United States Patent
Shelton, IV et al.

(10) Patent No.: US 12,016,566 B2
(45) Date of Patent: Jun. 25, 2024

(54) SURGICAL INSTRUMENT WITH ADAPTIVE FUNCTION CONTROLS

(71) Applicant: Cilag GmbH International, Zug (CH)

(72) Inventors: Frederick E. Shelton, IV, New Vienna, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 904 days.

(21) Appl. No.: 17/062,502

(22) Filed: Oct. 2, 2020

(65) Prior Publication Data

US 2022/0104821 A1    Apr. 7, 2022

(51) Int. Cl.
*A61B 17/064*    (2006.01)
*A61B 17/115*    (2006.01)
*A61B 17/00*    (2006.01)

(52) U.S. Cl.
CPC . *A61B 17/1155* (2013.01); *A61B 2017/00199* (2013.01); *A61B 2017/00221* (2013.01); *A61B 2560/0271* (2013.01)

(58) Field of Classification Search
CPC ................. A61B 17/1155; A61B 2017/00017
See application file for complete search history.

(56) References Cited

U.S. PATENT DOCUMENTS

| | | | |
|---|---|---|---|
| 6,352,532 B1 | 3/2002 | Kramer et al. | |
| 6,443,973 B1 | 9/2002 | Whitman | |
| 6,451,015 B1 | 9/2002 | Rittman, III et al. | |
| 7,032,798 B2 | 4/2006 | Whitman et al. | |
| 7,164,940 B2 | 1/2007 | Hareyama et al. | |
| 7,667,592 B2 | 2/2010 | Ohyama et al. | |
| 7,670,334 B2 | 3/2010 | Hueil et al. | |

(Continued)

FOREIGN PATENT DOCUMENTS

| | | |
|---|---|---|
| CA | 3089858 A1 | 8/2019 |
| EP | 2491872 A1 | 8/2012 |

(Continued)

OTHER PUBLICATIONS

U.S. Appl. No. 16/574,797, filed Sep. 18, 2019, Ethicon LLC.

(Continued)

*Primary Examiner* — Eyamindae C Jallow
(74) *Attorney, Agent, or Firm* — Condo Roccia Koptiw LLP

(57) ABSTRACT

A surgical instrument receives an indication to provide adaptive control of surgical instrument functions. The indication may indicate to provide adaptable staple height operating range, to control motors associated with tissue compression, and/or to operate using the operational parameters associated with previous surgical procedures. The surgical instrument may determine values for parameters associated with the identified function and adapt the control of the identified function based upon the determined parameters. The surgical instrument may adapt a display of staple height operating range based on parameters indicating a size of an anvil head. The surgical instrument may control motors associated with tissue compression based on parameters indicating force applied in the instrument. The surgical instrument may operate according to operational parameters identified by a surgical hub.

19 Claims, 61 Drawing Sheets

(56) References Cited

U.S. PATENT DOCUMENTS

| | | |
|---|---|---|
| 7,803,151 B2 | 9/2010 | Whitman |
| 7,833,219 B2 | 11/2010 | Tashiro et al. |
| 8,157,145 B2 | 4/2012 | Shelton, IV et al. |
| 8,255,045 B2 | 8/2012 | Gharib et al. |
| 8,476,227 B2 | 7/2013 | Kaplan et al. |
| 8,523,043 B2 | 9/2013 | Ullrich et al. |
| 8,608,045 B2 | 12/2013 | Smith et al. |
| 8,851,354 B2 | 10/2014 | Swensgard et al. |
| 8,918,207 B2 | 12/2014 | Prisco |
| 8,960,519 B2 | 2/2015 | Whitman et al. |
| 9,011,427 B2 | 4/2015 | Price et al. |
| 9,072,535 B2 | 7/2015 | Shelton, IV et al. |
| 9,123,155 B2 | 9/2015 | Cunningham et al. |
| 9,250,172 B2 | 2/2016 | Harris et al. |
| 9,283,054 B2 | 3/2016 | Morgan et al. |
| 9,345,481 B2 | 5/2016 | Hall et al. |
| 9,516,239 B2 | 12/2016 | Blanquart et al. |
| 9,538,962 B1 | 1/2017 | Hannaford et al. |
| 9,743,016 B2 | 8/2017 | Nestares et al. |
| 9,777,913 B2 | 10/2017 | Talbert et al. |
| 9,913,642 B2 | 3/2018 | Leimbach et al. |
| 10,244,991 B2 | 4/2019 | Shademan et al. |
| 10,492,783 B2 | 12/2019 | Shelton et al. |
| 10,639,037 B2 | 5/2020 | Shelton, IV et al. |
| 10,695,081 B2 | 6/2020 | Shelton, IV et al. |
| 10,881,399 B2 | 1/2021 | Shelton, IV et al. |
| 10,912,567 B2 | 2/2021 | Shelton, IV et al. |
| 11,123,074 B2 | 9/2021 | Adams et al. |
| 11,185,331 B2 | 11/2021 | Adams et al. |
| 11,284,963 B2 | 3/2022 | Shelton, IV et al. |
| 2004/0108825 A1 | 6/2004 | Lee et al. |
| 2005/0033117 A1 | 2/2005 | Ozaki et al. |
| 2005/0187576 A1 | 8/2005 | Whitman et al. |
| 2005/0206583 A1 | 9/2005 | Lemelson et al. |
| 2006/0076385 A1 | 4/2006 | Etter et al. |
| 2006/0082542 A1 | 4/2006 | Morita et al. |
| 2006/0184160 A1 | 8/2006 | Ozaki et al. |
| 2006/0273135 A1 | 12/2006 | Beetel |
| 2007/0055304 A1 | 3/2007 | Whitman |
| 2007/0151390 A1 | 7/2007 | Blumenkranz et al. |
| 2007/0225690 A1 | 9/2007 | Sekiguchi et al. |
| 2008/0319275 A1 | 12/2008 | Chiu et al. |
| 2009/0046146 A1 | 2/2009 | Hoyt |
| 2009/0090763 A1 | 4/2009 | Zemlok et al. |
| 2009/0128084 A1 | 5/2009 | Johnson et al. |
| 2009/0248022 A1 | 10/2009 | Falkenstein et al. |
| 2010/0096431 A1 | 4/2010 | Smith et al. |
| 2011/0095067 A1 | 4/2011 | Ohdaira |
| 2012/0138658 A1 | 6/2012 | Ullrich et al. |
| 2012/0182409 A1 | 7/2012 | Moriyama et al. |
| 2012/0211542 A1 | 8/2012 | Racenet |
| 2012/0248167 A1 | 10/2012 | Flanagan et al. |
| 2012/0253329 A1 | 10/2012 | Zemlok et al. |
| 2013/0116218 A1 | 5/2013 | Kaplan et al. |
| 2013/0197531 A1 | 8/2013 | Boukhny et al. |
| 2014/0087999 A1 | 3/2014 | Kaplan et al. |
| 2014/0160259 A1 | 6/2014 | Blanquart et al. |
| 2014/0160260 A1 | 6/2014 | Blanquart et al. |
| 2014/0160318 A1 | 6/2014 | Blanquart et al. |
| 2014/0160319 A1 | 6/2014 | Nestares et al. |
| 2014/0166728 A1 | 6/2014 | Swayze et al. |
| 2014/0214311 A1 | 7/2014 | Stevens et al. |
| 2014/0263541 A1 | 9/2014 | Leimbach et al. |
| 2014/0263551 A1 | 9/2014 | Hall et al. |
| 2014/0263552 A1 | 9/2014 | Hall et al. |
| 2014/0267655 A1 | 9/2014 | Richardson et al. |
| 2014/0268860 A1 | 9/2014 | Talbert et al. |
| 2015/0125447 A1 | 5/2015 | Heider |
| 2015/0182220 A1 | 7/2015 | Yates et al. |
| 2015/0223890 A1 | 8/2015 | Miller et al. |
| 2015/0342621 A1 | 12/2015 | Jackson, III |
| 2016/0066915 A1 | 3/2016 | Baber et al. |
| 2016/0066916 A1 | 3/2016 | Overmyer et al. |
| 2016/0100839 A1 | 4/2016 | Marczyk et al. |
| 2016/0171947 A1 | 6/2016 | Chen |
| 2016/0249919 A1 | 9/2016 | Savage et al. |
| 2016/0256156 A1 | 9/2016 | Shelton, IV et al. |
| 2016/0256184 A1 | 9/2016 | Shelton, IV et al. |
| 2016/0265938 A1 | 9/2016 | Hryb et al. |
| 2017/0086914 A1 | 3/2017 | Wiener et al. |
| 2017/0172381 A1 | 6/2017 | Morimoto |
| 2017/0199632 A1 | 7/2017 | Ohmura |
| 2017/0249431 A1 | 8/2017 | Shelton, IV et al. |
| 2017/0296169 A1 | 10/2017 | Yates et al. |
| 2017/0296178 A1 | 10/2017 | Miller et al. |
| 2017/0296213 A1 | 10/2017 | Swensgard et al. |
| 2017/0323062 A1 | 11/2017 | Djajadiningrat et al. |
| 2017/0333033 A1 | 11/2017 | Valentine et al. |
| 2018/0032130 A1 | 2/2018 | Meglan |
| 2018/0098049 A1 | 4/2018 | Sugano et al. |
| 2018/0098768 A1 | 4/2018 | Zhang et al. |
| 2018/0197624 A1 | 7/2018 | Robaina et al. |
| 2018/0329504 A1 | 11/2018 | Ziraknejad et al. |
| 2018/0353186 A1 | 12/2018 | Mozdzierz et al. |
| 2018/0360449 A1 | 12/2018 | Shelton, IV et al. |
| 2018/0360452 A1 | 12/2018 | Shelton et al. |
| 2018/0360460 A1 | 12/2018 | Mozdzierz et al. |
| 2019/0000446 A1 | 1/2019 | Shelton et al. |
| 2019/0000464 A1 | 1/2019 | Shelton, IV et al. |
| 2019/0000478 A1 | 1/2019 | Messerly et al. |
| 2019/0020420 A1 | 1/2019 | Zocher et al. |
| 2019/0099180 A1 | 4/2019 | Leimbach et al. |
| 2019/0104919 A1 | 4/2019 | Shelton, IV et al. |
| 2019/0125361 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0183591 A1 | 6/2019 | Johnson et al. |
| 2019/0200844 A1* | 7/2019 | Shelton, IV ........ H04L 63/1416 |
| 2019/0200906 A1 | 7/2019 | Shelton, IV et al. |
| 2019/0200981 A1* | 7/2019 | Harris ................ A61B 5/0022 |
| 2019/0200996 A1 | 7/2019 | Shelton et al. |
| 2019/0200997 A1* | 7/2019 | Shelton, IV ........... G16H 40/63 |
| 2019/0200998 A1 | 7/2019 | Shelton et al. |
| 2019/0201029 A1 | 7/2019 | Shelton, IV et al. |
| 2019/0201033 A1 | 7/2019 | Yates et al. |
| 2019/0201034 A1 | 7/2019 | Shelton et al. |
| 2019/0201044 A1 | 7/2019 | Shelton, IV et al. |
| 2019/0201102 A1 | 7/2019 | Shelton, IV et al. |
| 2019/0201104 A1 | 7/2019 | Shelton, IV et al. |
| 2019/0201115 A1 | 7/2019 | Shelton, IV et al. |
| 2019/0201119 A1 | 7/2019 | Harris et al. |
| 2019/0201122 A1 | 7/2019 | Shelton, IV et al. |
| 2019/0201129 A1 | 7/2019 | Shelton, IV et al. |
| 2019/0201136 A1 | 7/2019 | Shelton et al. |
| 2019/0201137 A1 | 7/2019 | Shelton et al. |
| 2019/0201140 A1 | 7/2019 | Yates et al. |
| 2019/0201141 A1 | 7/2019 | Shelton, IV et al. |
| 2019/0201144 A1 | 7/2019 | Shelton, IV et al. |
| 2019/0201146 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0206003 A1 | 7/2019 | Harris et al. |
| 2019/0206050 A1 | 7/2019 | Yates et al. |
| 2019/0206555 A1 | 7/2019 | Morgan et al. |
| 2019/0206562 A1* | 7/2019 | Shelton, IV ........ A61B 17/0206 |
| 2019/0206563 A1 | 7/2019 | Shelton et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton et al. |
| 2019/0250873 A1 | 8/2019 | Blume et al. |
| 2019/0314015 A1 | 10/2019 | Shelton, IV et al. |
| 2019/0388137 A1 | 12/2019 | Henrywood et al. |
| 2020/0078078 A1 | 3/2020 | Henderson et al. |
| 2020/0078079 A1 | 3/2020 | Morgan et al. |
| 2020/0162664 A1 | 5/2020 | Maeda et al. |
| 2020/0214571 A1 | 7/2020 | Bradbury et al. |
| 2020/0405304 A1 | 12/2020 | Mozdzierz et al. |
| 2020/0405311 A1* | 12/2020 | Shelton, IV ...... G06K 19/07758 |
| 2020/0405439 A1 | 12/2020 | Shelton et al. |
| 2021/0077110 A1 | 3/2021 | Adams et al. |
| 2021/0077111 A1 | 3/2021 | Adams et al. |
| 2021/0077112 A1 | 3/2021 | Adams et al. |
| 2021/0196384 A1 | 7/2021 | Shelton, IV et al. |
| 2021/0196423 A1 | 7/2021 | Shelton, IV et al. |

(56) References Cited

U.S. PATENT DOCUMENTS

| | | |
|---|---|---|
| 2021/0196425 A1 | 7/2021 | Shelton, IV et al. |
| 2021/0205027 A1 | 7/2021 | Leist |
| 2021/0401533 A1 | 12/2021 | Im |
| 2022/0022982 A1 | 1/2022 | Hares et al. |
| 2022/0025258 A1 | 1/2022 | Ichikawa et al. |
| 2022/0104694 A1 | 4/2022 | Shelton, IV et al. |
| 2022/0104713 A1 | 4/2022 | Shelton, IV |
| 2022/0104765 A1 | 4/2022 | Shelton, IV et al. |
| 2022/0104806 A1 | 4/2022 | Shelton, IV et al. |
| 2022/0104807 A1 | 4/2022 | Shelton, IV et al. |
| 2022/0104813 A1 | 4/2022 | Shelton, IV et al. |
| 2022/0104814 A1 | 4/2022 | Shelton, IV et al. |
| 2022/0104820 A1 | 4/2022 | Shelton, IV et al. |
| 2022/0104821 A1 | 4/2022 | Shelton, IV et al. |
| 2022/0104822 A1 | 4/2022 | Shelton, IV et al. |
| 2022/0104843 A1 | 4/2022 | Shelton, IV et al. |
| 2022/0104867 A1 | 4/2022 | Shelton, IV et al. |
| 2022/0104889 A1 | 4/2022 | Shelton, IV et al. |
| 2022/0104896 A1 | 4/2022 | Shelton, IV et al. |
| 2022/0104897 A1 | 4/2022 | Shelton, IV et al. |
| 2022/0104908 A1 | 4/2022 | Shelton, IV et al. |
| 2022/0104910 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0108783 A1 | 4/2022 | Shelton, IV et al. |
| 2022/0108788 A1 | 4/2022 | Shelton, IV et al. |
| 2022/0108789 A1 | 4/2022 | Shelton, IV et al. |

FOREIGN PATENT DOCUMENTS

| | | | |
|---|---|---|---|
| EP | 2659852 | A2 | 11/2013 |
| EP | 2789299 | A1 | 10/2014 |
| EP | 3061405 | A1 | 8/2016 |
| EP | 3064141 | A1 | 9/2016 |
| EP | 3412225 | A1 | 12/2018 |
| EP | 3449800 | A1 | 3/2019 |
| EP | 3466348 | A2 | 4/2019 |
| EP | 3506273 | A1 | 7/2019 |
| EP | 3506299 | A1 | 7/2019 |
| EP | 3547324 | A1 | 10/2019 |
| EP | 3628207 | A1 | 4/2020 |
| WO | 2015125447 | A1 | 8/2015 |
| WO | 2016171947 | A1 | 10/2016 |
| WO | WO 2019-130108 | A1 | 7/2019 |
| WO | WO-2019130088 | A1 * | 7/2019 ....... A61B 17/07207 |
| WO | 2019133140 | A9 | 9/2019 |
| WO | 2020/101283 | A1 | 5/2020 |
| WO | 2020/129916 | A1 | 6/2020 |
| WO | 2020/154351 | A1 | 7/2020 |

OTHER PUBLICATIONS

U.S. Appl. No. 16/574,281, filed Sep. 18, 2019, Ethicon LLC.
U.S. Appl. No. 17/062,504, filed Oct. 2, 2020, Shelton, et al.
U.S. Appl. No. 17/062,499, filed Oct. 2, 2020, Shelton, et al.
U.S. Appl. No. 17/062,496, filed Oct. 2, 2020, Shelton, et al.
"FPGA Fundamentals", Available at <https://www.ni.com/en-us/innovations/white-papers/08/fpga-fundamentals.html>, Jun. 17, 2020, pp. 1-9.
Google Scholar, "Google Scholar", 2 pages.
Slade, G. W., "The Fast Fourier Transform in Hardware: A Tutorial Based on an FPGA Implementation", Available at <http://web.mit.edu/>, Mar. 21, 2013, 27 pages.
WO 2020/101283 (A1), US 2021/0401533 (A1).
WO 2020/129916 (A1), US 2022/0025258 (A1).

* cited by examiner

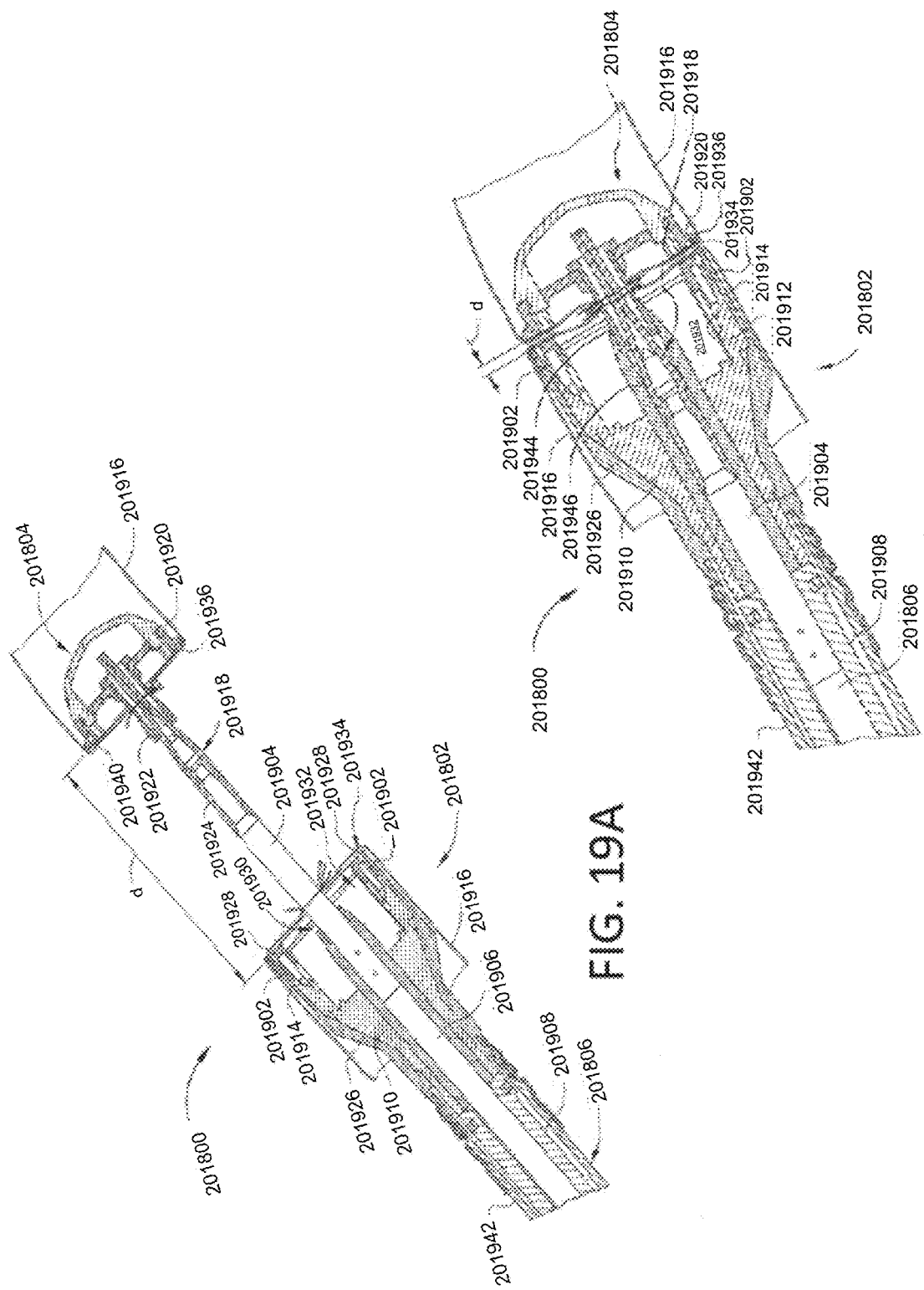

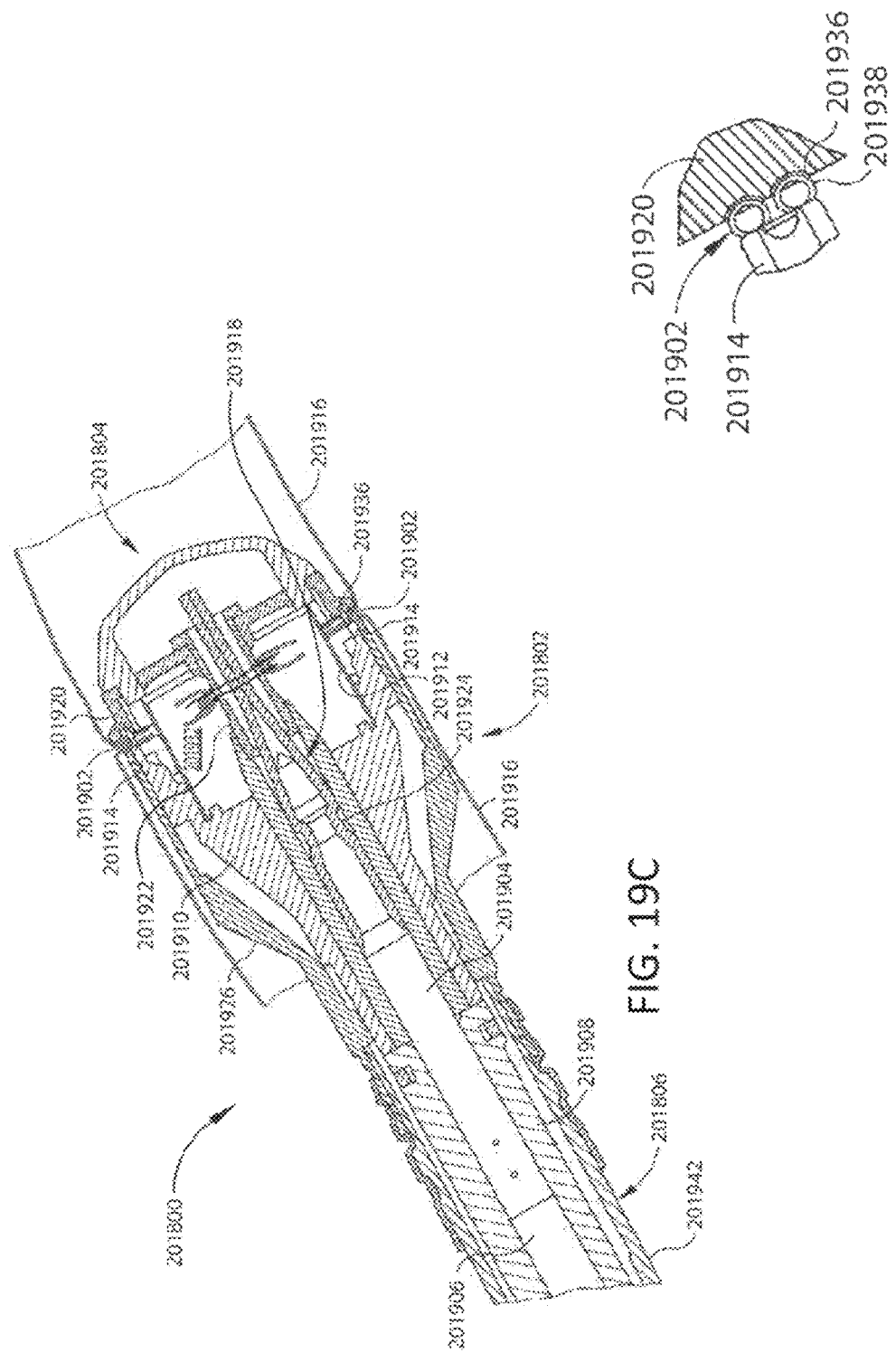

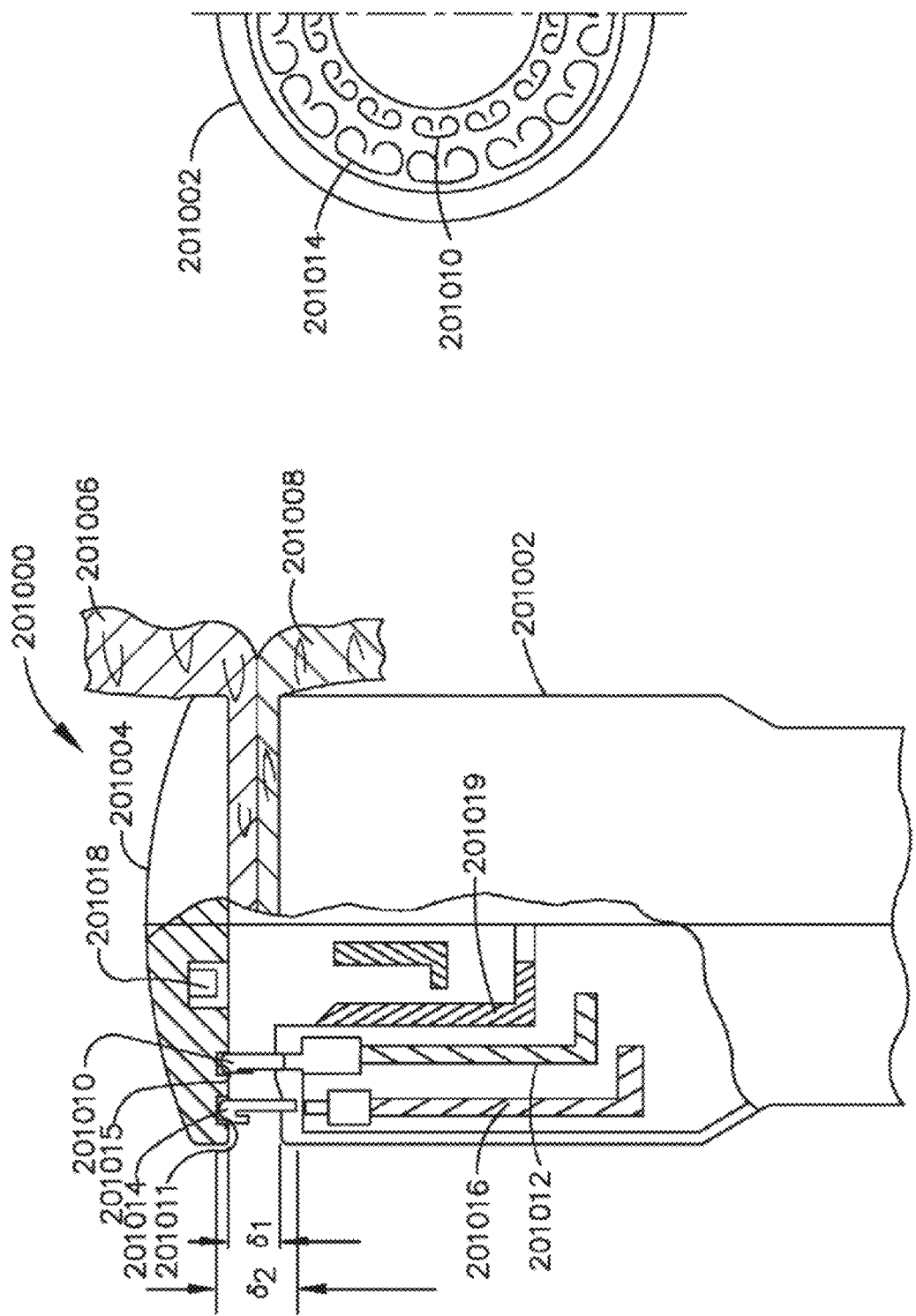

SURGICAL INSTRUMENT WITH ADAPTIVE FUNCTION CONTROLS

CROSS-REFERENCE TO RELATED APPLICATIONS

This application is related to the following, filed contemporaneously, the contents of each of which are incorporated by reference herein:

U.S. patent application Ser. No. 17/062,504, filed Oct. 2, 2020, titled METHOD FOR OPERATING TIERED OPERATION MODES IN A SURGICAL SYSTEM;

U.S. patent application Ser. No. 17/062,499, filed Oct. 2, 2020, titled SURGICAL INSTRUMENT WITH ADAPTIVE MOTOR CONTROL; and U.S. patent application Ser. No. 17/062,496, filed Oct. 2, 2020, titled SURGICAL INSTRUMENT WITH ADAPTIVE CONFIGURATION CONTROL.

BACKGROUND

Surgical instruments often comprise components or systems that operate to provide functions attendant to operation of the surgical instrument. For example, a surgical stapler may comprise a display adapted to provide feedback to an operator regarding the tissue compression. A surgical stapler may comprise a first motor that may provide force for clamping tissue, and a second motor that may provide force for driving a staple into the tissue.

SUMMARY

Systems and techniques are disclosed herein for adaptive control of surgical instrument functions. A surgical instrument may be configured to communicate with an external system such as, for example, a surgical hub. The surgical instrument may receive from the surgical hub an indication of one or more functions that are to be adaptively controlled by the surgical instrument. For example, a surgical stapler instrument may receive an indication to adaptively control a display of tissue compression. The surgical instrument may determine values for parameters associated with the identified function and adapt the control of the identified function based upon the determined parameters. A surgical stapler may receive an indication from the surgical hub to provide an adaptable representation of an operating range for tissue compression. In response to receiving the indication, the surgical stapler may determine one or more parameters associated with the surgical stapler. For example, the surgical stapler may determine parameters relating to the size of an anvil head of an end effector. The surgical stapler may modify the adaptable representation of the operating range for tissue compression based on the value of the parameters. For example, if the size of the anvil head is relatively small, the surgical stapler may modify the width of a band comprised in the adaptable representation of the operating range for tissue compression.

This Summary is provided to introduce a selection of concepts in a simplified form that are further described herein in the Detailed Description. This Summary is not intended to identify key features or essential features of the claimed subject matter, nor is it intended to be used to limit the scope of the claimed subject matter. Other features are described herein.

BRIEF DESCRIPTION OF THE DRAWINGS

FIG. 19A depicts an enlarged longitudinal cross-section view of a stapling head assembly of the instrument of FIG. 18 showing an anvil in an open position, in accordance with at least one aspect of the present disclosure.

FIG. 19B depicts an enlarged longitudinal cross-sectional view of the stapling head assembly of the instrument of FIG. 18 showing the anvil in a closed position, in accordance with at least one aspect of the present disclosure.

FIG. 19C depicts an enlarged longitudinal cross-sectional view of the stapling head assembly of the instrument of FIG. 18 showing a staple driver and blade in a fired position, in accordance with at least one aspect of the present disclosure.

FIG. 20 depicts an enlarged partial cross-sectional view of a staple formed against the anvil, in accordance with at least one aspect of the present disclosure.

FIG. 21 is a partial cutaway view of a powered circular stapling device comprising a circular stapling head assembly and an anvil, in accordance with at least one aspect of the present disclosure.

FIG. 22 is a partial top view of the circular stapling head assembly shown herein showing a first row of staples (inner staples) and a second row of staples (outer staples), in accordance with at least one aspect of the present disclosure.

DETAILED DESCRIPTION

Figure 1:
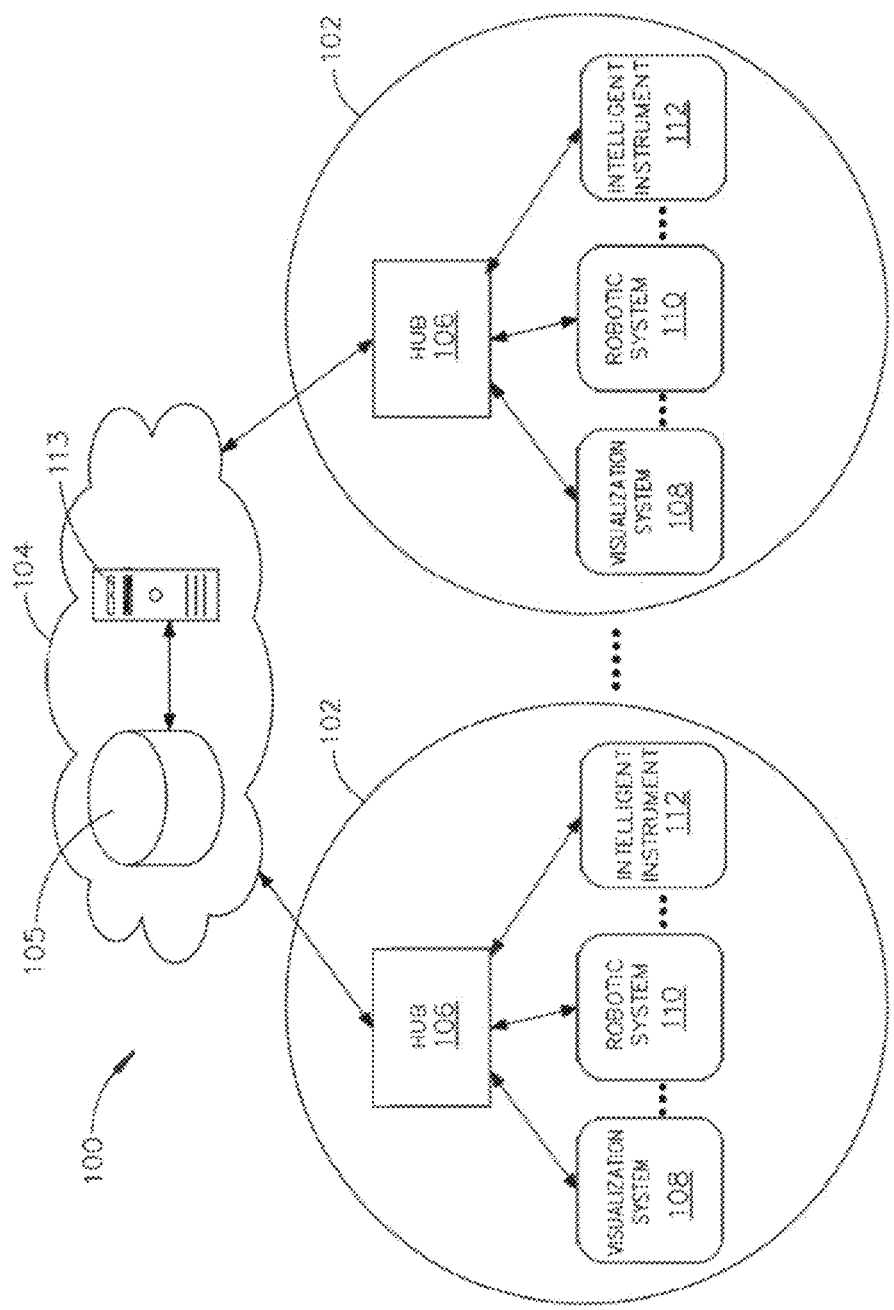
FIG. 1 is a block diagram of a computer-implemented interactive surgical system.

Applicant of the present application owns the following U.S. patent applications, patent publications, and patents, each of which is herein incorporated by reference in its entirety:

U.S. Patent Application Publication No. US 20190200981 (U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019;

U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018;

U.S. Patent Application Publication No. US20190206563A1 (U.S. patent application Ser. No. 16/209,465), titled Method for adaptive control schemes for surgical network control and interaction, filed Dec. 4, 2018;

U.S. Patent Application Publication No. US20190206562A1 (U.S. patent application Ser. No. 16/209,416), titled Method of hub communication, processing, display, and cloud analytics, filed Dec. 4, 2018;

U.S. Patent Application Publication No. US20190201034A1 (U.S. patent application Ser. No. 16/182,240), titled Powered stapling device configured to adjust force, advancement speed, and overall stroke of cutting member based on sensed parameter of firing or clamping, filed Nov. 6, 2018;

U.S. Patent Application Publication No. US20190200996A1 (U.S. patent application Ser. No. 16/182,229), titled ADJUSTMENT OF STAPLE HEIGHT OF AT LEAST ONE ROW OF STAPLES BASED ON THE SENSED TISSUE THICKNESS OR FORCE IN CLOSING, filed Nov. 6, 2018;

U.S. Patent Application Publication No. US20190200997A1 (U.S. patent application Ser. No. 16/182,234), titled Stapling device with both compulsory and discretionary lockouts based on sensed parameters, filed Nov. 6, 2018;

U.S. patent application Ser. No. 16/458,117, titled SURGICAL SYSTEM WITH RFID TAGS FOR UPDATING MOTOR ASSEMBLY PARAMETERS, filed Jun. 30, 2019;

U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018;

U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018;

U.S. Patent Application Publication No. 2017/0296213 (U.S. patent application Ser. No. 15/130,590), titled SYSTEMS AND METHODS FOR CONTROLLING A SURGICAL STAPLING AND CUTTING INSTRUMENT, published on Oct. 19, 2017;

U.S. Pat. No. 9,345,481, titled STAPLE CARTRIDGE TISSUE THICKNESS SENSOR SYSTEM, issued on May 24, 2016;

U.S. Patent Application Publication No. 2014/0263552 (U.S. patent application Ser. No. 13/800,067), titled STAPLE CARTRIDGE TISSUE THICKNESS SENSOR SYSTEM, published on Sep. 18, 2014;

U.S. Patent Application Publication No. US20180360452A1 (U.S. patent application Ser. No. 15/628,175), titled TECHNIQUES FOR ADAPTIVE CONTROL OF MOTOR VELOCITY OF A SURGICAL STAPLING AND CUTTING INSTRUMENT, filed Jun. 20, 2017;

U.S. Pat. No. 9,345,481, titled STAPLE CARTRIDGE TISSUE THICKNESS SENSOR SYSTEM, issued on May 24, 2016;

U.S. Patent Application Publication No. US20180360452A1 (U.S. patent application Ser. No.

15/628,175), titled TECHNIQUES FOR ADAPTIVE CONTROL OF MOTOR VELOCITY OF A SURGICAL STAPLING AND CUTTING INSTRUMENT, filed Jun. 20, 2017;

U.S. Patent Application Publication No. US20190000446A1 (U.S. patent application Ser. No. 15/636,829), titled CLOSED LOOP VELOCITY CONTROL TECHNIQUES FOR ROBOTIC SURGICAL INSTRUMENT, filed Jun. 29, 2017;

U.S. Patent Application Publication No. US20190099180A1 (U.S. patent application Ser. No. 15/720,852), titled SYSTEM AND METHODS FOR CONTROLLING A DISPLAY OF A SURGICAL INSTRUMENT, filed Sep. 29, 2017;

U.S. Patent Application Publication No. 2014/0166728 (U.S. patent application Ser. No. 13/716,318), entitled "Motor Driven Rotary Input Circular Stapler with Modular End Effector," published Jun. 19, 2014;

U.S. Pat. No. 9,250,172, titled Systems and methods for predicting metabolic and bariatric surgery outcomes, issued on Feb. 2, 2016;

U.S. Patent Application Publication No. US20130116218A1 (U.S. patent application Ser. No. 13/631,095), titled Methods and compositions of bile acids, published May 9, 2013;

U.S. Patent Application Publication No. US20140087999A1 (U.S. patent application Ser. No. 13/828,809), titled Clinical predictors of weight loss, published Mar. 27, 2014;

U.S. Pat. No. 8,476,227, titled Methods of activating a melanocortin-4 receptor pathway in obese subjects, issued Jul. 2, 2013;

U.S. patent application Ser. No. 16/574,773, titled METHOD FOR CALIBRATING MOVEMENTS OF ACTUATED MEMBERS OF POWERED SURGICAL STAPLER, filed Sep. 18, 2019;

U.S. patent application Ser. No. 16/574,797, titled METHOD FOR CONTROLLING CUTTING MEMBER ACTUATION FOR POWERED SURGICAL STAPLER, filed Sep. 18, 2019;

U.S. patent application Ser. No. 16/574,281, titled METHOD FOR CONTROLLING END EFFECTOR CLOSURE FOR POWERED SURGICAL STAPLER, filed Sep. 18, 2019;

U.S. Patent Application Publication No. US20190201119A1 (U.S. patent application Ser. No. 15/940,694), titled CLOUD-BASED MEDICAL ANALYTICS FOR MEDICAL FACILITY SEGMENTED INDIVIDUALIZATION OF INSTRUMENT FUNCTION, filed Mar. 29, 2018;

U.S. Pat. No. 10,492,783, titled SURGICAL INSTRUMENT WITH IMPROVED STOP/START CONTROL DURING A FIRING MOTION, issued on Dec. 3, 2019;

U.S. Patent Application Publication No. US20190200998A1 (U.S. patent application Ser. No. 16/209,491), titled METHOD FOR CIRCULAR STAPLER CONTROL ALGORITHM ADJUSTMENT BASED ON SITUATIONAL AWARENESS, filed Dec. 4, 2018; and U.S. Patent Application Publication No. US20190201140A1 (U.S. patent application Ser. No. 15/940,654), titled SURGICAL HUB SITUATIONAL AWARENESS, filed Mar. 29, 2018.

Systems and techniques are disclosed for controlling the communication capabilities between a surgical instrument such as, for example, a surgical stapler and a removeable component such as, for example, staple cartridge. A surgical instrument may determine one or more parameters associated with the surgical instrument and the removable component. For example, the surgical instrument may determine a parameter representing a software version associated with one of the surgical instrument or component. The surgical instrument may determine the type and degree of communication that may take place between the surgical instrument and the removable component based on the one or more parameters. For example, the surgical stapler may determine two-way communication may be performed between the surgical instrument and the removable component based upon a parameter indicating the surgical instrument and/or removable instrument comprise a recent software version.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
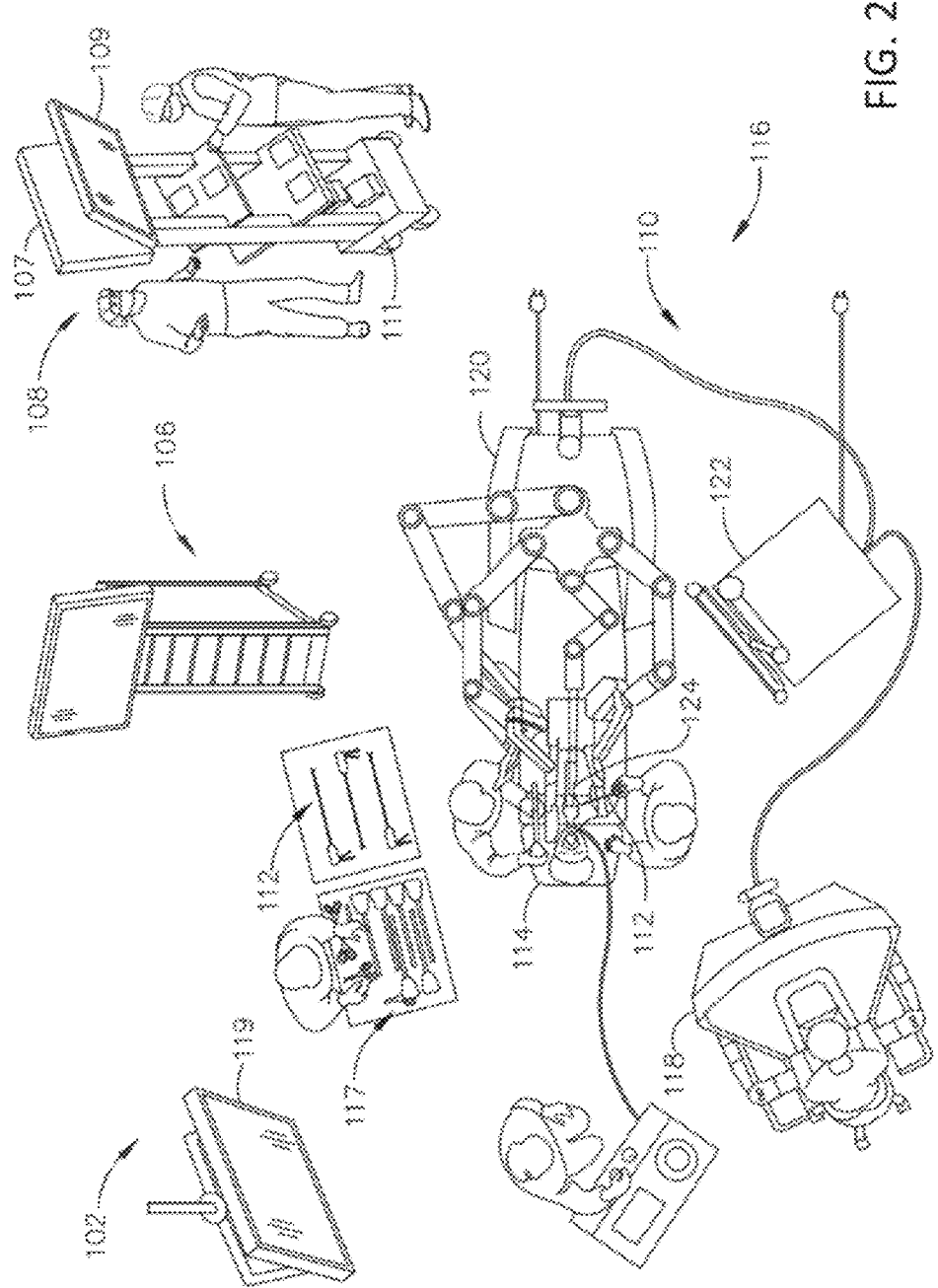
FIG. 2 shows an example surgical system being used to perform a surgical procedure in an operating room.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in US. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described in U.S. Patent Application Publication No. US 2019-0200844 A1 (U.S. patent application Ser. No. 16/209,385), tided METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
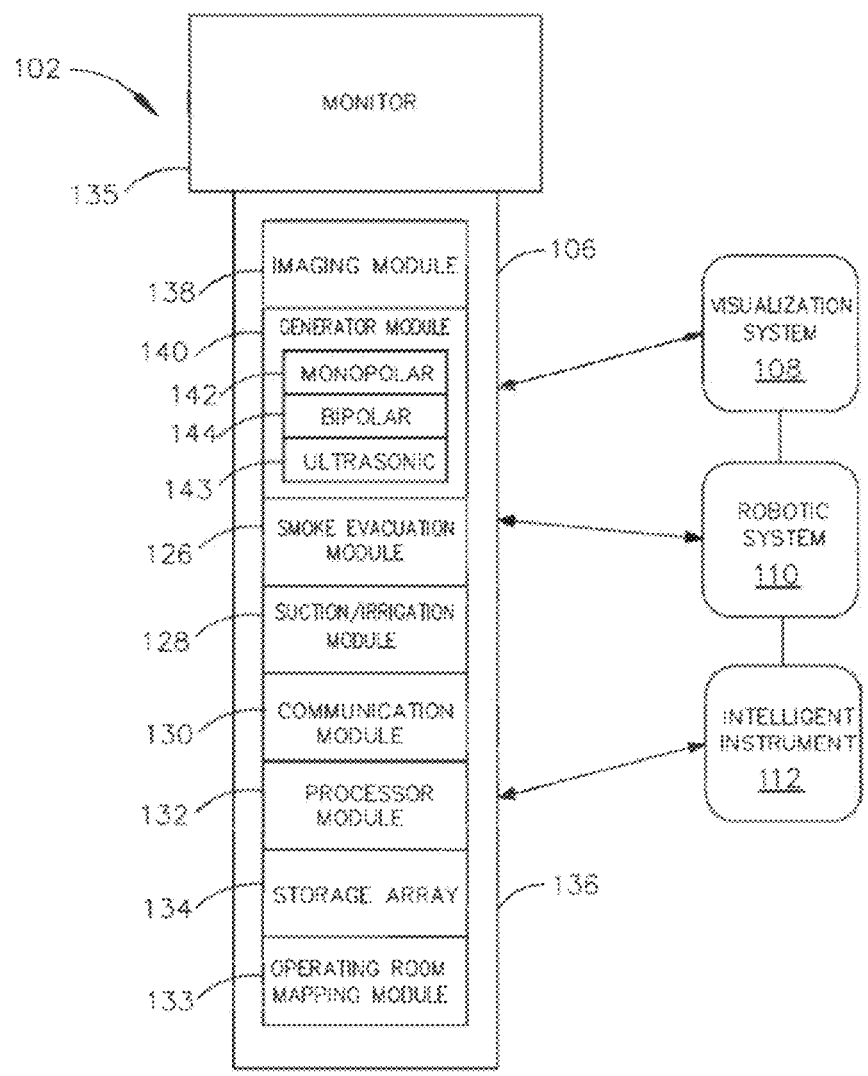
FIG. 3 shows an example surgical hub paired with a visualization system, a robotic system, and an intelligent instrument.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
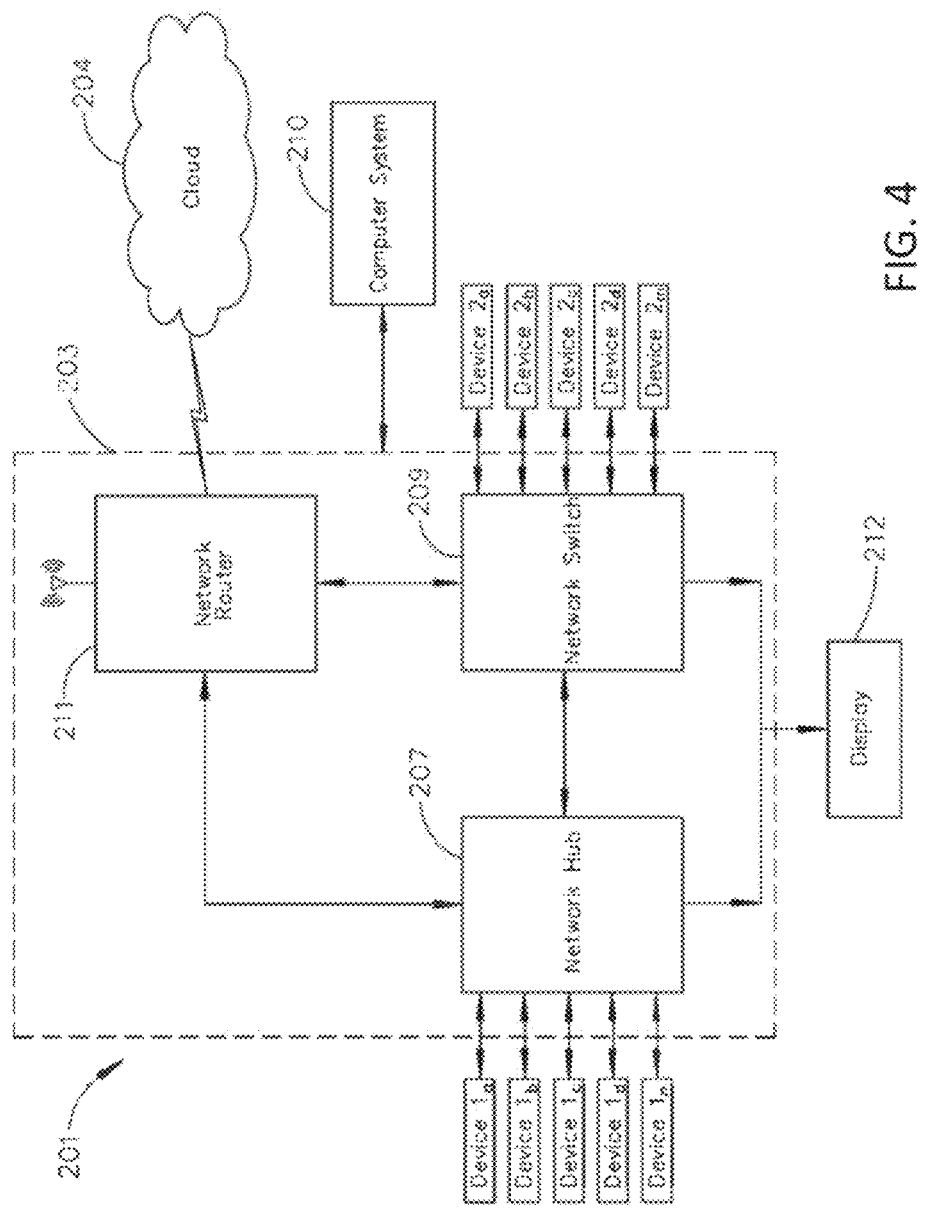
FIG. 4 illustrates a surgical data network having a communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (VIAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
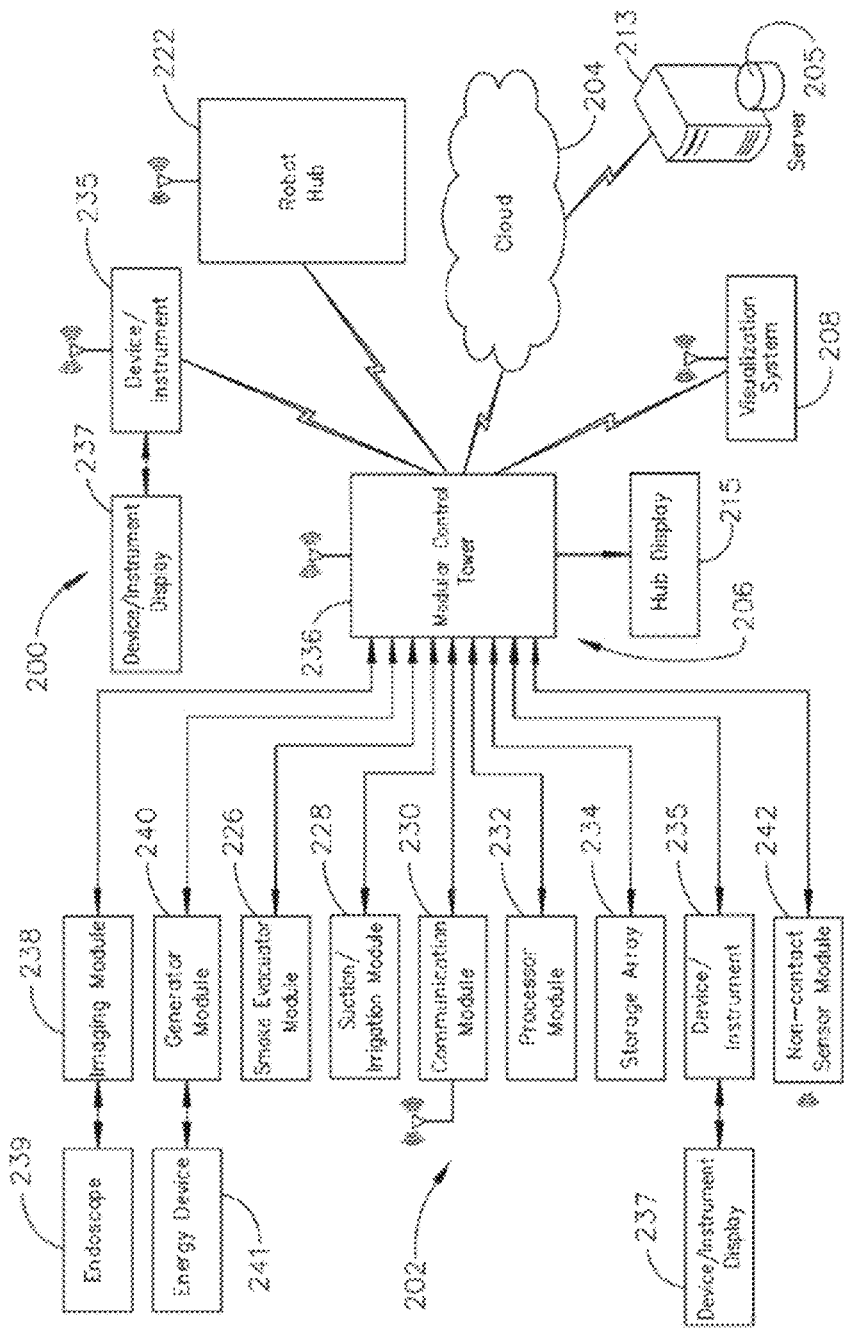
FIG. 5 illustrates an example computer-implemented interactive surgical system.
Figure 6:
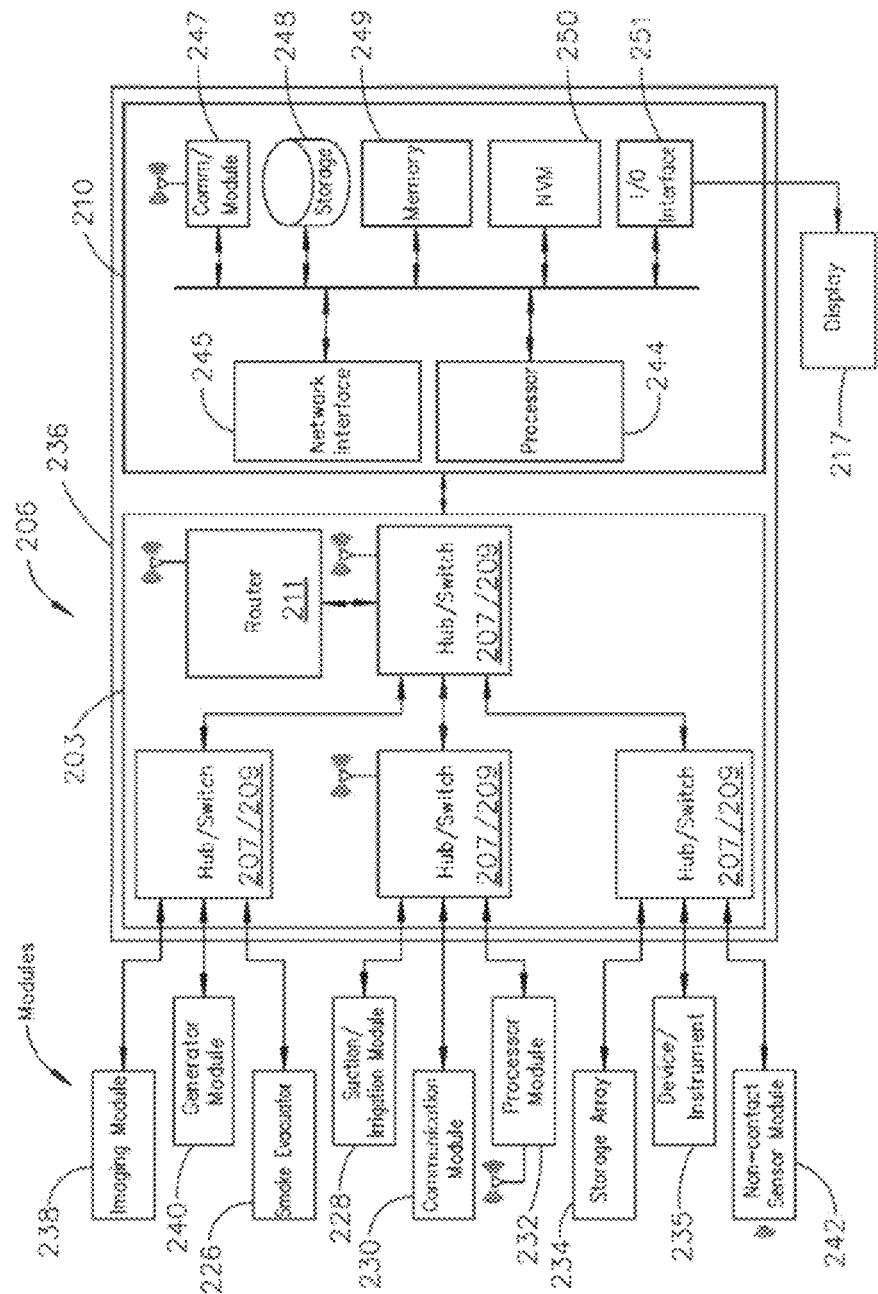
FIG. 6 illustrates an example surgical hub comprising a plurality of modules coupled to the modular control tower.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
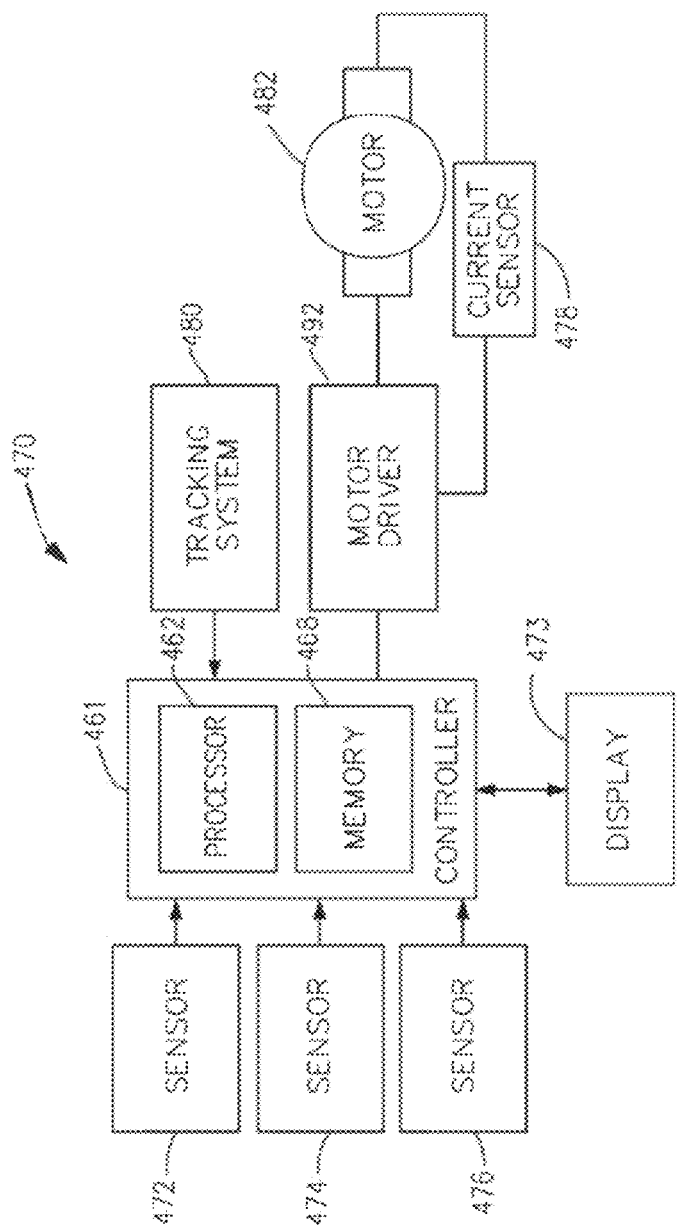
FIG. 7 illustrates an example surgical instrument or tool.

FIG. 7 illustrates a logic diagram of a control system 470 of a surgical instrument or tool in accordance with one or more aspects of the present disclosure. The system 470 may comprise a control circuit. The control circuit may include a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 may be configured to determine the position of the longitudinally movable displacement member. The position information may be provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 may display a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 may include a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, tided SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In some examples, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 may be a full-bridge controller for use with external N-channel power metal-oxide semiconductor field-effect transistors (MOSFETs) specifically designed for inductive loads, such as brush DC motors. The driver 492 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the lowside FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 may comprise a controlled motor drive circuit arrangement comprising a position sensor 472 according to one aspect of this disclosure. The position sensor 472 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 472 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches may be fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system may comprise a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 may be a low-voltage and low-power component and includes four Hall-effect elements in an area of the position sensor 472 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bitshift, and table lookup operations. The angle position, alarm bits, and magnetic field information may be transmitted over a standard serial communication interface, such as a serial peripheral interface (SPI) interface, to the microcontroller 461. The position sensor 472 may provide 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, tided STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, tided TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertial, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain can be converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force may be converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 474, such as, for example, a micro-strain gauge, that can be configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain can be converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub 203 as shown in FIGS. 5 and 6.

Figure 8:
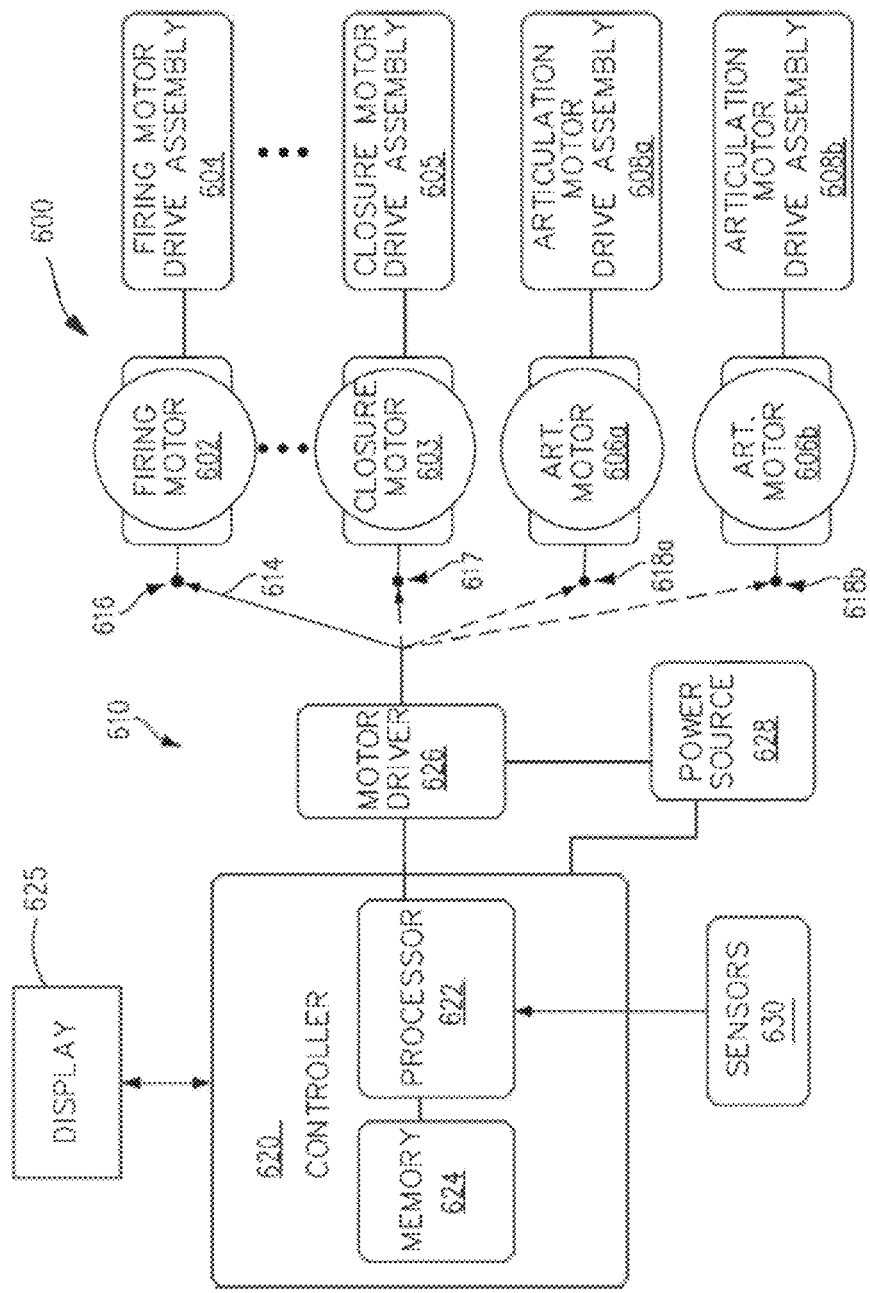
FIG. 8 illustrates an example surgical instrument or tool having motors that can be activated to perform various functions.

FIG. 8 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described herein, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 8, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 8, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described herein.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor can be a multipurpose, programmable device that accepts digital data as input, processes it according to instructions stored in its memory, and provides results as output. It can be an example of sequential digital logic, as it may have internal memory. Processors may operate on numbers and symbols represented in the binary numeral system.

The processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

The memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

One or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 9:
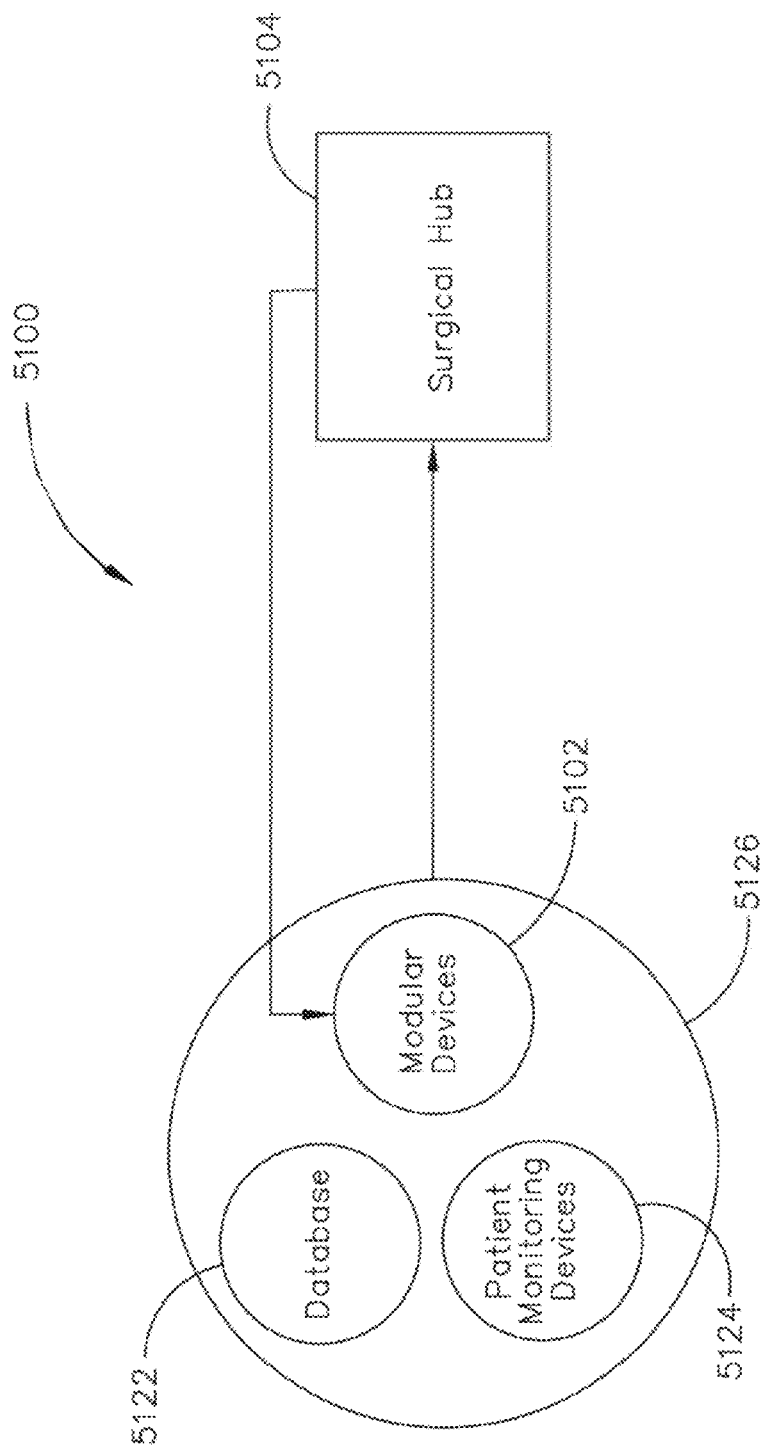
FIG. 9 is a diagram of an example situationally aware surgical system.

FIG. 9 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 10:
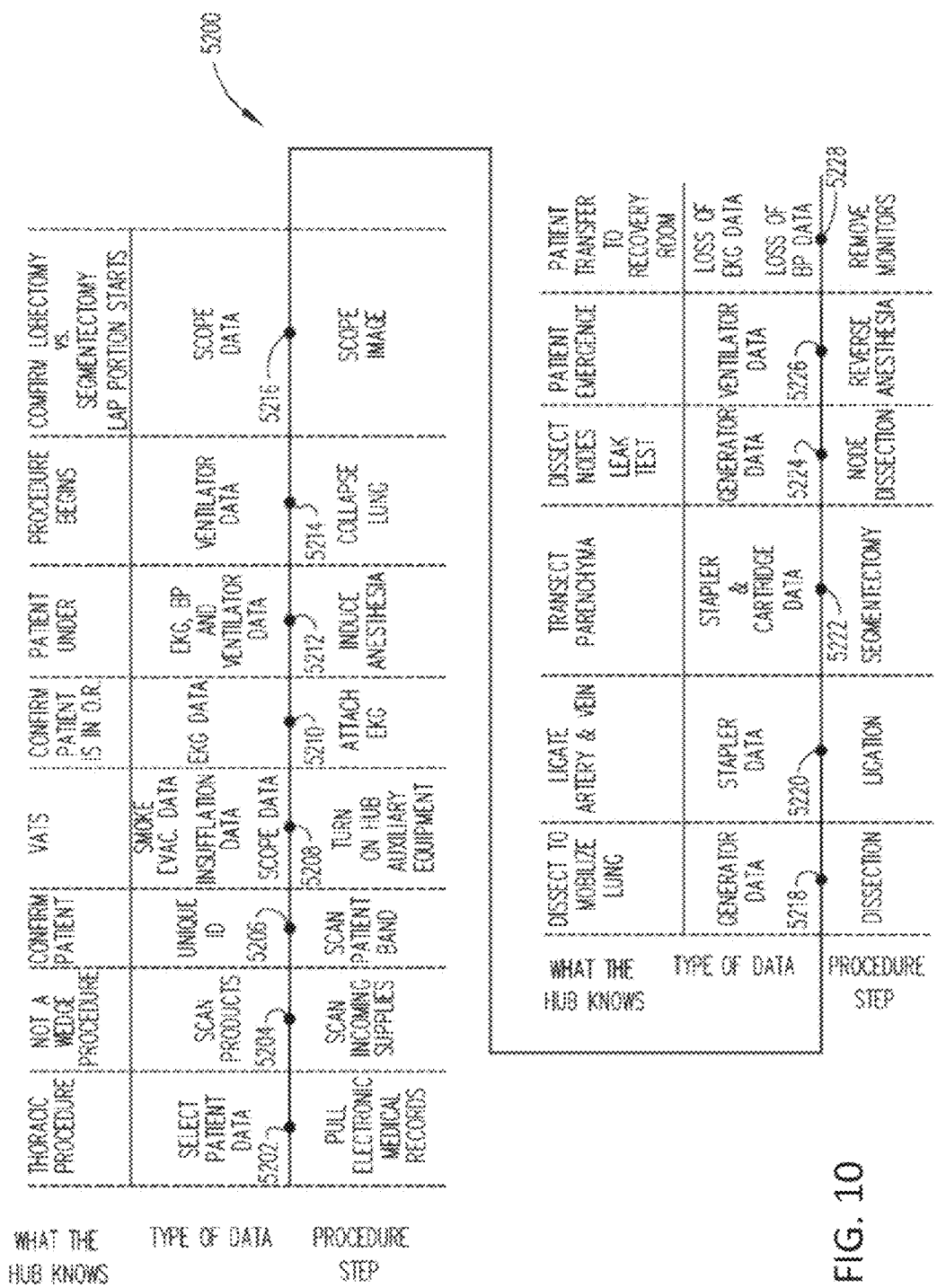
FIG. 10 illustrates an example timeline of an illustrative surgical procedure and the inferences that the surgical hub can make from the data detected at each step in the surgical procedure.

FIG. 10 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 9, reference should also be made to FIG. 9. The timeline 5200 may depict the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 may receive data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 can be able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described herein.

As the first step 5202 in this illustrative procedure, the hospital staff members may retrieve the patient's EMR from the hospital's EMR database. Based on select patient data in the EMR, the surgical hub 5104 determines that the procedure to be performed is a thoracic procedure. Second 5204, the staff members may scan the incoming medical supplies for the procedure. The surgical hub 5104 cross-references the scanned supplies with a list of supplies that can be utilized in various types of procedures and confirms that the mix of supplies corresponds to a thoracic procedure. Further, the surgical hub 5104 may also be able to determine that the procedure is not a wedge procedure (because the incoming supplies either lack certain supplies that are necessary for a thoracic wedge procedure or do not otherwise correspond to a thoracic wedge procedure). Third 5206, the medical personnel may scan the patient band via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that may be located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 may determine that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 may pair with the surgical hub 5104. As the surgical hub 5104 begins receiving data from the patient monitoring devices 5124, the surgical hub 5104 may confirm that the patient is in the operating theater, as described in the process 5207, for example. Sixth 5212, the medical personnel may induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof. for example. Upon completion of the sixth step 5212, the pre-operative portion of the lung segmentectomy procedure is completed and the operative portion begins.

Seventh 5214, the patient's lung that is being operated on may be collapsed (while ventilation is switched to the contralateral lung). The surgical hub 5104 can infer from the ventilator data that the patient's lung has been collapsed, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung can be the first operative step in this particular procedure. Eighth 5216, the medical imaging device 5108 (e.g., a scope) may be inserted and video from the medical imaging device may be initiated. The surgical hub 5104 may receive the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy may place the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. An example technique for performing a VATS lobectomy may utilize a single medical imaging device. An example technique for performing a VATS segmentectomy utilizes multiple cameras. An example technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team may begin the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team may proceed to the ligation step of the procedure. The surgical hub 5104 can infer that the surgeon is ligating arteries and veins because it may receive data from the surgical stapling and cutting instrument indicating that the instrument is being fired. Similar to the prior step, the surgical hub 5104 can derive this inference by cross-referencing the receipt of data from the surgical stapling and cutting instrument with the retrieved steps in the process. Eleventh 5222, the segmentectomy portion of the procedure can be performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (e.g., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure may begin.

Thirteenth 5226, the patient's anesthesia can be reversed. The surgical hub 5104 can infer that the patient is emerging from the anesthesia based on the ventilator data (i.e., the patient's breathing rate begins increasing), for example. Lastly, the fourteenth step 5228 may be that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 10, the patient data can also be utilized by a situationally aware surgical hub 5104 to generate control adjustments for the paired modular devices 5102.

Figure 11:
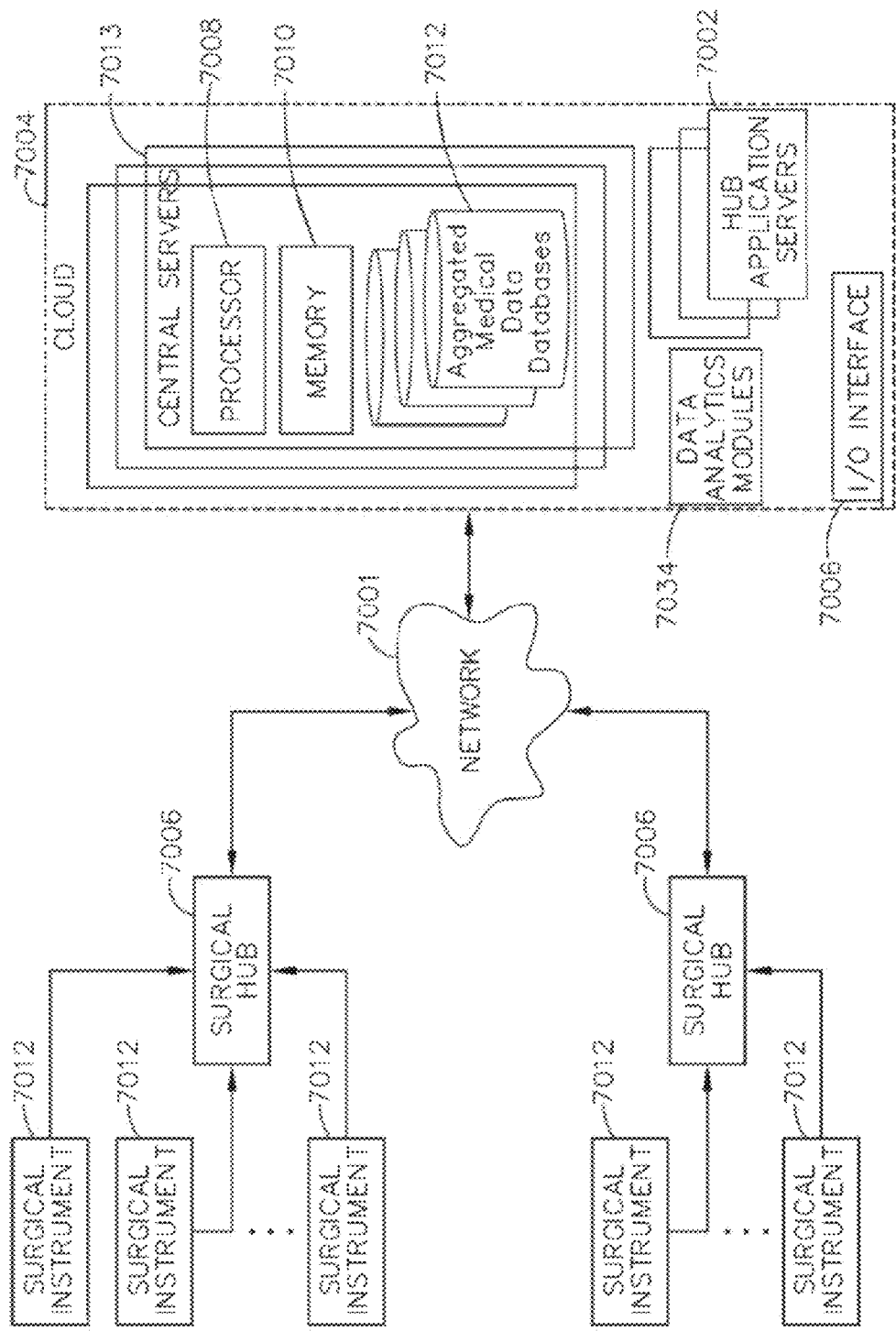
FIG. 11 is a block diagram of the computer-implemented interactive surgical system.

FIG. 11 is a block diagram of the computer-implemented interactive surgical system, in accordance with at least one aspect of the present disclosure. In one aspect, the computer-implemented interactive surgical system may be configured to monitor and analyze data related to the operation of various surgical systems that include surgical hubs, surgical instruments, robotic devices and operating theaters or healthcare facilities. The computer-implemented interactive surgical system may comprise a cloud-based analytics system. Although the cloud-based analytics system may be described as a surgical system, it may not be necessarily limited as such and could be a cloud-based medical system generally. As illustrated in FIG. 11, the cloud-based analytics system may comprise a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 may be communicatively coupled to one or more surgical instruments 7012. The hubs 7006 may also be communicatively coupled to the cloud 7004 of the computer-implemented interactive surgical system via the network 7001. The cloud 7004 may be a remote centralized source of hardware and software for storing, manipulating, and communicating data generated based on the operation of various surgical systems. As shown in FIG. 11, access to the cloud 7004 may be achieved via the network 7001, which may be the Internet or some other suitable computer network. Surgical hubs 7006 that may be coupled to the cloud 7004 can be considered the client side of the cloud computing system (i.e., cloud-based analytics system). Surgical instruments 7012 may be paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 11, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 may comprise one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also may comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7012 of the cloud 7004. In particular, the cloud 7004 may advantageously perform data analysis and operations on the aggregated data to yield insights and/or perform functions that individual hubs 7006 could not achieve on their own. To this end, as shown in FIG. 11, the cloud 7004 and the surgical hubs 7006 are communicatively coupled to transmit and receive information. The I/O interface 7006 is connected to the plurality of surgical hubs 7006 via the network 7001. In this way, the I/O interface 7006 can be configured to transfer information between the surgical hubs 7006 and the aggregated medical data databases 7011. Accordingly, the I/O interface 7006 may facilitate read/write operations of the cloud-based analytics system. Such read/write operations may be executed in response to requests from hubs 7006. These requests could be transmitted to the hubs 7006 through the hub applications. The I/O interface 7006 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 may be configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 12.

The particular cloud computing system configuration described in the present disclosure may be specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch-controlled user interfaces such that clinicians may control aspects of interaction between the surgical instruments 7012 and the cloud 7004. Other suitable user interfaces for control such as auditory controlled user interfaces can also be used.

Figure 12:
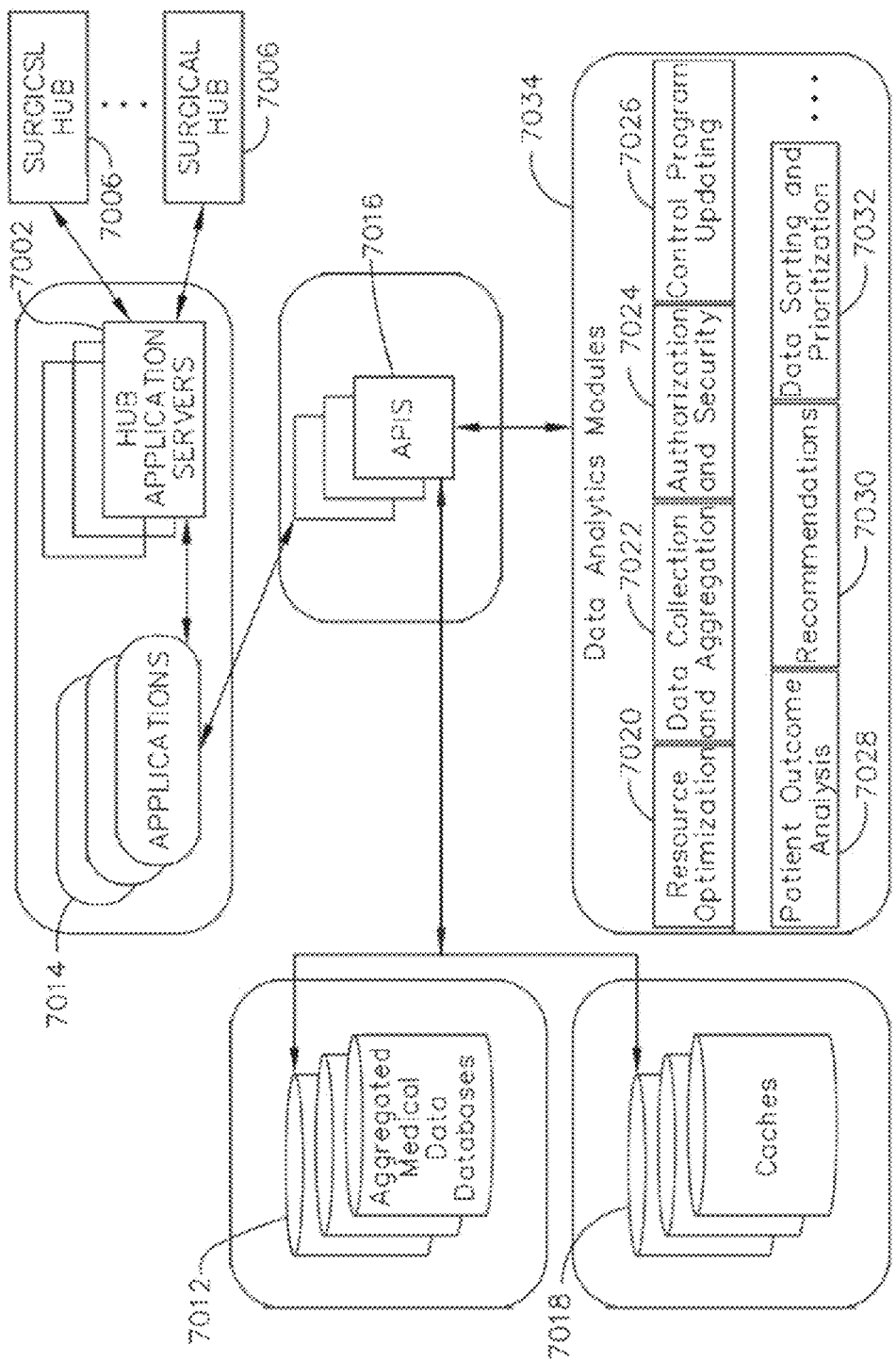
FIG. 12 illustrates the functional architecture of an example computer-implemented interactive surgical system.

FIG. 12 is a block diagram which illustrates the functional architecture of the computer-implemented interactive surgical system, in accordance with at least one aspect of the present disclosure. The cloud-based analytics system may include a plurality of data analytics modules 7034 that may be executed by the processors 7008 of the cloud 7004 for providing data analytic solutions to problems specifically arising in the medical field. As shown in FIG. 12, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 may define the set of protocols and routines corresponding to the hub applications 7014. Additionally, the APIs 7016 may manage the storing and retrieval of data into and from the aggregated medical databases 7012 for the operations of the applications 7014. The caches 7018 may also store data (e.g., temporarily) and may be coupled to the APIs 7016 for more efficient retrieval of data used by the applications 7014. The data analytics modules 7034 in FIG. 12 may include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules may be used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that may be transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, instruments 7012, and other devices that may comprise a "black list" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally, or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash-based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described herein to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 11 and 12 as one example of hardware and software implementation.

Figure 13:
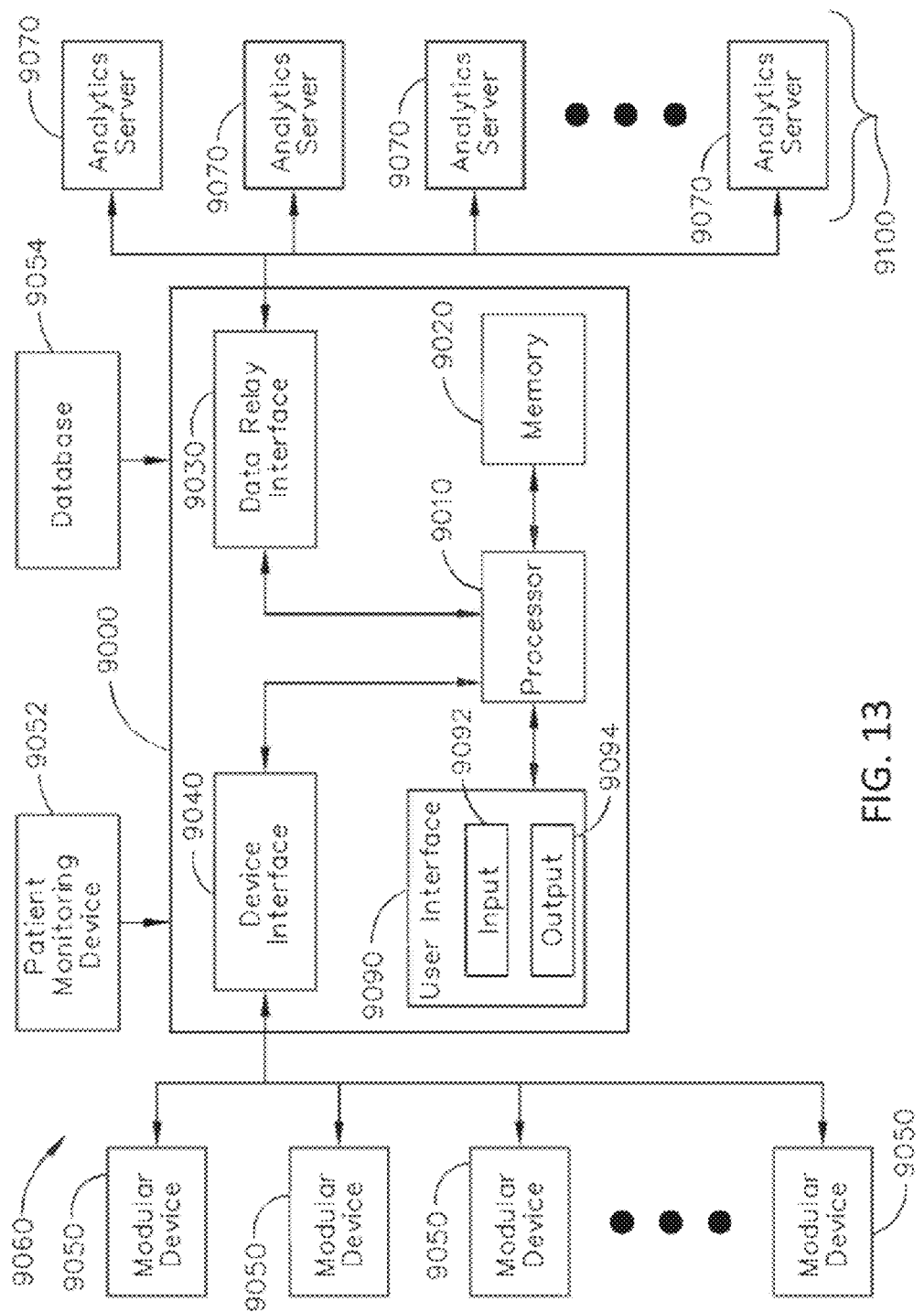
FIG. 13 illustrates an example computer-implemented interactive surgical system that is configured to adaptively generate control program updates for modular devices.

FIG. 13 illustrates a block diagram of a computer-implemented adaptive surgical system 9060 that is configured to adaptively generate control program updates for modular devices 9050, in accordance with at least one aspect of the present disclosure. In some exemplifications, the surgical system may include a surgical hub 9000, multiple modular devices 9050 communicably coupled to the surgical hub 9000, and an analytics system 9100 communicably coupled to the surgical hub 9000. Although a single surgical hub 9000 may be depicted, it should be noted that the surgical system 9060 can include any number of surgical hubs 9000, which can be connected to form a network of surgical hubs 9000 that are communicably coupled to the analytics system 9010. In some exemplifications, the surgical hub 9000 may include a processor 9010 coupled to a memory 9020 for executing instructions stored thereon and a data relay interface 9030 through which data is transmitted to the analytics system 9100. In some exemplifications, the surgical hub 9000 further may include a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further may include an interface 9040 for communicably coupling the modular devices 9050 to the surgical hub 9000. In one aspect, the interface 9040 may include a transceiver that is communicably connectable to the modular device 9050 via a wireless communication protocol. The modular devices 9050 can include, for example, surgical stapling and cutting instruments, electrosurgical instruments, ultrasonic instruments, insufflators, respirators, and display screens. In some exemplifications, the surgical hub 9000 can further be communicably coupled to one or more patient monitoring devices 9052, such as EKG monitors or BP monitors. In some exemplifications, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data may indicate how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In some exemplifications, the analytics system 9100 may include a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 may be connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 5-6.

Figure 14:
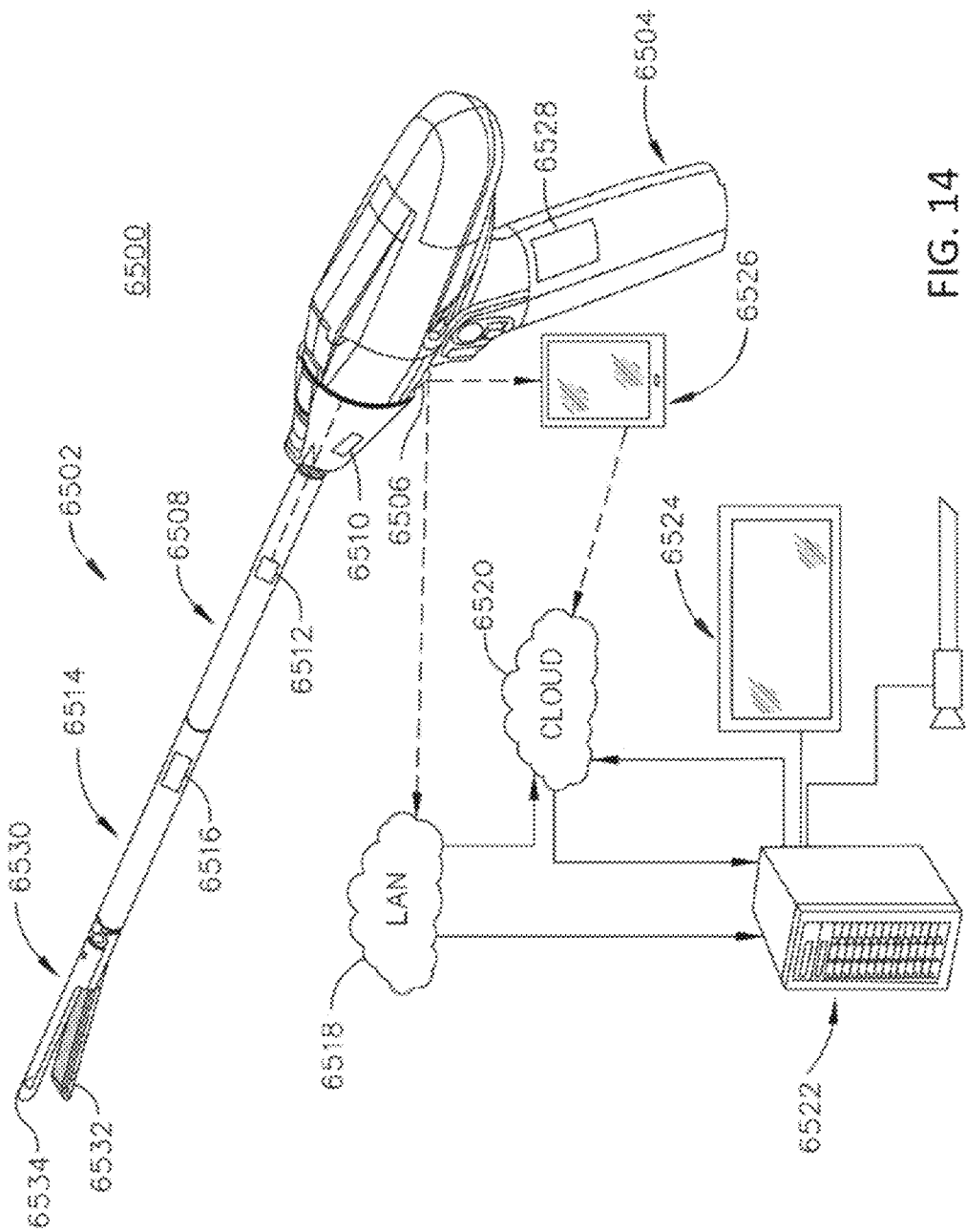
FIG. 14 illustrates an example surgical system that includes a handle having a controller and a motor, an adapter releasably coupled to the handle, and a loading unit releasably coupled to the adapter.

FIG. 14 provides a surgical system 6500 in accordance with the present disclosure and may include a surgical instrument 6502 that can be in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 may include a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 may include an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 may be configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more than one time prior to being replaced. The second jaw 6534 may include an anvil that deforms or otherwise secures the fasteners about tissue as the fasteners are ejected from the multi-fire fastener cartridge.

The handle 6504 may include a motor that is coupled to the drive shaft to affect rotation of the drive shaft. The handle 6504 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 may be in communication with a controller 6528 of the handle 6504 to selectively activate the motor to affect rotation of the drive shafts. The controller 6528 may be disposed within the handle 6504 and is configured to receive input from the control interface and adapter data from the adapter 6508 or loading unit data from the loading unit 6514. The controller 6528 may analyze the input from the control interface and the data received from the adapter 6508 and/or loading unit 6514 to selectively activate the motor. The handle 6504 may also include a display that is viewable by a clinician during use of the handle 6504. The display may be configured to display portions of the adapter or loading unit data before, during, or after firing of the instrument 6502.

The adapter 6508 may include an adapter identification device 6510 disposed therein and the loading unit 6514 includes a loading unit identification device 6516 disposed therein. The adapter identification device 6510 may be in communication with the controller 6528, and the loading unit identification device 6516 may be in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 may provide an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 can be configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 may include a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Figure 15:
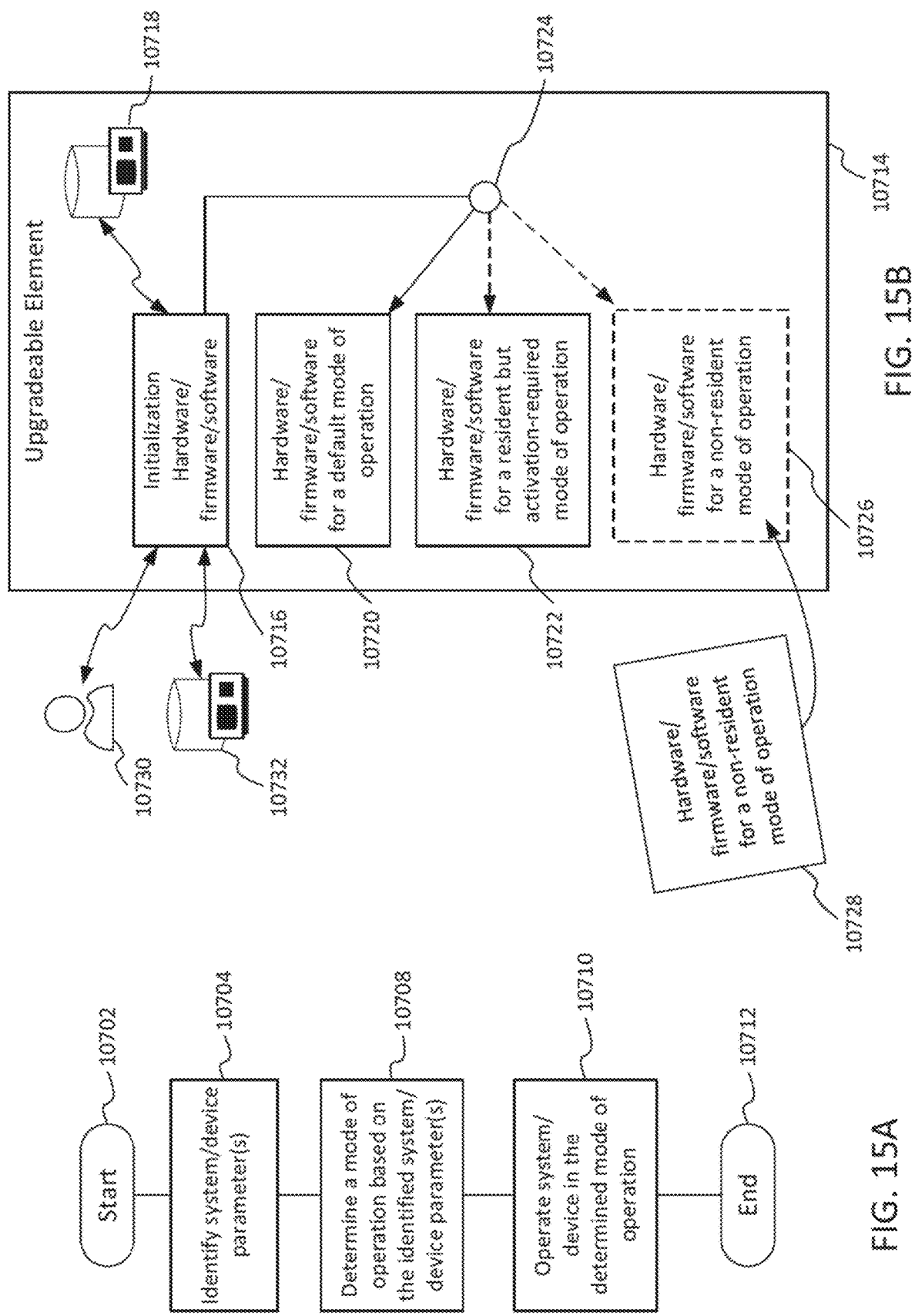
FIG. 15A illustrates an example flow for determining a mode of operation and operating in the determined mode.
FIG. 15B illustrates an example flow for changing a mode of operation.

FIG. 15A illustrates an example flow for determining a mode of operation and operating in the determined mode. The computer-implemented interactive surgical system and/or components and/or subsystems of the computer-implemented interactive surgical system may be configured to be updated. Such updates may include the inclusions of features and benefits that were not available to the user before the update. These updates may be established by any method of hardware, firmware, and software updates suitable for introducing the feature to the user. For example, replaceable/swappable (e.g., hot swappable) hardware components, flashable firmware devices, and updatable software systems may be used to update computer-implemented interactive surgical system and/or components and/or subsystems of the computer-implemented interactive surgical system.

The updates may be conditioned on any suitable criterion or set of criteria. For example, an update may be conditioned on one or more hardware capabilities of the system, such as processing capability, bandwidth, resolution, and the like. For example, the update may be conditioned on one or more software aspects, such as a purchase of certain software code. For example, the update may be conditioned on a purchased service tier. The service tier may represent a feature and/or a set of features the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, or the like.

At 10704, a system/device parameter may be identified. The system/device parameter may be any element or set of elements on which an update in conditioned. For example, the computer-implemented interactive surgical system may detect a certain bandwidth of communication between a modular device and a surgical hub. For example, the computer-implemented interactive surgical system may detect an indication of the purchase of certain service tier.

At 10708, a mode of operation may be determined based on the identified system/device parameter. This determination may be made by a process that maps system/device parameters to modes of operation. The process may be a manual and/or an automated process. The process may be the result of local computation and/or remote computation. For example, a client/server interaction may be used to determine the mode of operation based on the on the identified system/device parameter. For example, local software and/or locally embedded firmware may be used to determine the mode of operation based on the identified system/device parameter. For example, a hardware key, such as a secure microprocessor for example, may be used to determine the mode of operation based on the identified system/device parameter.

At 10710, operation may proceed in accordance with the determined mode of operation. For example, a system or device may proceed to operate in a default mode of operation. For example, a system or device may proceed to operate in an alternate mode of operation. The mode of operation may be directed by control hardware, firmware, and/or software already resident in the system or device. The mode of operation may be directed by control hardware, firmware, and/or software newly installed/updated.

FIG. 15B illustrates an example functional block diagram for changing a mode of operation. An upgradeable element 10714 may include an initialization component 10716. The initialization component 10716 may include any hardware, firmware, and/or software suitable determining a mode of operation. For example, the initialization component 10716 may be portion of a system or device start-up procedure. The initialization component 10716 may engage in an interaction to determine a mode of operation for the upgradeable element 10714. For example, the initialization component 10716 may interact with a user 10730, an external resource 10732, and/or a local resource 10718 for example. For example, the initialization component 10716 may receive a licensing key from the user 10730 to determine a mode of operation. The initialization component 10716 may query an external resource 10732, such as a server for example, with a serial number of the upgradable device 10714 to determine a mode of operation. For example, the initialization component 10716 may query a local resource 10718, such as a local query to determine an amount of available bandwidth and/or a local query of a hardware key for example, to determine a mode of operation.

The upgradeable element 10714 may include one or more operation components 10720, 10722, 10726, 10728 and an operational pointer 10724. The initialization component 10716 may direct the operational pointer 10724 to direct the operation of the upgradable element 10741 to the operation component 10720, 10722, 10726, 10728 that corresponds with the determined mode of operation. The initialization component 10716 may direct the operational pointer 10724 to direct the operation of the upgradable element to a default operation component 10720. For example, the default operation component 10720 may be selected on the condition of no other alternate mode of operation being determined. For example, the default operation component 10720 may be selected on the condition of a failure of the initialization component and/or interaction failure. The initialization component 10716 may direct the operational pointer 10724 to direct the operation of the upgradable element 10714 to a resident operation component 10722. For example, certain features may be resident in the upgradable component 10714 but require activation to be put into operation. The initialization component 10716 may direct the operational pointer 10724 to direct the operation of the upgradable element 10714 to install a new operation component 10728 and/or a new installed operation component 10726. For example, new software and/or firmware may be downloaded. The new software and or firmware may contain code to enable the features represented by the selected mode of operation. For example, a new hardware component may be installed to enable the selected mode of operation.

Figure 16:
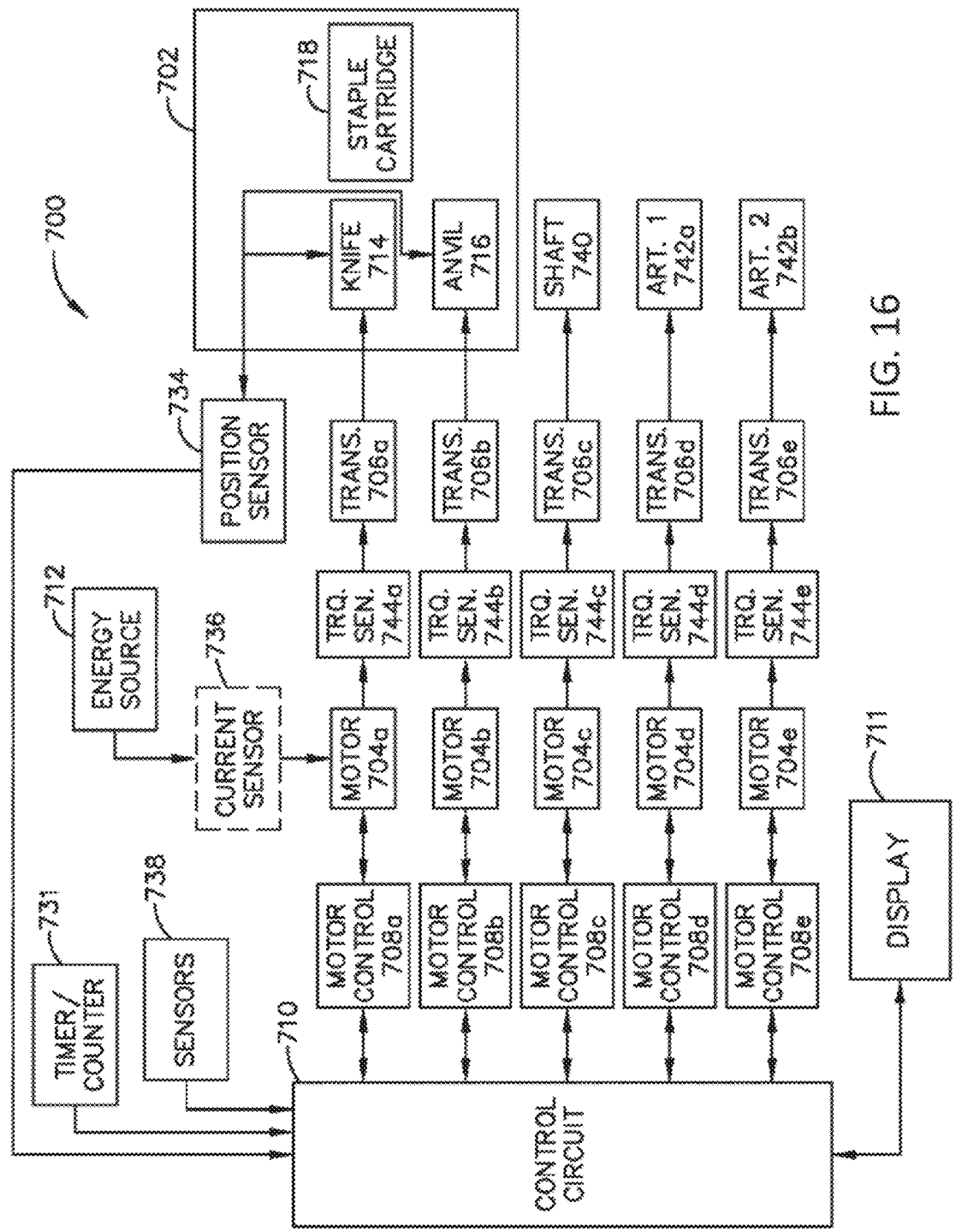
FIG. 16 is a schematic diagram of a surgical instrument configured to operate a surgical tool described herein, in accordance with at least one aspect of the present disclosure.

FIG. 16 is a schematic diagram of a surgical instrument 700 configured to operate a surgical tool described herein according to one aspect of this disclosure. The surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members. In one aspect, the surgical instrument 700 is representative of a hand held surgical instrument. In another aspect, the surgical instrument 700 is representative of a robotic surgical instrument. In other aspects, the surgical instrument 700 is representative of a combination of a hand held and robotic surgical instrument. In various aspects, the surgical stapler 700 may be representative of a linear stapler or a circular stapler.

In one aspect, the surgical instrument 700 comprises a control circuit 710 configured to control an anvil 716 and a knife 714 (or cutting element including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the knife 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the knife 714 as determined by the position sensor 734 with the output of the timer/counter 731 such that the control circuit 710 can determine the position of the knife 714 at a specific time (t) relative to a starting position or the time (t) when the knife 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742 a, 742 b.

In one aspect, the control circuit 710 may generate motor set point signals. The motor set point signals may be provided to various motor controllers 708 a-708 e. The motor controllers 708 a-708 e may comprise one or more circuits configured to provide motor drive signals to the motors 704 a-704 e to drive the motors 704 a-704 e as described herein. In some examples, the motors 704 a-704 e may be brushed DC electric motors. For example, the velocity of the motors 704 a-704 e may be proportional to the respective motor drive signals. In some examples, the motors 704 a-704 e may be brushless DC electric motors, and the respective motor drive signals may comprise a PWM signal provided to one or more stator windings of the motors 704 a-704 e. Also, in some examples, the motor controllers 708 a-708 e may be omitted and the control circuit 710 may generate the motor drive signals directly.

In one aspect, the control circuit 710 may initially operate each of the motors 704 a-704 e in an open-loop configuration for a first open-loop portion of a stroke of the displacement member. Based on the response of the surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704 a-704 e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704 a-704 e based on translation data describing a position of the displacement member in a closed-loop manner to translate the displacement member at a constant velocity.

In one aspect, the motors 704 a-704 e may receive power from an energy source 712. The energy source 712 may be a DC power supply driven by a main alternating current power source, a battery, a super capacitor, or any other suitable energy source. The motors 704 a-704 e may be mechanically coupled to individual movable mechanical elements such as the knife 714, anvil 716, shaft 740, articulation 742 a, and articulation 742 b via respective transmissions 706 a-706 e. The transmissions 706 a-706 e may include one or more gears or other linkage components to couple the motors 704 a-704 e to movable mechanical elements. A position sensor 734 may sense a position of the knife 714. The position sensor 734 may be or include any type of sensor that is capable of generating position data that indicate a position of the knife 714. In some examples, the position sensor 734 may include an encoder configured to provide a series of pulses to the control circuit 710 as the knife 714 translates distally and proximally. The control circuit 710 may track the pulses to determine the position of the knife 714. Other suitable position sensors may be used, including, for example, a proximity sensor. Other types of position sensors may provide other signals indicating motion of the knife 714. Also, in some examples, the position sensor 734 may be omitted. Where any of the motors 704 a-704 e is a stepper motor, the control circuit 710 may track the position of the knife 714 by aggregating the number and direction of steps that the motor 704 has been instructed to execute. The position sensor 734 may be located in the end effector 702 or at any other portion of the instrument. The outputs of each of the motors 704 a-704 e include a torque sensor 744 a-744 e to sense force and have an encoder to sense rotation of the drive shaft.

In one aspect, the control circuit 710 is configured to drive a firing member such as the knife 714 portion of the end effector 702. The control circuit 710 provides a motor set point to a motor control 708 a, which provides a drive signal to the motor 704 a. The output shaft of the motor 704 a is coupled to a torque sensor 744 a. The torque sensor 744 a is coupled to a transmission 706 a which is coupled to the knife 714. The transmission 706 a comprises movable mechanical elements such as rotating elements and a firing member to control the movement of the knife 714 distally and proximally along a longitudinal axis of the end effector 702. In one aspect, the motor 704 a may be coupled to the knife gear assembly, which includes a knife gear reduction set that includes a first knife drive gear and a second knife drive gear. A torque sensor 744 a provides a firing force feedback signal to the control circuit 710. The firing force signal represents the force required to fire or displace the knife 714. A position sensor 734 may be configured to provide the position of the knife 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708 a. In response to the firing signal, the motor 704 a may drive the firing member distally along the longitudinal axis of the end effector 702 from a proximal stroke start position to a stroke end position distal to the stroke start position. As the firing member translates distally, a knife 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708 *b*, which provides a drive signal to the motor 704 *b*. The output shaft of the motor 704 *b* is coupled to a torque sensor 744 *b*. The torque sensor 744 *b* is coupled to a transmission 706 *b* which is coupled to the anvil 716. The transmission 706 *b* comprises movable mechanical elements such as rotating elements and a closure member to control the movement of the anvil 716 from the open and closed positions. In one aspect, the motor 704 *b* is coupled to a closure gear assembly, which includes a closure reduction gear set that is supported in meshing engagement with the closure spur gear. The torque sensor 744 *b* provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708 *b*. In response to the closure signal, the motor 704 *b* advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708 *c*, which provides a drive signal to the motor 704 *c*. The output shaft of the motor 704 *c* is coupled to a torque sensor 744 *c*. The torque sensor 744 *c* is coupled to a transmission 706 *c* which is coupled to the shaft 740. The transmission 706 *c* comprises movable mechanical elements such as rotating elements to control the rotation of the shaft 740 clockwise or counterclockwise up to and over 360°. In one aspect, the motor 704 *c* is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744 *c* provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In a circular stapler implementation, the transmission 706 *c* element is coupled to the trocar to advance or retract the trocar. In one aspect, the shaft 740 is part of a closure system that comprises a trocar 201904 and a trocar actuator 201906 as discussed in more detail with reference to FIGS. 19A-19C hereinbelow. Accordingly, the control circuit 710 controls the motor control circuit 708 *c* to control the motor 704 *c* to advance or retract the trocar. A torque sensor 744 *c* is provided to measure the torque applied by the shaft of the motor 704 *c* to the transmission components 706 *c* employed in advancing and retracting the trocar. The position sensor 734 may include a variety of sensors to track the position of the trocar, the anvil 716, or the knife 714, or any combination thereof. Other sensors 738 may be employed to measure a variety of parameters including position or velocity of the trocar, the anvil 716, or the knife 714, or any combination thereof. The torque sensor 744 *c*, the position sensor 734, and the sensors 738 are coupled to the control circuit 710 as inputs to various processes for controlling the operation of the surgical instrument 700 in a desired manner.

In one aspect, the control circuit 710 is configured to articulate the end effector 702. The control circuit 710 provides a motor set point to a motor control 708 *d*, which provides a drive signal to the motor 704 *d*. The output shaft of the motor 704 *d* is coupled to a torque sensor 744 *d*. The torque sensor 744 *d* is coupled to a transmission 706 *d* which is coupled to an articulation member 742 *a*. The transmission 706 *d* comprises movable mechanical elements such as articulation elements to control the articulation of the end effector 702 ±65°. In one aspect, the motor 704 *d* is coupled to an articulation nut, which is rotatably journaled on the proximal end portion of the distal spine portion and is rotatably driven thereon by an articulation gear assembly. The torque sensor 744 *d* provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742 *a*, 742 *b*. These articulation members 742 *a*, 742 *b* are driven by separate disks on the robot interface (the rack) which are driven by the two motors 708 *d*, 708 *e*. When the separate firing motor 704 *a* is provided, each of articulation links 742 *a*, 742 *b* can be antagonistically driven with respect to the other link in order to provide a resistive holding motion and a load to the head when it is not moving and to provide an articulation motion as the head is articulated. The articulation members 742 *a*, 742 *b* attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704 *a*-704 *e* may comprise a brushed DC motor with a gearbox and mechanical links to a firing member, closure member, or articulation member. Another example includes electric motors 704 *a*-704 *e* that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704 *a*-704 *e*. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744 a-744 e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704 a-704 e. The force required to advance any of the movable mechanical elements such as the knife 714 corresponds to the current drawn by one of the motors 704 a-704 e. The force is converted to a digital signal and provided to the control circuit 710. The control circuit 710 can be configured to simulate the response of the actual system of the instrument in the software of the controller. A displacement member can be actuated to move a knife 714 in the end effector 702 at or near a target velocity. The surgical instrument 700 can include a feedback controller, which can be one of any feedback controllers, including, but not limited to a PID, a state feedback, a linear-quadratic (LQR), and/or an adaptive controller, for example. The surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, tided CLOSED LOOP VELOCITY CONTROL TECHNIQUES FOR ROBOTIC SURGICAL INSTRUMENT, filed Jun. 29, 2017, which is herein incorporated by reference in its entirety.

The surgical instrument 700 may comprise wired or wireless communication circuits to communicate with the modular communication hub as shown in FIGS. 1-6 and 9-13. The surgical instrument 700 may be the motorized circular stapling instrument 201800 (FIG. 18), 201000 (FIGS. 21-22).

Figure 17:
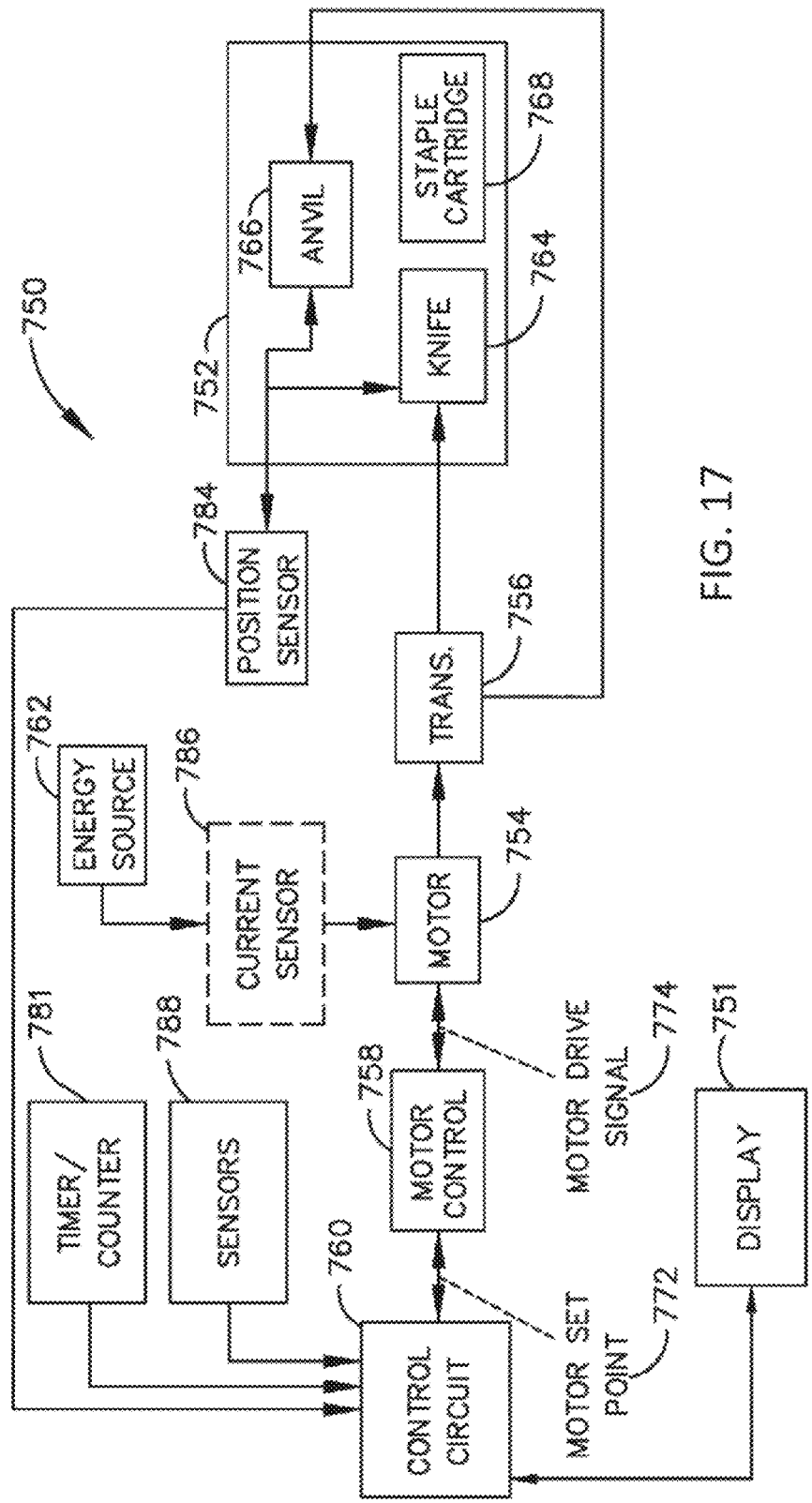
FIG. 17 illustrates a block diagram of a surgical instrument configured to control various functions, in accordance with at least one aspect of the present disclosure.

FIG. 17 illustrates a block diagram of a surgical instrument 750 configured to control various functions, according to one aspect of this disclosure. In one aspect, the surgical instrument 750 is programmed to control the distal translation of a displacement member such as the knife 764, or other suitable cutting element. The surgical instrument 750 comprises an end effector 752 that may comprise an anvil 766, a knife 764 (including a sharp cutting edge), and a removable staple cartridge 768.

The position, movement, displacement, and/or translation of a linear displacement member, such as the knife 764, can be measured by an absolute positioning system, sensor arrangement, and position sensor 784. Because the knife 764 is coupled to a longitudinally movable drive member, the position of the knife 764 can be determined by measuring the position of the longitudinally movable drive member employing the position sensor 784. Accordingly, in the following description, the position, displacement, and/or translation of the knife 764 can be achieved by the position sensor 784 as described herein. A control circuit 760 may be programmed to control the translation of the displacement member, such as the knife 764. The control circuit 760, in some examples, may comprise one or more microcontrollers, microprocessors, or other suitable processors for executing instructions that cause the processor or processors to control the displacement member, e.g., the knife 764, in the manner described. In one aspect, a timer/counter 781 provides an output signal, such as the elapsed time or a digital count, to the control circuit 760 to correlate the position of the knife 764 as determined by the position sensor 784 with the output of the timer/counter 781 such that the control circuit 760 can determine the position of the knife 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the knife 764 via a transmission 756. The transmission 756 may include one or more gears or other linkage components to couple the motor 754 to the knife 764. In one aspect, the transmission is coupled to a trocar actuator of a circular stapler to advance or retract the trocar. A position sensor 784 may sense a position of the knife 764, the trocar, or the anvil 766, or a combination thereof. The position sensor 784 may be or include any type of sensor that is capable of generating position data that indicate a position of the knife 764. In some examples, the position sensor 784 may include an encoder configured to provide a series of pulses to the control circuit 760 as the knife 764 translates distally and proximally. The control circuit 760 may track the pulses to determine the position of the knife 764. Other suitable position sensors may be used, including, for example, a proximity sensor. Other types of position sensors may provide other signals indicating motion of the knife 764. Also, in some examples, the position sensor 784 may be omitted. Where the motor 754 is a stepper motor, the control circuit 760 may track the position of the knife 764 by aggregating the number and direction of steps that the motor 754 has been instructed to execute. The position sensor 784 may be located in the end effector 752 or at any other portion of the instrument.

In a circular stapler implementation, the transmission 756 element may be coupled to the trocar to advance or retract the trocar, to the knife 764 to advance or retract the knife 764, or the anvil 766 to advance or retract the anvil 766. These functions may be implemented with a single motor using suitable clutching mechanism or may be implemented using separate motors as shown with reference to FIG. 16, for example. In one aspect, the transmission 756 is part of a closure system that comprises a trocar 201904 and a trocar actuator 201906 as discussed in more detail with reference to FIGS. 19A-19C hereinbelow. Accordingly, the control circuit 760 controls the motor control circuit 758 to control the motor 754 to advance or retract the trocar. Similarly, the motor 754 may be configured to advance or retract the knife 764 and advance or retract the anvil 766. A torque sensor may be provided to measure the torque applied by the shaft of the motor 754 to the transmission components 756 employed in advancing and retracting the trocar, the knife 764, or the anvil 766, or combinations thereof. The position sensor 784 may include a variety of sensors to track the position of the trocar, the knife 764, or the anvil 766, or any combination thereof. Other sensors 788 may be employed to measure a variety of parameters including position or velocity of the trocar, the knife 764, or the anvil 766, or any combination thereof. The torque sensor, the position sensor 784, and the sensors 788 are coupled to the control circuit 760 as inputs to various processes for controlling the operation of the surgical instrument 750 in a desired manner.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors. In one aspect, the sensors 788 may be configured to determine the position of a trocar of a circular stapler.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the knife 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a knife 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or knife 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, a knife 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the knife 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, tided SYSTEM AND METHODS FOR CONTROLLING A DISPLAY OF A SURGICAL INSTRUMENT, filed Sep. 29, 2017, which is herein incorporated by reference in its entirety.

The surgical instrument 750 may comprise wired or wireless communication circuits to communicate with the modular communication hub as shown in FIGS. 1-6 and 9-13. The surgical instrument 750 may be the motorized circular stapling instrument 201800 (FIG. 18), 201000 (FIGS. 21-22).

Figure 18:
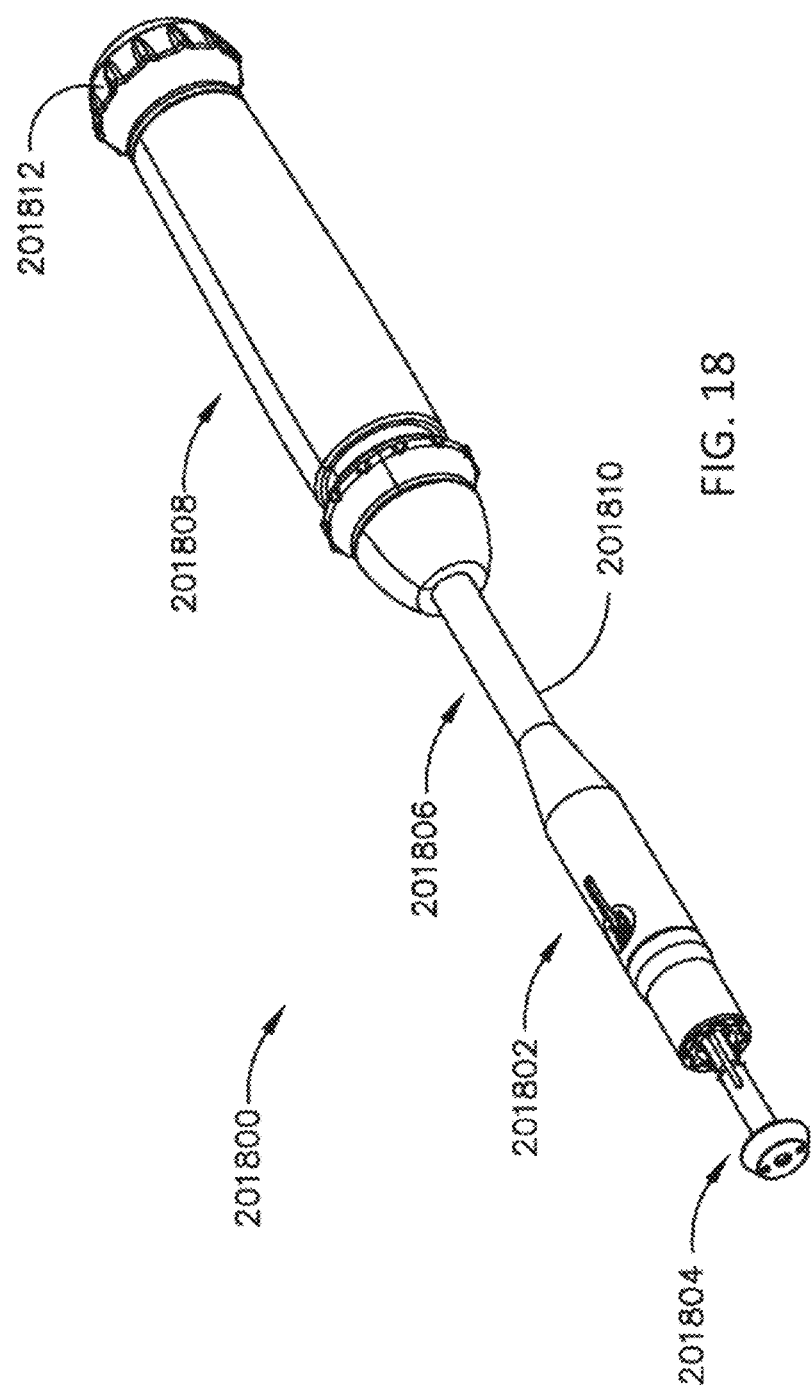
FIG. 18 depicts a perspective view of a circular stapling surgical instrument, in accordance with at least one aspect of the present disclosure.

FIG. 18 shows an example motorized circular stapling instrument 201800. The Instrument 201800 of this example comprises a stapling head assembly 201802, an anvil 201804, a shaft assembly 201806, a handle assembly 201808, and a rotation knob 201812. The stapling head assembly 201802 selectively couples with the anvil 201804. The stapling head assembly 201802 is operable to clamp tissue between staple pockets and staple forming pockets of the anvil 201804. The stapling head assembly 201802 comprises a cylindrical knife that is operable to sever tissue captured between stapling head assembly 201802 and the anvil 201804. The stapling head assembly 201802 drives staples through the tissue captured between stapling head assembly 201802 and the anvil 201804. The stapling instrument 201800 may be used to create a secure anastomosis (e.g., an end-to-end anastomosis) within a gastro-intestinal tract of a patient or elsewhere. An outer tubular member 201810 is coupled to the actuator handle assembly 201808. The outer tubular member 201810 provides a mechanical ground between the stapling head assembly 201802 and the handle assembly 201808.

The stapling head assembly 201802 is operable to clamp tissue, sever tissue, and staple tissue all in response to a single rotary input communicated via the shaft assembly 201806. Accordingly, actuation inputs translated linearly through shaft assembly 201806 are not required for the stapling head assembly 201802, though the stapling head assembly 201802 may comprise a translating clutch feature. By way of example only, at least part of stapling head assembly 201802 may be configured in accordance with at least some of the teachings of U.S. patent application Ser. No. 13/716,318, entitled "Motor Driven Rotary Input Circular Stapler with Modular End Effector," filed on Dec. 17, 2012, and published as U.S. Pat. Pub. No. 2014/0166728 on Jun. 19, 2014, the disclosure of which is incorporated by reference herein. Other suitable configurations for the stapling head assembly 201802 will be apparent to those of ordinary skill in the art in view of the teachings herein.

The shaft assembly 201806 couples the handle assembly 201808 with the stapling head assembly 201802. The shaft assembly 201806 comprises a single actuation feature, rotary driver actuator. Additional details about the handle assembly 201808 and the rotary driver actuator are disclosed in U.S. patent application Ser. No. 16/182,229, tided ADJUSTMENT OF STAPLE HEIGHT OF AT LEAST ONE ROW OF STAPLES BASED ON THE SENSED TISSUE THICKNESS OR FORCE IN CLOSING, filed Nov. 6, 2018, which is herein incorporated by reference in its entirety.

Referring now to FIGS. 19A-19C, in the present example, instrument 201800 comprises a closure system and a firing system. The closure system comprises a trocar 201904, a trocar actuator 201906, and a rotating knob 201812 (FIG. 18). As previously discussed, the rotation knob 201812 may be coupled to a motor to rotate the rotation knob 201812 in a clockwise or counterclockwise direction. An anvil 201804 may be coupled to a distal end of trocar 201904. Rotating knob 201812 is operable to longitudinally translate trocar 201904 relative to stapling head assembly 201802, thereby translating anvil 201804 when anvil 201804 is coupled to trocar 201904, to clamp tissue between anvil 201804 and stapling head assembly 201804. The firing system comprises a trigger, a trigger actuation assembly, a driver actuator

201908, and a staple driver 201910. Staple driver 201910 includes a cutting element, such as a knife 201912, configured to sever tissue when staple driver 201910 is actuated longitudinally. In addition, staples 201902 are positioned distal to a plurality of staple driving members 201914 of staple driver 201910 such that staple driver 201910 also drives staples 201902 distally when staple driver 201910 is actuated longitudinally. Thus, when staple driver 201910 is actuated via driver actuator 201908, knife 201912 members 201914 substantially simultaneously sever tissue 201916 and drive staples 201902 distally relative to stapling head assembly 201802 into tissue. The components and functionalities of the closure system and firing system will now be described in greater detail.

As shown in FIGS. 19A-19C, anvil 201804 is selectively coupleable to instrument 201800 to provide a surface against which staples 201902 may be bent to staple material contained between stapling head assembly 201802 and anvil 201804. Anvil 201804 of the present example is selectively coupleable to a trocar or pointed rod 201904 that extends distally relative to stapling head assembly 201802. Referring to FIGS. 19A-19C, anvil 201804 is selectively coupleable via the coupling of a proximal shaft 201918 of anvil 201904 to a distal tip of trocar 201904. Anvil 201804 comprises a generally circular anvil head 201920 and a proximal shaft 201918 extending proximally from anvil head 201920. In the example shown, proximal shaft 201918 comprises a tubular member 201922 having resiliently biased retaining clips 201924 to selectively couple anvil 201804 to trocar 201904, though this is merely optional, and it should be understood that other retention features for coupling anvil 201804 to trocar 201904 may be used as well. For example, C-clips, clamps, threading, pins, adhesives, etc. may be employed to couple anvil 201804 to trocar 201904. In addition, while anvil 201804 is described as selectively coupleable to trocar 201904, in some versions proximal shaft 201918 may include a one-way coupling feature such that anvil 201804 cannot be removed from trocar 201904 once anvil 201804 is attached. By way of example one-way features include barbs, one way snaps, collets, collars, tabs, bands, etc. Of course still other configurations for coupling anvil 201804 to trocar 201904 will be apparent to one of ordinary skill in the art in view of the teachings herein. For instance, trocar 201904 may instead be a hollow shaft and proximal shaft 201918 may comprise a sharpened rod that is insertable into the hollow shaft.

Anvil head 201920 of the present example comprises a plurality of staple forming pockets 201936 formed in a proximal face 201940 of anvil head 201920. Accordingly, when anvil 201804 is in the closed position and staples 201902 are driven out of stapling head assembly 201802 into staple forming pockets 201936, as shown in FIG. 19C, legs 201938 of staples 201902 are bent to form completed staples.

With anvil 201804 as a separate component, it should be understood that anvil 201804 may be inserted and secured to a portion of tissue 201916 prior to being coupled to stapling head assembly 201802. By way of example only, anvil 201804 may be inserted into and secured to a first tubular portion of tissue 201916 while instrument 201800 is inserted into and secured to a second tubular portion of tissue 201916. For instance, the first tubular portion of tissue 201916 may be sutured to or about a portion of anvil 201804, and the second tubular portion of tissue 201916 may be sutured to or about trocar 201904.

As shown in FIG. 19A, anvil 201804 is then coupled to trocar 201904. Trocar 201904 of the present example is shown in a distal most actuated position. Such an extended position for trocar 201904 may provide a larger area to which tissue 201916 may be coupled prior to attachment of anvil 201804. In addition, the extended position of trocar 20190400 may also provide for easier attachment of anvil 201804 to trocar 201904. Trocar 201904 further includes a tapered distal tip. Such a tip may be capable of piercing through tissue and/or aiding the insertion of anvil 201804 on to trocar 201904, though the tapered distal tip is merely optional. For instance, in other versions trocar 201904 may have a blunt tip. In addition, or in the alternative, trocar 201904 may include a magnetic portion (not shown) which may attract anvil 201804 towards trocar 201904. Of course still further configurations and arrangements for anvil 201804 and trocar 201904 will be apparent to one of ordinary skill in the art in view of the teachings herein.

When anvil 201804 is coupled to trocar 201904, the distance between a proximal face of the anvil 201804 and a distal face of stapling head assembly 201802 defines a gap distance d. Trocar 201904 of the present example is translatable longitudinally relative to stapling head assembly 201802 via an adjusting knob 201812 (FIG. 18) located at a proximal end of actuator handle assembly 201808 (FIG. 18), as will be described in greater detail below. Accordingly, when anvil 201804 is coupled to trocar 201904, rotation of adjusting knob 201812 enlarges or reduces gap distance d by actuating anvil 201804 relative to stapling head assembly 201802. For instance, as shown sequentially in FIGS. 19A-19B, anvil 201804 is shown actuating proximally relative to actuator handle assembly 201808 from an initial, open position to a closed position, thereby reducing the gap distance d and the distance between the two portions of tissue 201916 to be joined. Once the gap distance d is brought within a predetermined range, stapling head assembly 201802 may be fired, as shown in FIG. 19C, to staple and sever tissue 201916 between anvil 201804 and stapling head assembly 201802. Stapling head assembly 201802 is operable to staple and sever tissue 201916 by a trigger of actuator handle assembly 201808, as will be described in greater detail below.

Still referring to FIGS. 19A-19C, a user sutures a portion of tissue 201916 about tubular member 201944 such that anvil head 201920 is located within a portion of the tissue 201916 to be stapled. When tissue 201916 is attached to anvil 201804, retaining clips 201924 and a portion of tubular member 201922 protrude out from tissue 201916 such that the user may couple anvil 201804 to trocar 201904. With tissue 201916 coupled to trocar 201904 and/or another portion of stapling head assembly 201802, the user attaches anvil 201804 to trocar 201904 and actuates anvil 201804 proximally towards stapling head assembly 201802 to reduce the gap distance d. Once instrument 201800 is within the operating range, the user then staples together the ends of tissue 201916, thereby forming a substantially contiguous tubular portion of tissue 201916.

Stapling head assembly 201802 of the present example is coupled to a distal end of shaft assembly 201806 and comprises a tubular casing 201926 housing a slidable staple driver 201910 and a plurality of staples 201902 contained within staple pockets 201928. Shaft assembly 201806 of the present example comprises an outer tubular member 201942 and a driver actuator 201908. Staples 201902 and staple pockets 201928 are disposed in a circular array about tubular casing 201926. In the present example, staples 201902 and staple pockets 201928 are disposed in a pair of concentric annular rows of staples 201902 and staple pockets 201928. Staple driver 201910 is operable to actuate longitudinally within tubular casing 201926 in response to rotation of actuator handle assembly 201808 (FIG. 18). As shown in FIGS. 19A-19C, staple driver 201910 comprises a flared cylindrical member having a trocar opening 201930, a central recess 201932, and a plurality of members 201914 disposed circumferentially about central recess 201932 and extending distally relative to shaft assembly 201806. Each member 201914 is configured to contact and engage a corresponding staple 201902 of the plurality of staples 201902 within staple pockets 201928. Accordingly, when staple driver 201910 is actuated distally relative to actuator handle assembly 201808, each member 201914 drives a corresponding staple 201902 out of its staple pocket 201928 through a staple aperture 201934 formed in a distal end of tubular casing 201926. Because each member 201914 extends from staple driver 201910, the plurality of staples 201902 is driven out of stapling head assembly 201802 at substantially the same time. When anvil 201804 is in the closed position, staples 201902 are driven into staple forming pockets 201936 to bend legs 201938 of the staples 201902, thereby stapling the material located between anvil 201804 and stapling head assembly 201808. FIG. 20 depicts by way of example staple 201902 driven by a member 201914 into a staple forming pocket 201928 of anvil 201804 to bend legs 201938.

The motorized circular stapling instruments 201800, 201000 described herein with reference to FIGS. 18-21 may be controlled using any of the control circuits described in connection with FIGS. 7-8 and 16-17. For example, the control system 470 described with reference to FIG. 7. Further, the motorized circular stapling instrument 201800 may be employed in a hub and cloud environment as described in connection with FIGS. 1-6 and 9-13.

FIG. 21 is a partial cutaway view of a powered circular stapling device 201000 comprising a circular stapling head assembly 201002 and an anvil 201004, in accordance with at least one aspect of the present disclosure. The powered circular stapling device 20100 is shown clamping a first portion of tissue 201006 and a second portion of tissue 201008 between the anvil 201004 and the circular stapling head assembly 201002. Compression of the tissue 201006, 201008 between the anvil 201004 and the circular stapling head assembly 201002 is measured with a sensor 201018, such as a strain gauge, for example. The circular stapling head assembly 201002 also includes a knife 201019 that can be advanced at different rates to cut through tissue 201006, 201008 clamped between the anvil 201004 and the circular stapling head assembly 201002 after the inner and outer rows of staples 201010, 201014 are fired and formed against corresponding staple forming pockets 201011, 201015 of the anvil 201004.

FIG. 22 is a partial top view of the circular stapling head assembly 201002 shown in FIG. 21 showing a first row of staples 201010 (inner staples) and a second row of staples 201014 (outer staples), in accordance with at least one aspect of the present disclosure. The inner row of staples 201010 and the second row of staples 201014 are independently actuatable by first and second staple drivers 201012, 201016.

With reference now to FIGS. 21 and 22, once the tissue 201006, 201008 is clamped between the anvil 201004 and the circular stapling head assembly 201002, a first gap δ1 is set for the inner row of staples 201010 and a second gap δ2 is set for the outer row of staples 201014. As the tissue compression is increased or the tissue gap δ1, δ2 is decreased, and the nominal staple height for the center of a window is adjusted. The first staple driver 201012 drives the inner row of staples 201010 through the tissue 201006, 201008 and the inner row of staples 201010 are formed against the anvil 201004. Subsequently, the second staple driver 201016 independently drives the outer row of staples 201010 through the tissue 201006, 201008 and the outer row of staples 201014 are formed against the anvil 201004.

Figure 23:
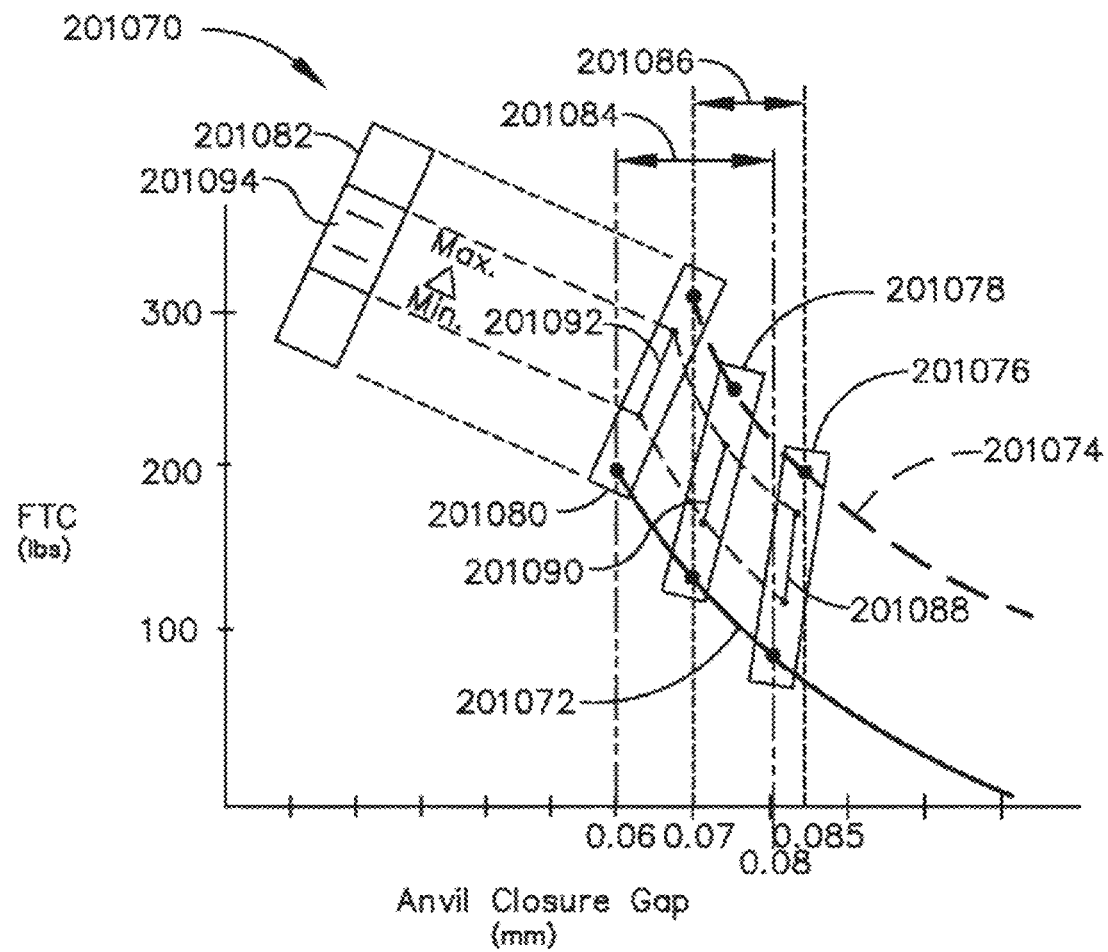
FIG. 23 is a graphical representation of viable staple firing range as indicated by usable staple height windows based on the tissue gap, closure force (FTC), or tissue creep stabilization sensed by the device or combinations thereof, in accordance with at least one aspect of the present disclosure.

The independently actuatable staple rows 201010, 201014 may be formed based on the FTC clamped by the anvil 201004 on the tissue 201006, 201008 or the tissue gap δ1, δ2 between the anvil 201004 clamp and the circular stapling head assembly 201002. Adjustment of the staple height of at least one row of staples based on the sensed tissue thickness or FTC focuses on the adjustment of a selection window based on tissue 201006, 201008 thickness/load in closing. In other aspects, the user adjustable range of selectable staple heights may be varied based on the tissue loading detected during an anvil 201004 retraction operation. As the tissue compression (e.g., FTC) is increased or the tissue gap δ1, δ2 is decreased the nominal staple height for the center of the window may be adjusted as described herein with reference to FIG. 23. In other aspects, the adjustment of the window range of acceptable staples is displayed as the compression is increased or the tissue gap decreased. In other aspects, once the tissue compression is completed then stabilization of the tissue, can further adjust the acceptable range based on the rate of tissue creep and time waited.

Figure 24:
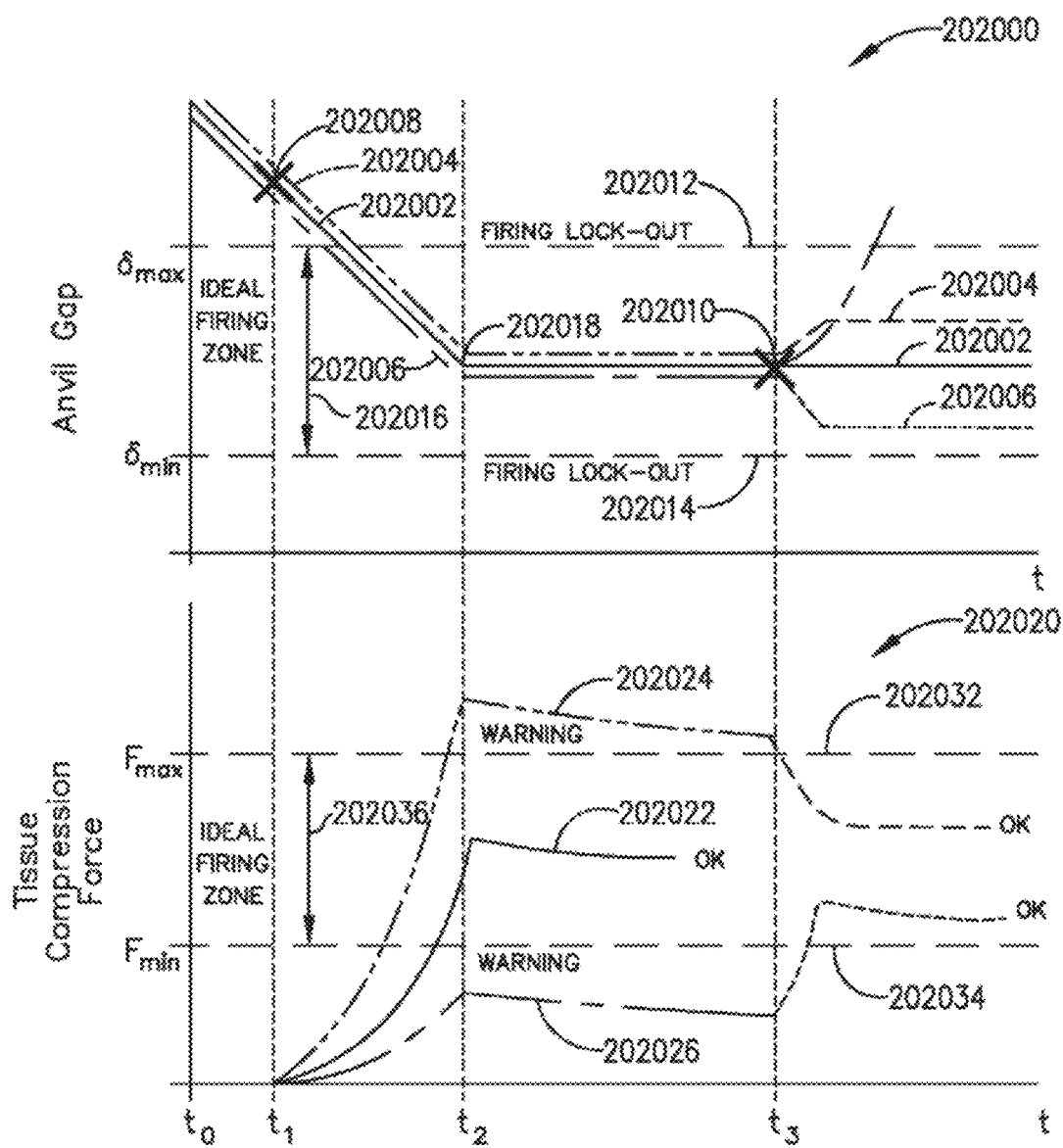
FIG. 24 is a graphical representation of a first pair of graphs depicting anvil gap and tissue compression force verse time for illustrative firings of a stapling instrument, in accordance with at least one aspect of the present disclosure.

FIG. 24 is a graphical representation of a first pair of graphs 202000, 202020 depicting anvil gap and tissue compression force F verse time for illustrative firings of a stapling instrument, in accordance with at least one aspect of the present disclosure. The tissue compression force F also may be expressed as force to close (FTC). The top graph 202000 depicts three separate anvil gap curves 202002, 202004, 202006 representative of anvil gap closure over time at three separate tissue compression forces, as shown in the bottom graph 202020, where anvil gap δ is shown along the vertical axis and time is shown along the horizontal axis. The anvil gap curves 202002, 202004, 202006 represent anvil closure of a powered circular stapling device 202080 (FIG. 26) as a function of time t for tissue of variable stiffness, constant thickness, and constant anvil gap δ, until adjustment(s) of the anvil gap δ are made by a control algorithm. A control algorithm implemented by any of the control circuits described herein with reference to FIGS. 7-8 and 16-17 can be configured to adjust the anvil gap according to the sensed tissue compression force F compared to one or more different thresholds. Additional details about the control circuits are disclosed in U.S. patent application Ser. No. 16/182,229, tided ADJUSTMENT OF STAPLE HEIGHT OF AT LEAST ONE ROW OF STAPLES BASED ON THE SENSED TISSUE THICKNESS OR FORCE IN CLOSING, filed Nov. 6, 2018, which is herein incorporated by reference in its entirety.

Figure 26:
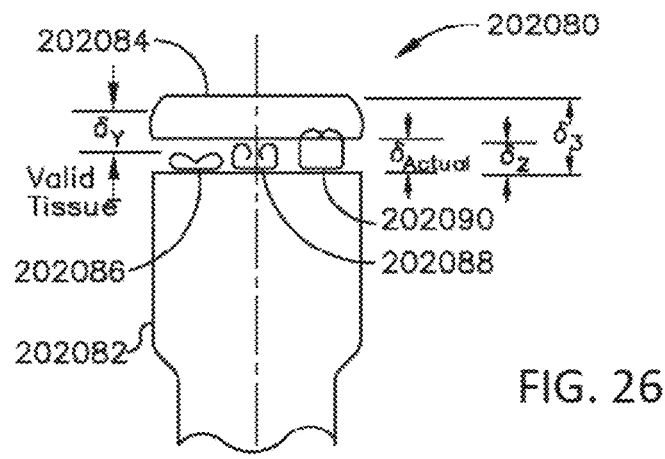
FIG. 26 is a schematic diagram of a powered circular stapling device illustrating valid tissue gap, actual gap, normal range gap, and out of range gap, in accordance with at least one aspect of the present disclosure.

Turning now briefly to FIG. 26, there is shown a schematic diagram of a powered circular stapling device 202080 illustrating valid tissue gap aγ, actual gap δactual, normal range gap δ2, and out of range gap δ3, in accordance with at least one aspect of the present disclosure. The powered circular stapling device 202080 includes a circular stapler 202082 and an anvil 202084, which is retracted from an open position to a closed position to clamp tissue between the anvil 201084 and the stapler 202082. Once the anvil 202084 is fully clamped on the tissue, there will be a gap δ defined between the anvil 202084 and the stapler 202082. When the circular stapler 202082 is fired (e.g., actuated), the staple formation is dependent upon the tissue gap δ. As shown in FIG. 26, for a normal range gap δ2, the staples

202088 are well formed. When the gap δ is too small, the staples 202086 are too tightly formed and when the gap δ is too large, the staples 202090 are too loosely formed.

Turning back now to FIG. 24, with reference to the top and bottom graphs 202000, 202020 and FIG. 26, at time t0 the anvil 201084 is initially open beyond the maximum anvil gap δmax before the anvil 201084 reaches the initial tissue contact point 202008 at time t1. As shown, due to constant tissue thickness, t1 is a common tissue contact point for tissue having variable tissue stiffness. At time t1, the anvil gap δ is still outside of the ideal firing zone 202016 shown between a maximum anvil gap δmax defining a upper firing lockout threshold 202012, and a minimum anvil gap δmin 202014, defining a lower firing lockout threshold 202014. From the initial tissue contact point 202008 at time t1 as the anvil 201084 continues to close the tissue compression force F starts to increase. The tissue compression force F will vary as a function of the biomechanical properties of tissue in terms of stiffness. As indicated in the bottom graph 202020, tissue of normal stiffness is represented by a first tissue compression force curve 202022, tissue of high stiffness is represented by a second tissue compression force curve 202024, and tissue of low stiffness is represented by a third tissue compression force curve 202026.

As the anvil 201084 continues to close between the maximum anvil gap δmax and the minimum anvil gap the anvil gap δ min, reaches a point of constant anvil gap 202018 at time t2. As shown in the lower graph 202020, at time t2 the tissue compression force F for tissue of normal stiffness represented by the first tissue compression force curve 202022 is within the ideal firing zone 202036, which is defined between a maximum compression force Fmax, defining an upper warning threshold 202032, and a minimum compression force Fmin, defining a lower warning threshold 202034. At time t2, the tissue compression force F for tissue of high stiffness represented by the second tissue compression force curve 202024 is above the upper warning threshold 202032 outside the ideal firing zone 202036 and the tissue compression force for tissue of low stiffness represented by the third tissue compression force curve 202026 is below the lower warning threshold 202034 outside the ideal firing zone 202036.

From time t2 to time t3, the anvil 201084 is maintained at a constant gap δ, as shown in the upper graph 202000, by the three anvil gap curves 202002, 202004, 202006. This period of constant gap δ, allows for tissue creep, as shown in the lower graph 202020, during which the average tissue compression force F slowly drops as shown by the three tissue compression force curves 202022, 202024, 202026. Tissue creep is a phase that is entered after tissue is grasped and the average tissue compression force F reaches a predetermined threshold and the closure motion of the anvil 201084 such that the anvil 201084 and the stapler 202082 hold the tissue therebetween for a predetermined time before initiating the firing phase in which the staples and knife are deployed. During the tissue creep phase the average tissue compression force F drops over the time period between t2 and t3. Tissue, in part because it is composed of solid and liquid material, tends to elongate when compressed. One way to account for this property is "tissue creep." When tissue is compressed, a certain amount of tissue creep can occur. Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep prior to firing.

With reference now also to FIG. 17, after a period where the anvil gap δ is maintained constant to allow for tissue creep, at time t3, prior to deploying the staples, the control circuit 760 at point 202010 determines whether a possible adjustment of the anvil 766 relative to the staple cartridge 764 (anvil 201804 and stapler 202084 in FIG. 26) is necessary. Accordingly, the control circuit 760 determines if the tissue compression force F is between the ideal firing zone 202036, above the maximum compression force Fmax threshold 202032, or below the minimum compression force Fmin threshold 202034 and makes any necessary adjustments to the anvil gap δ. If the tissue compression force F is between the ideal firing zone 202036, the control circuit 760 deploys the staples in the staple cartridge 768 and deploys the knife 764.

If the tissue compression force F is above the maximum compression force Fmax threshold 202032, the control circuit 760 is configured to register a warning that the compression force is too tight and to adjust the anvil gap δ, increase the wait time before firing, lower the firing speed, or enable a firing lockout, or any combination thereof. The control circuit 760 can adjust the anvil gap δ by advancing the anvil 766 distally, e.g. away, from the staple cartridge 768 (anvil 201804 and stapler 202084 in FIG. 26) to increase the anvil gap δ as shown by the segment of the anvil gap curve 2002004 beyond time t3. As shown by the segment of the tissue compression force curve 202024 beyond time t3, after the control circuit 760 increases the anvil gap δ, the tissue compression force F decreases into the ideal firing zone 202036.

If the tissue compression force F is below the minimum compression force Fmin threshold 202034, the control circuit 760 is configured to register a warning that the compression force is too loose and to adjust the anvil gap δ, proceed with caution, or enable a firing lockout, or any combination thereof. The control circuit 760 is configured to adjust the anvil gap δ by retracting the anvil 766 proximally, e.g. toward, the staple cartridge 768 (anvil 201804 and stapler 202084 in FIG. 26) to decrease the anvil gap δ as shown by the segment of the anvil gap curve 2002006 beyond time t3, As shown by the segment of the tissue compression force curve 202026 beyond time t3, after decreasing the anvil gap δ, the tissue compression force F increases into the ideal firing zone 202036.

Figure 25:
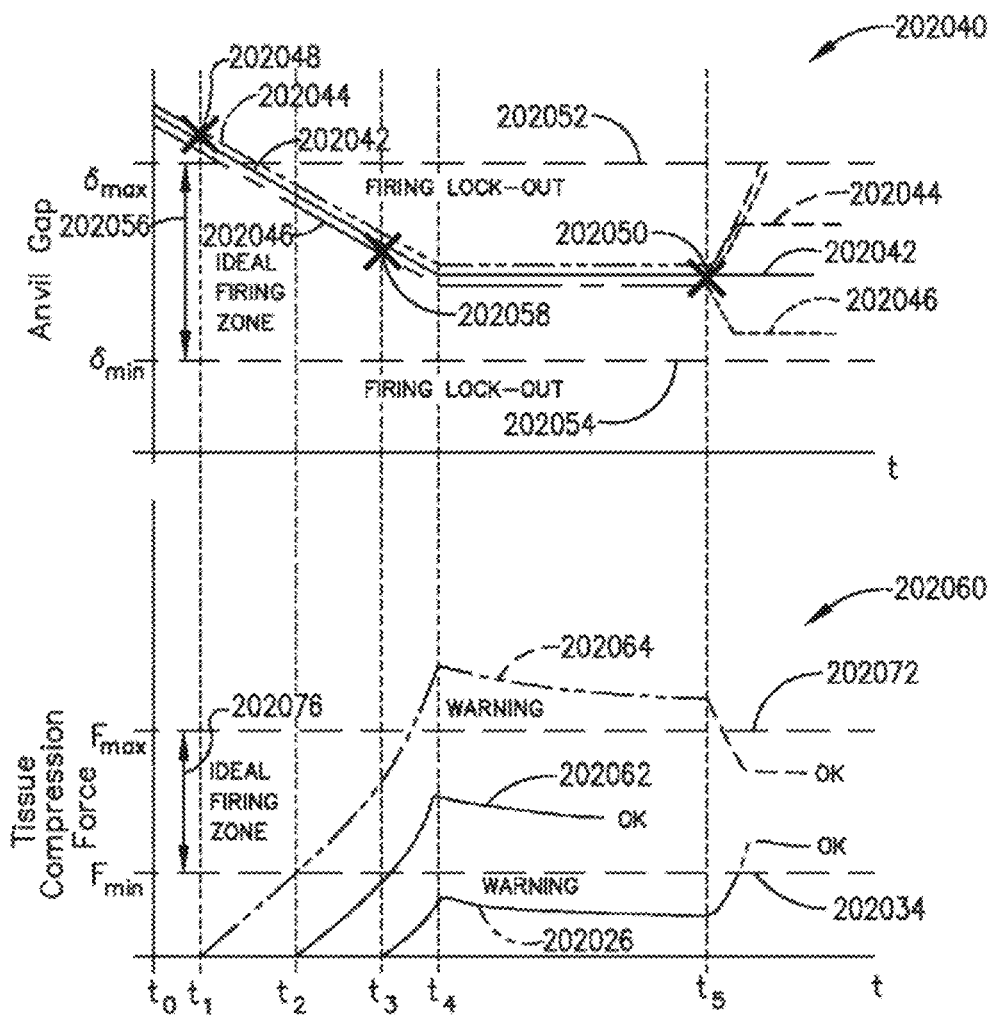
FIG. 25 is a graphical representation of a second pair of graphs depicting anvil gap and tissue compression force verse time for illustrative firings of a stapling instrument, in accordance with at least one aspect of the present disclosure.

Turning now to FIG. 25, there is shown a graphical representation of a second pair of graphs 202040, 202060 depicting anvil gap and tissue compression force F verse time for illustrative firings of a stapling instrument, in accordance with at least one aspect of the present disclosure. The top graph 202040 depicts three separate anvil gap curves 202042, 202046, 202046 representative of anvil gap closure over time at three separate tissue thicknesses, where anvil gap δ is shown along the vertical axis and time is shown along the horizontal axis. The anvil gap curves 202042, 202044, 202046 represent anvil closure of a powered circular stapling device 202080 (FIG. 26) as a function of time t for tissue of variable thickness, constant stiffness, and constant anvil gap δ, until adjustment(s) of the anvil gap δ are made by a control algorithm. A control algorithm implemented by any of the control circuits described herein with reference to FIGS. 7-8 and 16-17 can be configured to adjust the anvil gap according to the sensed tissue compression force F compared to one or more different thresholds.

With reference now to the top and bottom graphs 202040, 202060 and FIG. 26, at time t0 the anvil 201084 is initially open beyond the maximum anvil gap δmax before the anvil 201084 reaches a first tissue contact point 202048 for tissue of high thickness at time t1, where the tissue compression force curve 202064 for tissue of high thickness starts to increase. At time t1, the anvil gap δ is still outside of the ideal firing zone 202056 shown between a maximum anvil gap δ max, defining a upper firing lockout threshold 202052, and a minimum anvil gap δ min, defining a lower firing lockout threshold 202054. As shown, due to constant tissue stiffness and variable tissue thickness, the anvil 201084 contacts the tissue at different times. For example, time t1 is a first tissue contact point 202048 for tissue having high tissue thickness, time t2 is a second tissue contact point for tissue of normal thickness, and time t3 is a third tissue contact point 202058 for tissue of low thickness.

The first tissue compression force curve 202062 represents the compression force for tissue of normal thickness and starts to increase at time t2 when tissue of normal thickness initially contacts the anvil 201804. The second tissue compression force curve 202064 represents tissue of high thickness and starts to increase at time t1 when tissue of high thickness initially contacts the anvil 201804. The third tissue compression force curve 202066 represents tissue of low thickness and starts to increase at time t3 when tissue of low thickness initially contacts the anvil 201804. At the second and third tissue contact points at times t2 and t3, for tissue of normal and low thickness, the anvil gap δ is within the ideal firing zone 202056, 202076. The tissue compression force F will vary as a function of the biomechanical properties of tissue thickness. As indicated in the bottom graph 202040, tissue of normal thickness is represented by a first tissue compression force curve 202042, tissue of high thickness is represented by a second tissue compression force curve 202044, and tissue of low stiffness is represented by a third tissue compression force curve 202066. From the initial tissue contact points at times t1, t2, t3 as the anvil 201084 continues to close, the tissue compression forces for each curve 202062, 202064, 2020066 start to increase until time t4 where the anvil gap reaches a predetermined value and remains constant between t4 and t5 until the stapler 202082 is ready to fire.

As the anvil 201084 continues to close between the maximum anvil gap δ max and the minimum anvil gap δ min, the anvil gap δ reaches a point of constant anvil gap at time t4. As shown in the lower graph 202060, at time t4 the tissue compression force F for tissue of normal thickness represented by the first tissue compression force curve 202062 is within the ideal firing zone 202076, which is defined between a maximum compression force Fmax, defining an upper warning threshold 202072, and a minimum compression force Fmin, defining a lower warning threshold 202074. At time t4 the tissue compression force F for tissue of high thickness represented by the second tissue compression force curve 202064 is above the upper warning threshold 202072 outside the ideal firing zone 202076 and the tissue compression force F for tissue of low thickness represented by the third tissue compression force curve 202066 is below the lower warning threshold 202074 outside the ideal firing zone 202076.

From time t4 to time t5, the anvil 201084 is maintained at a constant gap δ, as shown in the upper graph 202040, by the three anvil gap curves 202042, 202044, 202046. This period of constant gap δ, allows for tissue creep, as shown in the lower graph 202060, during which the average tissue compression force F slowly drops as shown by the three tissue compression force curves 202062, 202064, 202066. Tissue creep is a phase that is entered after tissue is grasped and the average tissue compression force F reaches a predetermined threshold and the closure motion of the anvil 201084 such that the anvil 201084 and the stapler 202082 hold the tissue therebetween for a predetermined time before initiating the firing phase in which the staples and knife are deployed. During the tissue creep phase the average tissue compression force F drops over the time period between t2 and t3. Tissue, in part because it is composed of solid and liquid material, tends to elongate when compressed. One way to account for this property is "tissue creep." When tissue is compressed, a certain amount of tissue creep can occur. Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep prior to firing.

With reference now also to FIG. 17, after a period where the anvil gap δ is maintained constant to allow for tissue creep, at time t5, prior to deploying the staples, the control circuit 760 at point 202050 determines whether a possible adjustment of the anvil 766 relative to the staple cartridge 764 (anvil 201804 and stapler 202084 in FIG. 26) is necessary. Accordingly, the control circuit 760 determines if the tissue compression force F is between the ideal firing zone 202076, above the maximum compression force Fmax threshold 202072, or below the minimum compression force Fmin threshold 202074 and makes any necessary adjustments to the anvil gap δ. If the tissue compression force F is between the ideal firing zone 202076, the control circuit 760 deploys the staples in the staple cartridge 768 and deploys the knife 764.

If the tissue compression force F is above the maximum compression force Fmax threshold 202072, the control circuit 760 is configured to register a warning that the compression force is too tight and to adjust the anvil gap δ, increase the wait time before firing, lower the firing speed, or enable a firing lockout, or any combination thereof. The control circuit 760 can adjust the anvil gap δ by advancing the anvil 766 distally, e.g. away, from the staple cartridge 768 (anvil 201804 and stapler 202084 in FIG. 26) to increase the anvil gap δ as shown by the segment of the anvil gap curve 2002044 beyond time t5. As shown by the segment of the tissue compression force curve 202064 beyond time t5, after the control circuit 760 increases the anvil gap δ, the tissue compression force F decreases into the ideal firing zone 202076.

If the tissue compression force F is below the minimum compression force Fmin threshold 202074, the control circuit 760 is configured to register a warning that the compression force is too loose and can adjust the anvil gap δ, proceed with caution, or enable a firing lockout, or any combination thereof. The control circuit 760 is configured to adjust the anvil gap δ by retracting the anvil 766 proximally, e.g. toward, the staple cartridge 768 (anvil 201804 and stapler 202084 in FIG. 26) to decrease the anvil gap δ as shown by the segment of the anvil gap curve 202046 beyond time t5. As shown by the segment of the tissue compression force curve 202066 beyond time t5, after decreasing the anvil gap δ, the tissue compression force F increases into the ideal firing zone 202076.

With reference to FIGS. 24-25, in one aspect, the anvil gap δ may be determined by the controller 620 based on readings from the closure motor 603 as described with reference to FIG. 8, for example. In one aspect, the anvil gap δ may be determined by the control circuit 710 based on readings from the position sensor 734 coupled to the anvil 716 as described with reference to FIG. 16, for example. In one aspect, the anvil gap δ may be determined by the control circuit 760 based on readings from the position sensor 784 coupled to the anvil 766 as described with reference to FIG. 17, for example.

With reference to FIGS. 24-25, in one aspect, the tissue compression force F may be determined by the controller 620 based on readings from the closure motor 603 as described with reference to FIG. 8. For example, the tissue compression force F may be determined based on the current draw of the motor where higher current draw while closing the anvil is related to higher tissue compression force. In one aspect, the tissue compression force F may be determined by the control circuit 710 based on readings from sensors 738, such as strain gauges, coupled to the anvil 716 or the staple cartridge 718 as described with reference to FIG. 16, for example. In one aspect, the tissue compression force F may be determined by the control circuit 760 based on readings from the sensors 788, such as strain gauges, coupled to the anvil 766 as described with reference to FIGS. 17, for example.

Figure 27:
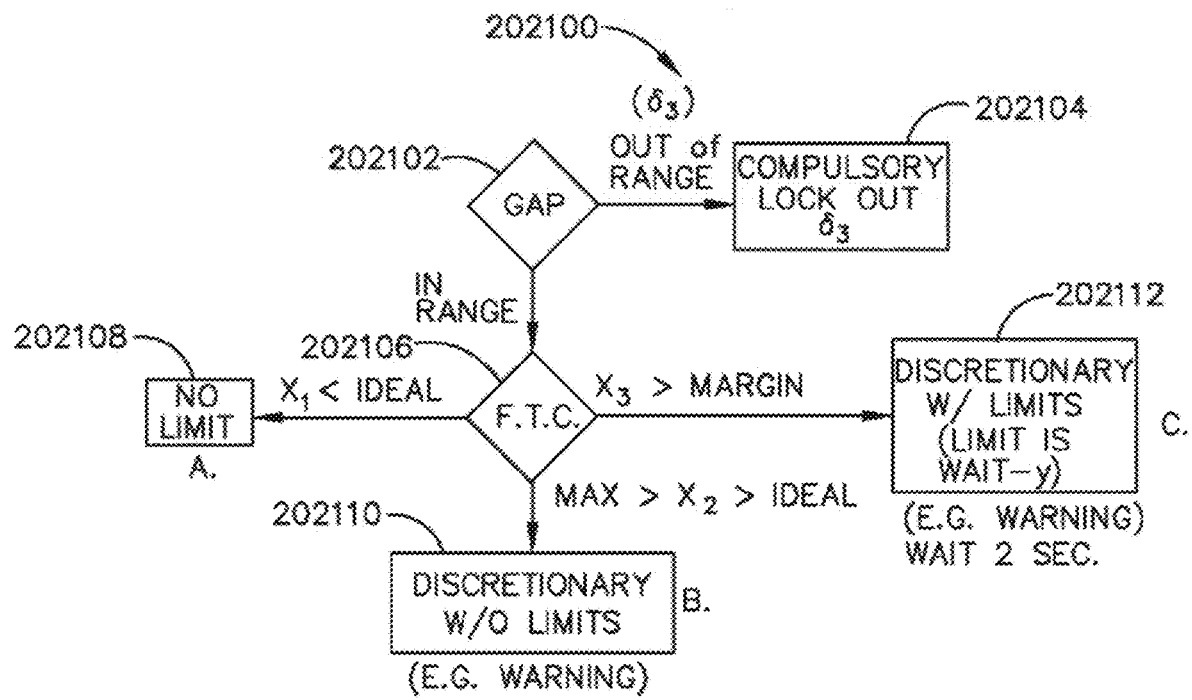
FIG. 27 is a logic flow diagram of a process depicting a control program or a logic configuration to provide discretionary or compulsory lockouts according to sensed parameters compared to thresholds, in accordance with at least one aspect of the present disclosure.

FIG. 27 is a logic flow diagram of a process 202100 depicting a control program or a logic configuration to provide discretionary or compulsory lockouts according to sensed parameters compared to thresholds, in accordance with at least one aspect of the present disclosure. As depicted in FIG. 27, according to a comparison of the measured anvil gap relative to one or more thresholds and the measured tissue compression force F (otherwise referred to as FTC) relative to one or more thresholds, a control algorithm can allow the instrument to be fired (e.g., actuated) without limitations, implement a discretionary lockout (e.g., provide a warning to the user), or implement a compulsory lockout of the instrument.

Accordingly, with reference to FIGS. 17, 26, and 27, the process 202100 will be described with reference to FIGS. 17-25. The control circuit 760 implements the algorithm to execute the process 202100 where the anvil 766 in FIG. 17 is shown as anvil 202084 in FIG. 26 and the staple cartridge 768 in FIG. 17 is shown as the stapler 202082 in FIG. 26. Additional details regarding the configuration and operation of a powered circular stapling device 202080 are described herein with reference to FIGS. 18-20. Turning back to the process 202100, the control circuit 760 determines the anvil gap δ as described in connection with FIGS. 24 and 25 based on readings from the position sensor 784 coupled to the anvil 766. When the anvil gap δ is δ3>δMax, the anvil gap is out of range and the control circuit 760 engages a compulsory lockout 202104. When the anvil gap δ is δMaX>δ2>δMin, the anvil gap δ is in range and the control circuit 760 determines 202106 the tissue compression force F (FTC) as described with reference to FIG. 29. As described above, the tissue compression force may be determined by the control circuit 760 based on readings from strain gauge sensors 788 coupled to the anvil 766 or the staple cartridge 768. Alternatively, tissue compression force may be determined based current draw by the motor 754.

Figure 29:
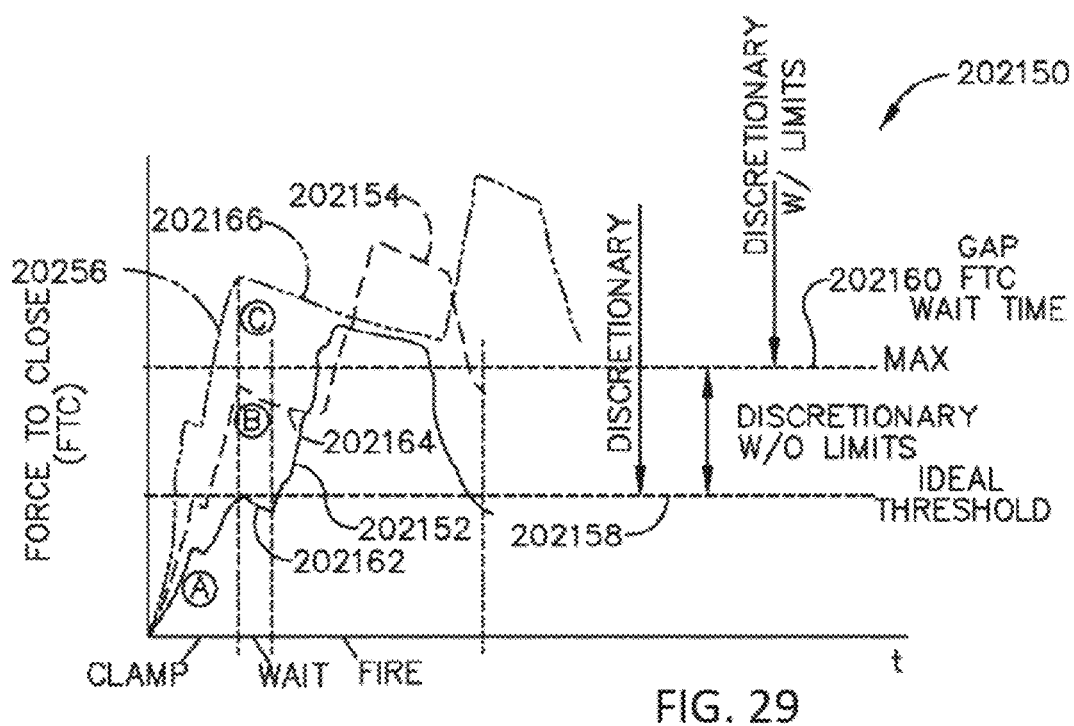
FIG. 29 is a graphical representation of three force to close (FTC) curves verse time, in accordance with at least one aspect of the present disclosure.

With reference now to FIGS. 27 and 29, when the FTC is less than an ideal FTC threshold (X1<Ideal FTC), zone A in FIG. 29, the control circuit 760 executes 202108 a no limits electronic lockout. When the FTC is between a maximum FTC threshold and the ideal FTC threshold (Max>X2>Ideal), zone B in FIG. 29, the control circuit 760 executes 202110 discretionary electronic lockouts without limits. In one aspect, under this condition, the control circuit 760 issues a warning in the form of a message or alert (audio, visual, tactile, etc.). When the FTC is greater than a maximum FTC threshold (X3>Margin), zone C in FIG. 29, the control circuit executes 202112 discretionary electronic lockouts with limits. Under this condition, the control circuit 760 issues a warning in the form of a message or alert (audio, visual, tactile, etc.) and applies a wait period before firing. In various aspects, the powered circular stapling device 202080 includes adjustable electronic lockouts as described herein, which can either prevent the actuation of the 202082 stapler or adjust the function of the powered circular stapling device 202080 based on a sensed condition and a secondary measure.

In one aspect, powered circular stapling device 202080 control algorithm described herein as the process 202100 can be configured to initiate discretionary and compulsory lockouts based on marginal and required conditions for the powered circular stapling device 202080 to operate. In one aspect, the process 202100 for the powered circular stapling device 202080 can be configured to implement both compulsory and discretionary lockouts based on sensed parameters within the system. A discretionary lockout pauses the automatic execution of a sequential operation, but can be overridden by the user input, for example. A compulsory lockout prevents the next sequential step, causing the user to back up a step of operation and resolve the lockout condition which induced the lockout, for example. In one aspect, both compulsory and discretionary lockouts can have both upper and lower bounded thresholds. Accordingly, the powered circular stapling device 202080 can comprise a combination of discretionary and compulsory lockouts.

In one aspect, powered circular stapling device 202080 control algorithm described herein as the process 202100 can be configured to adjust electronic lockouts that can either prevent the actuation of a system or adjust its function based on the sensed condition and a secondary measure. The sensed condition may be FTC, anvil displacement, gap δ, formation of staples and the secondary measure can include the severity of failure, a user input, or predefined comparison lookup table, for example.

In one aspect, the reaction of compulsory electronic lockouts is to prohibit the powered circular stapling device 202080 function until the situation is resolved. Conversely, the reaction to a discretionary lockout can be more subtle. For example, discretionary lockout could include a warning indication, an alert requiring user consent to proceed, a change in the rate or force of an actuation or wait time, or a prohibition of certain functions being performed until the situation is resolved or stabilized. In operation, compulsory conditions for the powered circular stapling device 202080 can include, for example, having the anvil 202084 fully seated before clamping or the stapler cartridge being loaded with staples before firing. Viable conditions for the powered circular stapling device 202080 can include, for example, being within the acceptable staple height for a given tissue thickness or a minimum tissue compression. Further, different conditions could have both discretionary and compulsory level thresholds on the same parameter, e.g., power level within the battery pack.

In one aspect, the powered circular stapling device 202080 can be configured to implement various control mechanisms to prevent or adjust the function of the powered circular stapling device 202080 based on the lockout type. In one aspect, compulsory lockouts could be solely electronic, mechanical interlocks, or a combination of the two. In various aspects having two lockouts, the lockouts could be redundant or optionally used based on the settings of the device. In one aspect, discretionary lockouts can be electronic lockouts so that they can be adjustable based on sensed parameters. For example, the discretionary lockouts could be a mechanical interlock that is electronically disabled or they could be a solely electronic lockout.

Figure 28:
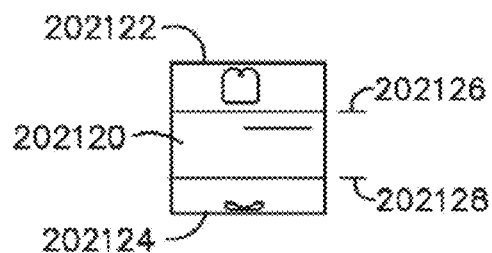
FIG. 28 is a diagram illustrating a range of tissue gaps and resulting staple forms, in accordance with at least one aspect of the present disclosure.

FIG. 28 is a diagram illustrating the anvil gap ranges and corresponding staple formation, in accordance with at least one aspect of the present disclosure. When the anvil gap 202120 is between an upper limit 202126 and a lower limit 202128, the staple formation is proper and within an acceptable range of staple heights for a given range of tissue thickness or minimum tissue compression force. When the anvil gap 202122 is greater than the upper limit 202126, the staple formation is loose. When the anvil gap 202124 is less than the lower limit 202128, the staple formation is tight.

FIG. 29 is a graphical representation 202150 of three force to close (FTC) curves 202152, 202154, 202156 verse time, in accordance with at least one aspect of the present disclosure. The FTC curves 202152, 202154, 202156 are divided into three phases: clamp, wait, and fire. The clamp phase has a common starting point, which means that the tissue has a common thickness and variable tissue stiffness as described in detail in FIG. 24. At the end of the clamp phase, there is a wait period before starting the fire phase to account for tissue creep.

The first FTC curve 202152 corresponds to tissue having a low tissue stiffness. During the clamping phase, the FTC curve 202152 exhibits a rise in tissue compression force that peaks below the ideal FTC threshold 202158 in zone A. At the end of the clamp phase, the powered circular stapling device 202080 (FIG. 26) waits a user controlled period 202162 before initiating the firing phase to account for tissue creep.

The second FTC curve 202154 corresponds to tissue having a normal tissue stiffness. During the clamping phase, the FTC curve 202154 exhibits a rise in tissue compression force that peaks between the ideal FTC threshold 202158 and the maximum FTC threshold 202160 in zone B. At the end of the clamp phase, the powered circular stapling device 202080 (FIG. 26) waits a user controlled period 202164 before initiating the firing phase to account for tissue creep.

The third FTC curve 202154 corresponds to tissue having a high tissue stiffness. During the clamping phase, the FTC curve 202156 exhibits a rise in tissue compression force that peaks above the maximum FTC threshold 202160 in zone C. At the end of the clamp phase, the powered circular stapling device 202080 (FIG. 26) controls a wait period 202166 before initiating the firing phase to account for tissue creep.

Figure 30:
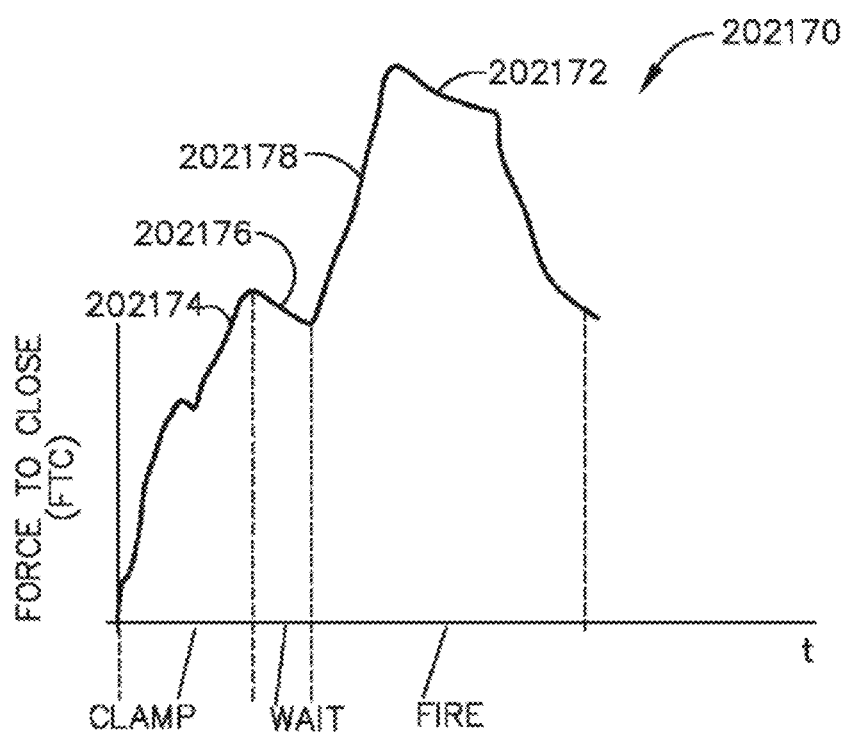
FIG. 30 is a detail graphical representation of a force to close (FTC) curve verse time, in accordance with at least one aspect of the present disclosure.

FIG. 30 is a detail graphical representation 202170 of a FTC curve 202172 verse time, in accordance with at least one aspect of the present disclosure. As shown, the FTC curve 202172 is divided over three phases: a clamp phase, a wait phase, and a fire phase. During the clamp phase, the FTC curve 202172 exhibits and increase in tissue compression force as indicated by the clamp phase segment 202174. After the clamp phase, there is a wait period 202176 before initiating the fire phase. The wait period 202176 may be either user controlled or device controlled depending on the value of the tissue compression force relative to ideal and maximum compression force thresholds. During the fire phase, the tissue compression force increases as shown by FTC curve segment 202178 and then drops.

Figure 31:
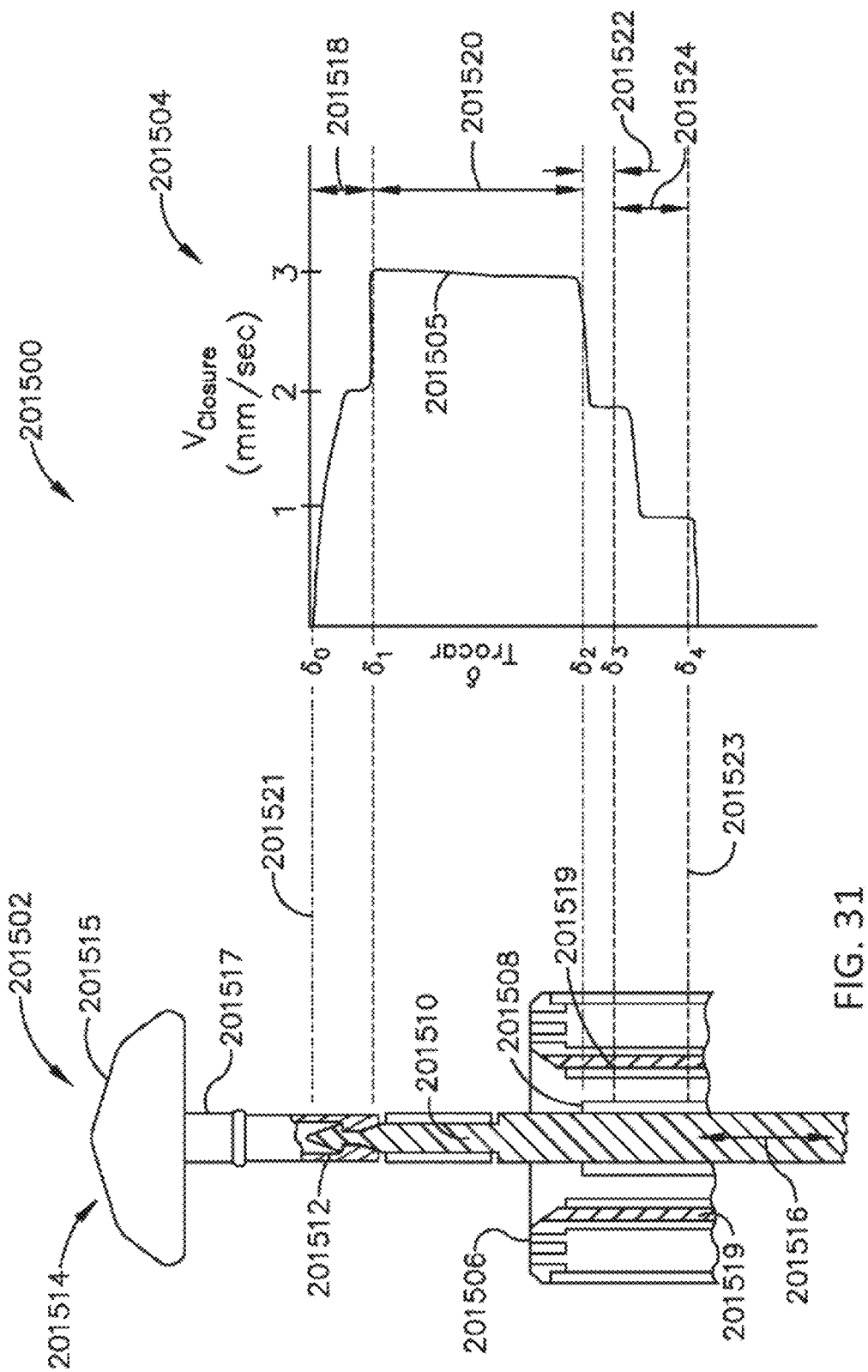
FIG. 31 is a diagram of graph and associated powered stapling device illustrating anvil closure rate adjustment at certain key points along a trocar's retraction stroke, in accordance with at least one aspect of the present disclosure.

In various aspects, the closure rate or direction of a circular stapler, or a combination thereof, can be adjusted based on the sensed attachment, relative to the fully attached state, of the anvil. In one aspect, the present disclosure provides a digitally enabled circular stapler algorithm for determining the variation the closure rate of the anvil at key locations of the trocar to ensure proper seating of the anvil on the trocar. FIG. 31 is a diagram 201500 of a powered stapling device 201502 and a graph 201504 illustrating the closure rate adjustment of an anvil 201514 portion of the powered stapling device 201502 at certain key points along the retraction stroke of a trocar 201510, in accordance with at least one aspect of the present disclosure. The powered stapling device 201502 is similar to the motorized circular stapling instrument 201800 described herein with reference to FIGS. 18-20, may be controlled using any of the control circuits described in connection with FIGS. 7-8 and 16-17, and may be employed in a hub and cloud environment as described in connection with FIGS. 1-6 and 9-13. The anvil 201514 includes an anvil head 201515 and an anvil shank 201517. The trocar 201510 can be advanced and retracted in the direction indicated by arrow 201516. In one aspect, the closure rate of the anvil 210514 can be adjusted at certain key points along the retraction stroke of the trocar 201510 to improve the final seating of the anvil 201514 on the trocar 201510 if the trocar 201510 is marginally attached but not fully attached to the anvil 201514.

The powered stapling device 201502, shown on the left side of FIG. 31, includes a circular stapling head assembly 201506 with a seating collar 201508 that receives the trocar 201510 therethrough. The trocar 201510 engages the anvil 201514 via a locking feature 201512. The trocar 210510 is movable, e.g., advanced and retracted, in the directions indicated by arrow 201516. A cutting element, such as a knife 201519, severs tissue when the circular stapling head assembly 201506 is driven towards the anvil 201514. In one aspect, the closure rate of the anvil 201514 can be adjusted at certain key points along the retraction stroke of the anvil 201510 in order to, for example, improve the final seating of the anvil 201514 on the trocar 201510 if the trocar 210510 is marginally attached but not fully attached to the anvil 201514. Accordingly, the closure rate of the anvil 201514 can be varied at key locations to ensure proper seating. The position or displacement of the trocar 210510 as it is advanced or retracted by a trocar actuator coupled to a motor may be detected by a plurality of proximity sensors disposed along the displacement path of the trocar 210510. In some aspects, the position or displacement of the trocar 210510 may be tracked using the tracking system 480 (FIG. 7) or the position sensors 734, 784 (FIGS. 16-17).

On the right side of FIG. 31, the graph 201504 illustrates the closure rate of the anvil 201514 as a function of the position of the trocar 201510 at certain key points, labeled as "δ Trocar" along the vertical axis and "Vclosure mm/sec" along the horizontal axis, in accordance with at least one aspect of the present disclosure. An anvil 201514 closure rate velocity profile curve 201505 is plotted as a function of the position of the trocar 201510. The closure rate of the anvil 201514 can be slow at a first zone 201518 to ensure proper attachment of the trocar 210510 to the anvil 201514, faster at a second zone 201520 during closure, slower again at a third zone 201522 to verify attachment, and then even slower at a fourth zone 201524 during application of a high closure load.

The anvil 201514 closure rate adjustment at certain key points along the trocar's 201510 retraction stroke improves the final seating of the anvil 201514 on the trocar 201510 if it marginally attached but not fully attached. At trocar 201510 position δ0 the anvil 201514 is in a fully open position 201521 and at trocar 201510 position δ4 the anvil 201514 is in a fully closed position 201523. Between the trocar 201510 fully open position 201521 δ0 and fully closed position δ4 the closure rate of the anvil 201514 is adjusted based on the position of the trocar 201510. For example, at the first zone 201518, as the trocar 201510 moves from the fully opened position 201521 δ0 to a first trocar 201510 position δ1, the closure rate of the anvil 201514 is slow (between 0-2 mm/sec) to ensure proper attachment of the anvil 201514 to the trocar 201510. At the second zone 201520, when the trocar 201510 moves from δ1 to δ2, the anvil 201514 is closed at a constant quick closure rate (3 mm/sec). When the trocar 201510 moves from δ2 to δ3 position, in the third zone 201522, the closure rate of the anvil 201514 is slowed to verify full attachment of the anvil 201514 to the trocar 201510. Finally, when the trocar 201510 moves from δ3 to δ4 position, in the fourth zone 201524, the closure rate of the anvil 201514 is slowed once again during high closure loads.

Figure 32:
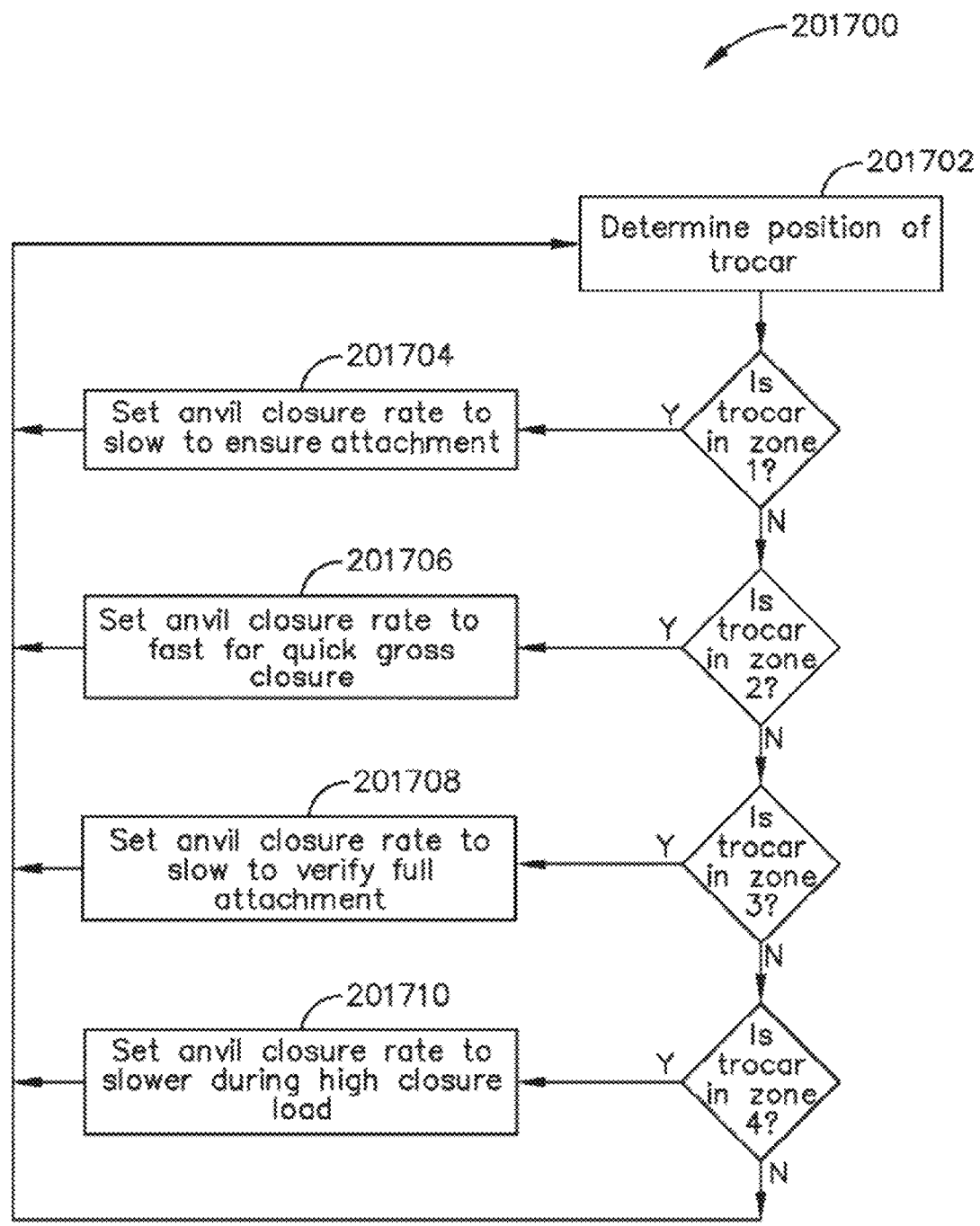
FIG. 32 is a logic flow diagram of a process depicting a control program or a logic configuration to adjust a closure rate of the anvil portion of the powered stapling device at certain key points along the retraction stroke of a trocar, in accordance with at least one aspect of the present disclosure.

FIG. 32 is a logic flow diagram of a process 201700 depicting a control program or a logic configuration to adjust a closure rate of the anvil 201514 portion of the powered stapling device 201502 at certain key points along the retraction stroke of a trocar 201510, in accordance with at least one aspect of the present disclosure. This process 201700 may be implemented with any of the control circuits described with reference to FIGS. 7-8 and 16-17. This process 201700 may be implemented in a hub or cloud computing environment described with reference to FIGS. 1-6 and 9-13, for example.

In particular, the process 201700 depicted in FIG. 32 will now be described with reference to the control circuit 760 of FIG. 17. The control circuit 760 determines 201702 the position of the trocar 201510 based on information received from position sensor 784. Alternatively, the position of the trocar 201510 may be determined based on information received from the sensors 788 or the timer/counter 781 circuit or a combination thereof. Based on the position of the trocar 201510, the control circuit 760 controls the closure rate of the anvil 201514 (Vclosure mm/sec) as a function of the position of the trocar 201510 at certain key points, in accordance with at least one aspect of the present disclosure. Accordingly, when the position of the trocar 201510 is located in a first zone 201518, where the anvil 201514 is attached to the trocar 201510, the process 201700 continues along the yes (Y) branch and the control circuit 760 sets 201704 the closure rate of the anvil 201514 to slow to ensure proper attachment of the trocar 210510 to the anvil 201514. Otherwise the process 201700 continues along the no (N) branch. When the position of the trocar 201510 is located in a second zone 201520, referred to as a quick gross closure zone, the process 201700 continues along the yes (Y) branch and the control circuit 760 sets 201706 the closure rate of the anvil 201514 to fast to rapidly close the anvil 201514. Otherwise the process 201700 continues along the no (N) branch. When the position of the trocar 201510 is located in a third zone 201522, referred to as a verification zone, the process continues along the yes (Y) branch and the control circuit 760 sets 201708 the closure rate of the anvil 201514 to slow to verify full attachment of the anvil 201514 to the trocar 201510. Otherwise the process 201700 continues along the no (N) branch. When the position of the trocar 201510 is located in a fourth zone 201524, referred to as a high closure load zone, the process 201700 continues along the yes (Y branch and the control circuit 760 sets 201710 the closure rate of the anvil 201514 to a slower rate than in the previous verification zone 201522 during the application of a high closure load. Once the anvil 201514 is fully closed trocar 201510 to capture tissue therebetween, the control circuit 760 actuates the knife 201519 to sever the tissue.

Figure 33:
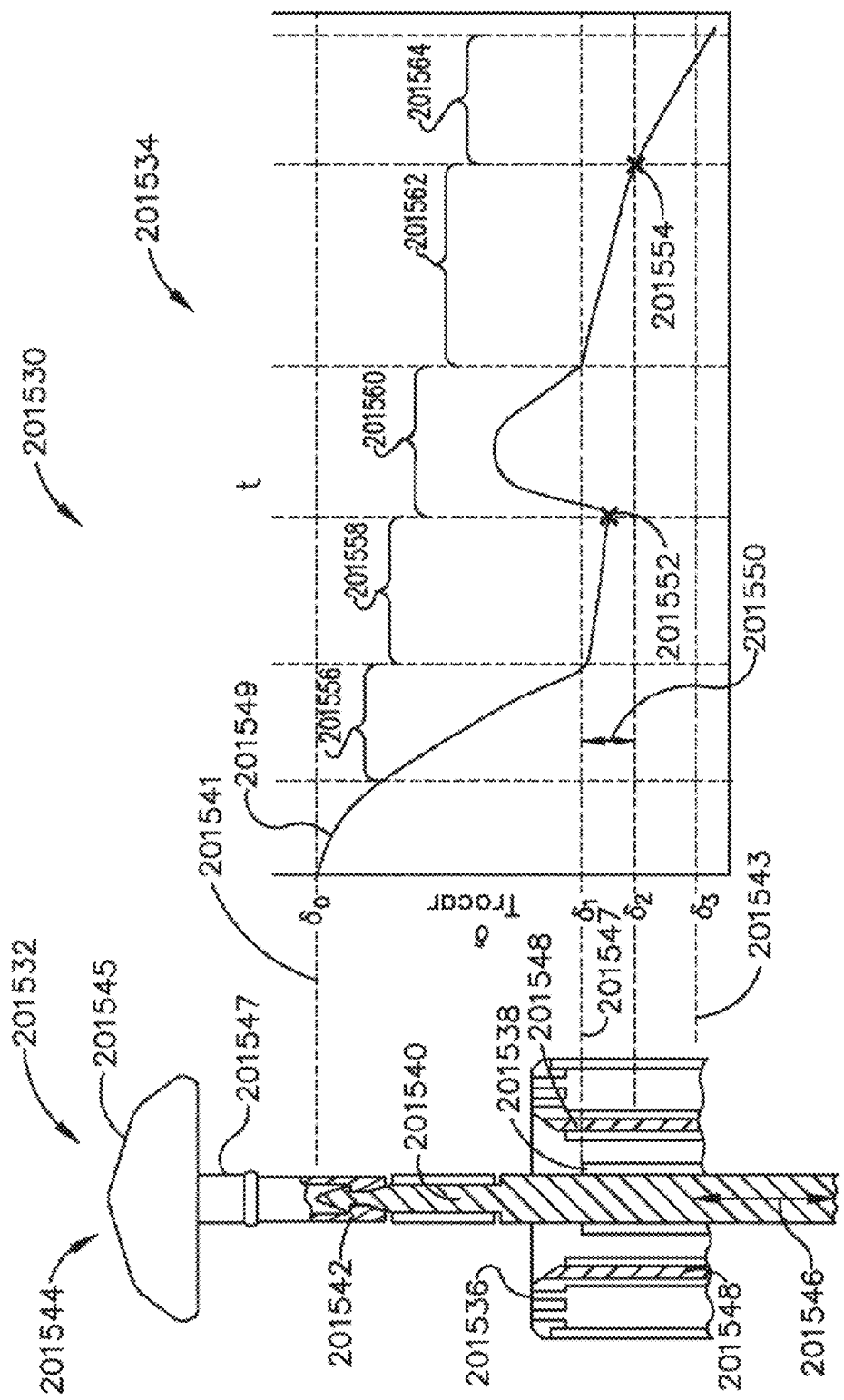
FIG. 33 is a diagram of graph and associated power stapling device diagram illustrating trocar position over time, in accordance with at least one aspect of the present disclosure.

In one aspect, the present disclosure provides a digitally enabled circular stapler adaptive algorithm for determining multi-directional seating motions on the trocar to drive the anvil into proper seating. FIG. 33 is a diagram 201530 of a powered stapling device 201532 and a graph 201534 illustrating detection of closure rates of the trocar 201540 and the anvil 201544, in accordance with at least one aspect of the present disclosure. The powered stapling device 201532 is similar to the motorized circular stapling instrument 201800 described herein with reference to FIGS. 18-21, may be controlled using any of the control circuits described in connection with FIGS. 7-8 and 16-17, and may be employed in a hub and cloud environment as described in connection with FIGS. 1-6 and 9-13. The anvil 201544 includes an anvil head 201545 and an anvil shank 201547. The trocar 201540 can be advanced and retracted in the direction indicated by arrow 201546. In one aspect, if the anvil shank 201547 is detected pulling loose from the trocar 201540, the powered stapling device 210530 could stop retraction or reverse and advance towards an open position 201541 until the instability of the anvil 201544 seating is resolved. If the anvil 201544 is pulled fully off, the powered stapling device 210530 could fully open 201541 indicating to the user to try re-attaching the anvil shank 201547 to the trocar 201540.

The powered stapling device 201532, shown on the left side of FIG. 33, includes a circular stapling head assembly 201536 with a seating collar 201538 that receives the trocar 201540 therethrough. The trocar 201540 engages the anvil 201544 via a locking feature 201542. The trocar 210540 is movable, e.g., advanced and retracted, in the directions indicated by arrow 201546. A cutting element, such as a knife 201548, severs tissue when the circular stapling head assembly 201536 is driven towards the anvil 201544.

In one aspect, the closure rates of the trocar 201540 and the anvil 201544 can be detected and any discrepancy between the closure rates of the two components could generate an automatic extension of the trocar 201540 and then retraction of the trocar 201540 in order to fully seat the anvil 201544 on the trocar 201540. In one aspect, any discrepancy between the closure rates of the trocar 201540 and the anvil 201544 may be provided to a control circuit or processor to operate a motor coupled to the trocar 201540 to generate an automatic extension of the trocar 201540 and then re-retraction in order to fully seat the anvil 201544 on the trocar 201540. If the anvil shank 201547 is detected pulling loose from the trocar 201540 the smart powered stapling device 201532 could stop retraction or even reverse and advance towards open until the instability of seating the anvil 201544 is resolved. If the anvil 201544 were pulled fully off it could even fully open indicating to the user to try re-attaching the anvil shank 201547 to the trocar 201540. As shown FIG. 33, the control algorithm can be configured to extend the trocar 201540 back towards the open position 201541 to reset the anvil 201544 if an anvil 201544 detachment is sensed, prior to then re-verifying attachment of the anvil 201544 and proceeding as normal upon confirming that the anvil 201544 is attached.

Accordingly, the system can be configured for multidirectional seating motions on the trocar 201540 to drive the anvil 201544 into proper seating. For example, if the anvil shank 201547 is detected as pulling loose from the trocar 201540, the smart powered stapling device 201530 could be configured to stop retraction or even reverse and advance towards open until the instability of seating the anvil 201544 is resolved. If the anvil 201544 were pulled fully off, the smart powered stapling device 201532 could even be configured to fully open, indicating to the user to try reattaching the anvil shank 201547 to the trocar 201540.

On the right side of FIG. 33, the graph 201534 illustrates the position of the trocar 201510 as a function of time at certain key points, labeled as "δ Trocar" along the vertical axis and "t" along the horizontal axis, in accordance with at least one aspect of the present disclosure. A trocar 201540 position profile curve 201549 is plotted as a function of time (t). With reference to the trocar 201540 position profile curve 201549, the trocar 201540 moves from a fully open position 201541 towards a fully closed position 201543 over a first period 201556 at a quick closure rate. During a second period 201558, the trocar 201540 moves into the verification zone 201547 where the anvil locking feature 201542 engages the seating collar 201538, at a slow rate to verify that the anvil locking feature 201542 has properly engaged the seating collar 201538. In the illustrated example, an anvil 201544 detached initiation is sensed at time 201552. Upon sensing that the anvil 201544 is detached, the trocar 201540 is advanced towards an open position and back over a third period 201560. The trocar 201540 then moves slowly during a fourth period 201562 until it is confirmed or verified that the anvil 201544 is attached to the trocar 201540 at time 201554. Thereafter, the trocar 201540 moves towards the closed position 201543 very slowly during a fifth period 201564 under high tissue load before the knife 201548 is advanced to sever the tissue captured between the anvil 201544 and the circular stapling head assembly 201536.

Figure 34:
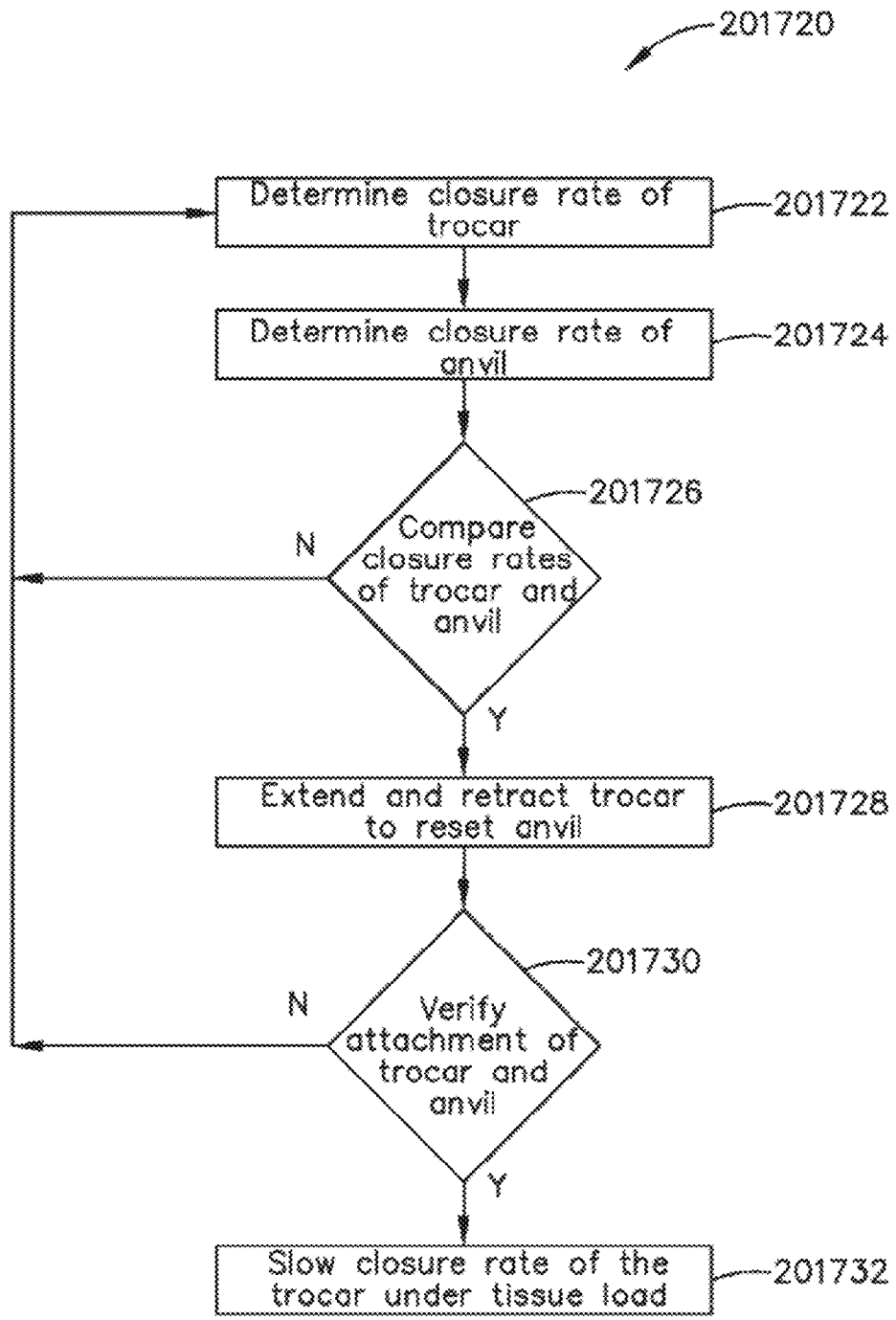
FIG. 34 is a logic flow diagram of a process depicting a control program or a logic configuration to detect multi-directional seating motions on the trocar to drive the anvil into proper seating, in accordance with at least one aspect of the present disclosure.

FIG. 34 is a logic flow diagram of a process 201720 depicting a control program or a logic configuration to detect multi-directional seating motions on the trocar 201540 to drive the anvil 201544 into proper seating, in accordance with at least one aspect of the present disclosure. This process 201720 may be implemented with any of the control circuits described herein with reference to FIGS. 7-8 and 16-17. This process 201720 may be implemented in a hub or cloud computing environment described with reference to FIGS. 1-6 and 9-13, for example.

In particular, the process 201720 depicted in FIG. 34 will now be described with reference to the control circuit 760 of FIG. 17. The control circuit 760 determines 201722 the closure rate of the trocar 201540 based on information received from position sensor 784. The control circuit 760 then determines 201724 the closure rate of the anvil 201544 based on information received from position sensor 784. Alternatively, the closure rate of the trocar 201540 or the anvil 201544 may be determined based on information received from the sensors 788 or the timer/counter 781 circuit or a combination thereof. The control circuit 760 compares 207126 the closure rates of the trocar 201540 and the anvil 201544. When there is no discrepancy between the closure rates of the trocar 201540 and the anvil 201544, the process 201720 continues along the no (N) branch and loops until there is a discrepancy between the closure rates of the trocar 201540 and the anvil 201544. When there is a discrepancy between the closure rates of the trocar 201540 and the anvil 201544, the process 201720 continues along the yes (Y) branch and the control circuit 760 extends and retracts 207128 the trocar 201540 to reset the anvil 201544. Subsequently, the process 201720 verifies 201130 the attachment of the trocar 201540 and anvil 201544. If the attachment is verified, the process 201720 continues along the yes (Y) branch and the control circuit 760 slows 207132 the closure rate of the trocar 201540 under tissue load. If the attachment is not verified, the process 201720 continues along the no (N) branch and loops until the attachment of the trocar 201540 to the anvil 201544 is verified. Once the anvil 201544 is fully closed on the trocar 201540 to capture tissue therebetween, the control circuit 760 actuates the knife 201548 to sever the tissue.

In various aspects, the knife speed of a circular stapler and end points can be adjusted based on the sensed toughness or thickness of the tissue between the anvil and cartridge. Accordingly, the circular stapler control algorithm can be configured to detect the tissue gap and force-to-fire to adjust the knife stroke and speed. In one aspect, the present disclosure provides a digitally enabled circular stapler adaptive algorithm for detecting tissue gap and force-to-fire to adjust knife stroke and knife speed, in accordance with at least one aspect of the present disclosure.

Figure 35:
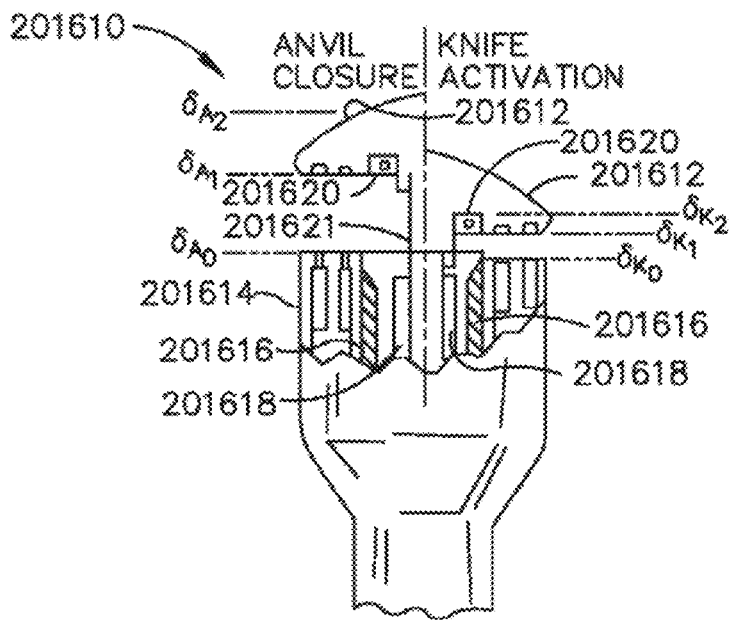
FIG. 35 is a partial schematic diagram of a circular powered stapling device showing anvil closure on the left side and knife 201616 actuation on the right side, in accordance with at least one aspect of the present disclosure.
Figure 36:
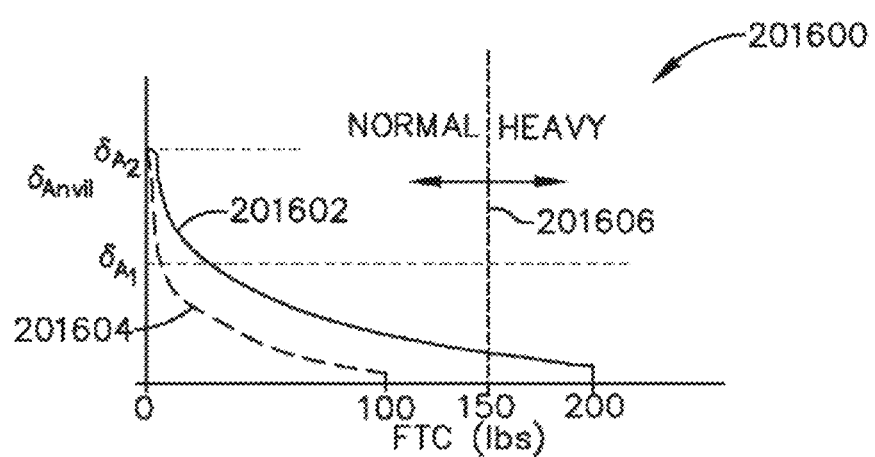
FIG. 36 is a graphical representation of anvil displacement (δAnvil) along the vertical axis as a function of force to close (FTC) a clamp along the horizontal axis, in accordance with at least one aspect of the present disclosure.
Figure 37:
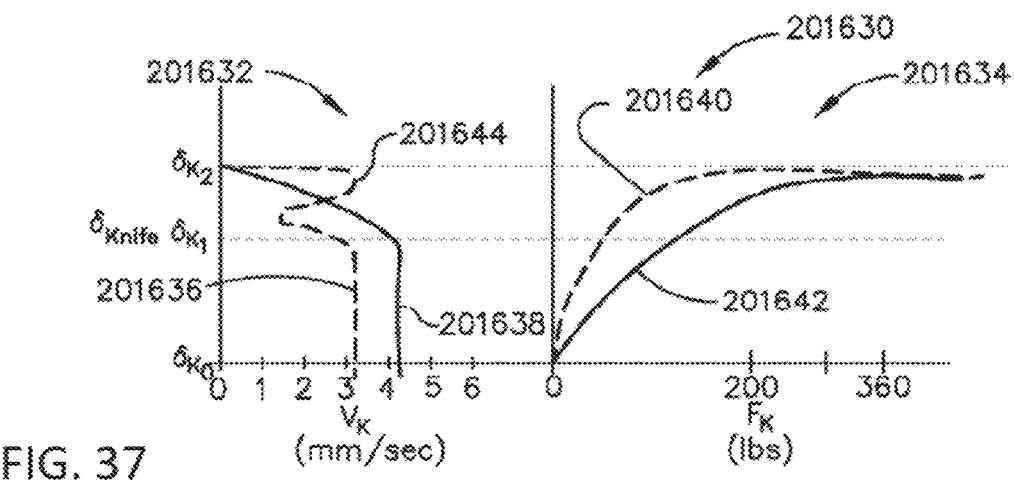
FIG. 37 is a graphical representation 201630 of knife 201616 displacement (δKnife) along the vertical axis as a function of knife 201616 velocity (VK mm/sec) along the horizontal axis on the left and also as a function of knife 201616 force (FK lbs) along the horizontal axis on the right, in accordance with at least one aspect of the present disclosure.

Generally, FIGS. 35-37 represent a circular powered stapling device 201610 and a series of graphs depicting force-to-close (FTC) a clamp relative to the position of the anvil 201612 (δAnvil) and knife 201616 velocity (VK) and knife 201616 force (FK) relative to the position of the knife 201616 (δKnife), in accordance with at least one aspect of the present disclosure. Using sensed data at different points along length of the shank 201621, a control algorithm can generate a map of tissue gap or reaction force vector of the anvil 201612, monitoring for a high or low side when compressed on tissue. When firing, the system measures forces acting on a compression element 201620 comprising a force sensor and adjusts to act evenly along the force vector of the shank to provide even and complete cutting.

In particular, FIG. 35 is a partial schematic diagram of a circular powered stapling device 201610 showing anvil 201612 closure on the left side and knife 201616 actuation on the right side, in accordance to at least one aspect of the present disclosure. The circular powered stapling device 201610 comprises an anvil 201612 that is movable from a fully open position δA2 to a fully closed position AG. An intermediate position δA1 represents the point at which the anvil 201612 contacts tissue located between the anvil 201612 and the circular stapler 201614. One or more position sensors located along the length of the anvil shank 201621 monitor the position of the anvil 201612. In one aspect, the position sensor may be located within the seating collar 201618. The compression element 201620 may comprise a force sensor, such as a strain gauge for example, to monitor the force applied to the tissue and to detect the point of initial contact of the anvil 201612 with the tissue, shown as intermediate position δA1. The position sensor and the force sensor interface with any of the control circuits described herein with reference to FIGS. 7-8 and 16-17, for example, which implement the circular stapler control algorithm. The circular powered stapling device 201610 also comprises a movable cutting element such as a knife 201616 that is movable from a fully retracted position δA0 to a fully extended position δA2 to achieve a complete tissue cut. The intermediate position δA1 of the knife 201616 represents the point at which the knife 201616 contacts with the compression element 201620 comprising a strain gauge or other contact or proximity sensor.

The power stapling device 201610 includes motors, sensors, and control circuits as described herein in connection with FIGS. 7-8 and 16-20. The motors are controlled by the control circuits to move the anvil 201612 and the knife 201616. One or more position sensors located on the power stapling device 201610 provide the position of the anvil 201612 and the knife 201616 to the control circuit. Additional sensors such as force sensors 201620 also provide tissue contact and force acting on the anvil 201612 and the knife 201616 to the control circuit. The control circuit employs the position of the anvil 201612, the position of the knife 201616, initial tissue contact, or force acting of the anvil 201612 or knife 201616 to implement the circular stapler control algorithm described hereinbelow in connection with FIG. 38.

FIG. 36 is a graphical representation 201600 of anvil 201612 displacement (δAnvil) along the vertical axis as a function of force-to-close (FTC) a clamp along the horizontal axis, in accordance with at least one aspect of the present disclosure. The vertical line represents a FTC threshold 201606 that indicates tissue toughness. The left side of the FTC threshold 201606 represents tissue having normal toughness and the right side of the FTC threshold 201606 represents tissue having heavy toughness. As the anvil 201612 is retracted from the fully open position δA2 to the intermediate position δA1, where the anvil 201612 initially contacts tissue, the FTC is substantially low (~0). As the anvil 201612 continues closing past this point towards the circular stapler 201614 to the fully retracted position δA0 minus the compressed tissue thickness, the FTC is nonlinear. Each tissue type from normal to heavy toughness will produce a different FTC curve. For example, the first FTC curve 201604, shown in broken line, spans from ~0 to ~100 lbs., where the maximum FTC is below the FTC threshold 201606. The second FTC curve 201602, shown in solid line, spans from ~0 to ~200 lbs., where the maximum FTC exceeds the FTC threshold 201606. As previously discussed, the FTC is measured by force sensors located in the compression element 201620 and coupled to the control circuit.

FIG. 37 is a graphical representation 201630 of knife 201616 displacement (δKnife) along the vertical axis as a function of knife 201616 velocity (VK mm/sec) along the horizontal axis on the left and also as a function of knife 201616 force (FK lbs) along the horizontal axis on the right, in accordance with at least one aspect of the present disclosure. On the left is a graphical representation 201632 of knife 201616 displacement (δKnife) along the vertical axis as a function of knife 201616 velocity (VK mm/sec) along the horizontal axis. On the right is a graphical representation 201634 of knife 201616 displacement (δKnife) along the vertical axis as a function of knife 201616 force (FK lbs) along the horizontal axis. The curves in dashed line 201638, 20142 in each of the graphical representations 201632, 201634 represent tissue of normal toughness whereas the curves in solid line 201636, 201640 represent tissue of heavy toughness.

Turning to the graphical representation 201632 on the left, for normal tissue toughness, as shown by the normal tissue knife velocity profile 201638, the initial velocity of the knife 201616 for normal tissue toughness starts at a first velocity, e.g., just over 4 mm/sec, at the initial knife position δK0. The knife 201616 continues at that velocity until it reaches knife position δK1 where the knife 201616 contacts tissue and slows the velocity of the knife 201616 as it cuts through the tissue until the knife 201616 reaches knife position δK2 indicating a complete cut and the control circuit stops the motor and hence stops the knife 201616. Turning to the graphical representation 201634 on the right, for normal tissue toughness, as shown by the normal tissue knife force curve 201642, the force acting on the knife 201616 is 0 lbs. at the initial knife position δK0 and varies nonlinearly until the knife 201616 reaches knife position δK2 until the cut is complete.

Turning to the graphical representation 201632 on the left, for heavy tissue toughness, as shown by the heavy tissue knife velocity profile 201636, the initial velocity of the knife 201616 for heavy tissue toughness starts at a second velocity, e.g., just over 3 mm/sec, which is lower relative to the first velocity, at the initial knife position δK0, which is less than the initial velocity for normal tissue toughness. The knife 201616 continues at that velocity until it reaches knife position δK1 where the knife 201616 contacts tissue. At this point the velocity of the knife 201616 starts to slow down nonlinearly as it cuts through the tissue for a short displacement of the knife 201616. The control circuit detects that the knife 201616 contacted tissue and in response increases the velocity of the motor to increase the velocity of the knife 201616, e.g., to the initial velocity until the knife 201616, until the knife 201616 reaches position δindicating a complete cut and the control circuit stops the motor and hence stops the knife 201616. This is shown as velocity spike 201644 to improve cutting of tissue of heavy toughness. Turning to the graphical representation 201634 on the right, for heavy tissue toughness, as shown by the heavy tissue knife force curve 201640, the force acting on the knife 201616 is 0 lbs. at the initial knife position δK0 and varies nonlinearly until the knife 201616 reaches knife position δK2 and the cut is complete. A comparison of the normal and heavy tissue knife force curves 201640, 201642 shows that, with lower velocity and adding the velocity spike 201644 shortly after tissue contact with the knife 201616, the knife 201616 experiences a lower force when cutting tissue of heavy toughness than it experiences when cutting tissue of normal toughness.

Figure 38:
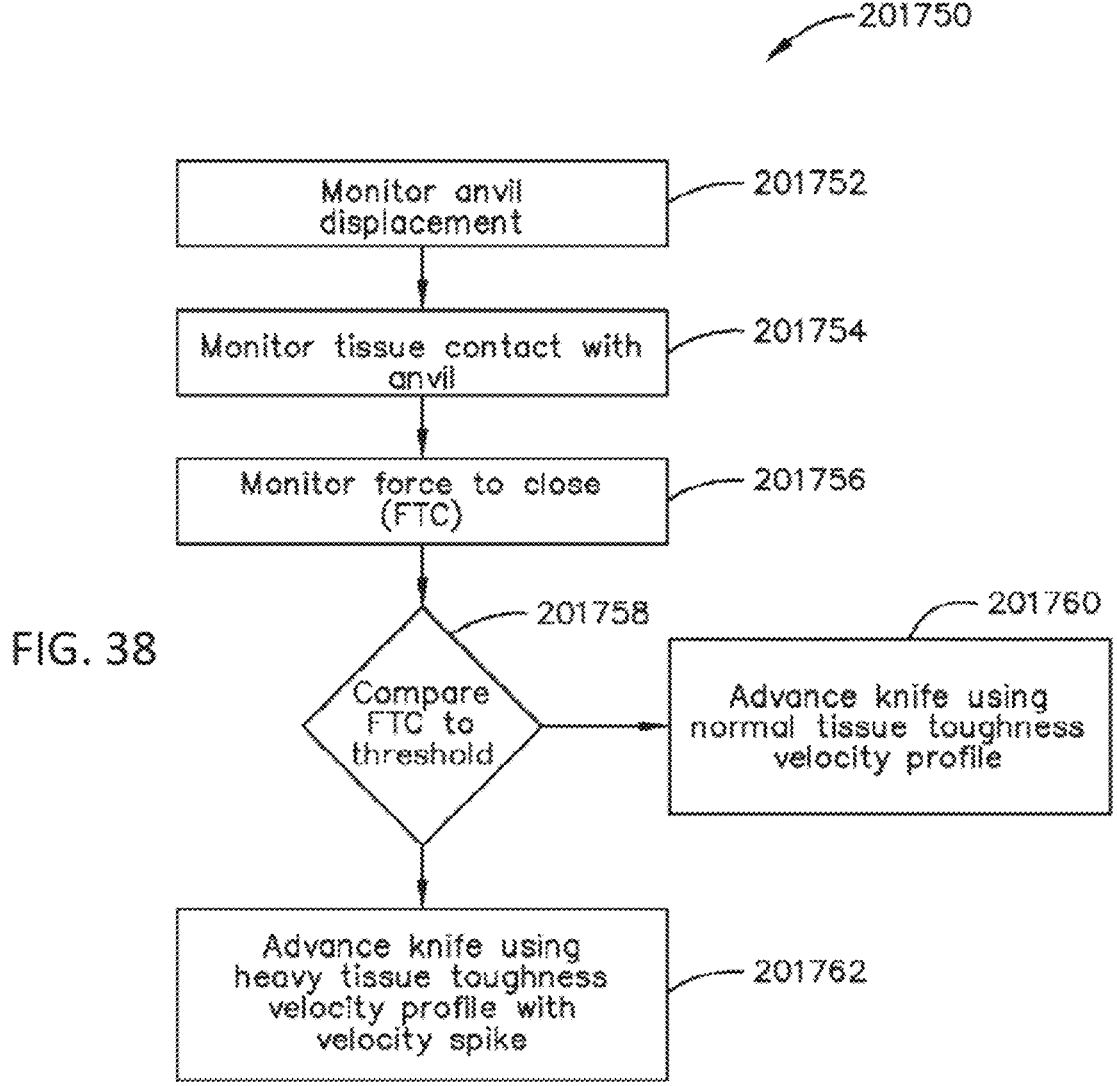
FIG. 38 is a logic flow diagram of a process depicting a control program or a logic configuration to detect the tissue gap and force-to-fire to adjust the knife stroke and speed, in accordance with at least one aspect of the present disclosure.

FIG. 38 is a logic flow diagram of a process 201720 depicting a control program or a logic configuration to detect the tissue gap and force-to-fire to adjust the knife stroke and speed, in accordance with at least one aspect of the present disclosure. This process 201750 may be implemented with any of the control circuits described with reference to FIGS. 7-8 and 16-17. This process 201750 may be implemented in a hub or cloud computing environment described with reference to FIGS. 1-6 and 9-13, for example.

In particular, the process 201750 depicted in FIG. 38 will now be described with reference to the control circuit 760 of FIG. 17 and the circular powered stapling device 201610 shown in FIGS. 35-37. The control circuit 760 monitors 201752 the displacement of the anvil 201612 based on position feedback received from the position sensor 784. As previously discussed, in one aspect, the position sensor 784 may be embedded in the shank 201612 of the anvil 201612. As the anvil 201612 is displaced, the control circuit 760 monitors 201754 contact of the anvil 201612 with tissue positioned between the anvil 201612 and the circular stapler 201614. In one aspect, tissue contact may be provided by a force sensor embedded in the compression element 201620. The force sensor is represented as the sensors 788 element of the surgical instrument 790 shown in FIG. 17. The force sensor 788 is employed to monitor 201756 the force-to-close (FTC) a clamp, which is the closing force of the anvil 201612 onto the tissue positioned between the anvil 201612 and the circular stapler 201614. The control circuit 760 compares 201758 the FTC to a predetermined threshold. When the FTC is below the predetermined threshold, the control circuit 760 sets the velocity of the motor 754 to advance 201760 the knife 201616 using a normal tissue toughness velocity profile 201638 as shown in FIG. 37. When the FTC is above the predetermined threshold, the control circuit 760 sets the velocity of the motor 754 to advance 201762 the knife 201616 using a heavy tissue toughness velocity profile 201636 with a velocity spike 201644 as shown in FIG. 37.

Figure 39:
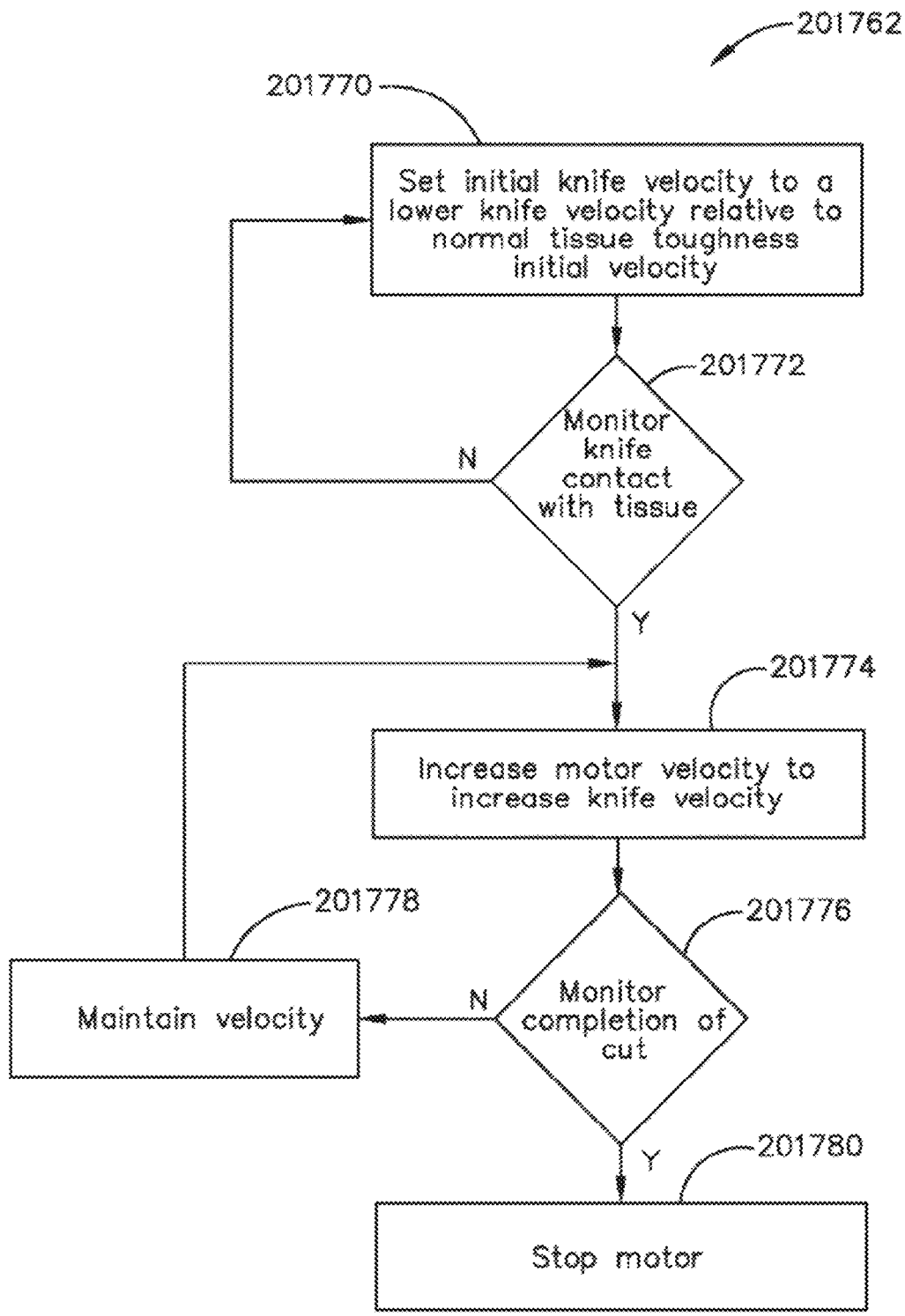
FIG. 39 is a logic flow diagram of a process depicting a control program or a logic configuration to advance the knife 201616 under a heavy tissue toughness velocity profile with a velocity spike as shown in FIG. 37, in accordance with at least one aspect of the present disclosure.

FIG. 39 is a logic flow diagram of a process 201762 depicting a control program or a logic configuration to advance 201762 the knife 201616 under a heavy tissue toughness velocity profile 201636 with a velocity spike

201644 as shown in FIG. 37, in accordance with at least one aspect of the present disclosure. This process 201762 may be implemented with any of the control circuits described with reference to FIGS. 7-8 and 16-17. This process 201750 may be implemented in a hub or cloud computing environment described with reference to FIGS. 1-6 and 9-13, for example.

In particular, the process 201762 depicted in FIG. 39 will now be described with reference to the control circuit 760 of FIG. 17 and the circular powered stapling device 201610 shown in FIGS. 35-37. When heavy tissue toughness is detected, the control circuit 760 sets 201770 the initial velocity of the knife 201616 a lower knife velocity relative to the knife velocity used for cutting normal tissue toughness. In one aspect, a slower knife velocity in heavy tissue toughness conditions promotes a better cut. The control circuit 760 monitors 201772 when the knife 201616 contacts the tissue. As previously discussed, tissue contact may be detected by a force sensor embedded in the compression element 201620. As shown in FIG. 37, when the knife 201616 contacts tissue the knife 201616 naturally slows down. Accordingly, once the control circuit 760 detects that the knife 201616 has contacted tissue, the tissue contact is detected, the control circuit 760 increases 201774 the velocity of the motor 754 to increase the velocity of the knife 201616 cutting through the tissue. The control circuit 760 monitors 201776 the completion of the cut and maintains 201778 the velocity of the motor 740 until completion of the cut is detected and then stops 201780 the motor 740.

Referring now to FIGS. 40-44, not only the amount and location of the tissue can affect the stapling outcome but also the nature, type, or state of the tissue. For example, irregular tissue distribution also manifests in situations that involve stapling previously stapled tissue such as, for example, in End-To End anastomosis procedures. Poor positioning and distribution of the previously stapled tissue within the end effector of a staple cartridge may cause the previously fired staple lines to be concentrated in one zone over another within the end effector, which negatively affects the outcome of such procedures.

Aspects of the present disclosure present a surgical stapling instrument that includes an end effector configured to staple tissue clamped between a first jaw and a second jaw of the end effector. In one aspect, positioning and orientation of previously stapled tissue within the end effector is determined by measuring and comparing tissue impedance at a number of predetermined zones within the end effector. In various aspects, tissue impedance measurements can also be utilized to identify overlapped layers of tissue and their position within an end effector.

Figure 40:
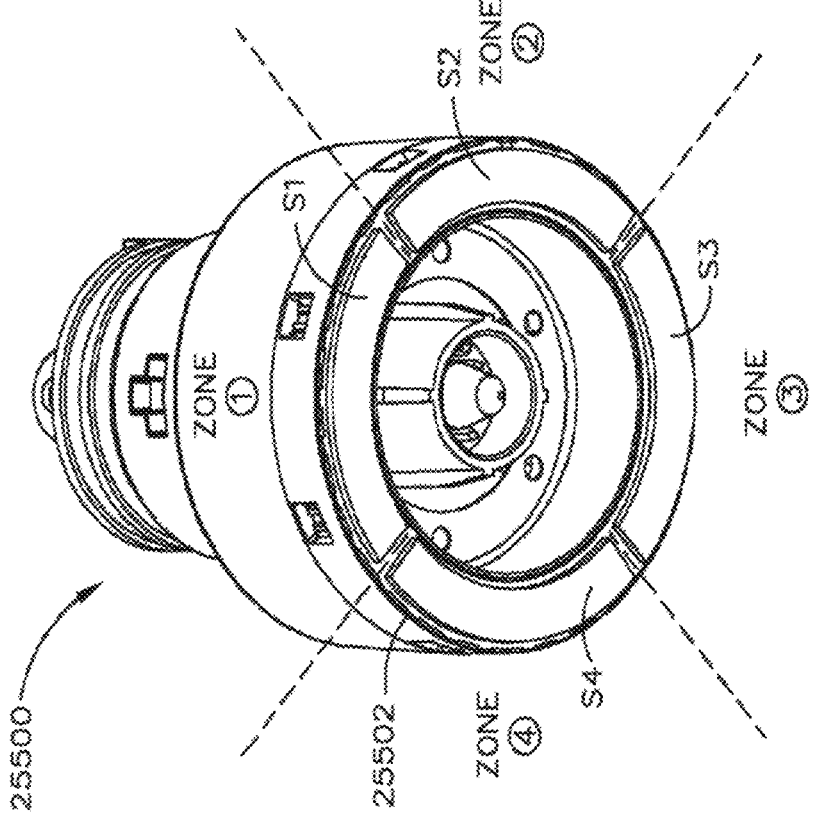
FIG. 40 illustrates a partial perspective view of a circular stapler showing a circular stapler trocar including a staple cartridge, which has four predetermined zones, in accordance with at least one aspect of the present disclosure.
Figure 42:
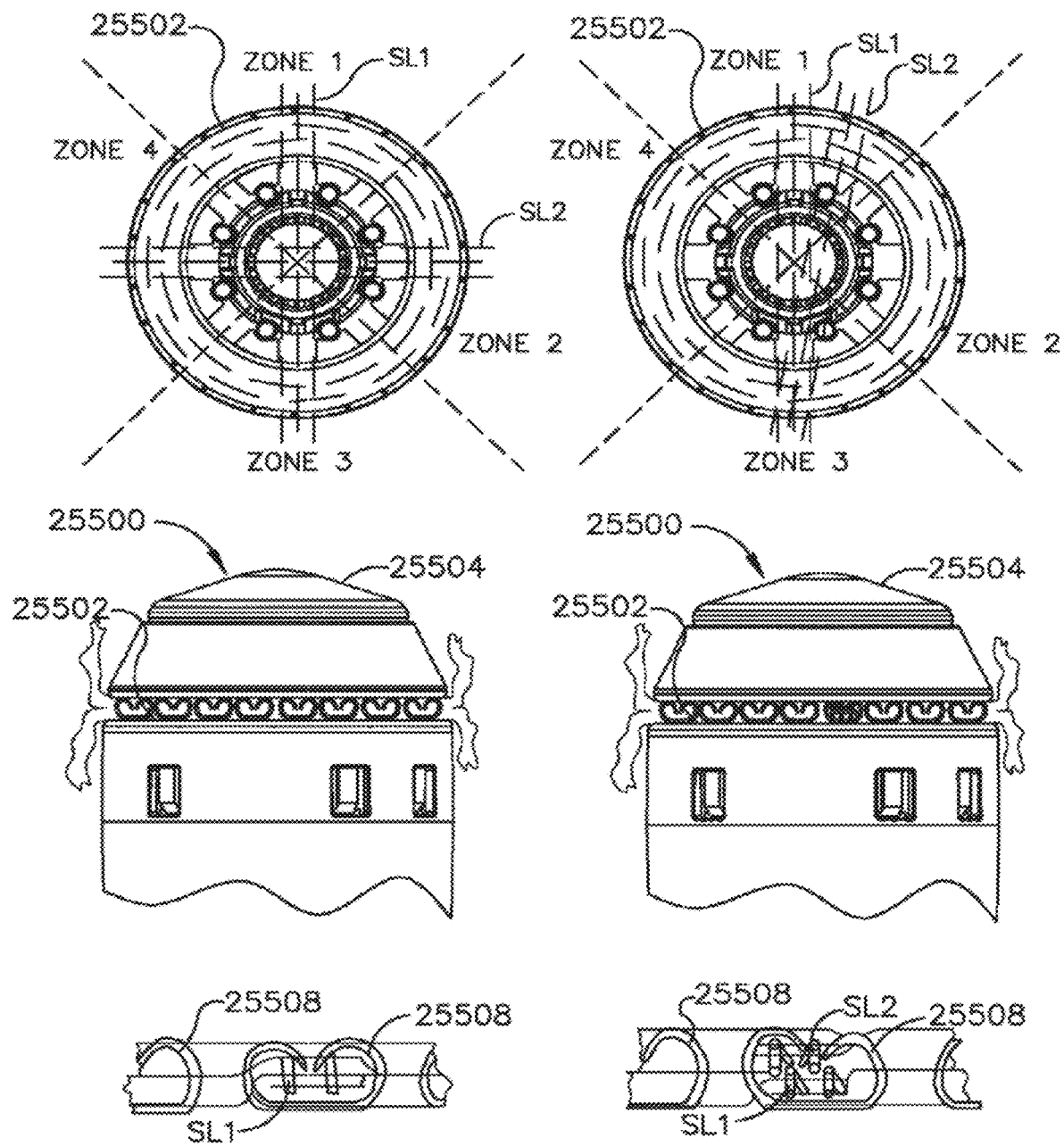
FIG. 42 illustrates, on the left, two tissues including previously deployed staples properly disposed onto the staple cartridge of FIG. 40, and on the right, two tissues including previously deployed staples properly disposed onto the staple cartridge of FIG. 40, in accordance with at least one aspect of the present disclosure.

FIGS. 40, 42 illustrate an end effector 25500 of a circular stapler that includes a staple cartridge 25502 and an anvil 25504 configured to grasp tissue therebetween. The anvil 25504 and staple cavities 25505 of the staple cartridge 25502 are removed from FIG. 40 to highlight other features of the end effector 25500. The staple cartridge 25502 includes four predetermined zones (Zone 1, Zone 2, Zone 3, Zone4) defined by sensing circuits (S1, S2, S3, S4), in accordance with the present disclosure.

Figure 41:
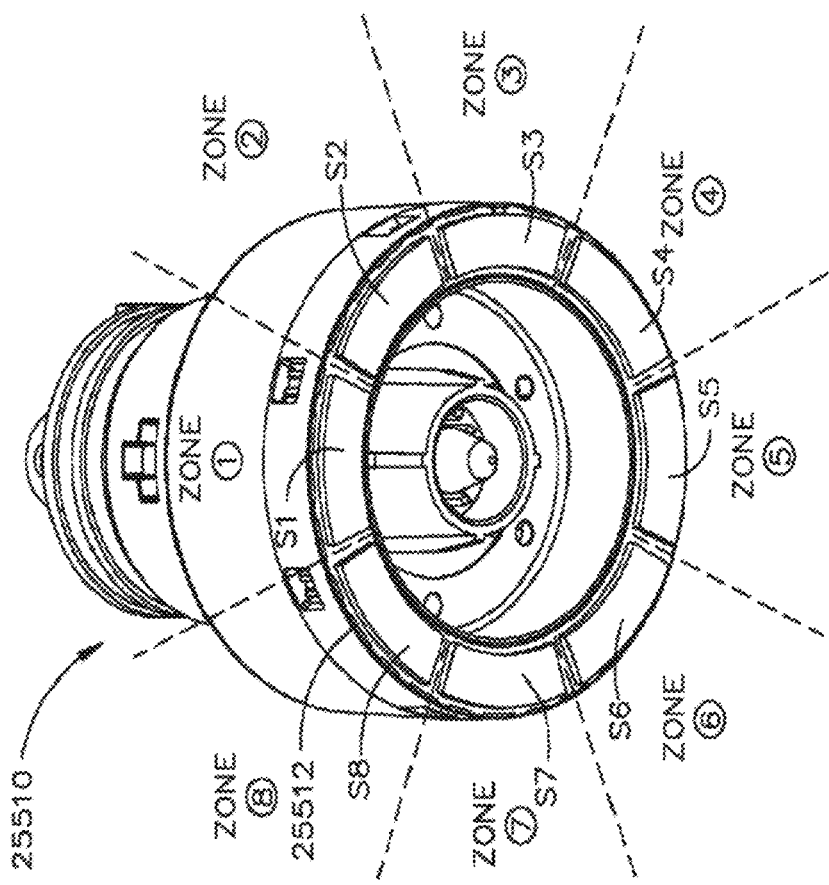
FIG. 41 illustrates a partial perspective view of a circular stapler showing a circular stapler trocar including a staple cartridge, which has eight predetermined zones, in accordance with at least one aspect of the present disclosure.

FIG. 41 illustrates another end effector 25510 of a circular stapler that includes staple cartridge 25512 and an anvil configured to grasp tissue therebetween. The anvil and staple cavities of the staple cartridge 25512 are removed to highlight other features of the end effector 25510. The staple cartridge 25512 includes eight predetermined zones (Zone 1-Zone 8) defined by sensing circuits (S1-S8), in accordance with the present disclosure. The zones defined in each of the circular staplers of FIGS. 40 and 41 are equal, or at least substantially equal, in size, and are arranged circumferentially around a longitudinal axis extending longitudinally through shafts of the circular staplers.

As described above, a previously stapled tissue is a tissue that includes staples that were previously deployed into the tissue. Circular staplers are often utilized in stapling previously stapled tissue to other previously stapled tissue (e.g. End-To-End Anastomosis procedures), as illustrated in FIG. 42.

The presence of the staples in tissue affects the tissue impedance as the staples usually have different conductivity than tissue. The present disclosure presents various tools and techniques for monitoring and comparing tissue impedances at the predetermined zones of an end effector (e.g. end effectors 25500, 25510) of a circular stapler to determine an optimal positioning and orientation of a previously-stapled tissue with respect to the end effector.

The examples on the left sides of FIG. 42 demonstrate properly positioned and oriented previously-stapled tissue with respect to predetermined zones of a circular stapler. The previously-stapled tissue properly extends through the center of the staple cartridge 25502, and only once intersects a predetermined zone. The bottom left side of FIG. 42 demonstrate staples 25508 of the staple cartridge 25502 deployed into properly positioned and oriented previously-stapled tissue.

The examples on the right sides of FIG. 42 demonstrate poorly positioned and oriented previously-stapled tissue. The previously-stapled tissue is off center or overlaps at one or more predetermined zones. The bottom right side of FIG. 42 demonstrate staples 25508 of the staple cartridge 25502 deployed into poorly positioned and oriented previously-stapled tissue.

As used in connection with FIGS. 40-44 a staple line may include multiple rows of staggered staples and typically includes two or three rows of staggered staples, without limitation. In the examples of FIG. 42, a circular stapler of FIG. 40 is utilized to staple two tissues that include previously deployed staple lines SL1, SL2. In the example to the left of FIG. 42, which represents properly positioned and orientated staple lines SL1, SL2, each of Zone 1 through Zone 4 receives a discrete portion of one of the staple lines SL1, SL2. The first staple line SL1 extends across Zone 2 and Zone 4, while the second staple line SL2, which intersects the first staple line SL1 at a central point, extends across Zone 1 and Zone 3. Accordingly, the measured impedances in the four zones will be equal, or at least substantially equal, to one another, and will be less than the impedance of an unstapled tissue.

On the contrary, in the example to the right of FIG. 42, which represents improperly positioned and orientated staple lines SL1, SL2, the staple lines SL1, SL2 overlap, or extend substantially on top of one another, across Zone 1 and Zone 3 yielding lower impedance measurements in zone 1 and Zone 3 as compared to Zone 2 and Zone 4.

Figure 43:
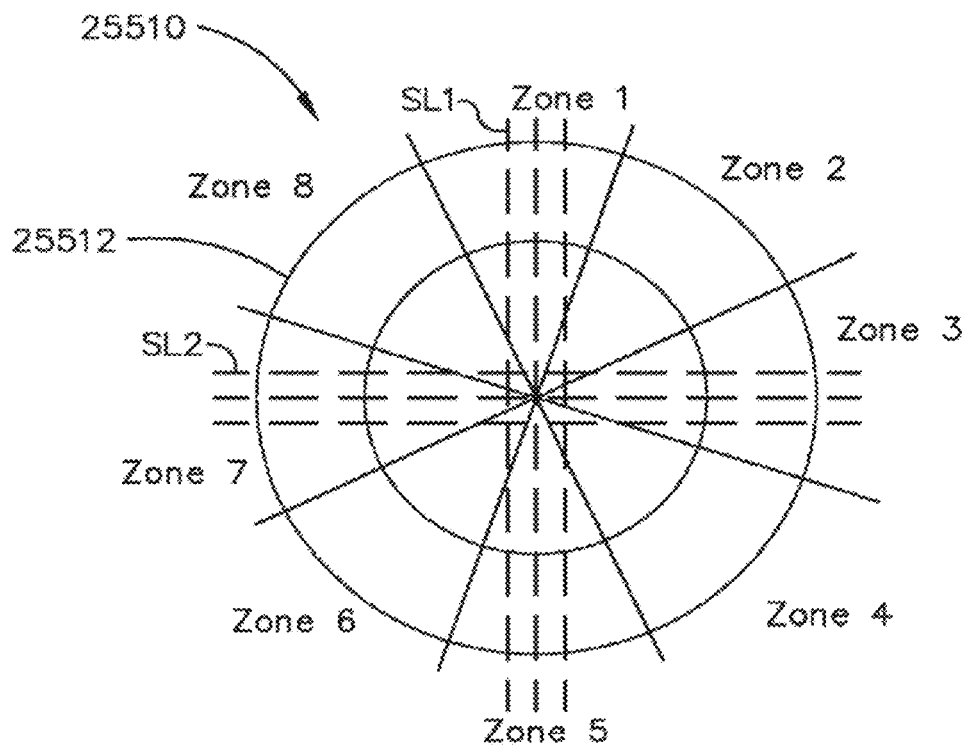
FIG. 43 illustrates two tissues including previously deployed staples properly disposed onto the staple cartridge of FIG. 41, in accordance with at least one aspect of the present disclosure.
Figure 44:
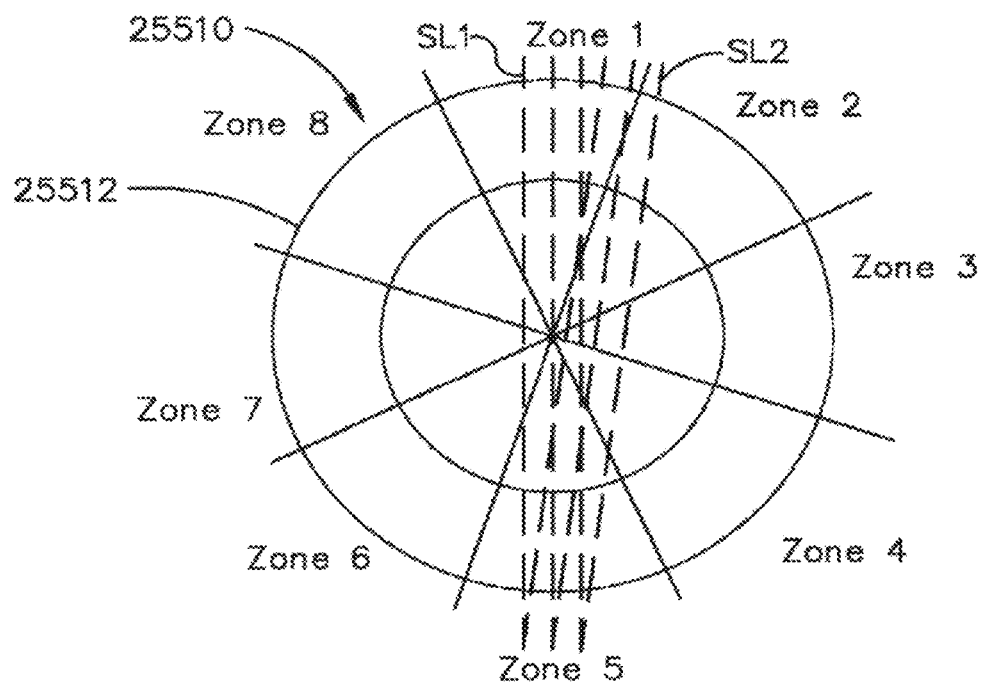
FIG. 44 illustrates two tissues including previously deployed staples improperly disposed onto the staple cartridge of FIG. 41, in accordance with at least one aspect of the present disclosure.

FIGS. 43 and 44 illustrate staple lines SL1, SL2 in an End-To-End anastomosis procedure performed by an end effector 25510 of a circular stapler that includes eight predetermined zones (zone 1: Zone 8) defined by eight sensing circuits S1-S8, as described above. The anvil of the end effector 25510 and staple cavities of the staple cartridge 25512 are removed from FIGS. 43 and 44 to highlight other features of the end effector 25510.

Figure 46:
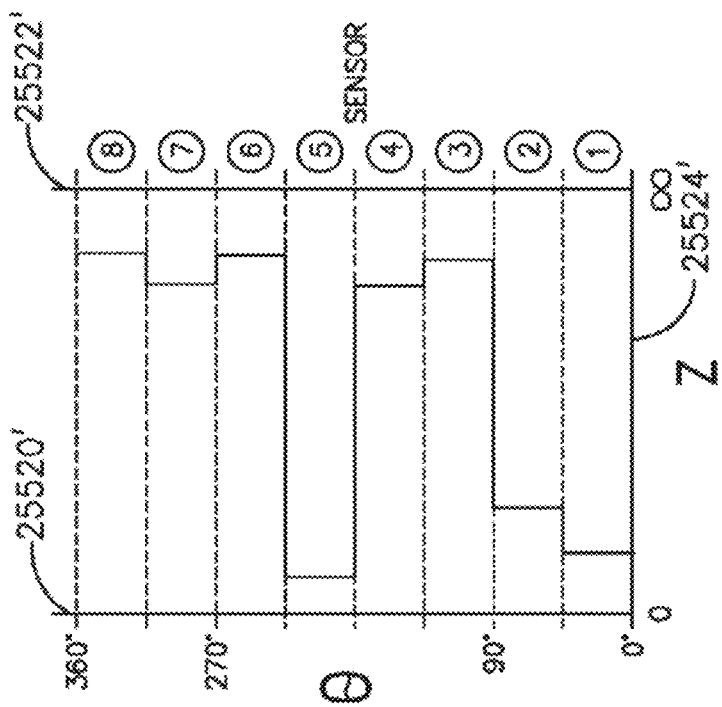
FIG. 46 is a graph depicting a tissue impedance signature of the improperly disposed tissues of FIG. 44, in accordance with at least one aspect of the present disclosure.
Figure 45:
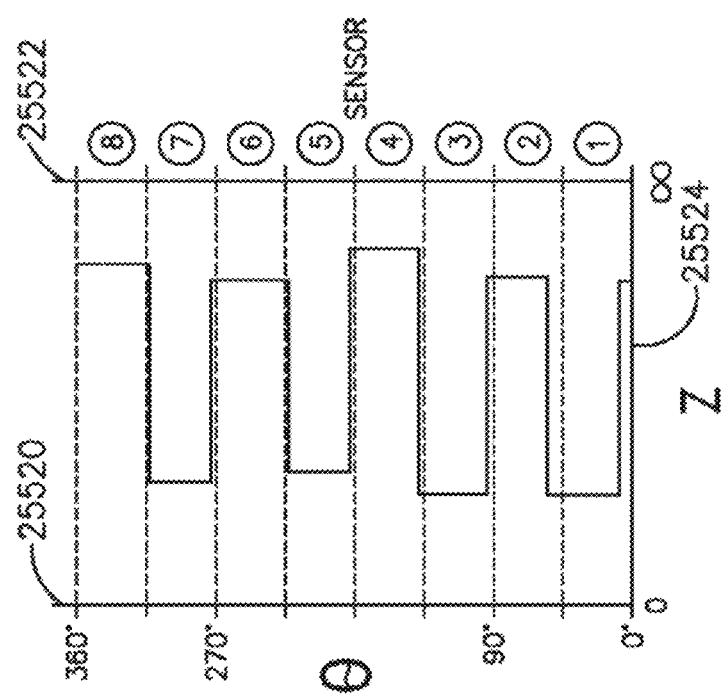
FIG. 45 is a graph depicting a tissue impedance signature of the properly disposed tissues of FIG. 43, in accordance with at least one aspect of the present disclosure.

FIGS. 45 and 46 illustrate measured tissue impedances based on sensor signals from the sensing circuits S1-S8. The individual measurements define tissue impedance signatures. Vertical axes 25520, 25520' represent an angle of orientation (θ), while vertical axes 25522, 25522' list corresponding predetermined zones (Zone 1: Zone 8). Tissue impedance (Z) is depicted on horizontal axes 25524, 25524'.

In the example of FIGS. 43 and 45, the impedance measurements represent properly positioned and orientated staple lines SL1, SL2. As illustrated in FIG. 43, the staple lines SL1, SL2 extend through Zone 1, Zone 3, Zone 5, and Zone 7, and only overlap at a central point of the staple cartridge 25512. Since the previously-stapled tissue is evenly distributed among Zone 1, Zone 3, Zone 5, and Zone 7, tissue impedance measurements at such zones are the same, or at least substantially the same, in magnitude, and are significantly less than tissue impedance measurements at Zone 2, Zone 4, Zone 6, and Zone 8, which did not receive previously-stapled tissue.

Conversely, in the example of FIGS. 44, 46, the impedance measurements represent improperly positioned and orientated staple lines SL1, SL2. The staple lines SL1, SL2 overlap on top of one another extending only through Zone 1 and Zone 5. Accordingly, tissue impedance measurements at Zone 1 and Zone 5 are significantly lower in magnitude than the remaining zones, which did not receive previously-stapled tissue.

Figure 47:
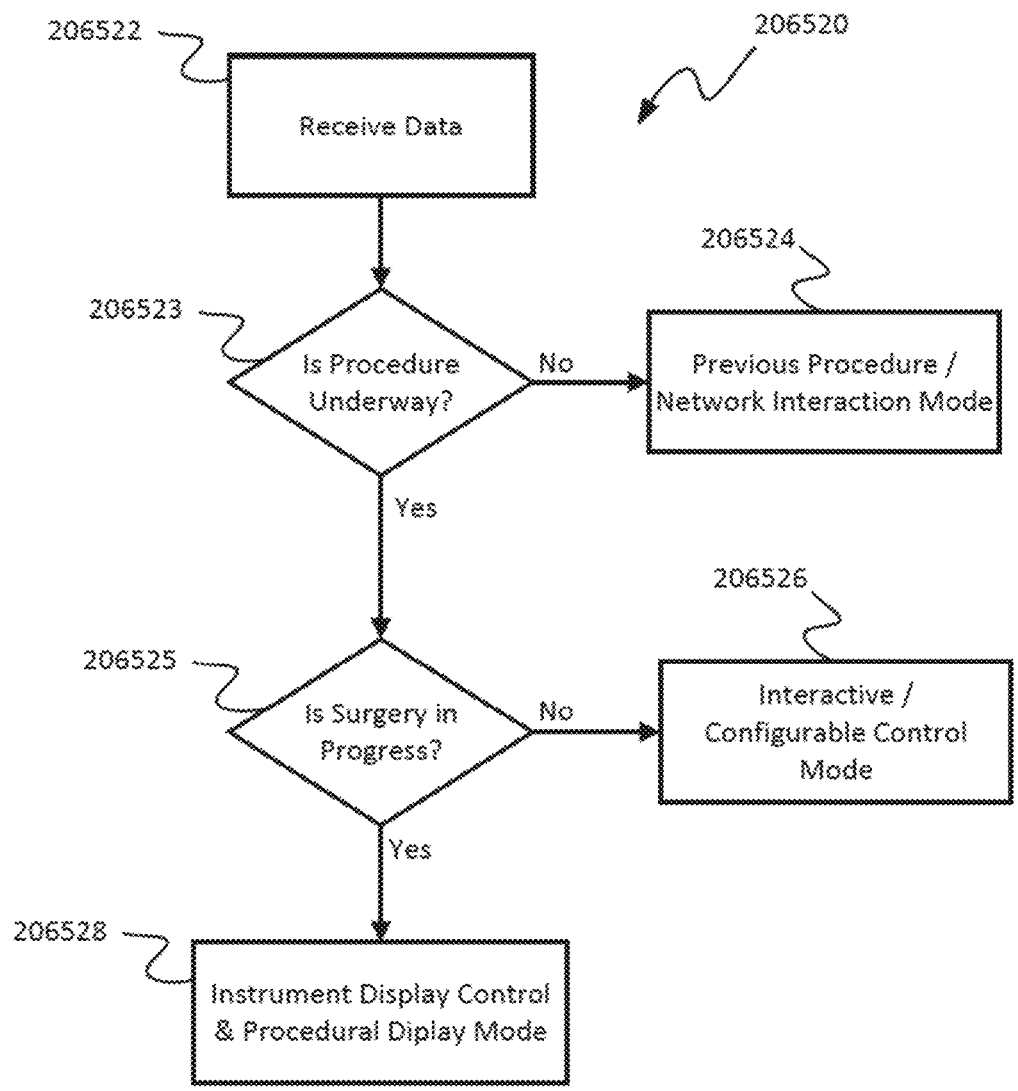
FIG. 47 is a logic flow diagram of a process depicting a control program or a logic configuration for selecting operational modes of a surgical hub, in accordance with at least one aspect of the present disclosure.

FIG. 47 illustrates is a logic flow diagram of a process 206520 depicting a control program or a logic configuration for selecting operational modes of a surgical hub 5104, in a surgical procedure, depending on a determined progress status of the surgical procedure. The process 2065520 can be performed by any suitable control circuit such as, for example, a control circuit of a surgical hub 5104. Data can be received 206522 from at least one data source, and may include patient data 206532 from a patient monitoring device, surgical staff data 206534 from a surgical staff detection device, modular device data 206536 from one or more modular devices and/or hospital data 206538 from a hospital database. The received 206522 data is processed by the surgical hub 5104 to determine a progress status of the surgical procedure. Additional details regarding determine whether surgery is process are disclosed in U.S. patent application Ser. No. 16/209,465, tided Method for adaptive control schemes for surgical network control and interaction, filed Dec. 4, 2018, which is herein incorporated by reference in its entirety.

As illustrated in FIG. 47, the received 206522 data can be utilized by the surgical hub 5104 to determine 206523 whether the surgical procedure is underway. If not, the surgical hub 5104 activates or selects a previous procedure/network interaction mode 206524. If, however, the surgical hub 5104 determines 206523 that the surgical procedure is underway, it further determines 206525 whether surgery is in progress. If not, the surgical hub 5104 activates or selects an interactive/configurable control mode 206526. If, however, the surgical hub 5104 determines 206525 that the surgery is in progress, the surgical hub 5104 activates or selects an instrument display control & procedural display mode 206528

The mode 206524 is more restrictive than the mode 206526, and the mode 206526 is more restrictive than the mode 206528. This arrangement is designed to take into consideration a user error in the form of inadvertent commands, for example. Before the surgical procedure starts, the mode 206524 only permits access to previous procedure data, and a limited interaction with a cloud-based system 104, 204, for example. During the preoperative steps, but before surgery is begun, the mode 206526 provides a less restrictive interface that permits a user to access and/or configure various parameters and/or controls without being able to use or activate such controls. In the least restrictive mode 206528, which is only available during surgery, the user is allowed to use or activate controls of certain modular devices depending on the surgical step being performed.

Figure 48:
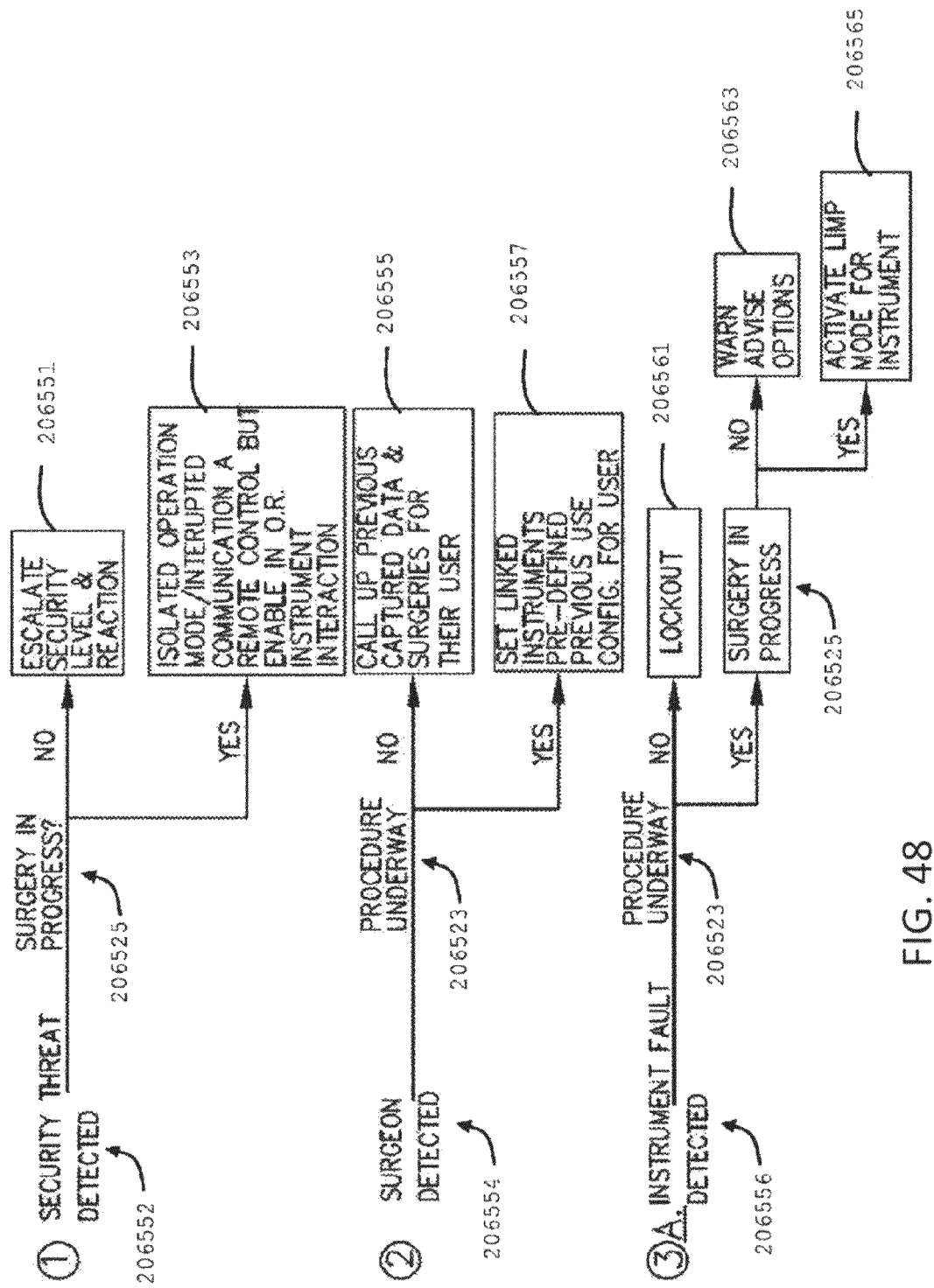
FIG. 48 is a logic flow diagram of a process depicting a control program or a logic configuration for responding to sensed parameters, in accordance with at least one aspect of the present disclosure.

Surgical hubs may receive data determinative of a situational parameter of surgical procedure and in response adjust response to sensed parameter based on determined situational parameter. In at least one example, as illustrated in FIG. 48, the sensed parameter can be detecting 206552 a security threat. In other examples, the sensed parameter can be detecting 206554 a surgeon. In other examples, the sensed parameter can be detecting 20559 an instrument fault such as, for example, a modular device.

Further to the above, responding to a detected 206552 security threat depends on whether surgery is progress, which can be determined 206525, as described above in connection with FIG. 47. If it is determined 206525 that surgery is in progress, an isolated operation mode 206553 can be activated. If surgery is not in progress, the current security level can escalated 206551 to a higher security level, and an appropriate reaction or response can be taken to address the detected 206552 security threat. Additional details regarding determine whether surgery is process are disclosed in U.S. patent application Ser. No. 16/209,465, tided Method for adaptive control schemes for surgical network control and interaction, filed Dec. 4, 2018.

In various examples, the isolated operation mode 206553 comprises interrupting communications with external systems such as, for example, the cloud-based system 104, 204. In certain examples, the communications interruption excludes local communications within an operating room such as, for example, instrument-to-instrument communications, instrument-to-surgical hub 106, 206 communications, and/or remote controller-to-instrument communications.

Referring still to FIG. 48, responding to a detected 206554 surgeon depends on whether the surgical procedure is underway, which can be determined 206523, as described above in connection with FIG. 47. If it is determined 206523 that a surgical procedure is underway, linked instruments can be set 206557 to pre-defined parameters based on previous use configurations for the detected 206554 surgeon, for example. If, however, a surgical procedure is not underway, previous captured data and/or previous surgeries data can be called up 206555, for example. Additional details regarding determine whether surgical procedure is underway is process are disclosed in U.S. patent application Ser. No. 16/209,465, tided Method for adaptive control schemes for surgical network control and interaction, filed Dec. 4, 2018, which is herein incorporated by reference in its entirety Referring still to FIG. 48, responding to a detected 206556 instrument fault depends on whether the surgical procedure is underway, and further depends on whether surgery is in progress which can be determined 206523, 206525, as described above in connection with FIG. 47. An instrument can be, for example, a modular device. If it is determined 206523 that a surgical procedure is underway, and it is further determined 206525 that surgery is in progress, a limp mode can be activated 206565 for the instrument. If, however, a surgical procedure is not underway, a lockout of the surgical instrument can be engaged 206561 to prevent the surgical instrument from being used. Furthermore, if it is determined 206523 that a surgical procedure is underway, but surgery is not in progress, an alert or warning can be issued 206563 by the surgical hub 5104 to the surgical staff, for example, advising options.

Figure 49:
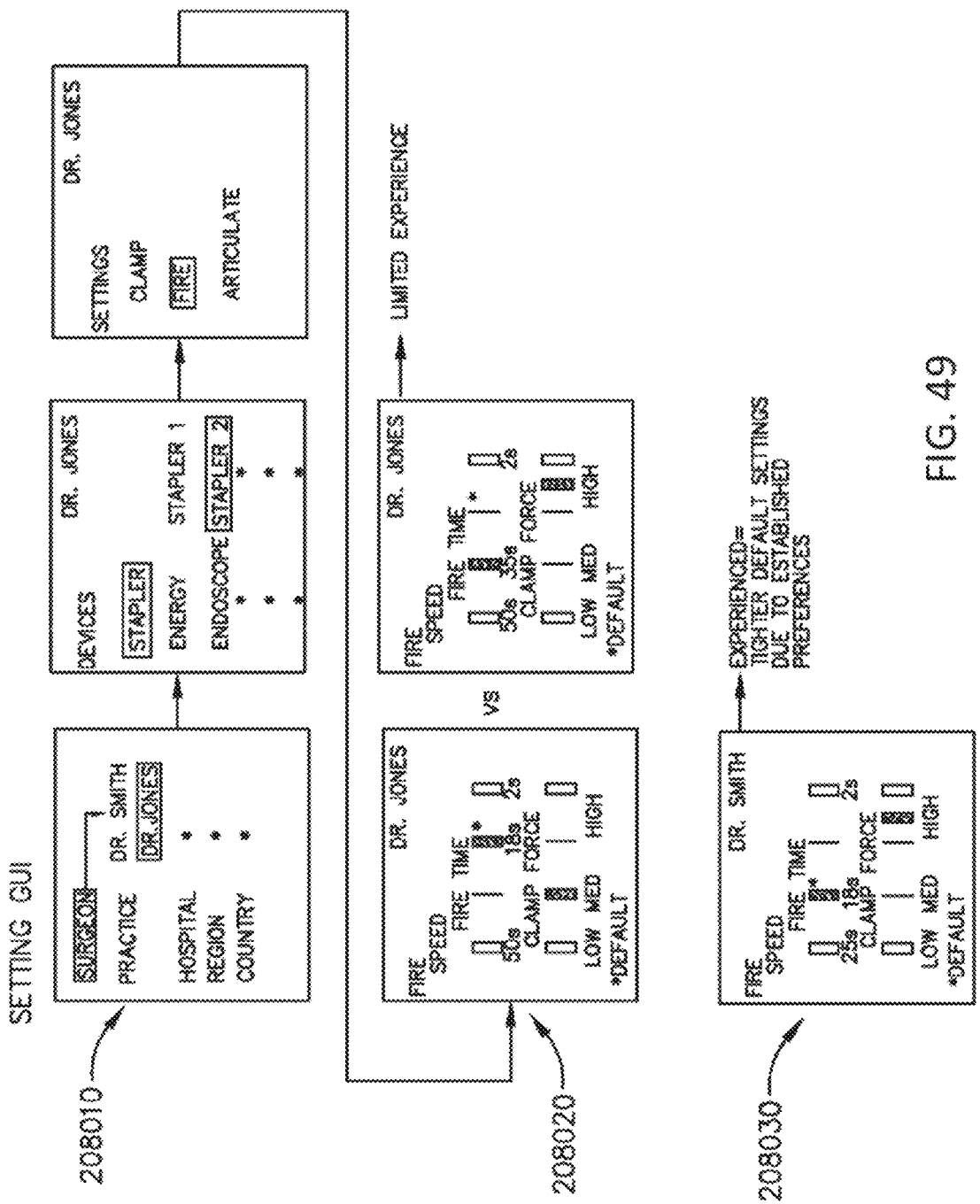
FIG. 49 is a diagram of a graphical user interface (GUI) for controlling various device parameters in accordance with at least one aspect of the present disclosure.

FIG. 49 depicts a GUI displaying a series of menus comprising selectable options to aid a clinician in operating a particular surgical instrument, such as the instrument 208100 (shown in FIG. 50), for example. In the illustrated example, a first series of displays 208010 depict multiple selectable menu options where, in this instance, a specific surgeon is selected, a specific instrument is selected, and a specific function is selected. In such an instance, a specific surgeon can be selected so that a control circuit, such as the control circuit 208103, for example, may load particular settings, such as learned adaptive limits, for example, for that particular surgeon. A specific instrument, such as the instrument 208100, for example, can be selected so as to allow the control circuit to load a specific control program to operate that instrument. This may include a specific adaptive-limiting program corresponding to a specific instrument and a specific surgeon. All of the selected options can be taken into account by the control circuit so as to load the correct control program(s) and/or settings for operating the desired device. In the illustrated example, the firing function of STAPLER 2 for Dr. Jones has been selected. These options may be automatically sensed by the control circuit and, in at least one instance, are not selected. For example, the information may already be delivered to the control circuit in a package corresponding to the particular procedure by a surgical hub (e.g. 102, 202), for example. In another instance, a surgeon may wear an identifier chip that a component of the control circuit can sense, a surgical robot, such as the surgical robot 110, for example, to which the instrument is attached may be able to automatically identify what instrument is attached to the operating arm of the robot 110, and/or the firing setting of the particular instrument may be identified by the robot based on an indirect input from the surgeon on a surgical robot control interface, for example.

Still referring to FIG. 49, two displays 208020 are depicted showing selectable, in at least one instance, options for Dr. Jones for the firing function of STAPLER 2. As can be seen in these displays 208020, firing time and clamp force are displayed and can be related to the overall firing speed of the instrument, such as the instrument 208100, for example. In this instance, Dr. Jones may have limited experience. Such experience can be known by the control circuit, such as the control circuit 208103, for example, based on information stored about Dr. Jones. In such an instance, the range of permitted values for the firing speed, whether they be selectable learned limits and/or selectable direct function parameters, may be larger than a range of permitted values allowed for an experienced surgeon. For example, a display 208030 is illustrated where Dr. Smith, a more experienced surgeon than Dr. Smith, is provided tighter default settings. This may occur due to the amount of repetitions a surgeon has with a particular instrument, such as the instrument 208100, for example. In at least one instance, a permitted value range indicating safer operation of a particular instrument may be provided to a surgeon with less experience where more a permitted value range indicating riskier operation of a particular instrument may be provided to a surgeon with more experience.

Figure 50:
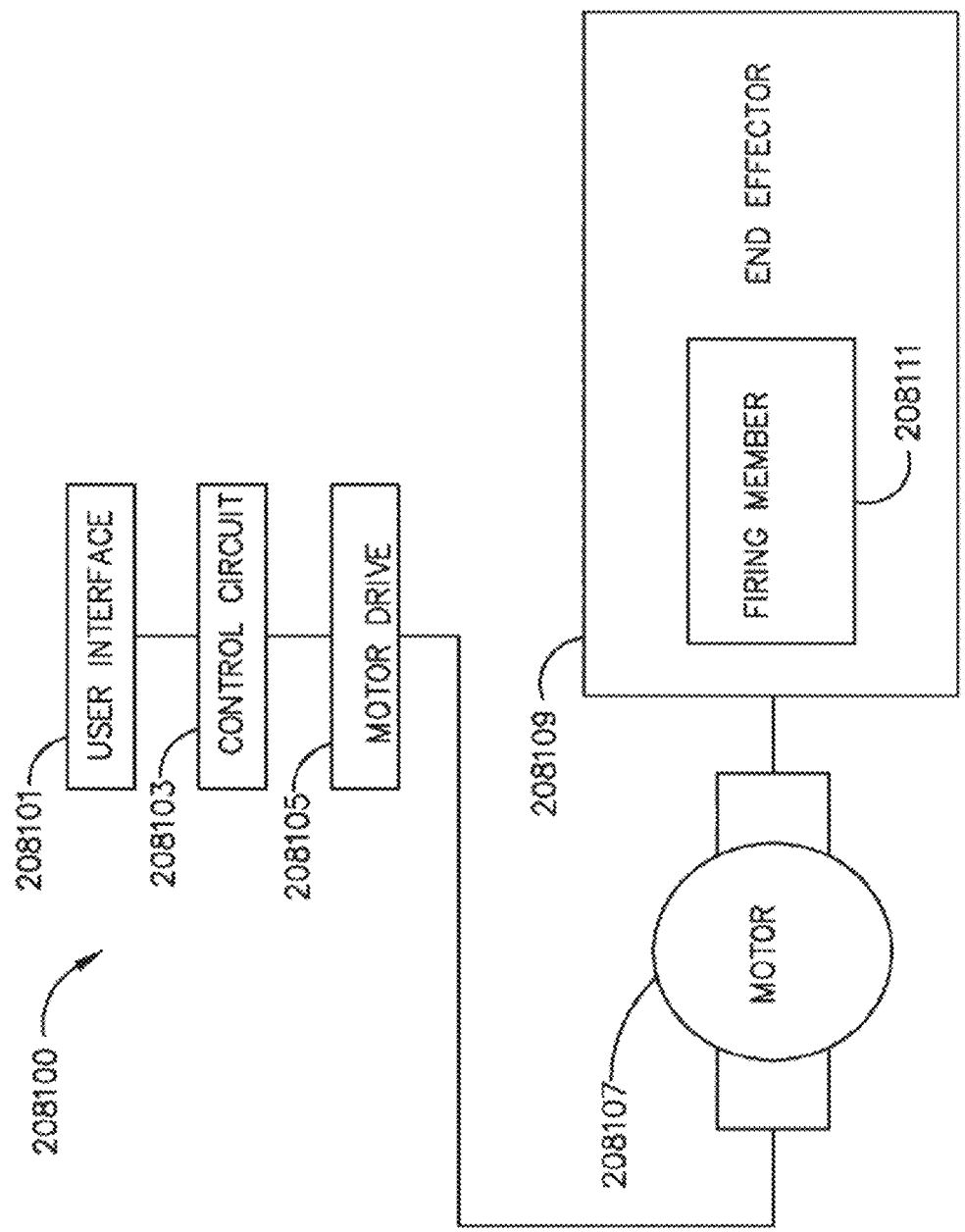
FIG. 50 is a block diagram depicting a surgical system in accordance with at least one aspect of the present disclosure.

FIG. 50 depicts a surgical instrument 208100 comprising a user interface 208101 and a control circuit 208103 configured to receive inputs from at the user interface 208101. The surgical instrument 208100 further comprises a motor driver 208105, a motor 208107 configured to be driven by the motor driver 208105 and controlled by the control circuit 208103, and an end effector 208109 comprising a firing member 208111 configured to be driven by the motor 208107. In at least one instance, various components of the surgical instrument 208100 may be substituted for an energy-based surgical instrument such as, for example, an ultrasonic surgical instrument. The control circuits described herein, such as the control circuit 208103, are configured to control any suitable end effector function, or parameter, powered by any suitable device. In at least one instance, the user interface 208101 comprises computer-based inputs rather than human-based inputs. For example, such computer-based inputs may originate from a surgical hub (e.g. 102, 202), for example. The surgical instrument 208100 can be employed with any of the systems, devices, and/or control circuits described herein. Various systems, devices, and/or control circuits described herein can be used for treating surgical patients. In the illustrated example, a surgical stapler can utilize a firing member, such as the firing member 208111, to cut the tissue of a patient and/or drive staples through tissue to fasten tissue during a surgical procedure. In such an instance, it can be advantageous to provide a control circuit capable of providing improved operation of the firing member. Any of the control circuits herein may provide such an advantage. In at least one instance, the firing member 208111 includes a firing assembly extending between the motor 208107 and the staples, for example, configured to be ejected by a sled. In at least one instance, the firing member 208111 includes one or more components of a firing assembly extending between the motor 208107 and the staples, for example, configured to be ejected by a sled.

Figure 51:
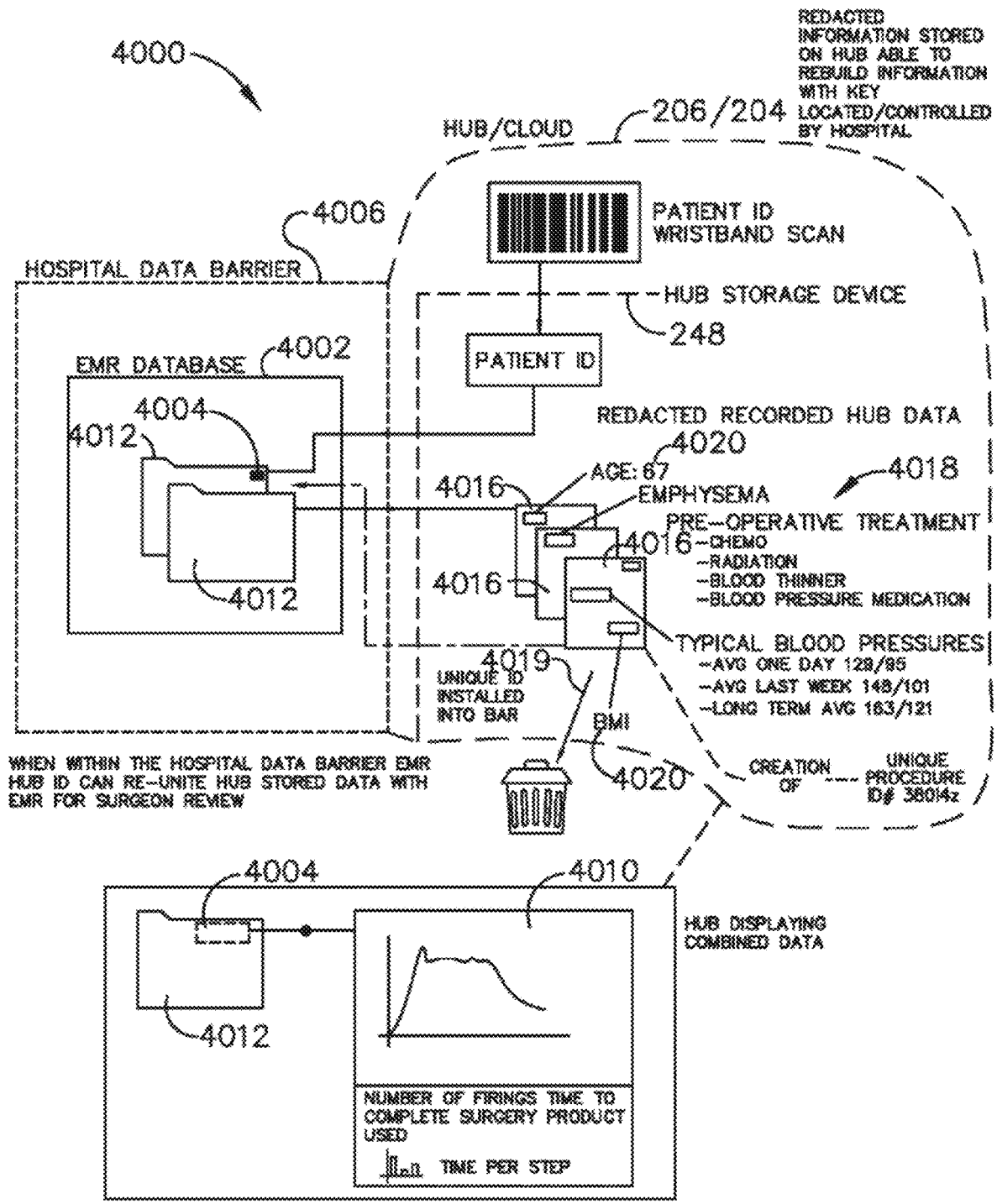
FIG. 51 is a diagram illustrating a technique for interacting with a patient Electronic Medical Record (EMR) database, in accordance with at least one aspect of the present disclosure.

FIG. 51 is a diagram 4000 illustrating a technique for interacting with a patient Electronic Medical Record (EMR) database 4002, according to one aspect of the present disclosure. In one aspect, the present disclosure provides a method of embedding a key 4004 within the EMR database 4002 located within the hospital or medical facility. A data barrier 4006 is provided to preserve patient data privacy and allows the reintegration of stripped and isolated data pairs, as described hereinbelow, from the surgical hub 106, 206 or the cloud 104, 204, to be reassembled. A schematic diagram of the surgical hub 206 is described generally in FIGS. 1-6 and 9-13. Therefore, in the description of FIG. 51, the reader is guided to FIGS. 1-6 and 9-13 for any implementation details of the surgical hub 206 that may be omitted here for conciseness and clarity of disclosure. Returning to FIG. 51, the method allows the users full access to all the data collected during a surgical procedure and patient information stored in the form of electronic medical records 4012. The reassembled data can be displayed on a monitor 4010 coupled to the surgical hub 206 or secondary monitors but is not permanently stored on any surgical hub storage device 248. The reassembled data is temporarily stored in a storage device 248 located either in the surgical hub 206 or the cloud 204 and is deleted at the end of its use and overwritten to insure it cannot be recovered. The key 4004 in the EMR database 4002 is used to reintegrate anonymized hub data back into full integrated patient electronic medical records 4012 data.

As shown in FIG. 51, the EMR database 4002 is located within the hospital data barrier 4006. The EMR database 4002 may be configured for storing, retrieving, and managing associative arrays, or other data structures known today as a dictionary or hash. Dictionaries contain a collection of objects, or records, which in turn have many different fields within them, each containing data. The patient electronic medical records 4012 may be stored and retrieved using a key 4004 that uniquely identifies the patient electronic medical record 4012, and is used to quickly find the data within the EMR database 4002. The key-value EMR database 4002 system treats the data as a single opaque collection which may have different fields for every record.

Information from the EMR database 4002 may be transmitted to the surgical hub 206 and the patient electronic medical records 4012 data is redacted and stripped before it is sent to an analytics system based either on the hub 206 or the cloud 204. An anonymous data file 4016 is created by redacting personal patient data and stripping relevant patient data 4018 from the patient electronic medical record 4012. As used herein, the redaction process includes deleting or removing personal patient information from the patient electronic medical record 4012 to create a redacted record that includes only anonymous patient data. A redacted record is a record from which sensitive patient information has been expunged. Un-redacted data may be deleted 4019. The relevant patient data 4018 may be referred to herein as stripped/extracted data 4018. The relevant patient data 4018 is used by the surgical hub 206 or cloud 204 processing engines for analytic purposes and may be stored on the storage device 248 of the surgical hub 206 or may be stored on the cloud 204 based analytics system storage device 205. The surgical hub anonymous data file 4016 can be rebuilt using a key 4004 stored in the EMR database 4002 to reintegrate the surgical hub anonymous data file 4016 back into a fully integrated patient electronic medical record 4012. The relevant patient data 4018 that is used in analytic processes may include information such as the patient's diagnoses of emphysema, pre-operative treatment (e.g., chemotherapy, radiation, blood thinner, blood pressure medication, etc.), typical blood pressures, or any data that alone cannot be used to ascertain the identity of the patient. Data 4020 to be redacted includes personal information removed from the patient electronic medical record 4012, may include age, employer, body mass index (BMI), or any data that can be used to ascertain the identity of the patient. The surgical hub 206 creates a unique anonymous procedure ID number (e.g., 380i4z), for example. Within the EMR database 4002 located in the hospital data barrier 4006, the surgical hub 206 can reunite the data in the anonymous data file 4016 stored on the surgical hub 206 storage device 248 with the data in the patient electronic medical record 4012 stored on the EMR database 4002 for surgeon review. The surgical hub 206 displays the combined patient electronic medical record 4012 on a display or monitor 4010 coupled to the surgical hub 206. Ultimately, un-redacted data is deleted 4019 from the surgical hub 206 storage 248.

Creation of a Hospital Data Barrier, Inside Which the Data from Hubs Can Be Compared Using Non-Anonymized Data and Outside of Which the Data Has to Be Stripped In one aspect, the present disclosure provides a surgical hub 206 as described in FIGS. 5 and 6, for example, where the surgical hub 206 comprises a processor 244; and a memory 249 coupled to the processor 244. The memory 249 stores instructions executable by the processor 244 to interrogate a surgical instrument 235, retrieve a first data set from the surgical instrument 235, interrogate a medical imaging device 238, retrieve a second data set from the medical imaging device 238, associate the first and second data sets by a key, and transmit the associated first and second data sets to a remote network, e.g., the cloud 204, outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

In another aspect, the first and second data sets define first and second data payloads in respective first and second data packets.

In various aspects, the present disclosure provides a control circuit to associate the first and second data sets by a key as described above. In various aspects, the present disclosure provides a non-transitory computer readable medium storing computer readable instructions which, when executed, causes a machine to associate the first and second data sets by a key as described above.

During a surgical procedure it would be desirable to monitor data associated with the surgical procedure to enable configuration and operation of instruments used during the procedure to improve surgical outcomes. The technical challenge is to retrieve the data in a manner that maintains the anonymity of the patient to maintain privacy of the data associated with the patient. The data may be used for conglomeration with other data without individualizing the data.

One solution provides a surgical hub 206 to interrogate an electronic medical records database 4002 for patient electronic medical records 4012 data, strip out desirable or relevant patient data 4018 from the patient electronic medical record 4012, and redact any personal information that could be used to identify the patient. The redaction technique removes any information that could be used to correlate the stripped relevant patient data 4018 to a specific patient, surgery, or time. The surgical hub 206 and the instruments 235 coupled to the surgical hub 206 can then be configured and operated based on the stripped relevant patient data 4018.

As disclosed in connection with FIG. 51, extracting (or stripping) relevant patient data 4018 from a patient electronic medical record 4012 while redacting any information that can be used to correlate the patient with the surgery or a scheduled time of the surgery enables the relevant patient data 4018 to be anonymized. The anonymous data file 4016 can then be sent to the cloud 204 for aggregation, processing, and manipulation. The anonymous data file 4016 can be used to configure the surgical instrument 235, or any of the modules shown in FIGS. 5 and 6 or the surgical hub 206 during the surgery based on the extracted anonymous data file 4016.

In one aspect, a hospital data barrier 4006 is created such that inside the data barrier 4006 data from various surgical hubs 206 can be compared using non-anonymized un-redacted data and outside the data barrier 4006 data from various surgical hubs 206 are stripped to maintain anonymity and protect the privacy of the patient and the surgeon. Additional details regarding this aspect are disclosed in U.S. patent application Ser. No. 16/209,385, tiled Method of hub communication, processing, storage and display, filed Dec. 4, 2018, which is herein incorporated by reference in its entirety.

In one aspect, the data from a surgical hub 206 can be exchanged between surgical hubs 206 (e.g., hub-to-hub, switch-to-switch, or router-to-router) to provide in-hospital analysis and display of the data. FIG. 1 shows an example of multiple hubs 106 in communication which each other and with the cloud 104. Additional details regarding this aspect are disclosed in U.S. patent application Ser. No. 16/209,385, tided Method of hub communication, processing, storage and display, filed Dec. 4, 2018.

In another aspect, an artificial time measure is substituted for a real time clock for all information stored internally within an instrument 235, a robot located in a robot hub 222, a surgical hub 206, and/or hospital computer equipment. The anonymized data, which may include anonymized patient and surgeon data, is transmitted to the server 213 in the cloud 204 and it is stored in the cloud storage device 205 coupled to the server 213. The substitution of an artificial real time clock enables anonymizing the patient data and surgeon data while maintaining data continuity. In one aspect, the instrument 235, robot hub 222, surgical hub 206, and/or the cloud 204 are configured to obscure patient identification (ID) while maintaining data Within the surgical hub 206, a local decipher key 4004 allows information retrieved from the surgical hub 206 itself to reinstate the real-time information from the anonymized data set located in the anonymous data file 4016. The data stored on the hub 206 or the cloud 204, however, cannot be reinstated to real-time information from the anonymized data set in the anonymous data file 4016. The key 4004 is held locally in the surgical hub 206 computer/storage device 248 in an encrypted format. The surgical hub 206 network processor ID is part of the decryption mechanism such that if the key 4004 and data is removed, the anonymized data set in the anonymous data file 4016 cannot be restored without being on the original surgical hub 206 computer/storage device 248.

Figure 52:
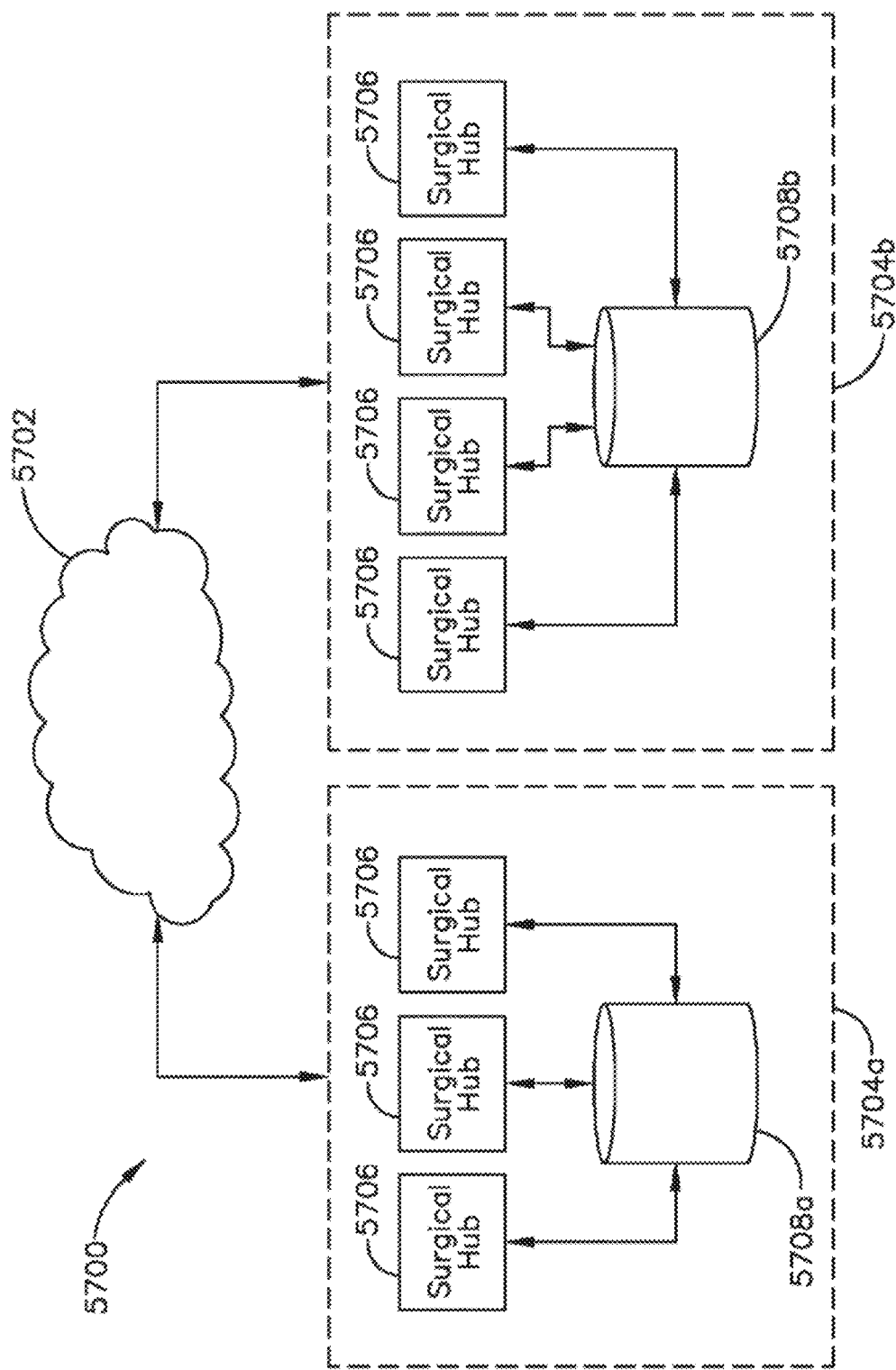
FIG. 52 illustrates a block diagram of a computer-implemented interactive surgical system, in accordance with at least one aspect of the present disclosure.

FIG. 52 illustrates a block diagram of a computer-implemented interactive surgical system 5700, in accordance with at least one aspect of the present disclosure. The system 5700 includes a number of surgical hubs 5706 that, as described above, are able to detect and track data related to surgical procedures that the surgical hubs 5706 (and the modular devices paired to the surgical hubs 5706) are utilized in connection with. In one exemplification, the surgical hubs 5706 are connected to form local networks such that the data being tracked by the surgical hubs 5706 is aggregated together across the network. The networks of surgical hubs 5706 can be associated with a medical facility, for example. The data aggregated from the network of surgical hubs 5706 can be analyzed to provide reports on data trends or recommendations. For example, the surgical hubs 5706 of a first medical facility 5704 *a* are communicably connected to a first local database 5708 *a* and the surgical hubs 5706 of a second medical facility 5704 *b* are communicably connected to a second local database 5708 *b*. The network of surgical hubs 5706 associated with the first medical facility 5704 *a* can be distinct from the network of surgical hubs 5706 associated with the second medical facility 5704 *b*, such that the aggregated data from each network of surgical hubs 5706 corresponds to each medical facility 5704 *a*, 5704 *b* individually. A surgical hub 5706 or another computer terminal communicably connected to the database 5708 *a*, 5708 *b* can be configured to provide reports or recommendations based on the aggregated data associated with the respective medical facility 5704 *a*, 5704 *b*. In this exemplification, the data tracked by the surgical hubs 5706 can be utilized to, for example, report whether a particular incidence of a surgical procedure deviated from the average in-network time to complete the particular procedure type.

In another exemplification, each surgical hub 5706 is configured to upload the tracked data to the cloud 5702, which then processes and aggregates the tracked data across multiple surgical hubs 5706, networks of surgical hubs 5706, and/or medical facilities 5704 *a*, 5704 *b* that are connected to the cloud 5702. Each surgical hub 5706 can then be utilized to provide reports or recommendations based on the aggregated data. In this exemplification, the data tracked by the surgical hubs 5706 can be utilized to, for example, report whether a particular incidence of a surgical procedure deviated from the average global time to complete the particular procedure type.

In another exemplification, each surgical hub 5706 can further be configured to access the cloud 5702 to compare locally tracked data to global data aggregated from all of the surgical hubs 5706 that are communicably connected to the cloud 5702. Each surgical hub 5706 can be configured to provide reports or recommendations based on the comparison between the tracked local data relative to local (i.e., in-network) or global norms. In this exemplification, the data tracked by the surgical hubs 5706 can be utilized to, for example, report whether a particular incidence of a surgical procedure deviated from either the average in-network time or the average global time to complete the particular procedure type.

In one exemplification, each surgical hub 5706 or another computer system local to the surgical hub 5706 is configured to locally aggregate the data tracked by the surgical hubs 5706, store the tracked data, and generate reports and/or recommendations according to the tracked data in response to queries. In cases where the surgical hub 5706 is connected to a medical facility network (which may include additional surgical hubs 5706), the surgical hub 5706 can be configured to compare the tracked data with the bulk medical facility data. The bulk medical facility data can include EMR data and aggregated data from the local network of surgical hubs 5706. In another exemplification, the cloud 5702 is configured to aggregate the data tracked by the surgical hubs 5706, store the tracked data, and generate reports and/or recommendations according to the tracked data in response to queries.

Each surgical hub 5706 can provide reports regarding trends in the data and/or provide recommendations on improving the efficiency or effectiveness of the surgical procedures being performed. In various exemplifications, the data trends and recommendations can be based on data tracked by the surgical hub 5706 itself, data tracked across a local medical facility network containing multiple surgical hubs 5706, or data tracked across a number of surgical hubs 5706 communicably connected to a cloud 5702. The recommendations provided by the surgical hub 5706 can describe, for example, particular surgical instruments or product mixes to utilize for particular surgical procedures based on correlations between the surgical instruments/product mixes and patient outcomes and procedural efficiency. The reports provided by the surgical hub 5706 can describe, for example, whether a particular surgical procedure was performed efficiently relative to local or global norms, whether a particular type of surgical procedure being performed at the medical facility is being performed efficiently relative to global norms, and the average time taken to complete a particular surgical procedure or step of a surgical procedure for a particular surgical team.

In one exemplification, each surgical hub 5706 is configured to determine when operating theater events occur (e.g., via a situational awareness system) and then track the length of time spent on each event. An operating theater event is an event that a surgical hub 5706 can detect or infer the occurrence of. An operating theater event can include, for example, a particular surgical procedure, a step or portion of a surgical procedure, or downtime between surgical procedures. The operating theater events can be categorized according to an event type, such as a type of surgical procedure being performed, so that the data from individual procedures can be aggregated together to form searchable data sets. In one exemplification, the surgical hub 5706 is configured to determine whether a surgical procedure is being performed and then track both the length of time spent between procedures (i.e., downtime) and the time spent on the procedures themselves. The surgical hub 5706 can further be configured to determine and track the time spent on each of the individual steps taken by the medical personnel (e.g., surgeons, nurses, orderlies) either between or during the surgical procedures. The surgical hub can determine when surgical procedures or different steps of surgical procedures are being performed via a situational awareness system, which is described in further detail above. Additional details regarding this aspect are disclosed in U.S. patent application Ser. No. 16/209,385, tided Method of hub communication, processing, storage and display, filed Dec. 4, 2018.

Figure 53:
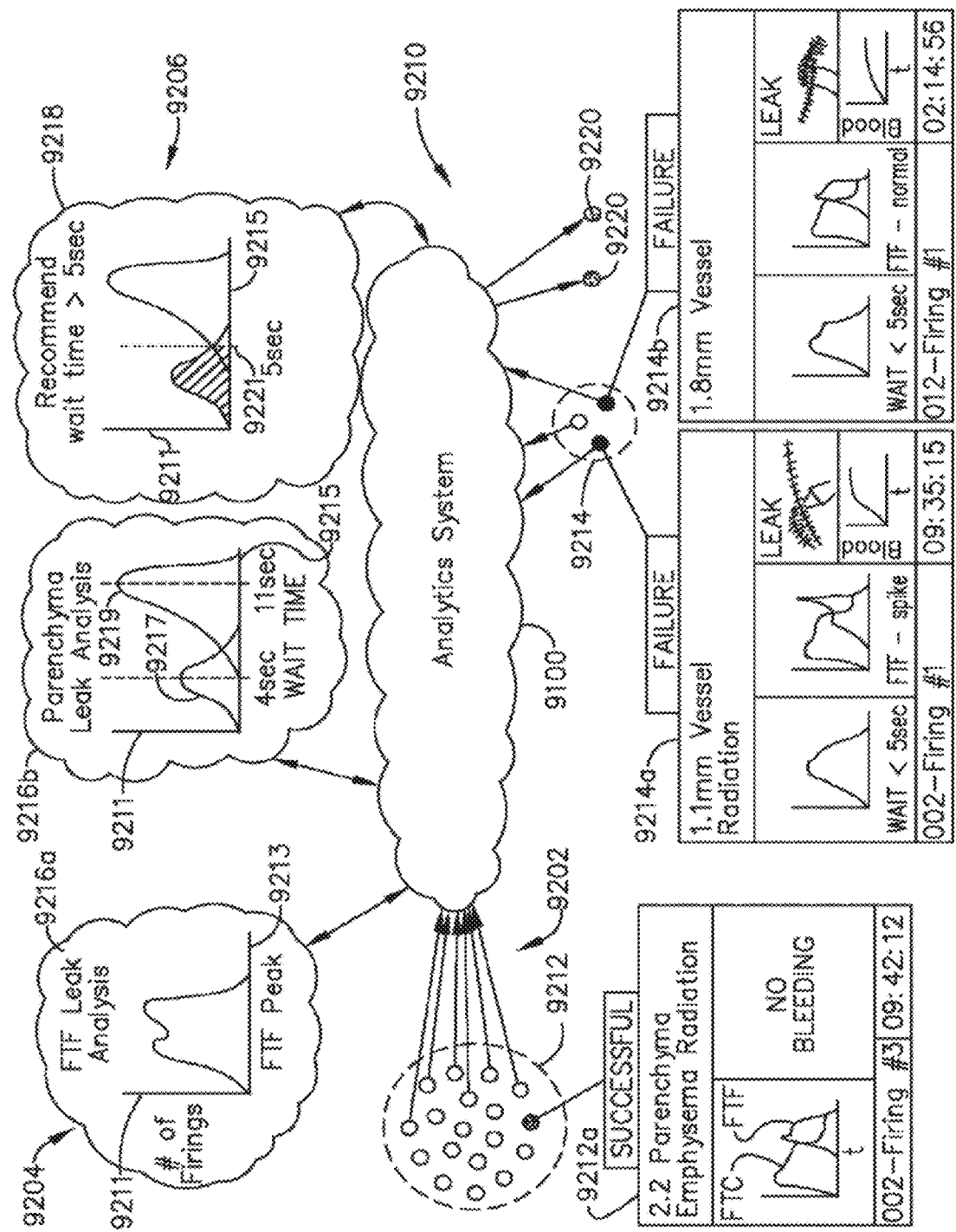
FIG. 53 illustrates a diagram of an illustrative analytics system updating a surgical instrument control program, in accordance with at least one aspect of the present disclosure

FIG. 53 illustrates a diagram of an illustrative analytics system 9100 updating a surgical instrument control program, in accordance with at least one aspect of the present disclosure. In one exemplification, a surgical hub 9000 or network of surgical hubs 9000 is communicably coupled to an analytics system 9100, as illustrated above in FIG. 13. The analytics system 9100 is configured to filter and analyze modular device 9050 data associated with surgical procedural outcome data to determine whether adjustments need to be made to the control programs of the modular devices 9050. The analytics system 9100 can then push updates to the modular devices 9050 through the surgical hubs 9000, as necessary. In the depicted exemplification, the analytics system 9100 comprises a cloud computing architecture. The modular device 9050 perioperative data received by the surgical 9000 hubs from their paired modular devices 9050 can include, for example, force to fire (i.e., the force required to advance a cutting member of a surgical stapling instrument through a tissue), force to close (i.e., the force required to clamp the jaws of a surgical stapling instrument on a tissue), the power algorithm (i.e., change in power over time of electrosurgical or ultrasonic instruments in response to the internal states of the instrument and/or tissue conditions), tissue properties (e.g., impedance, thickness, stiffness, etc.), tissue gap (i.e., the thickness of the tissue), and closure rate (i.e., the rate at which the jaws of the instrument clamped shut). It should be noted that the modular device 9050 data that is transmitted to the analytics system 9100 is not limited to a single type of data and can include multiple different data types paired with procedural outcome data. The procedural outcome data for a surgical procedure (or step thereof) can include, for example, whether there was bleeding at the surgical site, whether there was air or fluid leakage at the surgical site, and whether the staples of a particular staple line were formed properly. The procedural outcome data can further include or be associated with a positive or negative outcome, as determined by the surgical hub 9000 or the analytics system 9100, for example. The modular device 9050 data and the procedural outcome data corresponding to the modular device 9050 perioperative data can be paired together or otherwise associated with each other when they are uploaded to the analytics system 9100 so that the analytics system 9100 is able to recognize trends in procedural outcomes based on the underlying data of the modular devices 9050 that produced each particular outcome. In other words, the analytics system 9100 can aggregate the modular device 9050 data and the procedural outcome data to search for trends or patterns in the underlying device modular data 9050 that can indicate adjustments that can be made to the modular devices' 9050 control In the depicted exemplification, the analytics system 9100 executing the process 9200 described in connection with FIG. 13 is receiving 9202 modular device 9050 data and procedural outcome data. When transmitted to the analytics system 9100, the procedural outcome data can be associated or paired with the modular device 9050 data corresponding to the operation of the modular device 9050 that caused the particular procedural outcome. The modular device 9050 perioperative data and corresponding procedural outcome data can be referred to as a data pair. The data is depicted as including a first group 9212 of data associated with successful procedural outcomes and a second group 9214 of data associated with negative procedural outcomes. For this particular exemplification, a subset of the data 9212, 9214 received 9202 by the analytics system 9100 is highlighted to further elucidate the concepts discussed herein.

For a first data pair 9212 *a*, the modular device 9050 data includes the force to close (FTC) over time, the force to fire (FTF) over time, the tissue type (parenchyma), the tissue conditions (the tissue is from a patient suffering from emphysema and had been subject to radiation), what number firing this was for the instrument (third), an anonymized time stamp (to protect patient confidentiality while still allowing the analytics system to calculate elapsed time between firings and other such metrics), and an anonymized patient identifier (002). The procedural outcome data includes data indicating that there was no bleeding, which corresponds to a successful outcome (i.e., a successful firing of the surgical stapling instrument). For a second data pair 9212 *b*, the modular device 9050 data includes the wait time prior the instrument being fired (which corresponds to the first firing of the instrument), the FTC over time, the FTF over time (which indicates that there was a force spike near the end of the firing stroke), the tissue type (1.1 mm vessel), the tissue conditions (the tissue had been subject to radiation), what number firing this was for the instrument (first), an anonymized time stamp, and an anonymized patient identifier (002). The procedural outcome data includes data indicating that there was a leak, which corresponds to a negative outcome (i.e., a failed firing of the surgical stapling instrument). For a third data pair 9212 *c*, the modular device 9050 data includes the wait time prior the instrument being fired (which corresponds to the first firing of the instrument), the FTC over time, the FTF over time, the tissue type (1.8 mm vessel), the tissue conditions (no notable conditions), what number firing this was for the instrument (first), an anonymized time stamp, and an anonymized patient identifier (012). The procedural outcome data includes data indicating that there was a leak, which corresponds to a negative outcome (i.e., a failed firing of the surgical stapling instrument). It should be noted again that this data is intended solely for illustrative purposes to assist in the understanding of the concepts discussed herein and should not be interpreted to limit the data that is received and/or analyzed by the analytics system 9100 to generate control program updates.

When the analytics system 9100 receives 9202 perioperative data from the communicably connected surgical hubs 9000, the analytics system 9100 proceeds to aggregate and/or store the data according to the procedure type (or a step thereof) associated with the data, the type of the modular device 9050 that generated the data, and other such categories. By collating the data accordingly, the analytics system 9100 can analyze the data set to identify correlations between particular ways of controlling each particular type of modular device 9050 and positive or negative procedural outcomes. Based upon whether a particular manner of controlling a modular device 9050 correlates to positive or negative procedural outcomes, the analytics system 9100 can determine 9204 whether the control program for the type of modular device 9050 should be updated.

For this particular exemplification, the analytics system 9100 performs a first analysis 9216 of the data set by analyzing the peak FTF 9213 (i.e., the maximum FTF for each particular firing of a surgical stapling instrument) relative to the number of firings 9211 for each peak FTF value. In this exemplary case, the analytics system 9100 can determine that there is no particular correlation between the peak FTF 9213 and the occurrence of positive or negative outcomes for the particular data set. In other words, there are not distinct distributions for the peak FTF 9213 for positive and negative outcomes. As there is no particular correlation between peak FTF 9213 and positive or negative outcomes, the analytics system 9100 would thus determine that a control program update to address this variable is not necessary. Further, the analytics system 9100 performs a second analysis 9216 *b* of the data set by analyzing the wait time 9215 prior to the instrument being fired relative to the number of firings 9211. For this particular analysis 9216 *b*, the analytics system 9100 can determine that there is a distinct negative outcome distribution 9217 and a positive outcome distribution 9219. In this exemplary case, the negative outcome distribution 9217 has a mean of 4 seconds and the positive outcome distribution has a mean of 11 seconds. Thus, the analytics system 9100 can determine that there is a correlation between the wait time 9215 and the type of outcome for this surgical procedure step. Namely, the negative outcome distribution 9217 indicates that there is a relatively large rate of negative outcomes for wait times of 4 seconds or less. Based on this analysis 9216 *b* demonstrating that there is a large divergence between the negative outcome distribution 9217 and the positive outcome distribution 9219, the analytics system 9100 can then determine 9204 that a control program update should be generated 9208.

Once the analytics system 9100 analyzes the data set and determines 9204 that an adjustment to the control program of the particular module device 9050 that is the subject of the data set would improve the performance of the modular device 9050, the analytics system 9100 then generates 9208 a control program update accordingly. In this exemplary case, the analytics system 9100 can determine based on the analysis 9216 *b* of the data set that a control program update 9218 recommending a wait time of more than 5 seconds would prevent 90% of the distribution of the negative outcomes with a 95% confidence interval. Alternatively, the analytics system 9100 can determine based on the analysis 9216 *b* of the data set that a control program update 9218 recommending a wait time of more than 5 seconds would result in the rate of positive outcomes being greater than the rate of negative outcomes. The analytics system 9100 could thus determine that the particular type of surgical instrument should wait more than 5 seconds before being fired under the particular tissue conditions so that negative outcomes are less common than positive outcomes. Based on either or both of these constraints for generating 9208 *a* control program update that the analytics system 9100 determines are satisfied by the analysis 9216 *b*, the analytics system 9100 can generate 9208 a control program update 9218 for the surgical instrument that causes the surgical instrument, under the given circumstances, to either impose a 5 second or longer wait time before the particular surgical instrument can be fired or causes the surgical instrument to display a warning or recommendation to the user that indicates to the user that the user should wait at least 5 seconds before firing the instrument. Various other constraints can be utilized by the analytics system 9100 in determining whether to generate 9208 a control program update, such as whether a control program update would reduce the rate of negative outcomes by a certain percentage or whether a control program update maximizes the rate of positive outcomes.

After the control program update 9218 is generated 9208, the analytics system 9100 then transmits 9210 the control program update 9218 for the appropriate type of modular devices 9050 to the surgical hubs 9000. In one exemplification, when a modular device 9050 that corresponds to the control program update 9218 is next connected to a surgical hub 9000 that has downloaded the control program update 9218, the modular device 9050 then automatically downloads the update 9218. In another exemplification, the surgical hub 9000 controls the modular device 9050 according to the control program update 9218, rather than the control program update 9218 being transmitted directly to the modular device 9050 itself.

Figure 54:
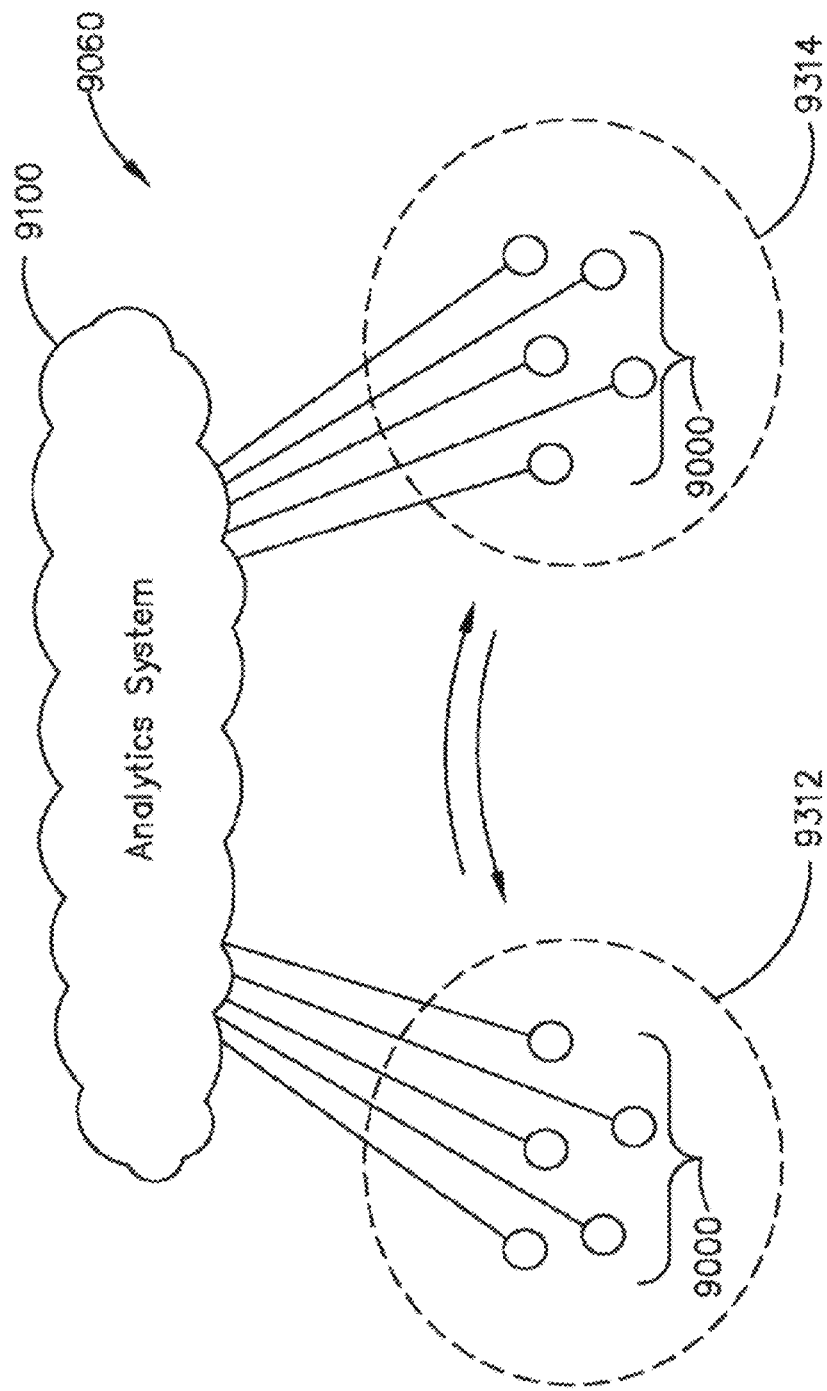
FIG. 54 illustrates a diagram of a computer-implemented interactive surgical system that is configured to adaptively generate control program updates for surgical hubs, in accordance with at least one aspect of the present disclosure

FIG. 54 illustrates a diagram of a computer-implemented adaptive surgical system 9060 that is configured to adaptively generate control program updates for surgical hubs 9000, in accordance with at least one aspect of the present disclosure. The surgical system 9060 includes several surgical hubs 9000 that are communicably coupled to the analytics system 9100. Subpopulations of surgical hubs 9000 (each of which can include individual surgical hubs 9000 or groups of surgical hubs 9000) within the overall population connected to the analytics system 9100 can exhibit different operational behaviors during the course of a surgical procedure. The differences in operational behavior between groups of surgical hubs 9000 within the population can result from the surgical hubs 9000 running different versions of their control program, by the surgical hubs' 9000 control programs being customized or programmed differently by local surgical staff, or by the local surgical staff manually controlling the surgical hubs 9000 differently. In the depicted example, the population of surgical hubs 9000 includes a first subpopulation 9312 that is exhibiting a first operational behavior and a second subpopulation 9314 that is exhibiting a second operational behavior for a particular task. Although the surgical hubs 9000 are divided into a pair of subpopulations 9312, 9314 in this particular example, there is no practical limit to the number of different behaviors exhibited within the population of surgical hubs 9000. The tasks that the surgical hubs 9000 can be executing include, for example, controlling a surgical instrument or analyzing a dataset in a particular manner.

The surgical hubs 9000 can be configured to transmit perioperative data pertaining to the operational behavior of the surgical hubs 9000 to the analytics system 9100. The perioperative data can include preoperative data, intraoperative data, and postoperative data. The preoperative data can include, for example, patient-specific information, such as demographics, health history, preexisting conditions, preoperative workup, medication history (i.e., medications currently and previously taken), genetic data (e.g., SNPs or gene expression data), EMR data, advanced imaging data (e.g., MRI, CT, or PET), metabolomics, and microbiome. Various additional types of patient-specific information that can be utilized by the analytics system 9100 are described by U.S. Pat. No. 9,250,172, U.S. patent application Ser. No. 13/631,095, U.S. patent application Ser. No. 13/828,809, and U.S. Pat. No. 8,476,227, each of which is incorporated by reference herein to the extent that they describe patient-specific information. The preoperative data can also include, for example, operating theater-specific information, such as geographic information, hospital location, operating theater location, operative staff performing the surgical procedure, the responsible surgeon, the number and type of modular devices 9050 and/or other surgical equipment that could potentially be used in the particular surgical procedure, the number and type of modular devices 9050 and/or other surgical equipment that are anticipated to be used in the particular surgical procedure, patient identification information, and the type of procedure being performed.

The intraoperative data can include, for example, modular device 9050 utilization (e.g., the number of firings by a surgical stapling instrument, the number of firings by an RF electrosurgical instrument or an ultrasonic instrument, or the number and types of stapler cartridges utilized), operating parameter data of the modular devices 9050 (e.g., the FTF curve for a surgical stapling instrument, a FTC curve for a surgical stapling instrument, the energy output of a generator, the internal pressure or pressure differential of a smoke evacuator), unexpected modular device 9050 utilization (i.e., the detection of the utilization of a modular device that is nonstandard for the procedure type), adjunctive therapies administered to the patient, and utilization of equipment other than the modular devices 9050 (e.g., sealants to address leaks). The intraoperative data can also include, for example, detectable misuse of a modular device 9050 and detectable off-label use of a modular device 9050.

The postoperative data can include, for example, a flag if the patient does not leave the operating theater and/or is sent for nonstandard postoperative care (e.g., a patient undergoing a routine bariatric procedure is sent to the ICU after the procedure), a postoperative patient evaluation relating to the surgical procedure (e.g., data relating to a spirometric performance after a thoracic surgery or data relating to a staple line leakage after bowel or bariatric procedures), data related to postoperative complications (e.g., transfusions or air leaks), or the patient's length of stay in the medical facility after the procedure. Because hospitals are increasingly being graded on readmission rates, complication rates, average length of stay, and other such surgical quality metrics, the postoperative data sources can be monitored by the analytics system 9100 either alone or in combination with surgical procedural outcome data (discussed below) to assess and institute updates to the controls programs of the surgical hubs 9000 and/or modular devices 9050.

In some exemplifications, the intraoperative and/or postoperative data can further include data pertaining to the outcome of each surgical procedure or a step of the surgical procedure. The surgical procedural outcome data can include whether a particular procedure or a particular step of a procedure had a positive or negative outcome. In some exemplifications, the surgical procedural outcome data can include procedure step and/or time stamped images of modular device 9050 performance, a flag indicating whether a modular device 9050 functioned properly, notes from the medical facility staff, or a flag for poor, suboptimal, or unacceptable modular device 9050 performance. The surgical procedural outcome data can, for example, be directly detected by the modular devices 9050 and/or surgical hub 9000 (e.g., a medical imaging device can visualize or detect bleeding), determined or inferred by a situational awareness system of the surgical hub 9000 as described in U.S. patent application Ser. No. 15/940,654, or retrieved from a database 9054 (e.g., an EMR database) by the surgical hub 9000 or the analytics system 9100. In some exemplifications, perioperative data including a flag indicating that a modular device 9050 failed or otherwise performed poorly during the course of a surgical procedure can be prioritized for communication to and/or analysis by the analytics system 9100.

In one exemplification, the perioperative data can be assembled on a procedure-by-procedure basis and uploaded by the surgical hubs 9000 to the analytics system 9100 for analysis thereby. The perioperative data indicates the manner in which the surgical hubs 9000 were programmed to operate or were manually controlled in association with a surgical procedure (i.e., the operational behavior of the surgical hubs 9000) because it indicates what actions the surgical hub 9000 took in response to various detected conditions, how the surgical hubs 9000 controlled the modular devices 9050, and what inferences the situationally aware surgical hubs 9000 derived from the received data. The analytics system 9100 can be configured to analyze the various types and combinations of preoperative, intraoperative, and post-operative data to determine whether a control program update should be generated and then push the update to the overall population or one or more subpopulations of surgical hubs 9000, as necessary.

Figure 55:
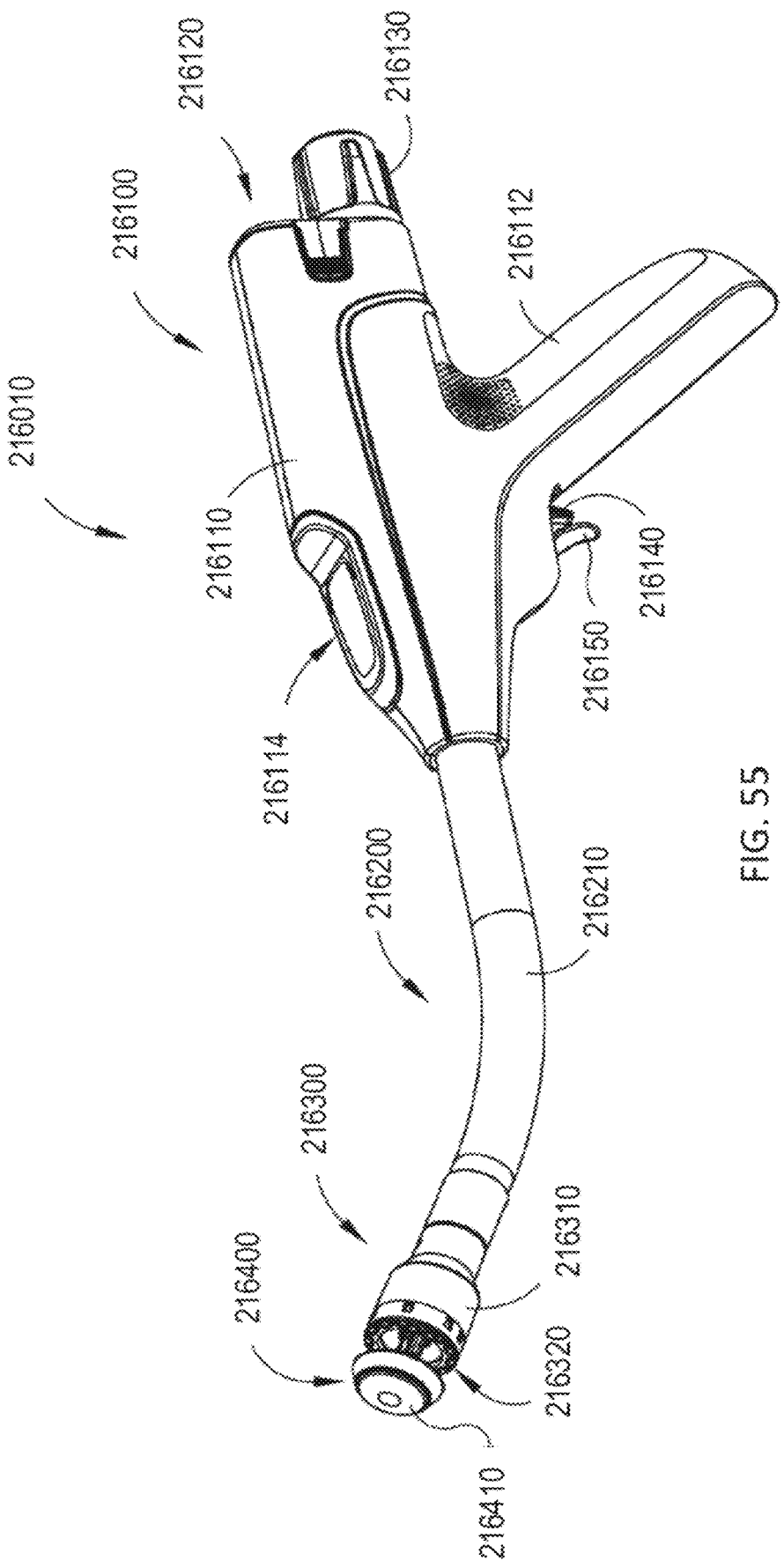
FIG. 55 depicts a perspective view of an exemplary circular stapler, in accordance with at least one aspect of the present disclosure
Figure 56:
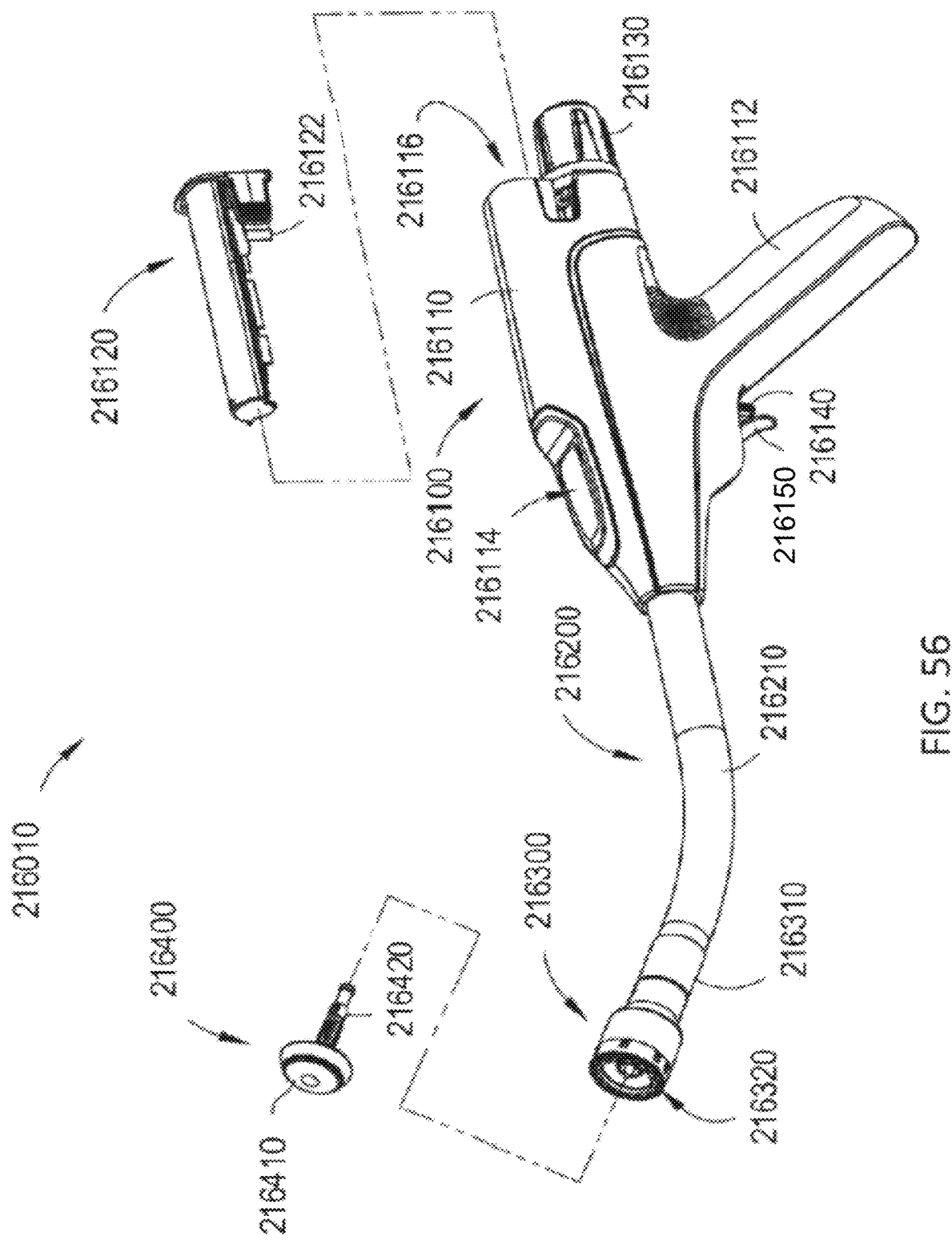
FIG. 56 depicts a perspective view of the circular stapler of FIG. 55, with a battery pack removed from a housing assembly and an anvil removed from a stapling head assembly, in accordance with at least one aspect of the present disclosure

FIGS. 55-56 depict an example surgical circular stapling instrument 216010 that can be adapted to include an RFID system and a control system thereof, in accordance with at least one aspect of the present disclosure. The stapling instrument 216010 may be used to provide an end-to-end anastomosis between two sections of an anatomical lumen such as a portion of a patient's digestive tract. Instrument 216010 of this example comprises a housing assembly 216100, a shaft assembly 216200, a stapling head assembly 216300, and an anvil 216400. Housing assembly 216100 comprises a casing 216110 defining an obliquely oriented pistol grip 216112. Although the housing assembly 216100 is depicted in the form of a handle, this is not limiting. In various instances, the housing assembly 216100 can be a component of a robotic system, for example.

Housing assembly 216100 further includes a window 216114 that permits viewing of a movable indicator needle. In some versions, a series of hash marks, colored regions, and/or other fixed indicators are positioned adjacent to window 216114 in order to provide a visual context for indicator needle, thereby facilitating operator evaluation of the position of needle within window 216114. The movement of the indicator needle corresponds to a closing motion of the anvil 216400 relative to the stapling head assembly 216300. The hash marks, colored regions, and/or other fixed indicators can define an optimal anvil closure zone for firing the instrument 216010. Accordingly, when the indicator needle is in the optimal anvil closure zone, the user may fire the instrument 216010. Various suitable alternative features and configurations for housing assembly 216100 will be apparent to those of ordinary skill in the art in view of the teachings herein.

Instrument 216010 of the present example further includes a power source which can be in the form of a battery pack 216120. Battery pack 216120 is operable to provide electrical power to a motor 216160 (shown in FIG. 57) in pistol grip 216112. In various aspects, battery pack 216120 is removable from housing assembly 216100. In particular, as shown in FIGS. 55-56, battery pack 216120 may be inserted into a socket 216116 defined by casing 216110. Once battery pack 216120 is fully inserted in socket 216116, latches 216122 of battery pack 216120 may resiliently engage interior features of casing 216110 to provide a snap fit. To remove battery pack 216120, the operator may press latches 216122 inwardly to disengage latches 216122 from the interior features of casing 216110 then pull battery pack 216120 proximally from socket 216116. It should be understood that battery pack 216120 and housing assembly 216100 may have complementary electrical contacts, pins and sockets, and/or other features that provide paths for electrical communication from battery pack 216120 to electrically powered components in housing assembly 216100 when battery pack 216120 is inserted in socket 216116. It should also be understood that, in some versions, battery pack 216120 is unitarily incorporated within housing assembly 216100 such that battery back 216120 cannot be removed from housing assembly 216100.

Shaft assembly 216200 extends distally from housing assembly 216100 and includes a preformed bend. In some versions, the preformed bend is configured to facilitate positioning of stapling head assembly 216300 within a patient's colon. Various suitable bend angles or radii that may be used will be apparent to those of ordinary skill in the art in view of the teachings herein. In some other versions, shaft assembly 216200 is straight, such that shaft assembly 216200 lacks a preformed bend. Various exemplary components that may be incorporated into shaft assembly 216200 will be described in greater detail below.

Stapling head assembly 216300 is located at the distal end of shaft assembly 216200. As shown in FIGS. 55-56, anvil 216400 is configured to removably couple with shaft assembly 216200, adjacent to stapling head assembly 216300. Anvil 216400 and stapling head assembly 216300 are configured to cooperate to manipulate tissue in three ways, including clamping the tissue, cutting the tissue, and stapling the tissue. A knob 216130 at the proximal end of housing assembly 216100 is rotatable relative to casing 216110 to provide precise clamping of the tissue between anvil 216400 and stapling head assembly 216300. When a safety trigger 216140 of housing assembly 216100 is pivoted away from a firing trigger 216150 of housing assembly 216100, firing trigger 216150 may be actuated to thereby provide cutting and stapling of the tissue.

In the following discussion of anvil 216400, the terms "distal" and "proximal" and variations thereof will be used with reference to the orientation of anvil 216400 when anvil 216400 is coupled with shaft assembly 216200 of instrument 216010. Thus, proximal features of anvil 216400 will be closer to the operator of instrument 216010; while distal features of anvil 216400 will be further from the operator of instrument 216010.

Figure 57:
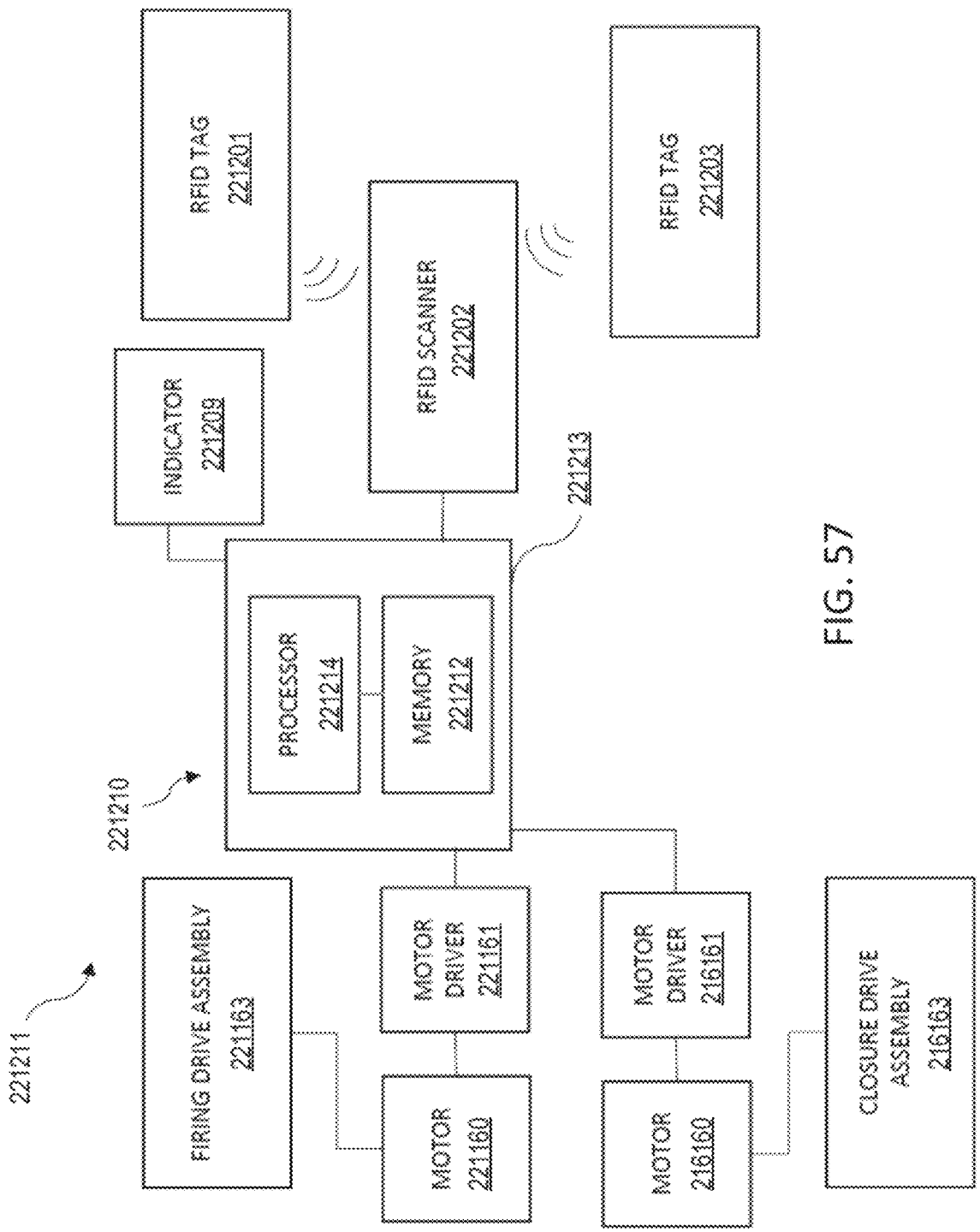
FIG. 57 depicts a control system of a surgical stapling instrument, in accordance with at least one aspect of the present disclosure.

FIG. 57 illustrates a logic diagram of a control system 221211 of a surgical instrument or tool in accordance with one or more aspects of the present disclosure. The control system 221211 includes a control circuit 221210 that can be integrated with the RFID scanner 221202 or can be coupled to, but positioned separately from, the RFID scanner 221202 in the housing assembly 216100, for example. The control circuit 221210 can be configured to receive input from the RFID scanner 221202 indicative of the information about a staple cartridge located on stapling head assembly 216300 that is stored in the RFID tag 221203 and/or information about the anvil 221200 that is stored in the RFID tag 221201.

In various examples, the RFID tag 221203 stores identification information of the staple cartridge and the RFID tag 221201 stores identification information of the anvil 221200. In such examples, the control circuit 221210 receives input from the RFID scanner 221202 indicative of the identification information of the staple cartridge and verifies the identity of the staple cartridge based on the input. Further, the control circuit 221210 receives input from RFID scanner 221202 indicative of the identification information of the anvil 221200 and verifies the identity of the anvil 221200 based on the input.

In at least one example, the control circuit 221210 includes a microcontroller 221213 that has a processor 221214 and a storage medium such as, for example, a memory 221212. The memory 221212 stores program instructions for performing various processes such as, for example, identity verification. The program instructions, when executed by the processor 221214, cause the processor 221214 to verify the identity of the staple cartridge and the identity of the anvil 221200 by comparing the identification information received from the RFID tags 221201, 221203 to identification information stored in the memory 221212 in the form of an identity database or table, for example.

In at least one example, the control circuit 221210 can be configured to check compatibility of the anvil 221200 with staple cartridge of the stapling head assembly 216300 based on input from the RFID scanner 221202. The processor 221214 can, for example, check the identity information of the anvil 221200 and the staple cartridge against a compatibility database or table stored in memory 221212.

In various examples, the memory 221212 comprises a local memory of the instrument 216010. In other examples, identity databases or tables and/or compatibility databases or tables can be downloaded from a remote server. In various aspects, the instrument 216010 may transmit the information received from RFID tags 221201, 221203 to a remote server that stores the databases or tables for performing the identity and/or compatibility checks remotely.

Referring to FIG. 57, motors 216160, 221160 are coupled to motor drivers 216161 and 221161, respectively, which are configured to control the operation of the motors 216160 and 221160 including the flow of electrical energy from a power source (e.g. battery pack 216120) to the motors 216160 and 221160. In various examples, the processor 221214 is coupled to the motors 216160, 221160 through the motor drivers 216161, 221161. In various forms, the motor 216160 and/or the motor 221160 may be a brushed direct current (DC) motor with a gearbox and mechanical links to effect a tissue treatment by a surgical end effector. In one aspect, motor drivers 216161, 221161 may be in the form of an A3941 available from Allegro Microsystems, Inc. Other motor drivers may be readily substituted for use with the control system 221211.

In various forms, the motors 216160, 221160 may be a brushed DC driving motor having a maximum rotational speed of approximately 25,000 RPM. In other arrangements, the motors 216160, 221160 may include a brushless motor, a cordless motor, a synchronous motor, a stepper motor, or any other suitable electric motor. The motor driver 216161, 221161 may comprise an H-bridge driver comprising field-effect transistors (FETs), for example. The motors 216160, 221160 can be powered by a power source. The power source may comprise a battery which may include a number of battery cells connected in series that can be used as the power source to power the surgical instrument or tool. In certain circumstances, the battery cells of the power source may be replaceable and/or rechargeable. In at least one example, the battery cells can be lithium-ion batteries which can be couplable to and separable from the power source.

In various aspects, a motor driver in accordance with the present disclosure may be a full-bridge controller for use with external N-channel power metal-oxide semiconductor field-effect transistors (VIOSFETs) specifically designed for inductive loads, such as brush DC motors. The motor driver may comprise a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system comprising an absolute positioning system.

In various aspects, one or more of the motors of the present disclosure can include a rotatable shaft that operably interfaces with a gear assembly that is mounted in meshing engagement with a set, or rack, of drive teeth on a displacement member of a firing drive assembly 221163 or a closure drive assembly 216163, for example. A sensor element may be operably coupled to a gear assembly such that a single revolution of the position sensor element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable a closure member, firing member, firing bar, I-beam, or combinations thereof.

In certain examples, as illustrated in FIG. 57, transition of the anvil 216400 to a closed configuration with the stapling head assembly 216300 is driven by the motor 221160. In such examples, the control circuit 221210 permits the motor 221160 to drive closure of the anvil 216400 if proper orientation, full seating, and/or proper identity of the anvil 216400 is detected by the control circuit 221210 based on input from the RFID scanner 221202 and/or RFID scanner 221204, as described above. Accordingly, a detected failure at establishing one or more of proper orientation, full seating, and/or proper identity of the anvil 216400 causes the control circuit 221210 to prevent the motor 221160 from starting and/or completing closure of the anvil 216400.

In certain examples, the control circuit 221210 permits the motor 216160 to drive staple firing and advancement of the cylindrical knife member if staple cartridge-anvil compatibility is confirmed based on the information stored in the RFID tags 221201, 221203 as reported by RFID scanners 221202. Conversely, the control circuit 221210 is configured to prevent the motor 216160 from driving staple firing and advancement of the cylindrical knife member if the staple cartridge-anvil compatibility cannot be established based on the information stored in the RFID tags 221201, 221203 as reported by RFID scanners 221202.

In various examples, antennas of one or more of the RFID tags 221201, 221203 and the RFID scanner 221202 may be supplemented with booster antennas that are engaged upon connection. In various examples, the antennas of active RFID tags on the surgical instrument 216010 such as, for example, the RFID tag 221201 and RFID tag 221203 can be cut during normal operation of the surgical instrument 216010 in planned manner. The lost signals from such RFID tags can signify completion of a surgical task.

In various aspects, an RFID tag can be positioned along the pathway of the cylindrical knife member. The RFID tag may transmit a signal through its antenna to the RFID scanner 221202, for example. When the antenna is severed by the knife member, the signal is lost. The signal loss can confirm advancement of the knife member.

In one example, the RFID tag is positioned on a breakable washer of the anvil 216400. In such example, the breakable washer is broken by the knife member toward the end of a full distal range of motion of the knife member. The knife member cuts the antenna of the RFID tag while breaking the breakable washer. When the antenna is severed, the signal transmitted from the RFID tag to the RFID scanner 221202, for example, is lost. The RFID scanner 221202 can be coupled to the control circuit 221210, and can report the signal loss to the control circuit 221210. The signal loss is interpreted by the control circuit 221210 to indicate completion of a firing sequence of the surgical instrument 216010.

In various aspects, as described above greater detail, a surgical instrument such as, for example, the instrument 216010 includes an anvil 216400 movable toward a stapling head assembly 216300 to capture tissue therebetween in a closed configuration. The tissue is then stapled and cut in a firing sequence of the surgical instrument 216010. The instrument 216010 further includes an RFID tag such as, for example, the RFID tag 221201 and an RFID scanner such as, for example, the RFID scanner 221202 that is configured to read and/or write to the RFID tag 221201. The RFID tag 221201 and the RFID scanner 221202 define an RFID system that can be employed by a control circuit 221210 to determine a characteristic of the tissue based on the RF signal backscatter from the tissue.

The positions of the RFID tag 221201 and the RFID scanner 221202 with respect to the tissue grasped between the anvil 216400 and the stapling head assembly 216300 can be selected for optimal measurements of the RF signal backscatter. In at least one example, the RFID tag 221201 and the RFID scanner 221202 can be positioned on opposite sides of the tissue.

The RF signal from the backscatter data can be gathered and correlated with known tissue characteristics to permit tissue analysis. In various aspects, the spectral characteristics of the backscatter data can be analyzed to determine various characteristics of the tissue. In at least one example, the backscatter data is employed to identify boundary features within the tissue. In at least one example, the backscatter data can be used to assess thickness of the tissue grasped between the anvil 216400 and the stapling head assembly 216300.

Applicant discloses systems and techniques for adaptive control of surgical instrument functions. A surgical instrument may be configured to communicate with an external system such as, for example, a surgical hub. The surgical hub may generate, and the surgical instrument may receive, an indication of one or more functions to be adaptively controlled by the surgical instrument. For example, a surgical stapler instrument may receive an indication to adaptively control a display of staple height operating range and/or to adaptively control motorized features of the surgical instrument. The surgical instrument may determine values for parameters associated with the identified function and adapt the control of the identified function based upon the determined parameters. The surgical instrument may modify its operation of the one or more controlled functions based upon the parameters. The surgical instrument may communicate additional information such as additional parameter values to the external system and may receive further input regarding continued control of the indicated one or more functions.

Figure 58:
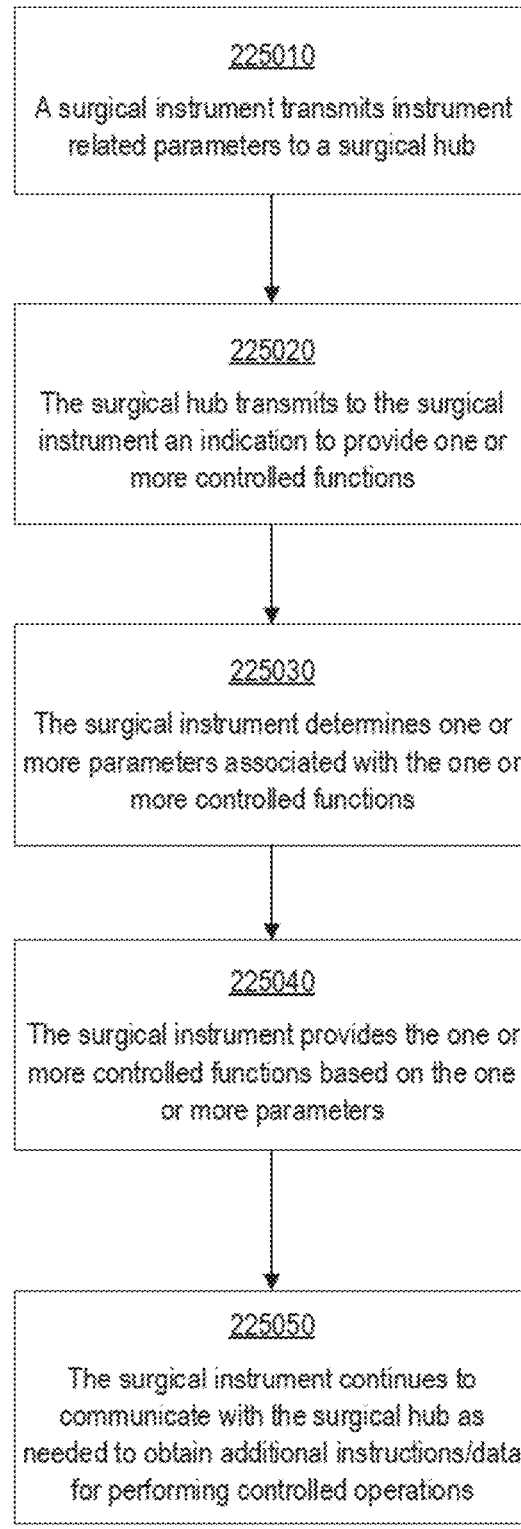
FIG. 58 depicts a flow chart of example processing for adaptive control of surgical instrument functions.

FIG. 58 depicts a flow chart of example processing for adaptive control of surgical instrument functions. As shown, at 225010, a surgical instrument may establish communication with an external system such as, for example, a surgical hub system. The surgical instrument may communicate parameters associated with the surgical instrument to the surgical hub. For example, the surgical instrument may communicate an indication of hardware comprised in the device, software operating on the device, and/or any other relevant information relating to the surgical instrument and its use.

The surgical hub system may use the identity of the surgical instrument and the one or more parameter values received from the surgical instrument to determine one or more functions that the surgical instrument may control during its processing. For example, if the parameters indicate the surgical instrument is a surgical circular stapler with an interchangeable end effector, the surgical hub system may determine that the surgical instrument should provide adaptive control of the staple height operating range. If the parameters indicate the surgical instrument is a surgical circular stapler of a type that has been used in previous surgical procedures for which the surgical hub system has relevant operating or operational parameters, the surgical hub system may determine that the surgical instrument should provide control of its system using operational parameters derived from prior surgical procedures.

At 225020, the surgical hub system transmits, and the surgical instrument receives, an indication to provide one or more controlled functions from the surgical hub system. The indication may be communicated in any suitable manner including, for example, as parameters. The indication may indicate to the surgical instrument to provide, for example, an adaptive staple height operating range, adaptive control of motorized tissue compression, and/or device control using operational parameters associated with previous surgical procedures.

At 225030, the surgical instrument may determine one or more parameters associated with the one or more controlled functions that were indicated in the communication from the surgical hub system. For example, if the surgical instrument has received an indication to provide an adaptive staple height operating range, the surgical instrument may determine parameters relating to the size of an anvil head associated with an end effector of the surgical instrument. If the surgical instrument has received an indication to provide adaptable control of a motor associated with force applied by a tissue compression anvil, the surgical instrument may monitor for an indication that a force to insert a staple is being applied. If the surgical instrument has received an indication to use operational parameters from previously completed surgical procedures, the surgical instrument may determine operational parameters from previous procedures by requesting and receiving the operational parameters from the surgical hub system.

At 225040, the surgical instrument may provide the one or more controlled functions indicated in the communication from the surgical hub based upon the determine parameters. For example, the surgical instrument may provide an adaptable staple height operating range based upon the parameters indicating a size of the anvil head of an end effector. If the anvil head is relatively small or large, the staple height operating range may be modified from a default representation. If the surgical instrument has received an indication to provide control of motors adapted for tissue compression, upon receiving data indicating a staple is being or is about to be inserted, the surgical instrument may control the motor to increase force applied to provide compression at the appropriate time and for the appropriate duration. If the surgical instrument has received an indication to provide control based upon operational parameters associated with previously completed surgical procedures, the surgical instrument may use the received operational parameters to perform its operations.

At 225050, the surgical instrument may continue to communicate with the surgical hub system as needed to provide additional parameters and information regarding its status and operation to the surgical hub and to receive additional instructions and data for performing controlled operations from the surgical hub.

Figure 59:
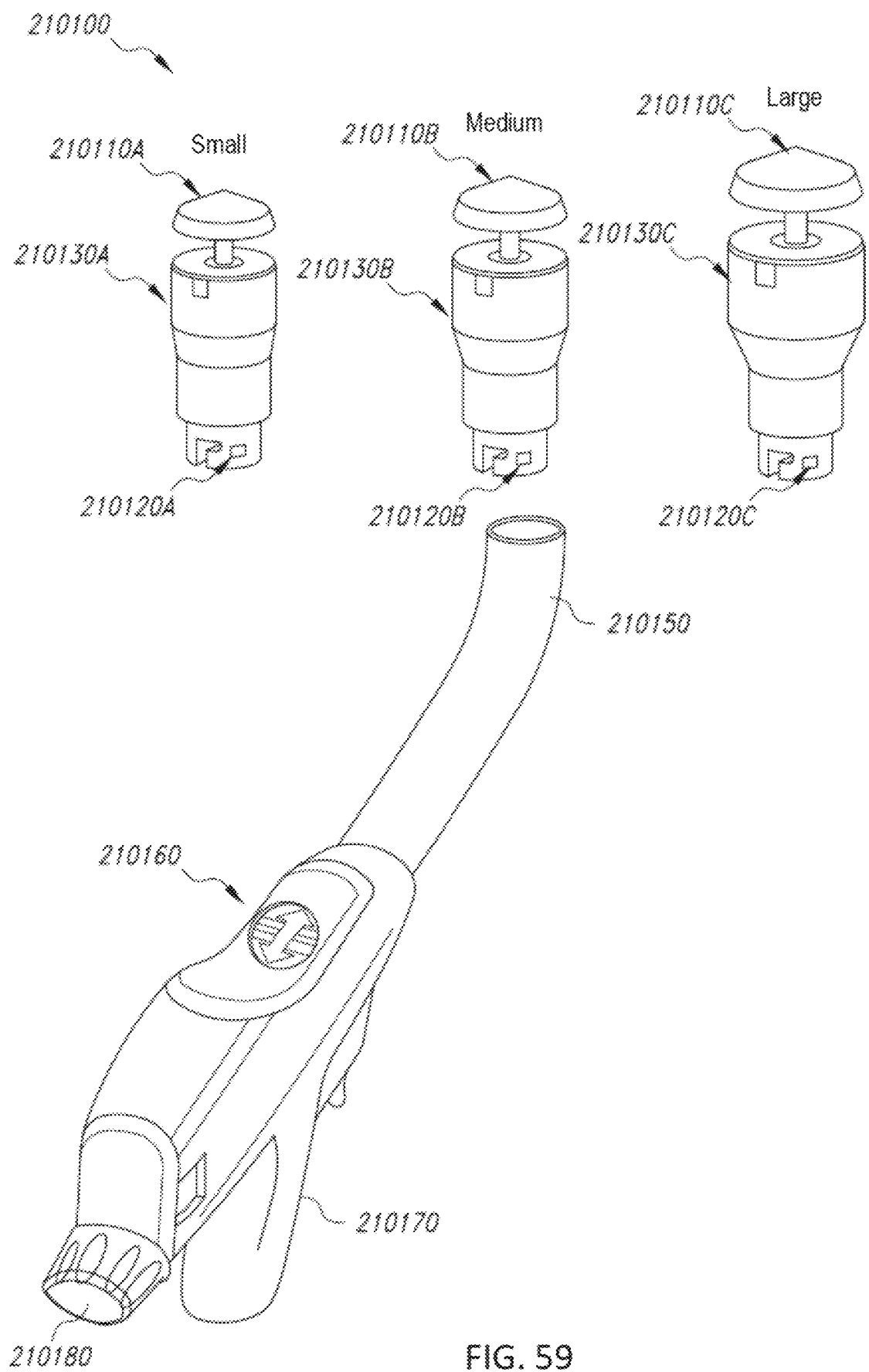
FIG. 59 illustrates an example motorized circular stapling instrument in accordance with at least one aspect of the present disclosure.

A surgical instrument may receive an indication from the surgical hub to provide an adaptable stable height operating range. FIG. 59 depicts an example motorized circular stapling instrument 210100. The example motorized circular stapling instrument 210100 may include structure may be adapted to perform functions as described in connection with instrument 201800 appearing in FIG. 18 and in connection with instrument 216010 appearing in FIG. 55. The circular stapling instrument 210100 may include a shaft assembly 210150, a handle assembly 210170, and a rotation knob 210180. The shaft assembly 210150, handle assembly 210170, and rotation knob 210180 may operate as described in connection with 201806, 201808, and 201812, respectively, in connection with the instrument 201800. The shaft assembly 210150, handle assembly 210170, and rotation knob 210180 may operate as described in connection with 216200, 216100, and 216130, respectively, in the instrument 216010.

The shaft assembly 210150 may be configured to be attached to and operate with one or more end effectors. The end effectors may include end effectors of different configurations. For example, the end effectors may be configured with different sizes, different shapes, different functionality, and the like. The end effectors may be configured for different tissue types and/or for different conditions of a particular tissue type, for example.

The end effector may include an anvil, such as 201804 or 216400. The end effector may include a head assembly 201802. The shaft assembly 210150 may be configured to operate with head assemblies of different sizes. For example, the shaft assembly 210150 may be configured to operate with a small-sized anvil 210110A. The shaft assembly 210150 may be configured to operate with a small-sized stapling head assembly 210130A. The shaft assembly 210150 may be configured to operate with a medium-sized (e.g., the standard size) anvil 210110B. The shaft assembly 210150 may be configured to operate with a medium-sized (e.g., the standard size) stapling head assembly 210130B. The shaft assembly 210150 may be configured to operate with a large-sized anvil 210110C. The shaft assembly 210150 may be configured to operate with a large-sized stapling head assembly 210130C.

Each stapling head assembly 210130A-C may include a respective data storage element 210120A-C. For example, stapling head assembly 210130B may include data storage element 210120B. The data storage element 210130B may be configured to store data and to transmit the stored data. The data may be transmitted via a wired and/or wireless connection. The data storage element 210120B may store data and/or information pertaining to the respective anvil 210110B and/or the stapling head assembly 210130B. The data may comprise data identifying the type of the stapling head assembly (e.g., motorized circular stapler head assembly), characteristics of the anvil 210110B (e.g., the anvil head's size, such as the diameter), the status of the stapling head assembly (e.g., whether staples have been fired), and/or the like.

The data storage element 210120B may include any device, system, and/or subsystem suitable for storing and/or providing stored data. For example, the data storage element 210120B may comprise an RFID micro-transponder and/or an RFID chip including a digital signature. The data storage element 210120B may include a battery-assisted passive RFID tag. A battery-assisted passive RFD tag may exhibit improved range and signal length (e.g., as compared to RFID micro-transponders and/or RFID chips). The data storage element 210120B may include a writable section that may be used to store data described herein. The data may be written to the writable section via a control circuit of the instrument 210100 such as is described in connection with FIGS. 7-8 and 16-17. The writable section may be read by a sensor of instrument 210100. For example, when a staple is fired, the instrument 210100 may write data indicative of the fired staple event to the writeable section. The instrument 210100 (or another instrument, for example) may subsequently read the data indicative of the fired staple event from the writeable section. This data writing and reading may enable the instrument 210100 to inform the user and/or other related systems of the staple firing history.

The stapling head assemblies 210130A and 210130C may include data storage elements 210120A and 210120C, respectively. The data storage elements 210120A and 210120C may function and be implemented as described with reference to the data storage element 210120B.

The stapling head assemblies 210130A, 210130B, and 210130C may each include a respective staple cartridge. A staple cartridge may include predetermined zones. The predetermined zones may be defined by sensing circuits. The predetermined zones may, via the sensing circuits, enable measurement of tissue impedance. The stapling head assemblies may include a stapling head assembly such as is illustrated in FIG. 40 or FIG. 41. As illustrated in FIG. 41, the staple cartridge 25512 may comprise eight predetermined zones (Zone 1-Zone 8) defined by sensing circuits ($S_1$-$S_8$). The zones defined in the circular staplers of FIGS. 40 and 41 may be equal, or at least substantially equal, in size, and may be arranged circumferentially around a longitudinal axis extending longitudinally through shafts of the circular staplers. FIG. 45 illustrates an example where tissue impedance measurements on the staple cartridge 25512 are substantially similar in magnitude, in Zone 1, Zone 3, Zone 5, and Zone 7, which may have received previously-stapled tissue. Significantly higher tissue impedance measurements on the staple cartridge 25512 may be substantially uniform in magnitude in Zone 2, Zone 4, Zone 6, and Zone 8, which may not have received previously-stapled tissue. FIG. 46 illustrates tissue impedance measurements unevenly distributed among the zones.

The handle assembly 210170 may include a motor as described with reference to instrument 201800. The handle assembly 210170 may include a plurality of motors as described in FIGS. 8, 16, 17, and 57. For example, the handle assembly 210170 may include at least a separately controlled anvil closure motor (e.g., closure motor 603 shown in FIG. 8 and motor 216160 shown in FIG. 57) and a separately controlled firing motor (e.g., firing motor 602 shown in FIG. 8 and motor 221160 shown in FIG. 57).

The handle assembly 210170 may comprise a graphical representation of an adaptable staple height operating range 210160, which also may be referred to as a representation of an operating range for tissue compression. The adaptable staple height operating range 210160 may operate similar to window 216114 as described in connection with FIGS. 55-56. The graphical representation may include variable staple height windows (such as, for example, those described with reference to variable staple height windows 201076, 201078, 201080, 201082 in FIG. 23). The graphical representation may include variable staple firing ranges (such as, for example, those described with reference to staple firing ranges 201088, 201090, 201092 in FIG. 23). The adaptable staple height operating range 210160 may be adapted based on one or more parameters sensed by the instrument 210100. The adaptable staple height operating range 210160 may be adapted based on one or more previously used parameter configurations.

Figure 60:
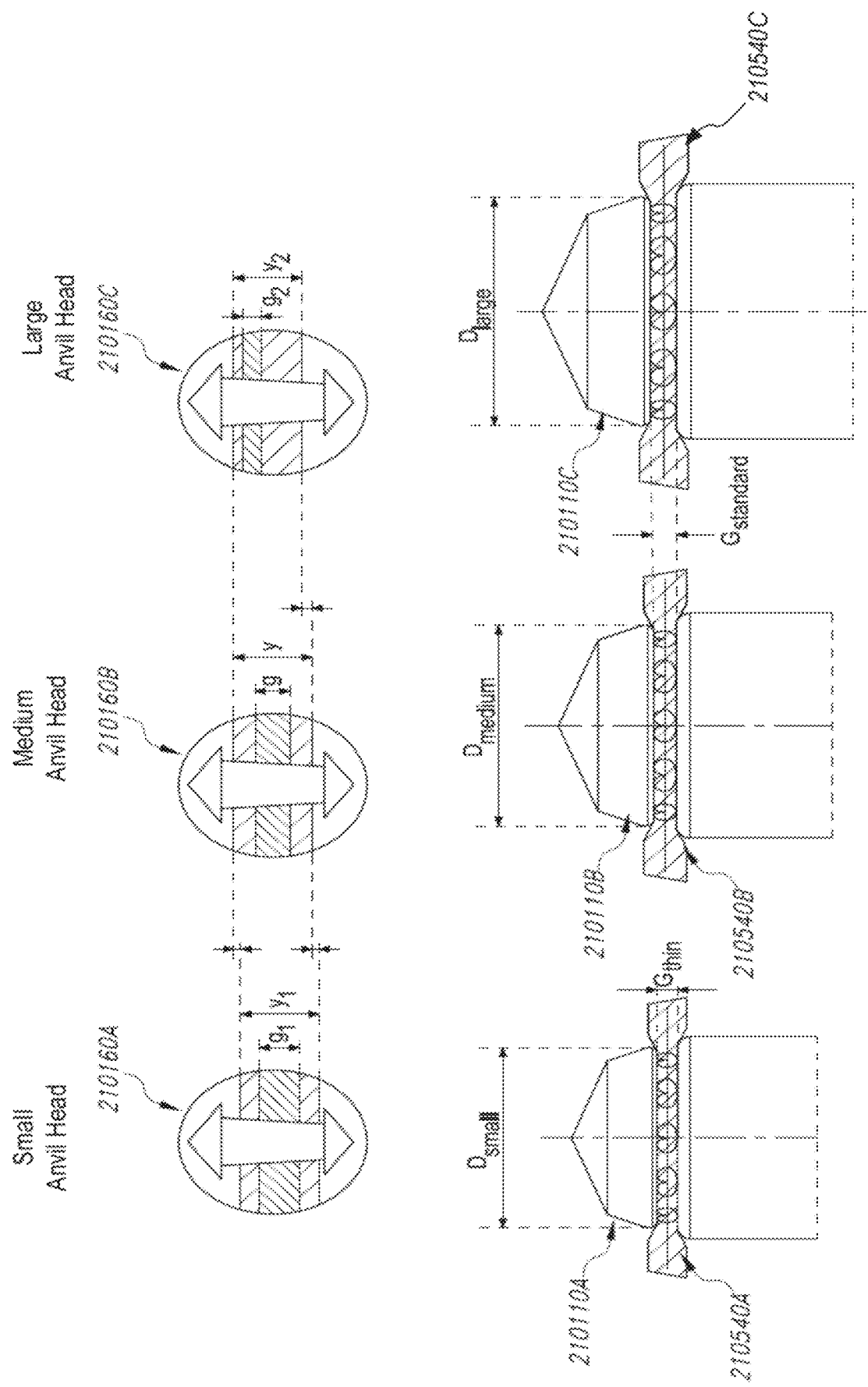
FIG. 60 illustrates an example representation of an adaptable staple height operating range displaying on an example motorized circular stapling instrument.

The adaptable staple height operating range 210160 may operate as described in connection with FIGS. 60-63. FIG. 60 illustrates an example representation of an adaptable staple height operating range displayed as it might appear on an example motorized circular stapling instrument 210100. A control circuit may enable the adaptable staple height operating range 210160. The adaptable staple height operating range 210160 may be adapted according to a mode, such as a stroke control mode, a load control mode, and/or a previous-configuration control mode, for example. The adaptable staple height operating range 210160 may be adapted according to a mode in a tiered system of operation modes. Mode selection (e.g., whether the instrument 210100 operates in a stroke control mode, a load control mode, or a previous-configuration control mode) may be determined by a system parameter that the instrument 210100 receives from an external system. For example, the instrument 210100 may be linked (e.g., paired) with a surgical hub in an operating room and may receive configuration information from the surgical hub. An indication which may be, for example, a system parameter, may be transmitted from the surgical hub to the instrument 210100. The system parameter may indicate to the instrument 210100 to operate in a particular control mode. The instrument 210100 may determine to operate in one of the stroke control mode, load control mode, or a previous-configuration control mode based on the received system parameter. The system parameter may be a setting associated with one or more of the following: a medical professional (e.g., a surgeon); a particular patient and/or class of patients; a medical facility or an institution; a subscription level and/or purchased software tier; or the like.

Figure 61:
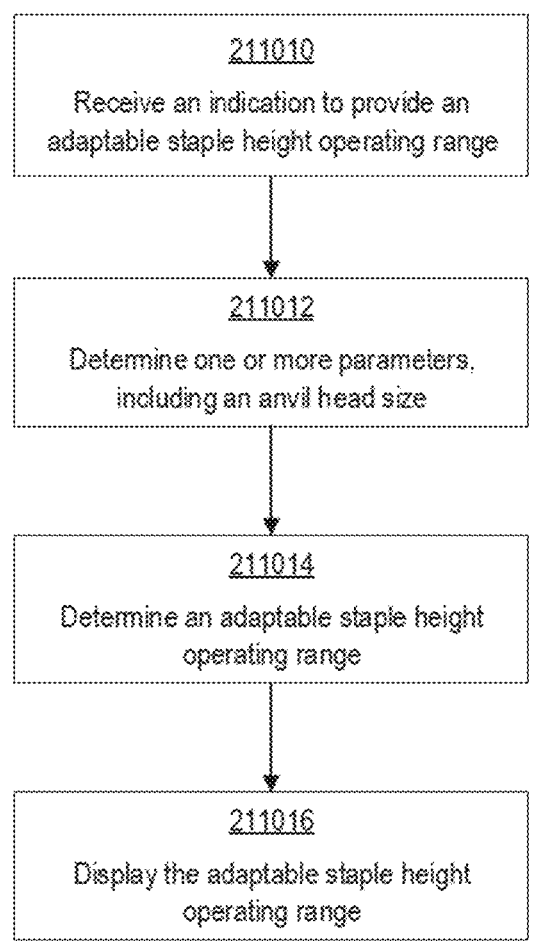
FIG. 61 is an example flow diagram of an example motorized circular stapling instrument operating in a stroke control operation mode.

FIG. 61 is a flow diagram depicting example processing for providing an adaptable staple height operating range while the motorized circular stapling instrument operates in a stroke control operation mode. At 211010, a surgical circular stapler 211000, which may an instrument 210100, may receive an indication, which may comprise a system parameter, to provide an adaptable staple height operating range (illustrated at 210160 in FIG. 59 and at 210160A-C in FIG. 60) while operating in a stroke control mode. The stroke control mode may refer to adapting the adaptable staple height operating range 210160 at least based on the stroke position of the anvil and the anvil head size during, for example, tissue clamping. For example, when a medium-sized anvil head 210110B with a medium-sized diameter ($D_{medium}$) is selected to operate with the surgical circular stapler 211000, at 211012, the surgical circular stapler's control circuitry may determine the $D_{medium}$ diameter size from the value stored in the data storage element 210120B (as shown in FIG. 59).

At 211014, the surgical circular stapler may use the determined size of the anvil head, e.g., medium, to determine that a standard adaptable staple height operating range 210160B should be presented. The standard adaptable staple height operating range 210160B may include a standard viable (e.g., workable) staple height range represented by a yellow zone y and a standard viable staple firing range represented by a green zone g. As shown in FIG. 60, the yellow zone represents a first laterally extending band and the green zone represents a second laterally extending band positioned within the first laterally extending band.

When the large-sized anvil head 210110C with a large-sized diameter ($D_{large}$) is selected to operate with the surgical circular stapler 211000, at 211012, the surgical circular stapler's 211000 control circuit may determine the $D_{large}$ diameter size from the value stored in data storage element 210120C (shown in FIG. 59). At 211014, the surgical circular stapler may use the determined size of the anvil head, i.e., large, to determine that an adaptable staple height operating range 210160C should be presented. Referring to FIG. 60, the adaptable staple height operating range 210160C may include a viable staple height range represented by a yellow zone $y_2$ and a viable staple firing range represented by a green zone $g_2$. A viable staple height range may be referred to as an adaptable viable staple height range. A viable staple firing range may be referred to as an adaptable viable staple firing range and/or adaptable staple firing range. The tissue 210540C being clamped on by the anvil head 210110C may have the same tissue thickness $G_{standard}$ as the tissue 210540B clamped by the anvil head 210110B. The surgical circular stapler 211000 may determine the adaptable staple height operating range 210160C by shifting up the standard yellow zone y and the standard green zone g to be yellow zone $y_2$ and the green zone $g_2$, respectively. As compared with the standard yellow, the laterally extending band representing the yellow zone, y2, may be compressed or narrower. As compared with the standard green zone, the laterally extending band representing green zone, g2, may be shifted upwards. The shift may be due to $D_{large}$ being larger than $D_{medium}$ and result from the same anvil closure force effecting a higher staple height when clamping with a large anvil head. Such an effect may be due to a large anvil head size with a larger clamping surface area requiring a larger anvil closure force to effect the same staple height. The surgical circular stapler 211000 may determine the adaptable staple height operating range 210160C by determining a narrower $y_2$ and a narrower green zone $g_2$ than the standard yellow zone y and the standard green zone g, respectively. Such adaptation may be caused by a higher staple height being effected when clamping with a large anvil head given the same clamping force. The unavailable lower staple height range renders the yellow zone and the green zone narrower.

When the small-sized anvil head 210110A with a small-sized diameter ($D_{small}$) is selected to operate with the surgical circular stapler 211000, at 211012, the surgical circular stapler's 211000 control circuit may determine the $D_{small}$ diameter size from the value stored in data storage element 210120A (shown in FIG. 59). At 211014, the surgical circular stapler may determine an adaptable staple height operating range 210160A. The adaptable staple height operating range 210160A may include a viable staple height range represented by a yellow zone $y_1$ and a viable staple firing range represented by a green zone $g_1$. The tissue 210540C being clamped by the anvil head 210110C may have a thinner tissue thickness $G_{thin}$ (corresponding to a longer anvil stroke relative to the fully open stroke position) of the tissue 210540A as compared to the tissue thickness $G_{standard}$ (corresponding to a shorter anvil stroke relative to the fully open stroke position) of the tissue 210540B clamped by the anvil head 210110B. The surgical circular stapler 211000 may determine the adaptable staple height operating range 210160A by shifting down the standard yellow zone y and the standard green zone g to be yellow zone $y_1$ and the green zone $g_1$, respectively. As compared with the standard yellow, the laterally extending band representing the yellow zone, y, may be shifted downward. As compared with the standard green zone, the laterally extending band representing green zone, g1, may be wider. The surgical circular stapler 211000 may determine the adaptable staple height operating range 210160A by determining a wider green zone $g_1$ than the standard green zone g. Such adaptation may be due to $D_{small}$ being smaller than $D_{medium}$ because the same anvil closure force may effect a lower staple height when clamping with a smaller anvil head. Such an effect may be due to a smaller anvil head size with a smaller clamping surface area requiring a smaller anvil closure force to effect the same staple height. Such adaptation may also be due to the thinner tissue thickness $G_{thin}$ of the tissue 210540A than the tissue thickness $G_{standard}$ of the tissue 210540B being clamped on by the anvil head 210110B which corresponds to a smaller anvil gap at the beginning of tissue clamping.

At 211016, the surgical circular stapler may display the adaptable staple height operating range.

Figure 62:
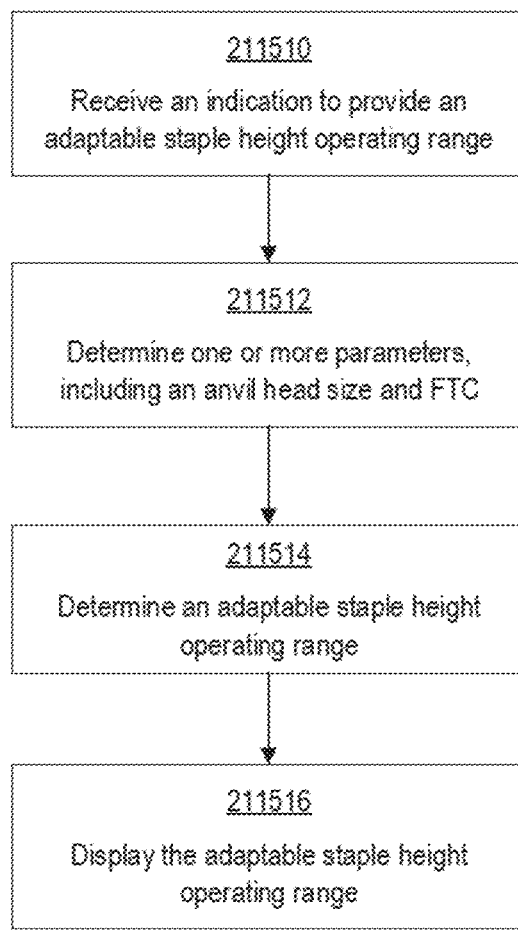
FIG. 62 is an example flow diagram of an example motorized circular stapling instrument operating in a load control operation mode.

FIG. 62 depicts a flow diagram of example processing for providing an adaptable staple height operating range while the motorized circular stapling instrument operates in a load control operation mode. At 211510, the surgical circular stapler may receive an indication, which may be a system parameter, to provide an adaptable staple height operating range (illustrated at 210160 in FIG. 59 and at 210160A-C in FIG. 60) in a load control mode. The load control mode may refer to adapting the adaptable staple height operating range 210160 based on a force-to-close (FTC) (e.g., sensed motor load as a proxy for FTC) during tissue clamping and tissue creep/wait phase, in addition to the anvil head size and the stroke position of the anvil.

During tissue clamping, when the small-sized anvil head 210110A with a small-sized diameter ($D_{small}$) is selected to operate with the surgical circular stapler 211000, at 211512, the surgical circular stapler's 211000 control circuit may determine the FTC in addition to determining the $D_{small}$ parameter and sensing the tissue thickness $G_{thin}$ upon the anvil head 210110A's initial contact with the tissue 210540A as described at 211012 in connection with FIG. 61. At 211514, the surgical circular stapler 211000 may determine an adaptable staple height operating range and, at

211516, may display the adaptable staple height operating range. Such adaptable staple height operating range may be a further adaptation from that described at 211014 with reference to FIG. 61. For example, given a same tissue thickness, the determined FTC during tissue clamping may vary depending on variable tissue stiffness as described between times $t_1$ and $t_2$ in the Tissue Compression Force v. Time function graph in FIG. 24 herein. In the example of the tissue compression force curve 202026 that corresponds to tissue of low stiffness, because a lower FTC is sensed, the yellow zone and the green zone of the adaptable staple height operating range may shift further down as compared to tissue of normal stiffness. In the example of the tissue compression force curve 202024 that corresponds to tissue of high stiffness, because a higher FTC is sensed, the yellow zone and the green zone of the adaptable staple height operating range may shift up as compared tissue of normal stiffness.

At 211014, given a same anvil gap, the determined FTC during tissue creep/wait phase may vary depending on variable tissue stiffness as described between $t_2$ and $t_3$ in the Tissue Compression Force v. Time function graph in FIG. 24 herein. If the example tissue compression force curves 202022, 202024, 202026 were to be applied, because a decreased FTC is sensed, the yellow zone and the green zone of the adaptable staple height operating range may shift further down during tissue creep/wait phase as compared to the yellow zone and the green zone as determined during tissue clamping.

Figure 64:
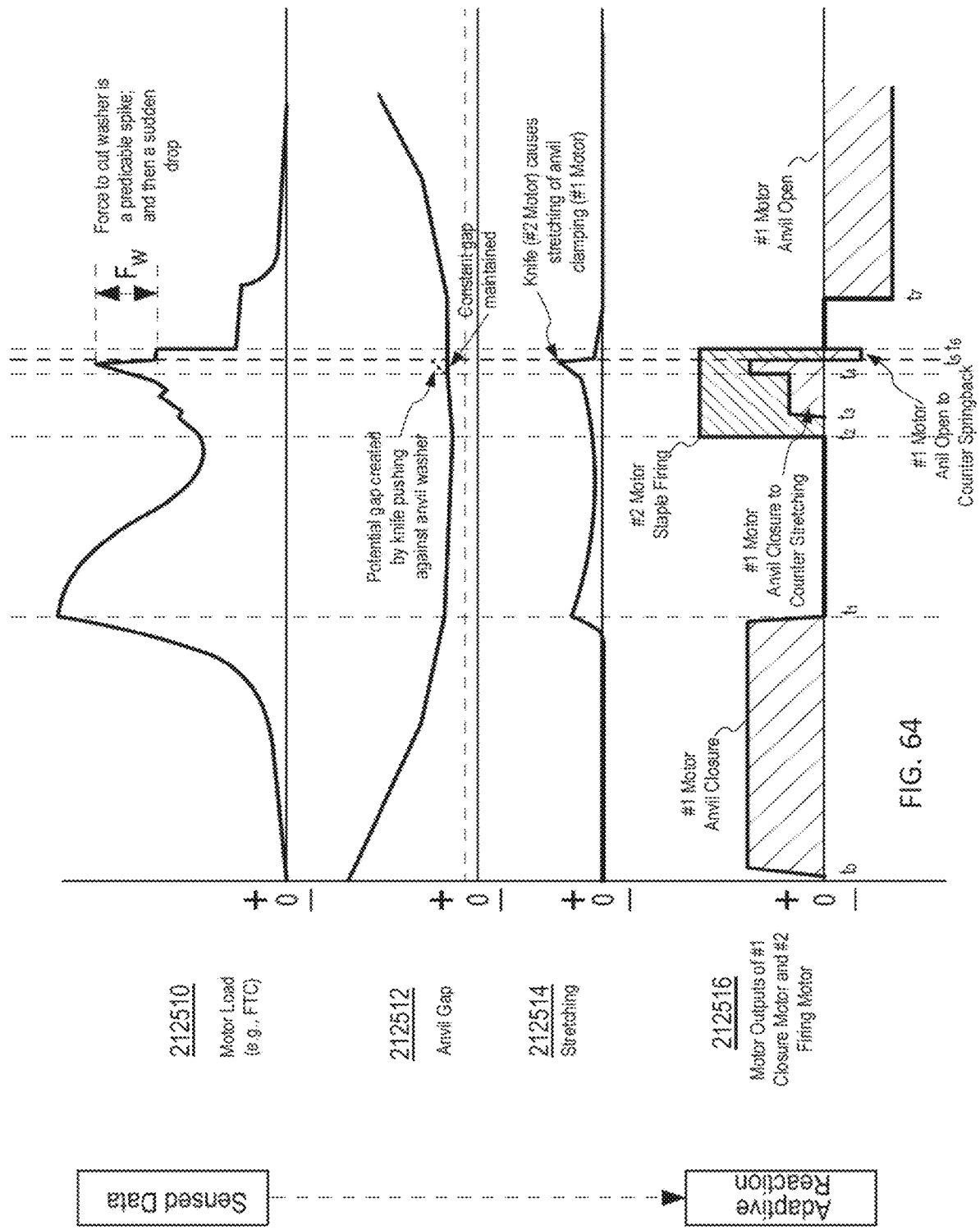
FIG. 64 is an example diagram illustrating various aspects of an example motorized circular stapling instrument operating using adaptive motor control in a load control operation mode.

A surgical instrument may receive an indication from the surgical hub to provide adaptive motor control. FIG. 64 is a diagram illustrating various aspects of an example motorized circular stapling instrument operating using adaptive motor control in a load control operation mode. FIG. 64 illustrates that the surgical circular stapler 211000, such as the instrument 210100, may be used in a surgical procedure to maintain a constant anvil gap during staple firing/tissue cutting by dynamically adapting the anvil closure motor's (described in FIG. 59) output to the firing motor's (as described in FIG. 59) output. Such adaptation may counter a force generated by the firing motor with a force in the opposite direction generated by the anvil closure motor. Both forces may be applied on the anvil to maintain a constant anvil gap. Graph 212510 depicts sensed motor load for the anvil closure motor (e.g., FTC) and sensed motor load for the firing motor (e.g., force to fire (FTF) or force to advance knife (FAK)) versus time. Graph 211512 depicts sensed anvil gap versus time. Graph 211514 depicts sensed tissue stretching versus time. Graph 211516 depicts motor output (e.g., power, current, and/or torque) of the anvil closure motor and the firing motor versus time.

Figure 65:
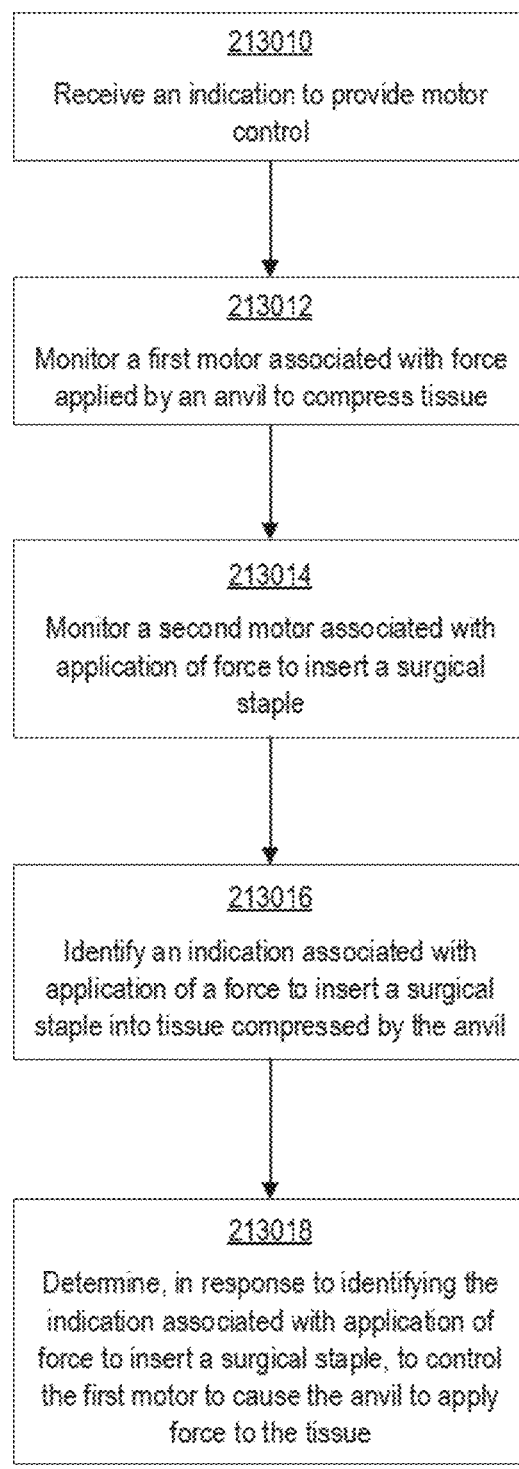
FIG. 65 is an example flow diagram of an example motorized circular stapling instrument operating with adaptive motor control in a load control operation mode.

FIG. 65 depicts a flow diagram of an example motorized circular stapling instrument operating using adaptive motor control in a load control operation mode. At 213010, a surgical circular stapler 211000, such as the instrument 210100, may receive an indication to provide motor control. For example, the surgical circular stapler may receive a system parameter for setting load control mode.

At 213012, the surgical circular stapler 211000 may monitor a first motor associated with force applied by an anvil to compress tissue (e.g., the anvil closure motor described herein). In the example surgical processing described in connection with FIG. 64, at t0 (e.g., when the anvil senses an initial contact with the tissue), the surgical circular stapler's 211000 control circuit may start monitoring the stroke position of the anvil by, for example, sensing the anvil gap as illustrated in graph 212512. The control circuit may also start monitoring the motor load for the anvil closure motor as illustrated in graph 212510. As the anvil gap decreases, the control circuit may cause the anvil closure motor to start generating a constant output ("first anvil closure motor output") to effect motorized tissue clamping as illustrated in graph 212516. Consequently, the control circuit may start sensing an increasing motor load (e.g., FTC) for the anvil closure motor as illustrated in graph 212510. In such manner, the surgical circular stapler 211000 may monitor the anvil closure motor's motor load.

Referring to FIG. 64, at t1, the surgical circular stapler's 211000 control circuit may sense the anvil gap has stopped decreasing and remains constant, and in response may cause the anvil closure motor to stop generating the first anvil closure motor output to end motorized tissue clamping and allow tissue creep/wait phase to start as illustrated in graph 212516. As the control circuit continues to monitor the anvil closure motor's motor load, the control circuit may sense a decreasing motor load (e.g., FTC) and then sense a constant motor load (e.g., FTC) as tissue creep stabilization is reached at t2 as illustrated in graph 212510. In such manner, the surgical circular stapler 211000 further monitors the anvil closure motor's motor load. Between t0 and t2, graph 212514 illustrates tissue stretch increasing at the end of tissue clamping, reaching a maximum at time t1, decreasing as tissue creep starts, and becoming constant at t2.

At 213014 in FIG. 65, the surgical circular stapler 211000 may monitor a second motor associated with application of force to insert a surgical staple (e.g. the firing motor described herein). In the example surgical procedure depicted in FIG. 64, at t2, the surgical circular stapler's 211000 control circuit may cause the firing motor to start generating a constant output ("first firing motor output") upon, for example, an instrument operator (e.g., a surgeon) triggering staple firing as illustrated in graph 212516. In response, the control circuit may start monitoring the motor load for the firing motor as illustrated in graph 212510, in addition to monitoring the constant motor load for the anvil closure motor starting at t2. In such manner, the surgical circular stapler 211000 monitors the firing motor's motor load.

At 213016 in FIG. 65, the surgical circular stapler 211000 may identify an indication associated with application of a force to insert a surgical staple into tissue compressed by the anvil. For example, continuing with the timeline illustrated in FIG. 64, at t2, as the surgical circular stapler's 211000 control circuit starts monitoring the motor load for the firing motor, the control circuit may start sensing an increasing motor load (e.g., FTF) for the firing motor as illustrated in graph 212510 resulting from the first firing motor output. In such manner, the surgical circular stapler 211000 may identify an indication associated with application of a force for staple firing. Graph 212514 illustrates the tissue stretch increasing starting at t2 as the motor load (e.g., FTF) for the firing motor increases.

At 213018 in FIG. 65, the surgical circular stapler 211000 may determine, in response to identifying the indication associated with application of force to insert a surgical staple, to control the first motor to cause the anvil to apply force to the tissue. Continuing with the timeline illustrated in FIG. 64, at t3, the surgical circular stapler's 211000 control circuit senses an increasing motor load (e.g., FTF) for the firing motor. In response, the control circuit may generate a constant output ("second anvil closure motor output"). The second anvil closure motor output may effect a force for anvil closure in order to counter the increasing tissue stretching described at 213016 and thereby maintain a constant anvil gap. The surgical circular stapler 211000 controls the anvil closure motor to apply a force for anvil closure in response to identifying an indication of application of a force for staple firing.

As a further example of processing at 213016 and 213018, in FIG. 65, and continuing with the timeline illustrated in FIG. 64, at t4, the instrument's 210100 advancing knife may make the initial contact with the breakable washer (as described in connection with FIG. 57). Upon sensing the initial contact, the surgical circular stapler's 211000 control circuit may cause the anvil closure motor to generate a higher constant output ("third anvil closure motor output") than the second anvil closure motor output. The third anvil closure motor output may effect a higher force for anvil closure for a brief period to counter the anticipated additional force spike to be applied on the anvil as the knife pushes and cuts through the breakable washer as illustrated in graph 212516. The period may end at t5 when the breakable washer is cut. The surgical circular stapler 211000 thereby further controls the anvil closure motor to apply a force for anvil closure in response to identifying an indication of application of a force for staple firing (i.e., the force for cutting through the breakable washer).

In FIG. 64, an increased motor load spike sensed, $F_w$, that corresponds to the force applied by the knife as it cuts through the breakable washer and the countering anvil closure force effected by the anvil closure motor are depicted in graph 212510. This is yet another example of FIG. 65's steps 213012 and 213014 for monitoring the motor for anvil closure and the motor for staple firing, respectively. In graph 212514 between t4 and t5, an increased tissue stretching is depicted as another effect of the force applied by the knife cutting through the breakable washer. As illustrated with a dotted line in FIG. 64, between t4 and t5, graph 212512 depicts a potential increased anvil gap that may be caused by the force applied by the knife cutting through breakable washer had the third anvil closure motor output not been generated. In such manner, a constant anvil gap may be maintained as the knife pushes and cuts through the breakable washer.

Between t5 and t6, illustrated in graph 21516, is another generated anvil closure motor output ("fourth anvil closure motor output") for a very brief period to effect a force for anvil opening. Such force may be used to counter the force the knife applies on the breakable washer in the anvil closing direction as the knife retracts to its seated position after having cut through the breakable washer.

Between t6 and t7, a period is depicted before the anvil gap increases upon an instrument operator initiating an anvil stroke to open the anvil. At t7, as the surgical circular stapler's 211000 control circuit senses an increasing anvil gap, the control circuit causes the anvil closure motor to generate another constant output ("fifth anvil closure motor output") to effect motorized anvil opening.

Figure 66:
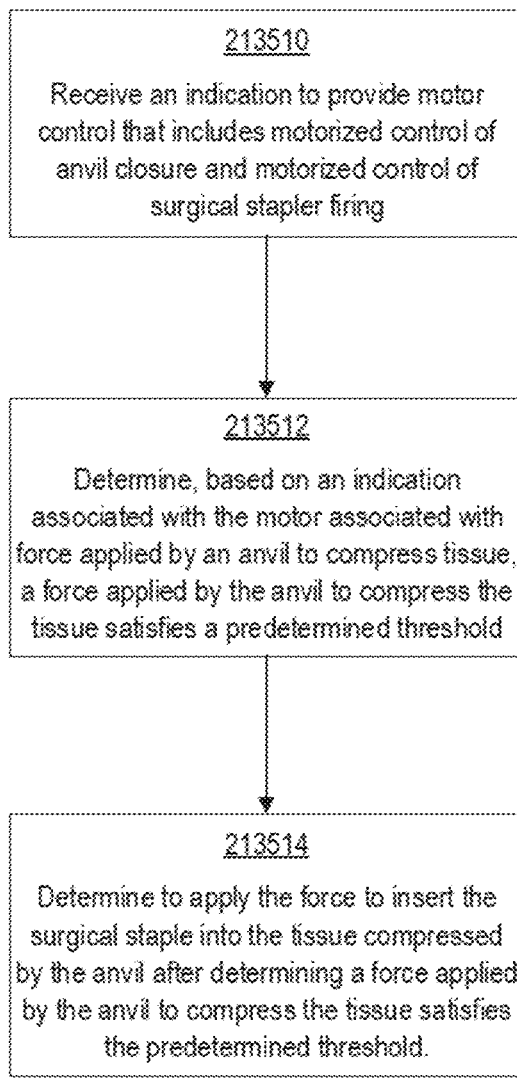
FIG. 66 is another example flow diagram of an example motorized circular stapling instrument operating in a load control operation mode.
Figure 67:
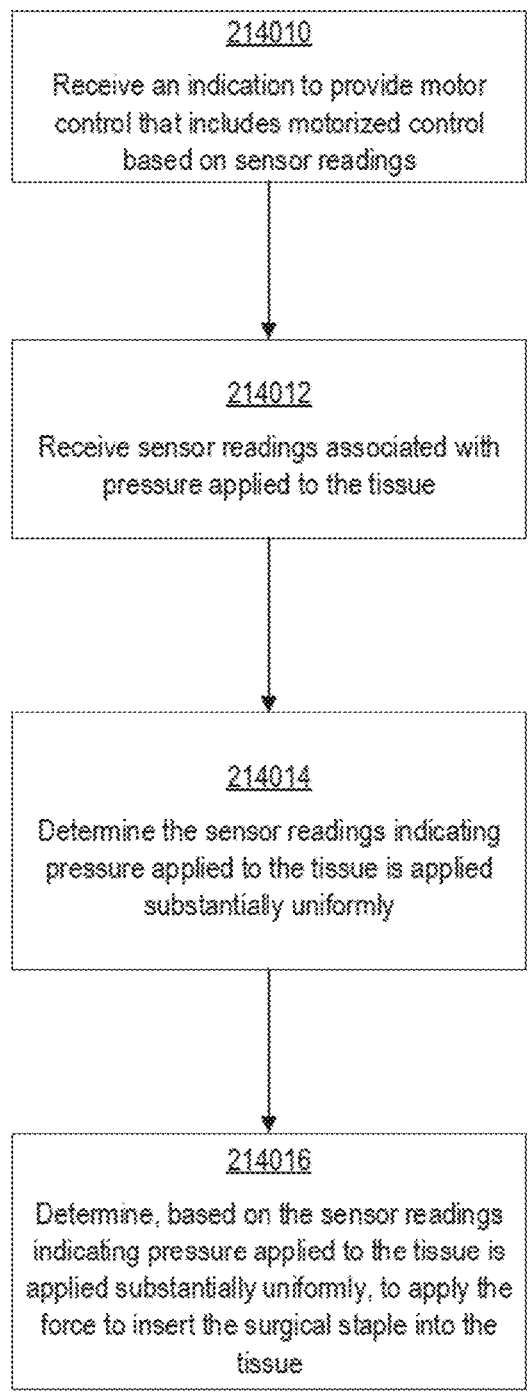
FIG. 67 is another example flow diagram of an example motorized circular stapling instrument operating in a load control operation mode.
Figure 68:
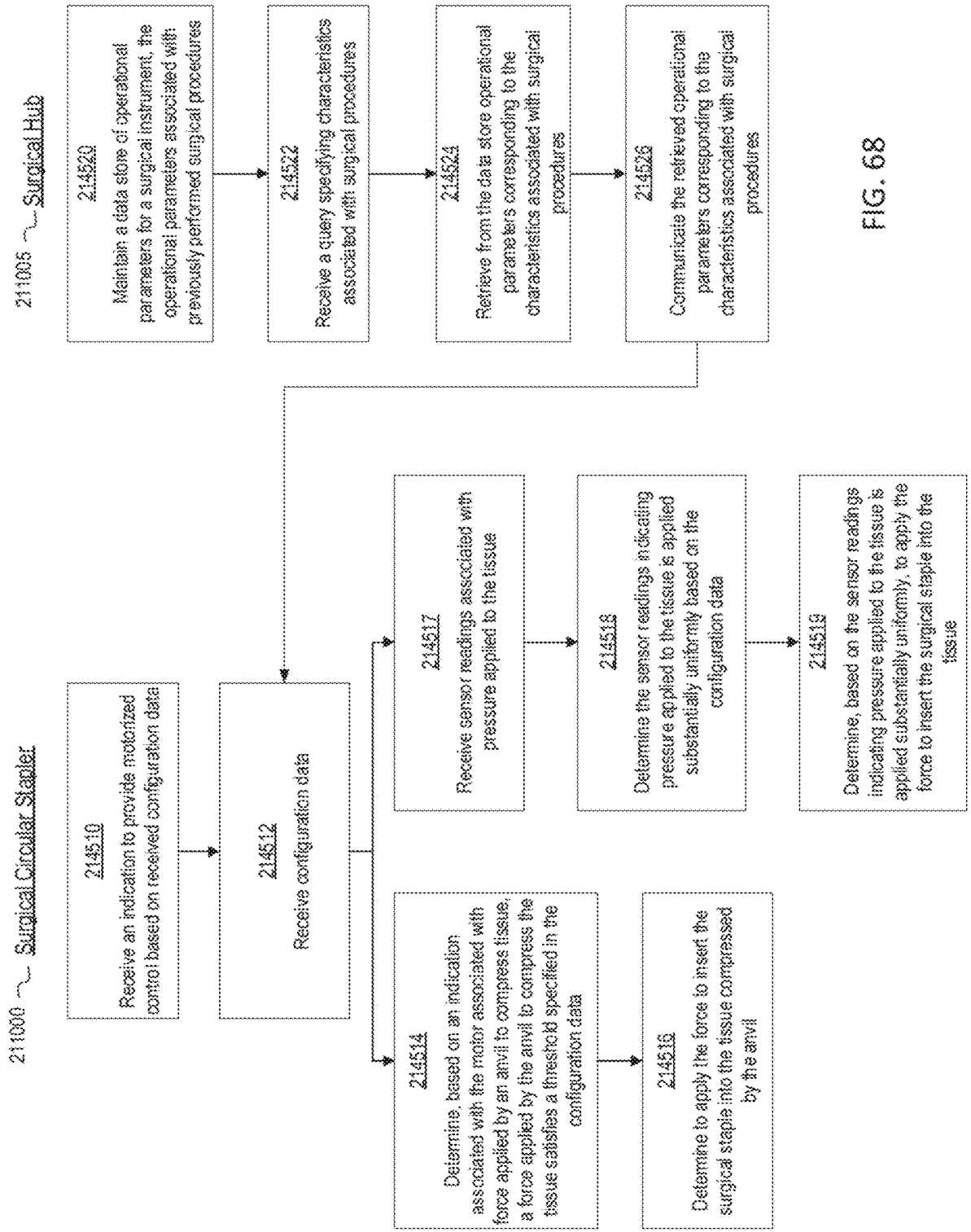
FIG. 68 is another example flow diagram of an example motorized circular stapling instrument operating in a previous-configuration control operation mode.

FIGS. 66-68 depict flow diagrams for processing associated with three sub-modes in a tiered system of operation modes under which the instrument 210100 operates in the load control mode. FIG. 66 illustrates the instrument 210100 operating under a sub-mode, e.g., the default sub-mode, where the motor load for the anvil closure motor (e.g., current drawn by the motor as a proxy for FTC) may be statically measured to ensure the instrument 210100 satisfies a predetermined criteria for staple firing ("static measurement sub-mode"). FIG. 67 illustrates the instrument 210100 operating under a sub-mode where sensor readings may be repeatedly measured to ensure the instrument 210100 satisfies a predetermined criteria for staple firing ("repeated sensor measurement sub-mode"). FIG. 68 illustrates the instrument 210100 operating under a sub-mode, which is the previous-configuration control mode described above with reference to FIGS. 60-63, where the predetermined criteria described in FIGS. 66 and 67 may be preconfigured with previously used configurations which may be stored in an external system, such as a surgical hub. Mode selection for such sub-modes may be determined by a system parameter as described above.

Referring to FIG. 66, in the example of load control mode's static measurement sub-mode, at 213510, the surgical circular stapler 211000, which may be the instrument 210100, may receive an indication to provide motor control that includes motorized control of anvil closure and motorized control of surgical stapler firing. For example, the system parameter for setting the surgical circular stapler 211000 to operate in load control mode described herein may, by default, serve as such indication.

At 213512, the surgical circular stapler 211000 may determine, based on an indication associated with the first motor, that a force applied by the anvil to compress the tissue satisfies a predetermined threshold. For example, an indication associated with the motor associated with force applied by an anvil to compress tissue may be a motor load for the surgical circular stapler's 211000 anvil closure motor. The motor load may be sensed at the end of the tissue creep/wait phase. The sensed motor load may be a tissue compression force (also referred to as FTC) with a magnitude that is within a predetermined range, such as the tissue compression force curve 202022 between t2 and t3 (i.e., a tissue creep/wait phase) that lies within a range from $F_{min}$ to $F_{max}$, i.e., ideal firing zone 202036, as illustrated in FIG. 24. The tissue compression force curve 202062 between t4 and t5 (i.e., a tissue creep/wait phase) that lies within a range from $F_{mm}$ to $F_{max}$ illustrated in FIG. 25 may be another such example.

At 213514, the surgical circular stapler 211000 may determine to apply the force to insert the surgical staple into the tissue compressed by the anvil after determining a force applied by the anvil to compress the tissue satisfies a predetermined threshold. For example, the surgical circular stapler's 211000 control circuit may be configured, similar to the control circuit 760 described in FIG. 24, to deploy the staples in the staple cartridge upon the surgical circular stapler's 211000 control circuit determining the tissue compression force F is within an ideal firing zone, such as the ideal firing zone 202036 in FIG. 24.

FIG. 67 illustrates the load control mode's repeated sensor measurement sub-mode. At 214010, the surgical circular stapler 211000 may receive an indication to provide motor control that includes motorized control based on sensor readings. A system parameter described herein for setting the surgical circular stapler 211000 to operate in load control mode's repeated sensor measurement sub-mode may serve as such indication.

At 214012, the surgical circular stapler 211000 may receive sensor readings associated with pressure applied to the tissue. For example, as described in FIG. 59 the surgical circular stapler's 211000 control circuit may receive tissue impedance measurements from predetermined zones on the staple cartridge as illustrated in FIGS. 40-41.

At 214014, the surgical circular stapler 211000 may determine the sensor readings indicating pressure applied to the tissue is applied substantially uniformly. For example, as described in connection with FIG. 59, the surgical circular stapler's 211000 control circuit may determine that tissue impedance measurements are substantially uniform as illustrated in FIG. 45. This determination may be based on a predetermined threshold that defines how much each predetermined zone's tissue impedance measurement may deviate from other zones and still be considered uniform. The surgical circular stapler's 211000 control circuit may be configured to perform tissue impedance measurements repeatedly (e.g., once per a pre-determined number of seconds) to determine the tissue impedance measurements are substantially uniform over a period of time, such as during tissue creep, including when tissue creep stabilization is reached.

At 214016, the surgical circular stapler 211000 may determine, based on the sensor readings indicating pressure applied to the tissue is applied substantially uniformly, to apply the force to insert the surgical staple into the tissue. For example, after the surgical circular stapler's 211000 control circuit determines the tissue impedance measurements are substantially uniform in the staple cartridge's predetermined zones as illustrated in FIG. 45 when tissue creep stabilization is reached, the surgical circular stapler's 211000 control circuit may deploy the staples in the staple cartridge when, for example, sensed motor load for the anvil closure motor (such as tissue compression F illustrated in FIG. 24) is also within an ideal firing zone as illustrated in FIG. 24.

Figure 69:
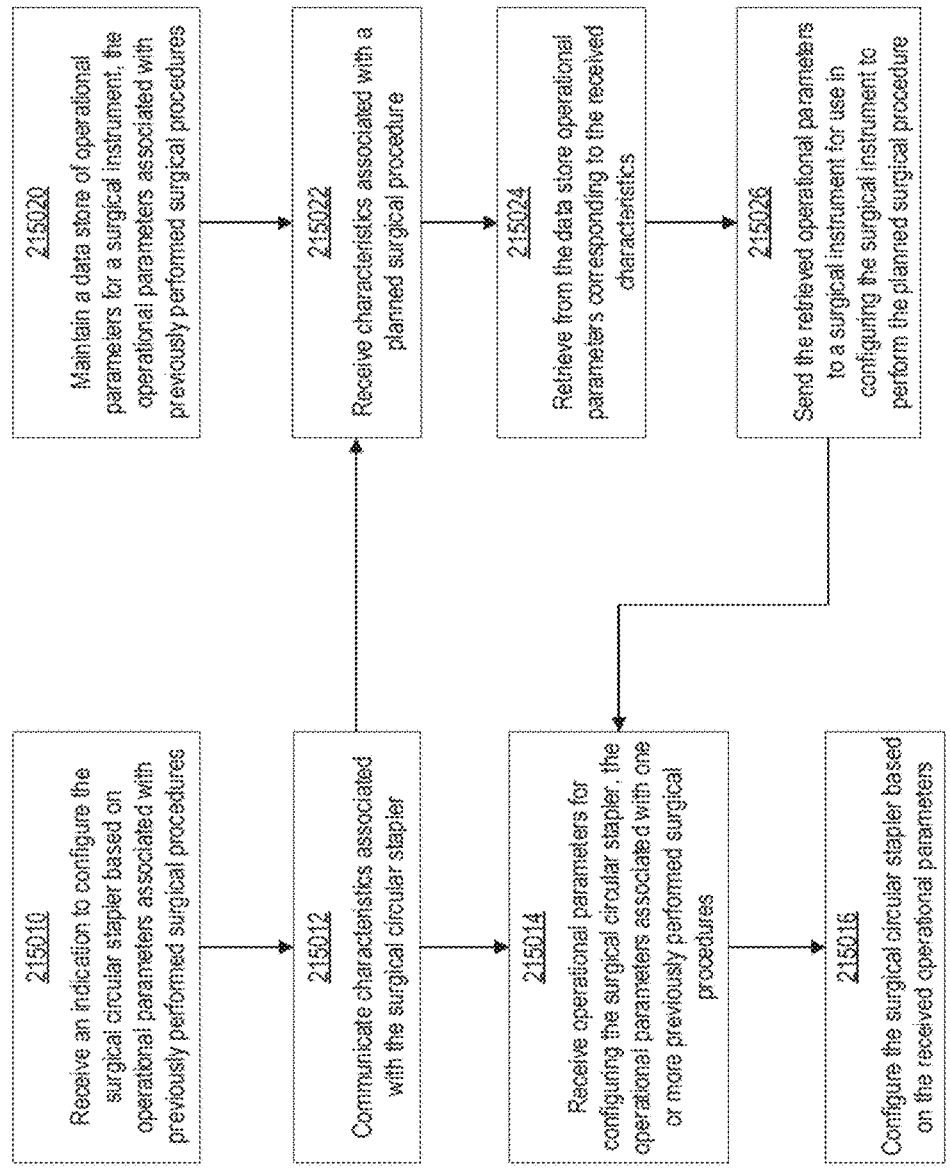
FIG. 69 is another example flow diagram of an example motorized circular stapling instrument operating in a previous-configuration control operation mode.

A surgical instrument may receive an indication from the surgical hub to provide control using operating or operational parameters associated with previously performed procedures. FIG. 69 is a functional flow diagram associated with an example previous-configuration control mode. The previous-configuration control mode may include processes and functionality as described herein with reference to FIGS. 60-63 and with reference to FIGS. 64-68.

Referring to FIG. 69, at 215020, a surgical hub 215005, which may be, for example, a surgical hub as described in connection with FIGS. 1-6 and 9-13, may maintain a data store of relevant data including operational parameters for a surgical instrument such as a surgical circular stapler 211000. The operational parameters may comprise "previous operational parameters" or "previous operating parameters" which may be parameters associated with previously performed surgical procedures. As described in connection with FIGS. 53 and 54, operational parameters that a surgical hub may receive from surgical instruments and store locally may comprise, for example, force-to-close (FTC) curve versus time (FTC curve), force-to-fire (FTF) curve versus time (FTF curve), anvil closure rate, tissue properties (e.g., impedance, thickness, stiffness, etc.), as well as others.

The operational parameters that may be relevant to the operation of a surgical circular stapler 2111000 and may be provided to a stapler by a surgical hub, may vary depending upon the operational mode of the stapler. For example, operational parameters used in stroke control mode surgical procedures may include, for example, the following: stroke control mode indicator, anvil head size, tissue thickness, viable staple height range, viable staple firing range, and wait time before staple firing phase. Operational parameters used in load control mode in an example surgical procedure may include, for example, the following: load control mode indicator, anvil head size, tissue thickness, tissue stiffness, viable staple height range, viable staple firing range, and wait time before staple firing phase. Operational parameters used in previous-configuration control mode in an example surgical procedure may include, for example, the following: previous-configuration control mode indicator, anvil head size, tissue thickness, tissue stiffness, viable staple height range, viable staple firing range, and wait time before staple firing phase.

The combination of parameters used for a procedure and which might be provided by a surgical hub to a surgical instrument may vary. For example, the combination of operational parameters used in the load control mode in an example surgical procedure may include, for example, the following: load control mode indicator, anvil head size, tissue thickness, tissue stiffness, viable staple height range, viable staple firing range, maximum FTC and minimum FTC allowed for staple firing, FTC curve, FTF curve, anvil closure motor output curve (e.g., graph 212516 shown in FIG. 64), firing motor output curve (e.g., graph 212516 shown in FIG. 64). In another example, the combination of operational parameters used in the load control mode in an example surgical procedure may include, for example, the following: load control mode indicator, repeated sensor measurement sub-mode indicator, anvil head size, tissue thickness, tissue stiffness, frequency of repeated measurement, tissue impedance for each predetermined zone on staple cartridge upon staple firing, viable staple height range, viable staple firing range, maximum FTC and minimum FTC allowed for staple firing, FTC curve, FTF curve, anvil closure motor output curve (e.g., graph 212516 shown in FIG. 64), firing motor output curve (e.g., graph 212516 shown in FIG. 64). In another example, the combination of operational parameters used in the load control mode in an example surgical procedure may include: previous-configuration control mode indicator, anvil head size, tissue thickness, tissue stiffness, sensor zone's tissue impedance uniformity deviation threshold, frequency of repeated sensor measurement, viable staple height range, viable staple firing range, maximum FTC and minimum FTC allowed for staple firing, FTC curve, FTF curve, anvil closure motor output curve (e.g., graph 212516 shown in FIG. 64), firing motor output curve (e.g., graph 212516 shown in FIG. 64).

Previous operational parameters for a surgical procedure may be stored along with a procedural outcome associated with a step of the procedure or the overall procedure. As described in in connection with FIG. 53, an example outcome may be whether there was bleeding at the surgical site. Another example may be whether the staples of a particular staple line were formed properly for the staple firing step of the procedure. As described in FIG. 53, procedural outcome may be further analyzed to be associated with a positive or negative outcome and such analyzed procedural outcome may be stored along with previous operational parameters.

Previous operational parameters for a surgical procedure may be stored along with an instrument operator identifier and/or patient parameters. As described in FIG. 54, for example, a responsible surgeon may be stored. As described in connection with FIG. 51, the patient parameters may be from patient records from an Electronic Medical Record database (EMR) and, after an anonymization process, may be stored in a surgical hub, such as the surgical hub 215005. Examples of patient parameters may include: the patient's diagnoses of emphysema, pre-operative treatment (e.g., chemotherapy, radiation, blood thinner, blood pressure medication, etc.), typical blood pressures, and etc.

Previous operational parameters may be operational parameter aggregate data based on multiple previous surgical procedures. As described in FIG. 52, for example, previous operational parameters from multiple previous surgical procedures may be aggregated locally at a surgical hub (e.g., the surgical hub 215005), aggregated across a network of surgical hubs (e.g., surgical hubs like the surgical hub 215005) associated with a medical facility, or aggregated globally at the cloud 5702. An example aggregate data may be operational parameter averages of surgical procedures with the same procedure type, similar patient parameters, and similar operational parameters (e.g., tissue properties) such as, for example, wait time (before staple firing phase) average at a surgical hub locally, at a medical facility, and globally at the cloud 5702. Another example aggregate data may further aggregate the above operational parameter averages based on procedural outcomes, such as the wait time average at a medical facility only for procedures with no malformed staples or generally with a positive outcome.

Referring to FIG. 69, as shown on the left side of the figure, the surgical circular stapler 211000 that is linked with the surgical hub 211005 may receive an indication to configure the surgical circular stapler based on operational parameters associated with previously performed surgical procedures. Such indication may be the system parameter as described in FIG. 63 to set the surgical circular stapler 211000 to operate in previous-configuration control mode. The surgical circular stapler 211000 and the surgical hub 211005 may be linked in an operating room in preparation for a planned surgical procedure.

At 215012, the surgical circular stapler 211000 may communicate to a linked surgical hub, such as the surgical hub 211005, characteristics associated with the surgical circular stapler 211000. For example, the surgical circular stapler 211000 may be operating with an end effector with an anvil, such as 210110B (shown in FIG. 59), and a staple heading assembly, such as 210130B (shown in FIG. 59). In such example, the surgical circular stapler 211000 may transmit a previous-configuration control mode indicator and an indication of medium anvil head size to the surgical hub 211005.

At 215022, the surgical hub 211005 may receive characteristics associated with a planned surgical procedure. Continuing with the example at 215012, the surgical hub 211005 may receive a previous-configuration control mode indicator and medium anvil head size transmitted from the surgical circular stapler 211000.

At 215024, the surgical hub 211005 may retrieve from the data store operational parameters corresponding to the received characteristics from the surgical circular stapler 211000. At 215022, the surgical hub 211005 may retrieve from the datastore the operational parameters used in the last surgical procedure performed by the instrument operator (e.g., the responsible surgeon for the planned surgical procedure) where a surgical circular stapler was used, the surgical circular stapler operation mode was a load control mode, and the anvil head size was medium. In such example, the retrieved operational parameters may include: a load control mode indicator, a medium anvil head size, normal tissue thickness, normal tissue stiffness, viable staple height range, viable staple firing range, a maximum FTC and a minimum FTC allowed for staple firing, a FTC curve, a FTF curve, an anvil closure motor output curve, a firing motor output curve.

At 215026, the surgical hub 211005 may send the retrieved operational parameters at 212024 to the surgical circular stapler 211000 for use in configuring the surgical circular stapler 211000 to perform the planned surgical procedure. In response, at 215014, the surgical circular stapler 211000 may receive from the surgical hub 211005 the retrieved operational parameters at 212024.

At 215016, the surgical circular stapler 211000 may be preconfigured using the received operational parameters at 215014 as the default operational parameters. Given the received operational parameters at 215014, the surgical circular stapler 211000 may be preconfigured to operate with the received viable staple height range, viable staple firing range, a maximum FTC and a minimum FTC allowed for staple firing, a FTC curve, a FTF curve, an anvil closure motor output curve, a firing motor output curve, when the tissue to be operated in the planned surgical procedure has the matching tissue properties, that is, a tissue with normal thickness and normal stiffness.

Figure 70:
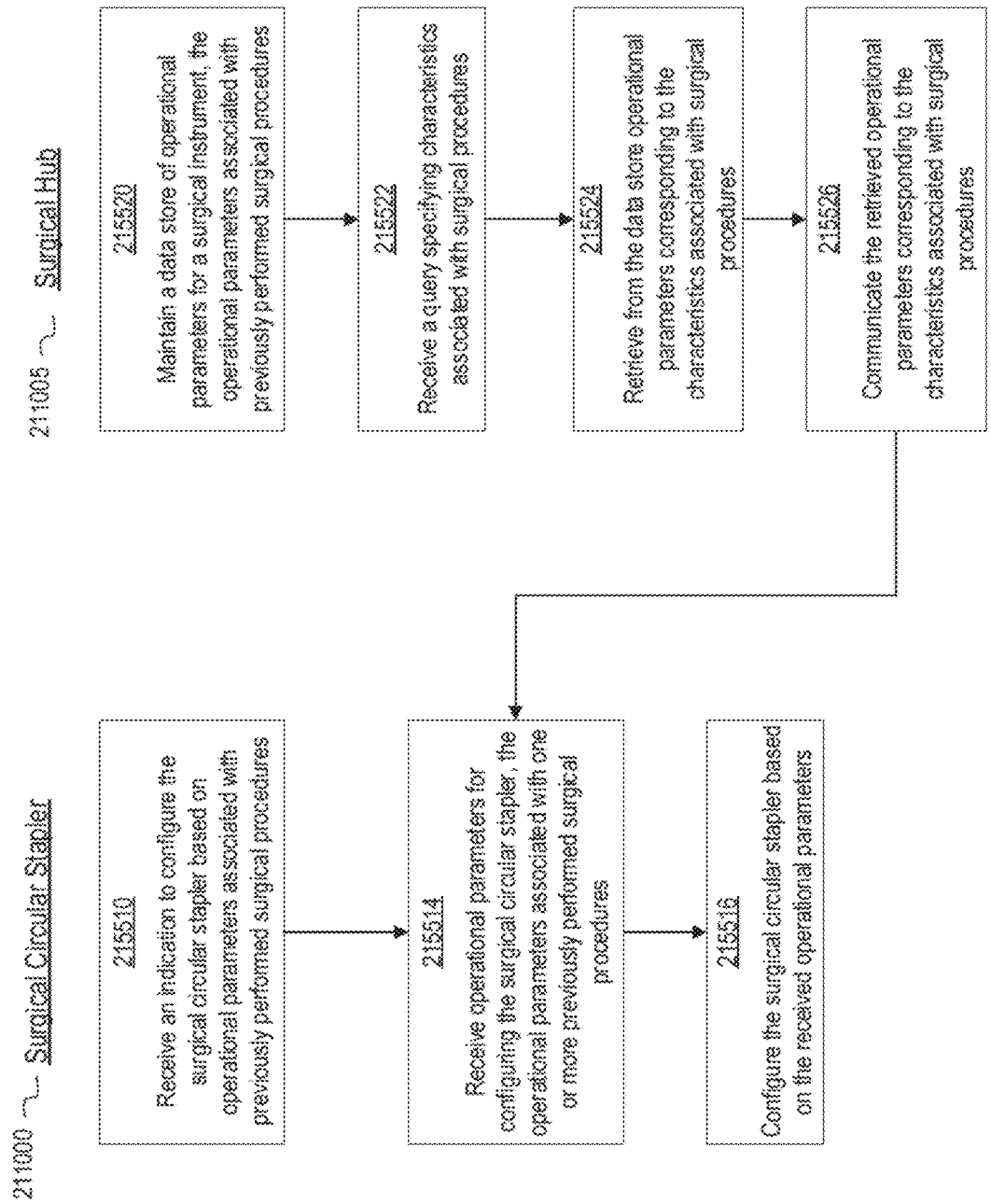
FIG. 70 is another example flow diagram of an example motorized circular stapling instrument operating in a previous-configuration control operation mode.

FIG. 70 is a flow chart corresponding to another example process for a surgical circular stapler 211000 to be configured to operate a previous-configuration control mode as described herein with reference to FIGS. 60-63 and 64-68.

At 215520, the surgical hub 215005 may maintain a data store of operational parameters that are associated with previously performed surgical procedures, as described at 215020 in FIG. 69.

At 215510, the surgical circular stapler 211000 may receive an indication to configure the surgical circular stapler based on operational parameters associated with previously performed surgical procedures as described at 211005 in FIG. 69.

At 215522, the surgical hub 215005 may receive a query specifying characteristics associated with surgical procedures. For example, the instrument operator as described in FIG. 69 may initiate a query on the surgical hub 215005 against the data store with the same characteristics received from the surgical circular stapler 211000 to retrieve operational parameters used in surgical procedures previously performed by the instrument operator as described at 215022 in FIG. 69. The instrument operator may initiate the query using a graphical user interface (GUI) located on the surgical hub 215005. FIG. 49 provides an example GUI that may be located on a surgical hub that may provide the ability for an instrument operator to interact with the surgical hub.

The instrument operator may initiate a query to obtain aggregated operational parameters to preconfigure the surgical circular stapler 211000. An example of aggregated operational parameters may be a medical facility (where surgical hub 215005 is located) average for viable staple height range and viable staple firing range for tissue with normal thickness where a surgical circular stapler with medium-sized anvil head size was used, the operation mode was a load control mode, and the procedural outcome was positive. At 215524, the surgical hub 215005 may retrieve from the data store matching operational parameters as described at 215024 in FIG. 69. At 215526, the surgical hub 215005 may send the retrieved operational parameters to the surgical circular stapler 211000, as described at 215026 in FIG. 69. At 215514, the surgical circular stapler 211000 may receive the retrieved operational parameters as described at 215014 in FIG. 69. At 215516, the surgical circular stapler 211000 may be preconfigured using the received operational parameters at 215514, as described at 215014 in FIG. 69. In such example, the surgical circular stapler 211000 may be preconfigured to operate with the received medical facility average for viable staple height range and viable staple firing range among other operational parameters.

Figure 63:
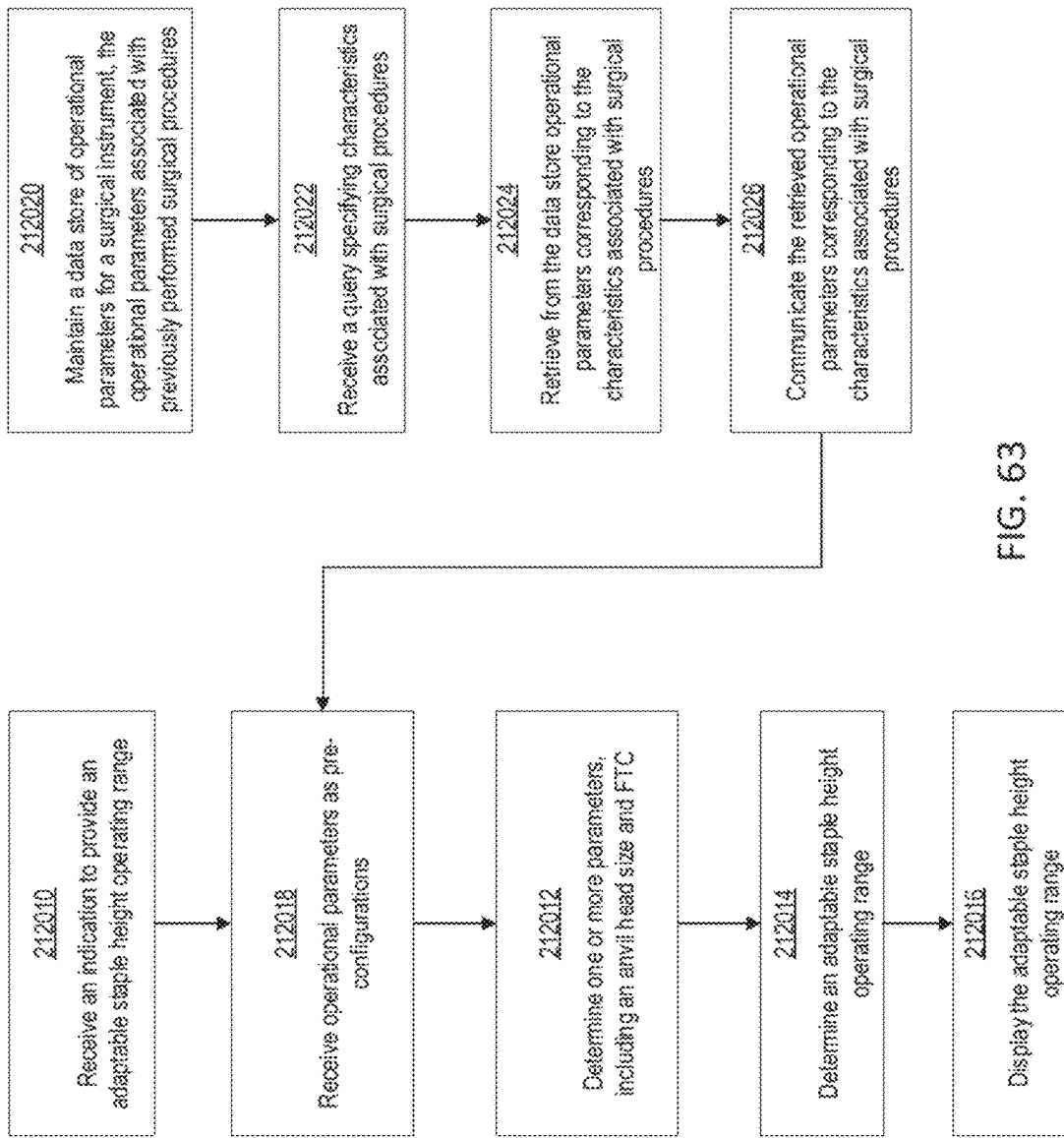
FIG. 63 is an example flow diagram of an example motorized circular stapling instrument operating in a previous-configuration control operation mode.

FIG. 63 depicts processing for preconfiguring the surgical circular stapler 211000 to provide an adaptable representation of an operating range for tissue compression using previous operational parameters retrieved from the surgical hub 215005 based on an instrument operator's query against the surgical hub's 215005 data store, at 212022, 212024, 212026, and 212018, as described in FIG. 70. After preconfiguring the surgical circular stapler 211000, it may be operated in effectively the load control mode at 212012, 212014, and 212016 as described in FIG. 62.

FIG. 68 depicts processing for preconfiguring the surgical circular stapler 211000 to provide motorized control in the load control mode with previous operational parameters retrieved from the surgical hub 215005 based on an instrument operator's query against the surgical hub's 215005 data store, at 214522, 214524, 214526, and 214512, as described in FIG. 70. After being preconfigured, the surgical circular stapler 211000 may be operated in both the "static measurement" sub-mode and "repeated sensor measurement" sub-mode under the local control mode as described in FIG. 66 and FIG. 67, respectively, at 214514, 214516, 214517, 214518, and 214519.

Accordingly, systems and techniques for adaptive control of surgical instrument functions have been disclosed. A surgical instrument may be configured to communicate with an external system such as, for example, a surgical hub. The surgical hub may generate, and the surgical instrument may receive, an indication of one or more functions to be adaptively controlled by the surgical instrument. For example, a surgical stapler instrument may receive an indication to adaptively control a display of staple height operating range and/or to adaptively control motorized features of the surgical instrument. The surgical instrument may determine values for parameters associated with the identified function and adapt the control of the identified function based upon the determined parameters. The surgical instrument may modify its operation of the one or more controlled functions based upon the parameters. The surgical instrument may communicate additional information such as additional parameter values to the external system and may receive further input regarding continued control of the indicated one or more functions.

The invention claimed is:

1. A surgical stapler comprising:
a processor configured to:
receive an indication to provide one or more controlled functions, the indication to provide the one or more controlled functions comprising an indication to provide adaptable control of a motor associated with application of force by a tissue compression anvil;
determine one or more parameters associated with the one or more controlled functions, the one or more parameters indicating a force to insert a surgical staple is being applied; and
provide, based on the one or more parameters, the one or more controlled functions,
wherein the processor configured to provide, based on the one or more parameters, the one or more controlled functions is configured to, based on the one or more parameters indicating the force to insert the surgical staple is being applied, control the motor to increase force applied by the tissue compression anvil while the force to insert the surgical staple is being applied.

2. The surgical stapler of claim 1,
wherein the processor is further configured to communicate parameters associated with the surgical stapler to a system; and
wherein the indication to provide the one or more controlled functions is based at least in part on the parameters associated with the surgical stapler.

3. The surgical stapler of claim 1,
wherein the processor configured to provide, based on the one or more parameters, the one or more controlled functions is further configured to modify operation of the one or more controlled functions based on the one or more parameters.

4. The surgical stapler of claim 1,
wherein the indication to provide the one or more controlled functions comprises an indication to provide one or more of an adaptable staple height operating range or configure the surgical stapler based on operational parameters associated with previously performed surgical procedures.

5. The surgical stapler of claim 1,
wherein the processor configured to receive the indication to provide the one or more controlled functions is further configured to receive an indication to provide an adaptable staple height operating range;
wherein the processor configured to determine the one or more parameters associated with the one or more controlled functions is further configured to determine a size of an anvil associated with an end effector; and
wherein the processor configured to provide, based on the one or more parameters, the one or more controlled functions is further configured to determine, based on the size of the anvil associated with the end effector, the adaptable staple height operating range is modified relative to a default adaptable staple height operating range.

6. A surgical circular stapler comprising:
a display; and
a processor communicatively coupled with the display, the processor configured to:
receive an indication to provide an adaptable staple height operating range;
determine one or more parameters associated with the surgical circular stapler;
determine the adaptable staple height operating range based on the one or more parameters of the surgical circular stapler; and
present on the display the adaptable staple height operating range.

7. The surgical circular stapler of claim 6,
wherein the processor configured to receive the indication to provide the adaptable staple height operating range is configured to receive the indication from an external system.

8. The surgical circular stapler of claim 6,
wherein the processor configured to determine the one or more parameters associated with the surgical circular stapler is configured to determine a size of an end effector head.

9. The surgical circular stapler of claim 8,
wherein the processor configured to determine the adaptable staple height operating range based on the one or more parameters of the surgical circular stapler is configured to determine, based on the size of the end effector head, the adaptable staple height operating range is modified relative to a default adaptable staple height operating range.

10. The surgical circular stapler of claim 9,
wherein the processor configured to determine the adaptable staple height operating range is modified relative to the default adaptable staple height operating range is configured to determine the adaptable staple height operating range is shifted relative to the default adaptable staple height operating range.

11. The surgical circular stapler of claim 6,
wherein the processor configured to determine the one or more parameters associated with the surgical circular stapler is configured to determine a force during tissue compression; and
wherein the processor configured to determine the adaptable staple height operating range based on the one or more parameters of the surgical circular stapler is configured to determine, based on the force during tissue compression, the adaptable staple height operating range is modified relative to a default adaptable staple height operating range.

12. The surgical circular stapler of claim 6,
wherein the indication to provide the adaptable staple height operating range comprises an indication to provide an adaptable staple height operating range as applied in a previous procedure;
wherein the processor configured to determine the one or more parameters f associated with the surgical circular stapler is configured to receive, from a surgical hub, one or more operational parameters associated with the adaptable staple height operating range as applied in the previous procedure; and
wherein the processor configured to determine the adaptable staple height operating range based on the one or more parameters of the surgical circular stapler is configured to:
set a default adaptable staple height operating range using the one or more operational parameters associated with the adaptable staple height operating range as applied in the previous procedure; and
determine the adaptable staple height operating range using the default adaptable staple height operating range.

13. A surgical stapler comprising:
an end effector having an anvil head;
a display; and
a processor communicatively coupled with the display, the processor configured to:
receive an indication to provide an adaptable staple height operating range;
determine one or more parameters associated with a size of the anvil head;
determine the adaptable staple height operating range based on the one or more parameters associated with the size of the anvil head; and
present on the display the adaptable staple height operating range.

14. The surgical stapler of claim 13,
wherein the processor is further configured to determine based on the one or more parameters associated with the size of the anvil head that the size of the anvil head is relatively small; and
wherein the processor configured to determine the adaptable staple height operating range based on the one or more parameters associated with the size of the anvil head is configured to determine the adaptable staple height operating range is modified relative to a default adaptable staple height operating range.

15. The surgical stapler of claim 14,
wherein the adaptable staple height operating range comprises a first laterally extending band and a second laterally extending band, the second laterally extending band positioned within the first laterally extending band;
wherein the processor configured to determine the adaptable staple height operating range is modified relative to the default adaptable staple height operating range is configured to:
determine the first laterally extending band is substantially similar in width to a first laterally extending band associated with the default adaptable staple height operating range; and
determine the second laterally extending band is wider than a second laterally extending band associated with the default adaptable staple height operating range.

16. The surgical stapler of claim 15,
wherein the processor configured to determine the adaptable staple height operating range is modified relative to the default adaptable staple height operating range is configured to determine the first laterally extending band is shifted downward relative to the first laterally extending band associated with the default adaptable staple height operating range.

17. The surgical stapler of claim 13,
wherein the processor is further configured to determine based on the one or more parameters associated with the size of the anvil head that the size of the anvil head is relatively large; and
wherein the processor configured to determine the adaptable staple height operating range based on the one or more parameters associated with the size of the anvil head is configured to determine the adaptable staple height operating range is modified relative to a default adaptable staple height operating range.

18. The surgical stapler of claim 17,
wherein the adaptable staple height operating range comprises a first laterally extending band and a second laterally extending band, the second laterally extending band positioned within the first laterally extending band; and
wherein the processor configured to determine the adaptable staple height operating range is modified relative to the default adaptable staple height operating range is configured to:
determine the first laterally extending band is narrower than a first laterally extending band associated with the default adaptable staple height operating range; and
determine the second laterally extending band is narrower than a second laterally extending band associated with the default adaptable staple height operating range.

19. The surgical stapler of claim 18,
wherein the processor configured to determine the adaptable staple height operating range is modified relative to the default adaptable staple height operating range is configured to determine the second laterally extending band is shifted upward relative to the second laterally extending band associated with the default adaptable staple height operating range.

* * * * *